United States Patent
Schmitz et al.

(10) Patent No.: US 8,475,483 B2
(45) Date of Patent: Jul. 2, 2013

(54) SELECTIVE TISSUE REMOVAL TOOL FOR USE IN MEDICAL APPLICATIONS AND METHODS FOR MAKING AND USING

(75) Inventors: Gregory P. Schmitz, Los Gatos, CA (US); Eric C. Miller, Los Gatos, CA (US); Richard T. Chen, Woodland Hills, CA (US); Ming-Ting Wu, Northridge, CA (US)

(73) Assignee: Microfabrica Inc., Van Nuys, CA (US)

( * ) Notice: Subject to any disclaimer, the term of this patent is extended or adjusted under 35 U.S.C. 154(b) by 0 days.

(21) Appl. No.: 13/289,994

(22) Filed: Nov. 4, 2011

(65) Prior Publication Data

US 2012/0053606 A1 Mar. 1, 2012

Related U.S. Application Data

(63) Continuation of application No. 13/007,578, filed on Jan. 14, 2011, which is a continuation-in-part of application No. 12/490,295, filed on Jun. 23, 2009, said application No. 13/007,578 is a continuation-in-part of application No. 12/490,301, filed on Jun. 23, 2009.

(60) Provisional application No. 61/075,006, filed on Jun. 23, 2008, provisional application No. 61/164,864, filed on Mar. 30, 2009, provisional application No. 61/164,883, filed on Mar. 30, 2009, provisional application No. 61/408,558, filed on Oct. 29, 2010.

(51) Int. Cl.
*A61B 17/32* (2006.01)
*A61B 17/56* (2006.01)

(52) U.S. Cl.
USPC .............. 606/170; 606/82; 606/167; 606/180

(58) Field of Classification Search
USPC ...... 606/79–85, 159, 166–180; 600/562–572; 30/166.3, 369, 370, 502
See application file for complete search history.

(56) References Cited

U.S. PATENT DOCUMENTS

| 2,259,015 A | 10/1941 | Anderson et al. |
| 2,455,655 A * | 12/1948 | Carroll .......................... 606/178 |
| 3,404,677 A | 10/1968 | Springer |
| 3,882,872 A | 5/1975 | Douvas et al. |

(Continued)

FOREIGN PATENT DOCUMENTS

WO    WO 2008/037984 A2    4/2008

OTHER PUBLICATIONS

Cohen at al.; EFAB: Batch production of functional, fully-dense metal parts with micron-scale features; Proc 9th, Solid Freeform Fabrication; Univ. of Texas at Austin; pp. 161-168; Aug. 1998.

(Continued)

*Primary Examiner* — Kathleen Holwerda
(74) *Attorney, Agent, or Firm* — Shay Glenn LLP

(57) ABSTRACT

The present disclosure relates generally to the field of tissue removal and more particularly to methods and devices for use in medical applications involving selective tissue removal. One exemplary method includes the steps of providing a tissue cutting instrument capable of distinguishing between target tissue to be removed and non-target tissue, urging the instrument against the target tissue and the non-target tissue, and allowing the instrument to cut the target tissue while automatically avoiding cutting of non-target tissue. Various tools for carrying out this method are also described.

27 Claims, 100 Drawing Sheets

U.S. PATENT DOCUMENTS

| | | | |
|---|---|---|---|
| 3,937,222 A | | 2/1976 | Banko |
| 4,621,637 A | | 11/1986 | Fishbein |
| 4,747,821 A | * | 5/1988 | Kensey et al. .................. 604/22 |
| 4,842,578 A | | 6/1989 | Johnson et al. |
| 4,844,363 A | | 7/1989 | Garnier et al. |
| 4,943,296 A | * | 7/1990 | Funakubo et al. ............ 606/166 |
| 5,019,088 A | | 5/1991 | Farr |
| 5,084,052 A | | 1/1992 | Jacobs |
| 5,141,168 A | | 8/1992 | Pepper |
| 5,181,433 A | | 1/1993 | Ueno et al. |
| 5,190,637 A | | 3/1993 | Guckel |
| 5,226,909 A | | 7/1993 | Evans et al. |
| 5,284,486 A | | 2/1994 | Kotula et al. |
| 5,378,583 A | | 1/1995 | Guckel et al. |
| 5,411,511 A | * | 5/1995 | Hall .............................. 606/166 |
| 5,465,444 A | | 11/1995 | Bigler et al. |
| 5,484,112 A | | 1/1996 | Koenig |
| 5,496,668 A | | 3/1996 | Guckel et al. |
| 5,522,829 A | | 6/1996 | Michalos |
| 5,576,147 A | | 11/1996 | Guckel et al. |
| 5,591,187 A | | 1/1997 | Dekel |
| 5,601,556 A | | 2/1997 | Pisharodi |
| 5,618,293 A | | 4/1997 | Sample et al. |
| 5,643,304 A | * | 7/1997 | Schechter et al. ............ 606/171 |
| 5,662,284 A | | 9/1997 | Koenig |
| 5,685,838 A | | 11/1997 | Peters et al. |
| 5,695,510 A | * | 12/1997 | Hood ........................... 606/169 |
| 5,718,618 A | | 2/1998 | Guckel et al. |
| 5,725,530 A | | 3/1998 | Popken |
| 5,782,848 A | * | 7/1998 | Lennox ......................... 606/159 |
| 5,788,169 A | | 8/1998 | Koenig |
| 5,823,990 A | * | 10/1998 | Henley ........................... 604/22 |
| 5,846,244 A | | 12/1998 | Cripe |
| 5,866,281 A | | 2/1999 | Guckel et al. |
| 5,908,719 A | | 6/1999 | Guckel et al. |
| 5,910,150 A | | 6/1999 | Saadat |
| 5,916,231 A | | 6/1999 | Bays |
| 5,928,158 A | * | 7/1999 | Aristides ...................... 600/547 |
| 5,928,161 A | * | 7/1999 | Krulevitch et al. ........... 600/564 |
| 5,957,881 A | | 9/1999 | Peters et al. |
| 6,001,112 A | | 12/1999 | Taylor |
| 6,010,477 A | | 1/2000 | Bays |
| 6,013,991 A | | 1/2000 | Philipp |
| 6,027,630 A | | 2/2000 | Cohen |
| 6,063,088 A | | 5/2000 | Winslow |
| 6,221,088 B1 | | 4/2001 | Bays |
| 6,293,957 B1 | | 9/2001 | Peters et al. |
| 6,447,525 B2 | | 9/2002 | Follmer et al. |
| 6,475,369 B1 | | 11/2002 | Cohen |
| 6,517,544 B1 | | 2/2003 | Michelson |
| 6,565,588 B1 | | 5/2003 | Clement et al. |
| 6,572,742 B1 | | 6/2003 | Cohen |
| 6,613,972 B2 | | 9/2003 | Cohen et al. |
| 6,666,874 B2 | | 12/2003 | Heitzmann et al. |
| 6,761,723 B2 | | 7/2004 | Buttermann et al. |
| 6,790,377 B1 | | 9/2004 | Cohen |
| 6,951,456 B2 | | 10/2005 | Cohen et al. |
| 7,160,304 B2 | | 1/2007 | Michelson |
| 7,163,614 B2 | | 1/2007 | Cohen |
| 7,195,989 B2 | | 3/2007 | Lockard et al. |
| 7,229,544 B2 | | 6/2007 | Cohen |
| 7,235,088 B2 | | 6/2007 | Pintor et al. |
| 7,239,219 B2 | | 7/2007 | Brown et al. |
| 7,252,861 B2 | | 8/2007 | Smalley |
| 7,479,147 B2 | | 1/2009 | Honeycutt et al. |
| 7,699,790 B2 | | 4/2010 | Simpson |
| 2004/0138672 A1 | | 7/2004 | Michelson |
| 2005/0021065 A1 | * | 1/2005 | Yamada et al. ............... 606/169 |
| 2005/0029109 A1 | | 2/2005 | Zhang et al. |
| 2005/0059905 A1 | | 3/2005 | Boock et al. |
| 2005/0222598 A1 | * | 10/2005 | Ho et al. ........................ 606/171 |
| 2006/0184175 A1 | | 8/2006 | Schomer et al. |
| 2006/0200152 A1 | | 9/2006 | Karubian et al. |
| 2006/0212060 A1 | | 9/2006 | Hacker et al. |
| 2006/0217730 A1 | | 9/2006 | Termanini |
| 2006/0229646 A1 | | 10/2006 | Sparks |
| 2006/0241566 A1 | | 10/2006 | Moon et al. |
| 2006/0282065 A1 | | 12/2006 | Cohen |
| 2007/0073303 A1 | | 3/2007 | Namba |
| 2007/0100361 A1 | | 5/2007 | Cohen |
| 2007/0197895 A1 | | 8/2007 | Nycz et al. |
| 2007/0198038 A1 | | 8/2007 | Cohen et al. |
| 2007/0219459 A1 | | 9/2007 | Cohen |
| 2007/0260253 A1 | | 11/2007 | Johnson et al. |
| 2007/0265648 A1 | | 11/2007 | Cohen |
| 2008/0004643 A1 | | 1/2008 | To et al. |
| 2008/0161809 A1 | | 7/2008 | Schmitz et al. |
| 2008/0249553 A1 | | 10/2008 | Gruber et al. |
| 2009/0012524 A1 | | 1/2009 | Dower |
| 2009/0018565 A1 | | 1/2009 | To et al. |
| 2010/0010492 A1 | | 1/2010 | Lockard et al. |
| 2010/0010525 A1 | | 1/2010 | Lockard et al. |

OTHER PUBLICATIONS

Cohen at al.; EFAB: low-cost automated electrochemical batch fabrication of arbritary 3-D microstructures; Micromachining and Microfabrication Process Technology, SPIE 1999 Symposium on Micromachining and Microfabrication; 11 pgs.; Sep. 1999.

Cohen at al.; EFAB: Rapid, low-cost desktop micromachining of high aspect ratio true 3-D MEMS; Proc. 12th, IEEE Micro Electro Mechanical Systems Workshop; IEEE; pp. 244-251; Jan. 1999.

Cohen, Adam L.; 3-D micromachining by electrochemical fabrication; Micromachine Devices; pp. 6-7; Mar. 1999.

Cohen, Adam L.; Electrochemical Fabrication (EFAB}); MEMS Handbook; Chapter 19; CRC Press LLC; pp. 19-1-19-23; 2002.

Microfabrication—rapid prototyping's killer application?; Rapid Prototyping Report; vol. 9; No. 6; pp. 1-5; Jun. 1999.

SSI Shredding Systems; www.ssiworld.com; 16 pgs.; Sep. 24, 2009 (downloaded).

Tseng et al.; EFAB: high aspect ratio, arbitrary 3-D metal microstructures using a low -cost automated batch process; 3rd Int'l. Workshop on High Aspect Ratio Microstructure Technology (HARMST99); Kazusa, Japan; 4 pgs.; Jun. 1999.

Tseng at al.; EFAB; high aspect ratio, arbitrary 3-D metal microstructures using a low -cost automated batch process; Microelectromechanical Systems (MEMS); vol. 1; ASME 1999 (Int'l. Mechanical Engineering Congress and Exposition; 6 pgs.; Nov. 1999.

Zhang et al.; EFAB: rapid desktop manufacturing of true 3-D microstructures; Proc. 2nd Int'l. Conf. on Integrated MicroNanotechnology for Space Applications; The Aerospace Co.; 11 pgs.; Apr. 1999.

Lockard et al.; U.S. Appl. No. 12/491,220 entitled "Miniature Shredding Tool for Use in Medical Applications and Methods for Making," filed Jun. 24, 2009.

Schmitz et al.; U.S. Appl. No. 13/007,578 entitled "Selective Tissue Removal Tool for Use in Medical Applications and Methods for Making and Using," filed Jan. 14, 2011.

Chen et al.; U.S. Appl. No. 13/388,653 entitled "Concentric Cutting Devices for Use in Minimally Invasive Medical Procedures." filed Apr. 16, 2012.

Schmitz et al.; U.S. Appl. No. 13/535,197 entitled "MEMS Micro Debrider Devices and Methods of Tissue Removal," filed Jun. 27, 2012.

* cited by examiner

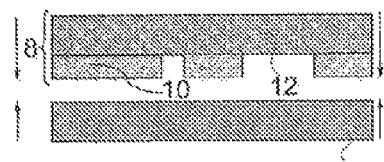
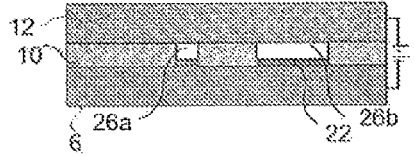
FIG. 1A (PRIOR ART)   FIG. 1B (PRIOR ART)
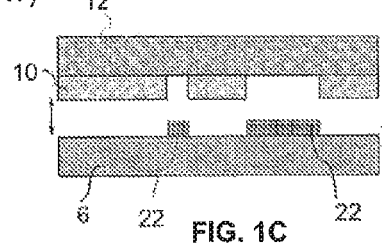
FIG. 1C (PRIOR ART)
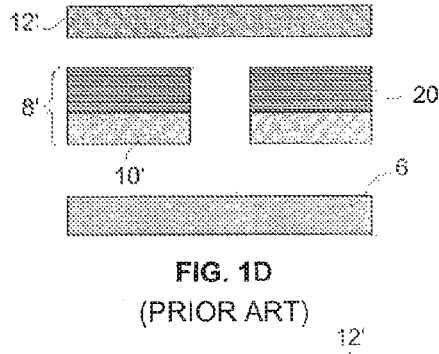
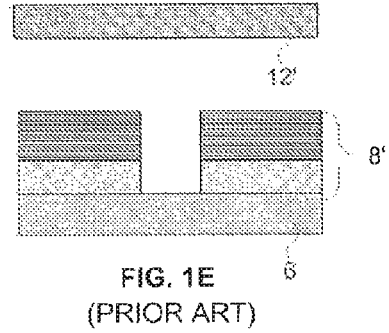
FIG. 1D (PRIOR ART)   FIG. 1E (PRIOR ART)
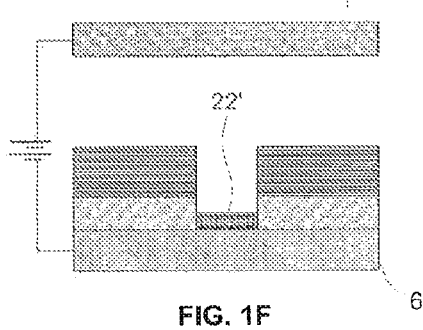
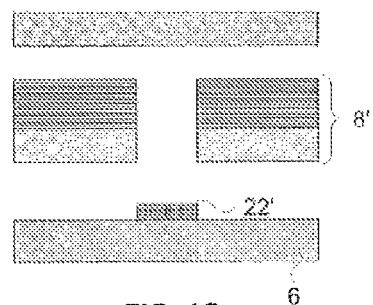
FIG. 1F (PRIOR ART)   FIG. 1G (PRIOR ART)

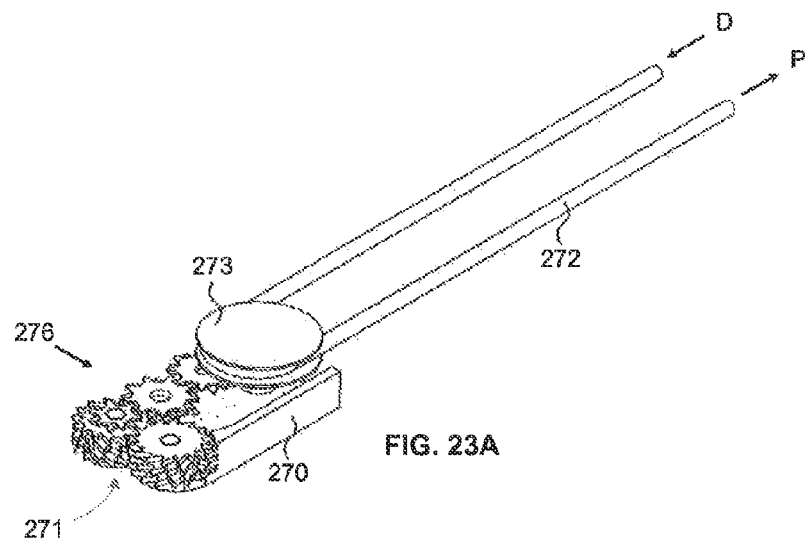
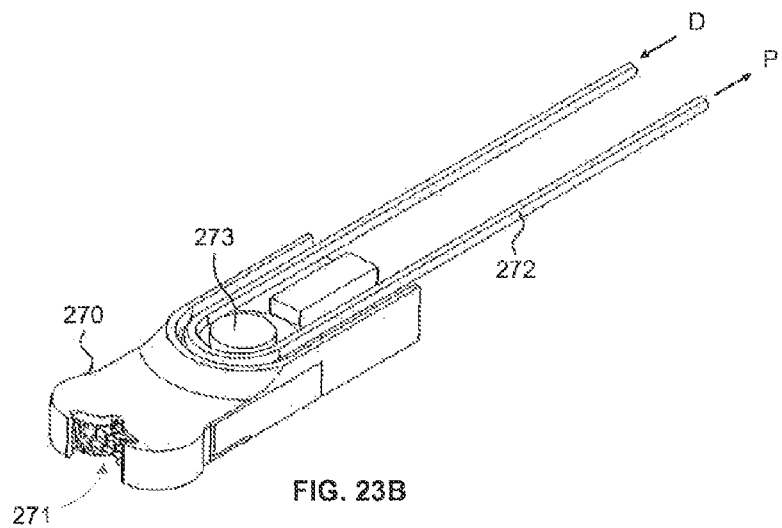

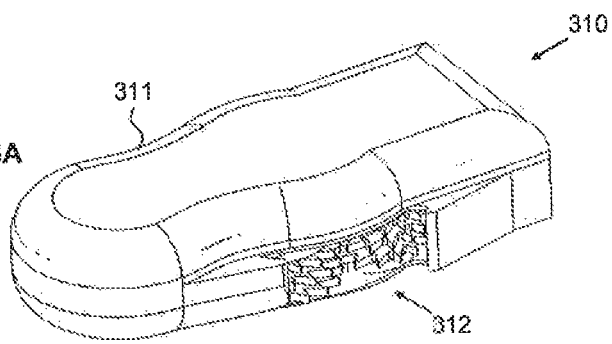
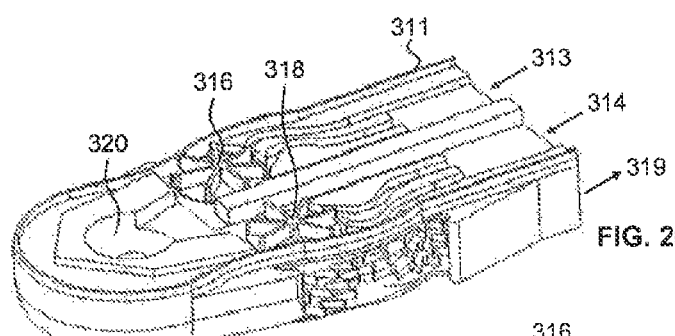
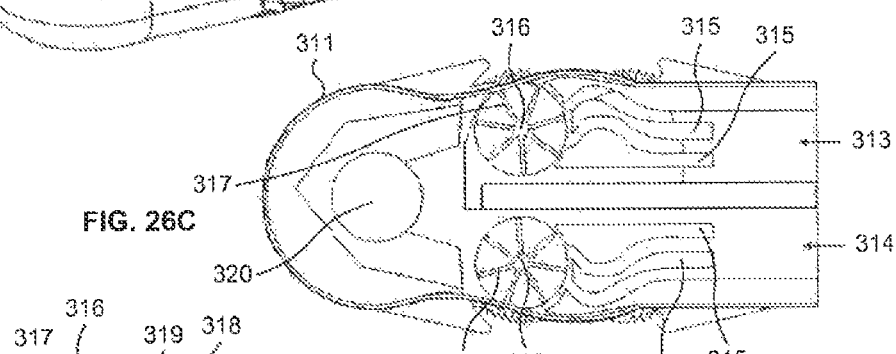
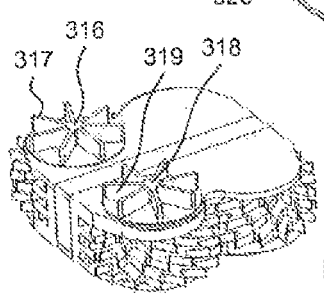
FIG. 26A
FIG. 26B
FIG. 26C
FIG. 26D

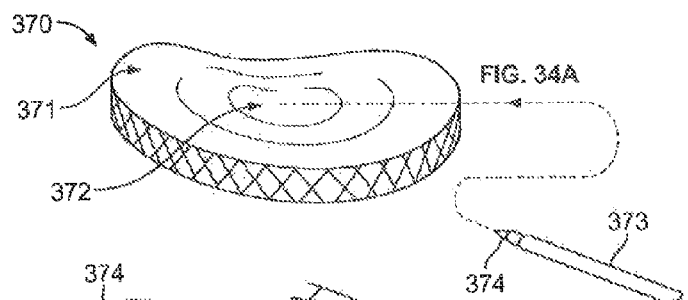
FIG. 34A
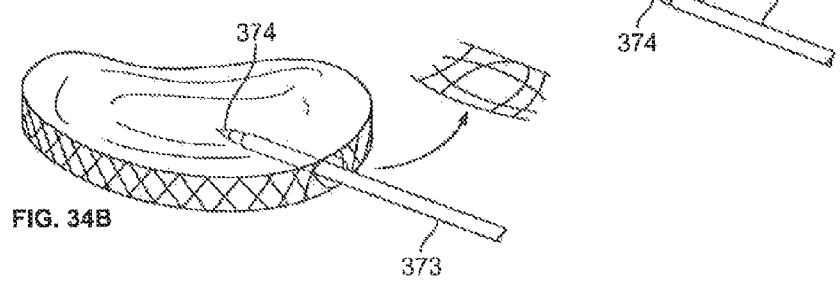
FIG. 34B
FIG. 34C
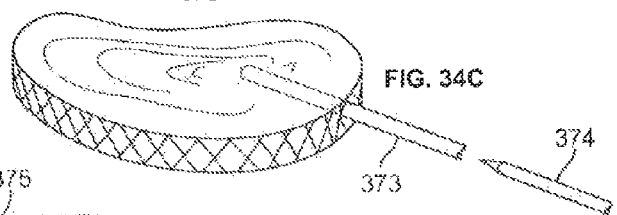
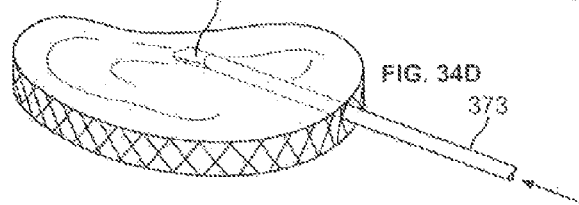
FIG. 34D
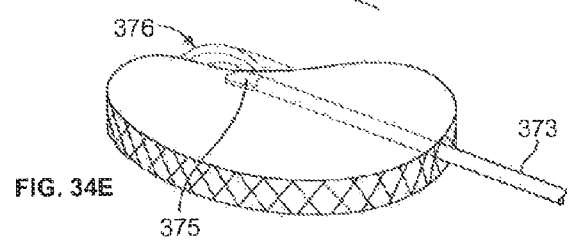
FIG. 34E

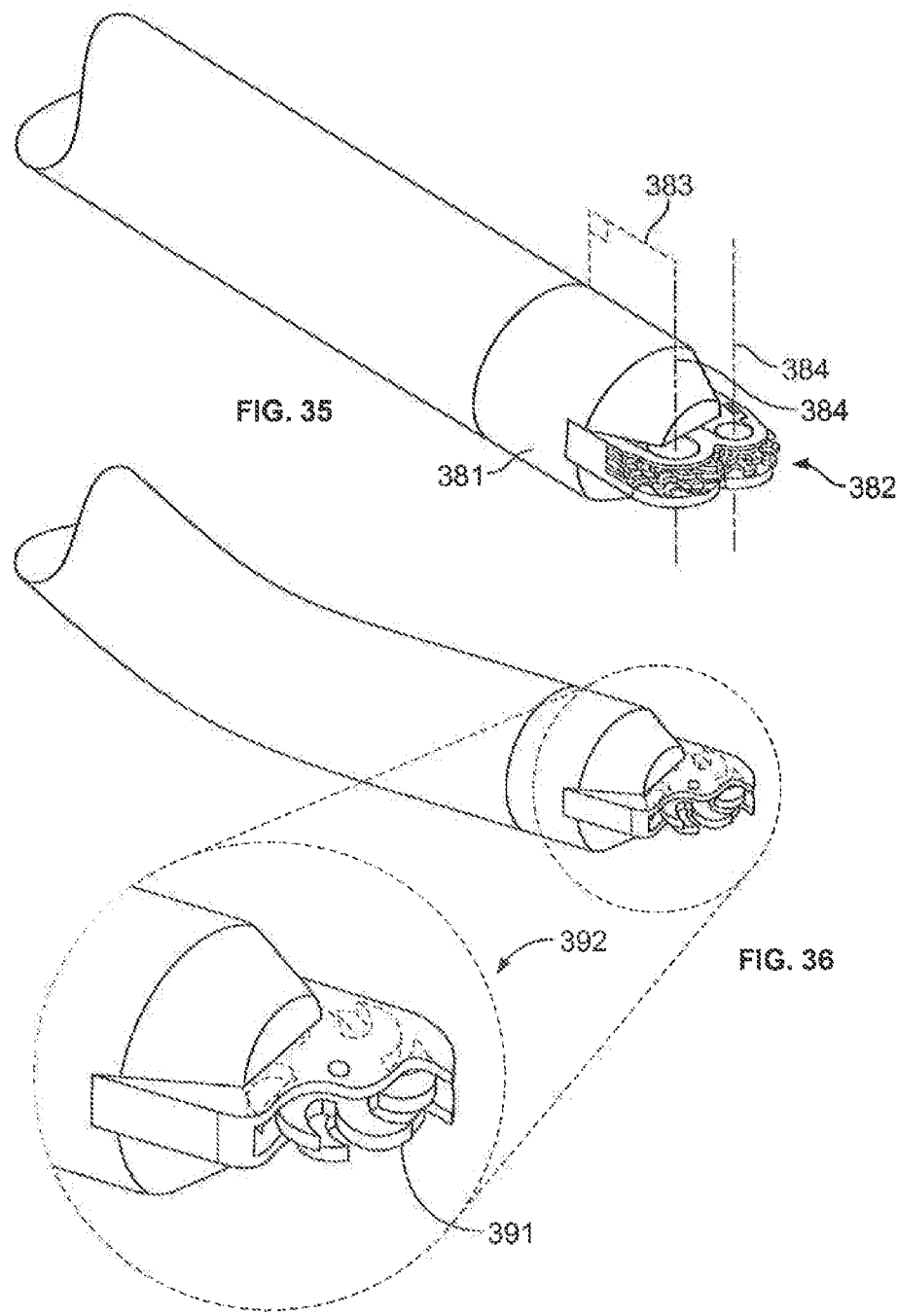

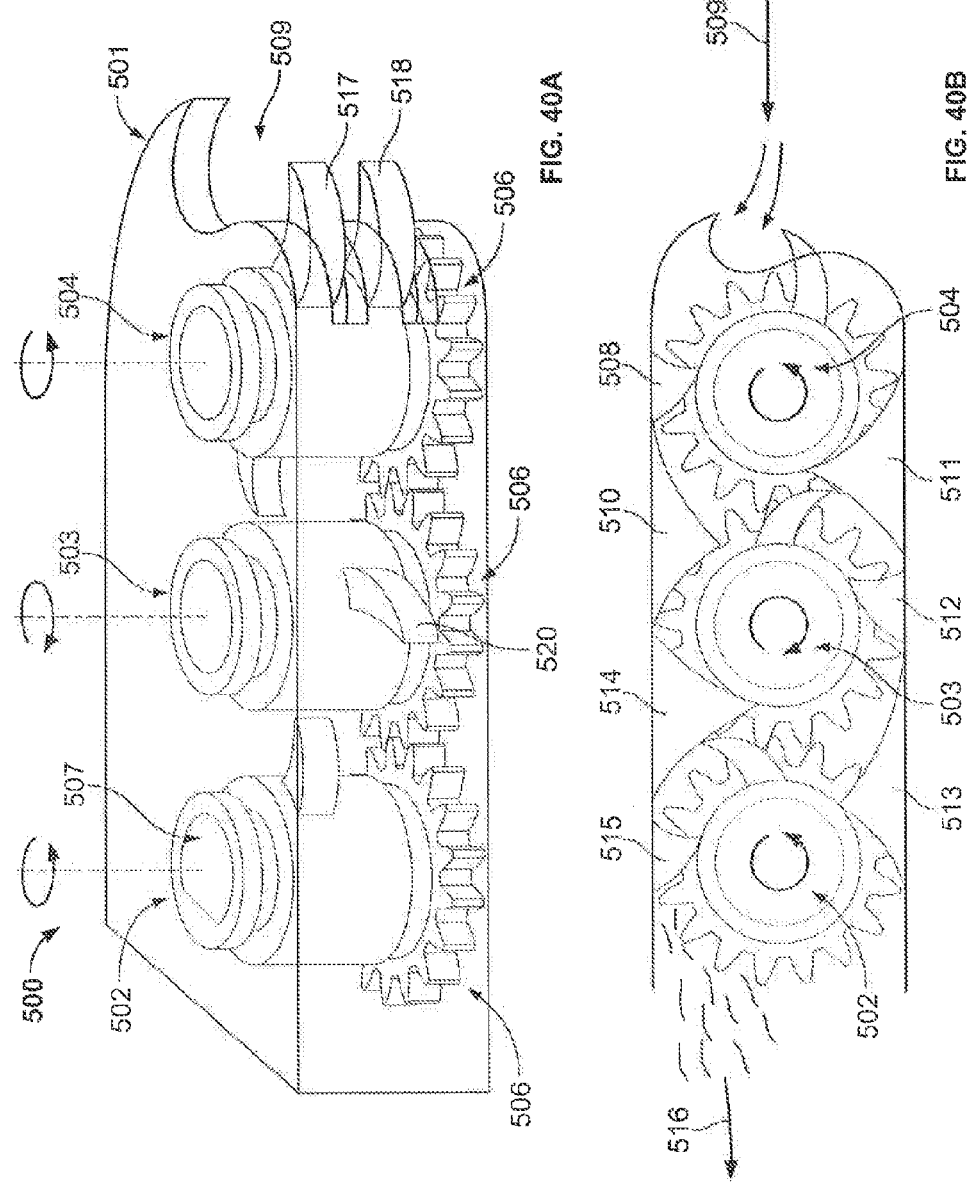

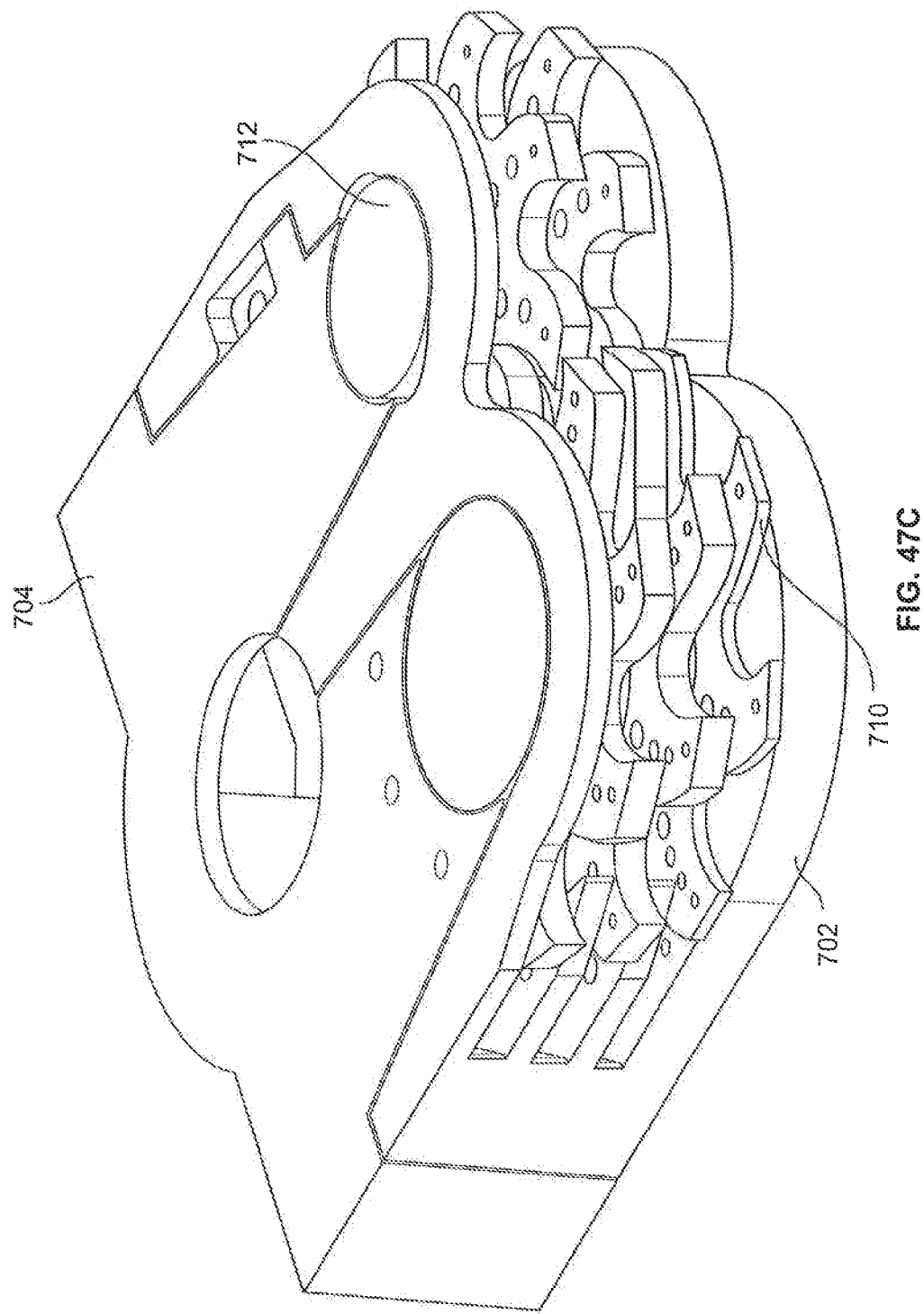

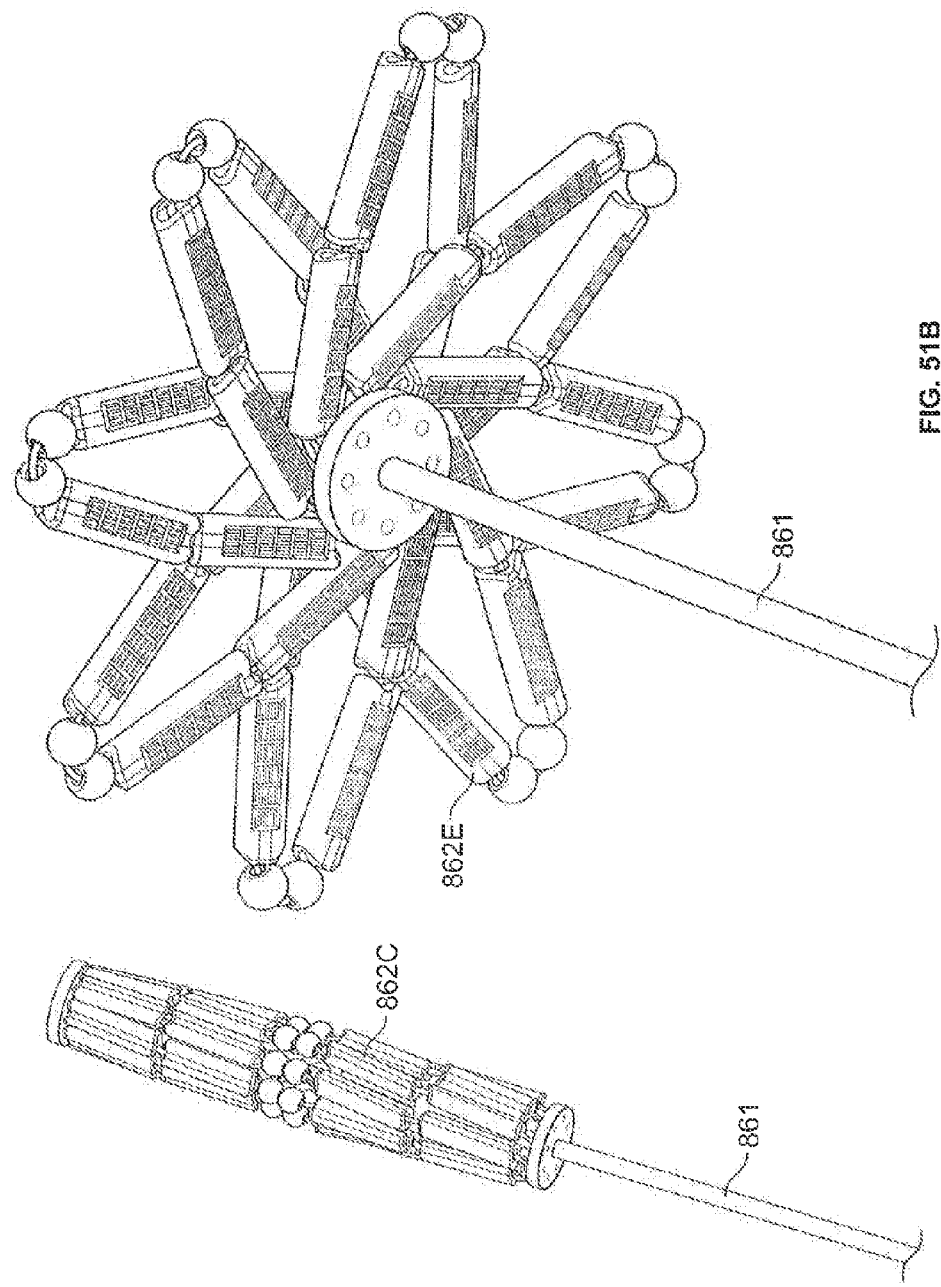

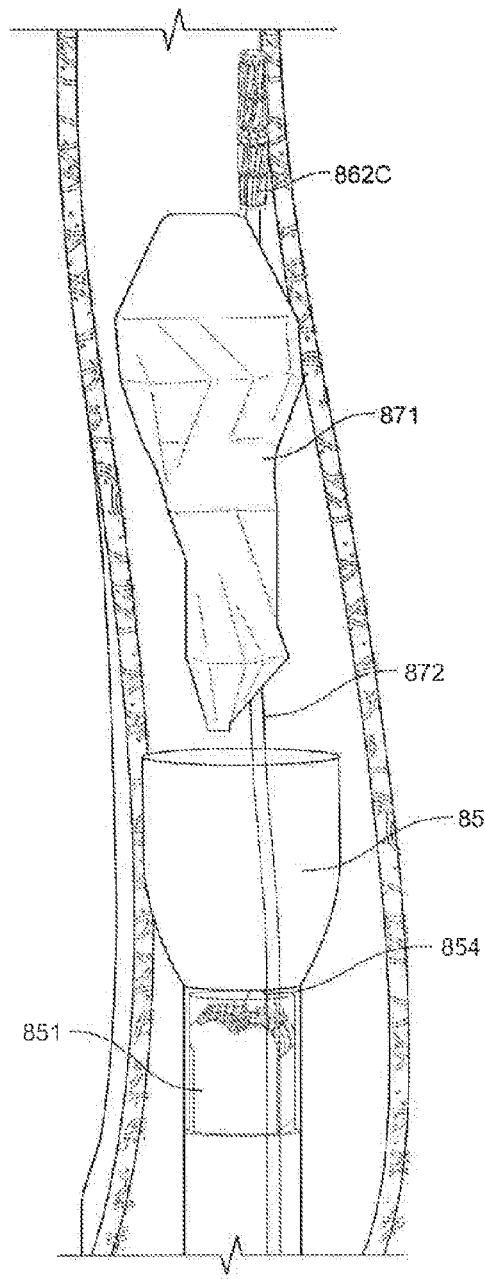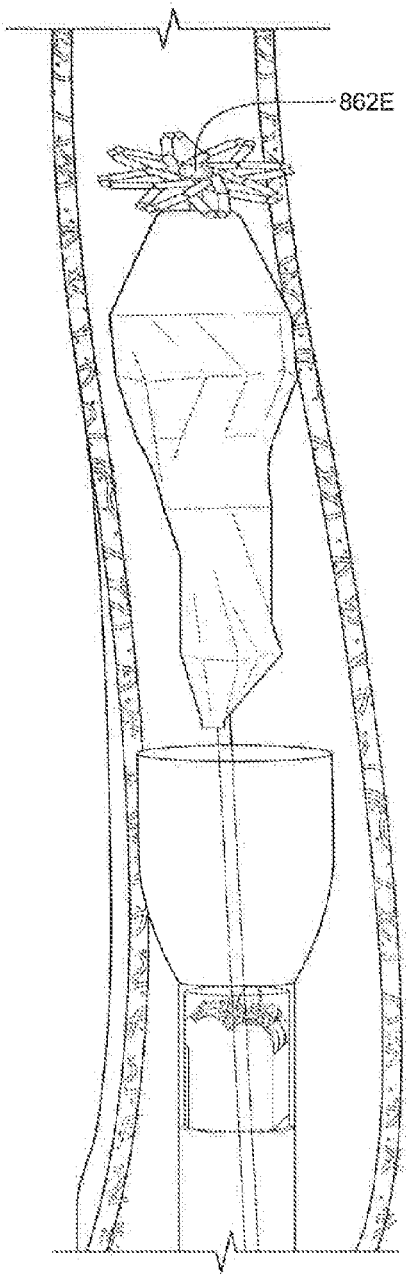

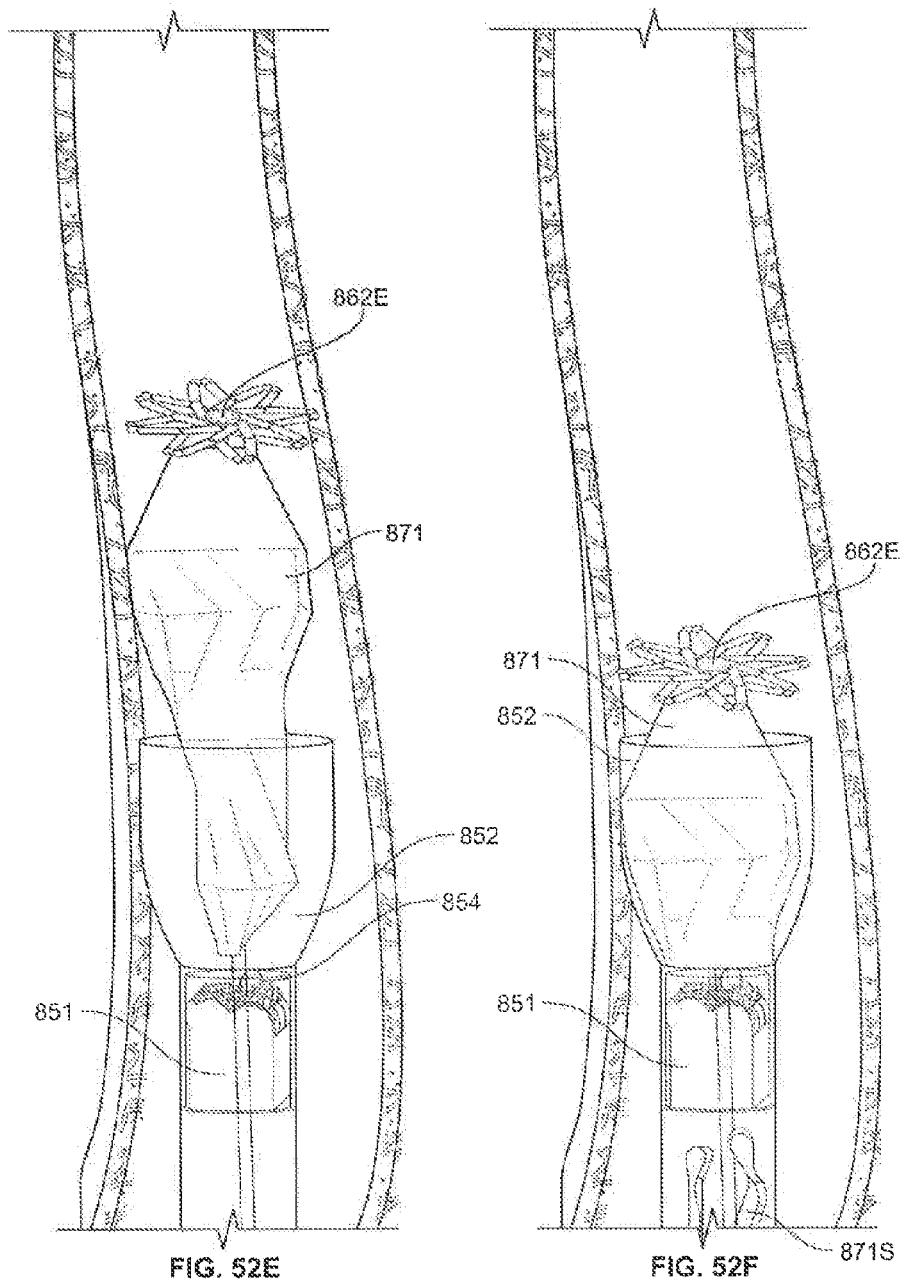

Design 1
Standard
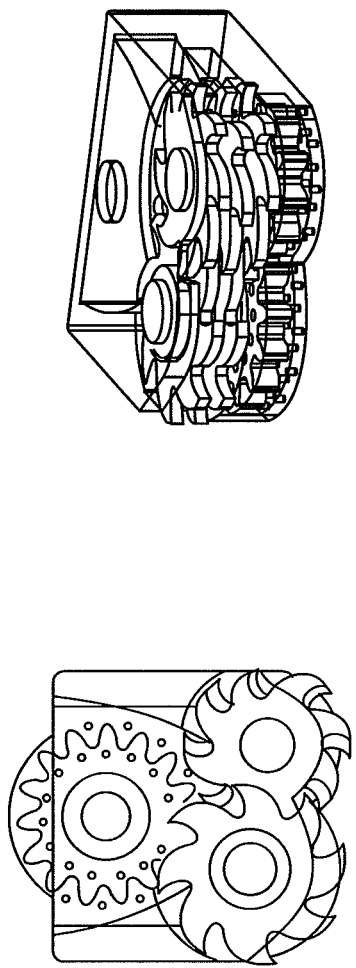
| | Left | Right |
|---|---|---|
| Rings | No | |
| Gap between blades | 30 | 30 |
| Axle diameter | 458 | 458 |
| Blade type | Coarse | Coarse |
| # Teeth | 8 | 8 |
| Diameter of blade | 1660 | 1450 |
| Top Protrusion | 293 | 252 |
| Bottom Protrusion | 53 | 90 |
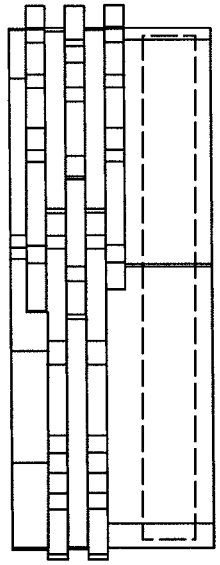
FIG. 66A

Design 2
Shear Blades
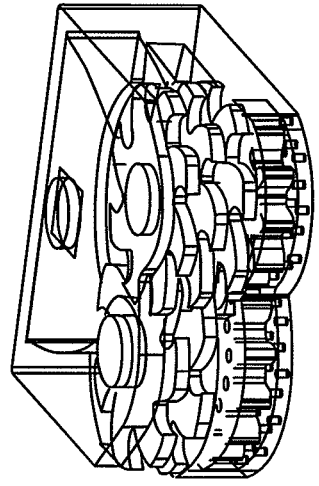
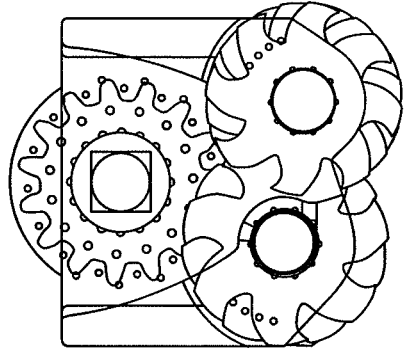
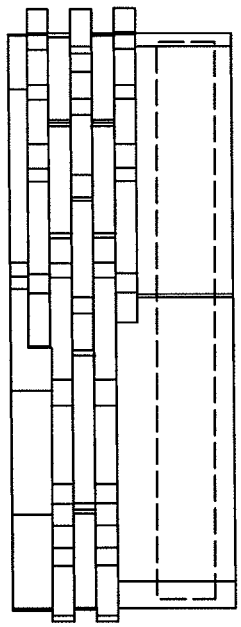
|  | Left | Right |
|---|---|---|
| Rings | Yes | |
| Gap between blades | 0 | 0 |
| Axle diameter | 458 | 458 |
| Blade type | Coarse | Coarse |
| # Teeth | 7 | 8 |
| Diameter of blade | 1550 | 1460 |
| Top Protrusion | 225 | 270 |
| Bottom Protrusion | -15 | 98 |
FIG. 66B

Design 3
2 Coarse in phase; 3 Fine offset layers
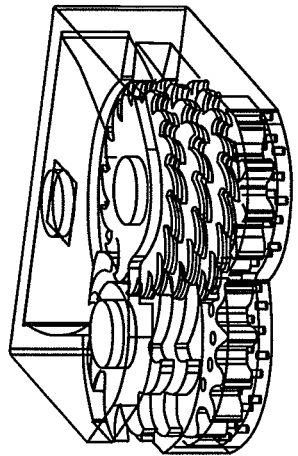
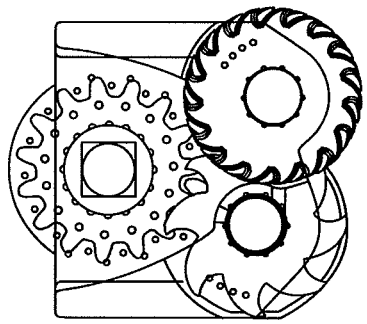
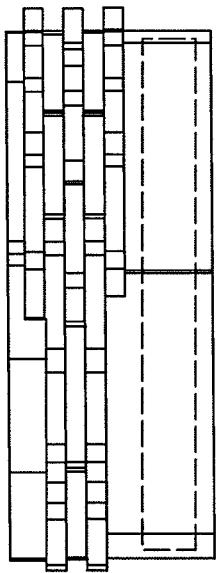
| Rings | Left | Right |
|---|---|---|
| Gap between blades | 30 | 30 |
| Axle diameter | 458 | 458 |
| Blade type | Coarse | Fine/Offset |
| # Teeth | 8 | 17 |
| Diameter of blade | 1530 | 1474 |
| Top Protrusion | 230 | 268 |
| Bottom Protrusion | 10 | 107 |
FIG. 66C

Design 4
2 Coarse out of phase; 3 Fine offset layers

| | Left | Right |
|---|---|---|
| Rings | Yes | |
| Gap between blades | 30 | 30 |
| Axle diameter | 458 | 458 |
| Blade type | Coarse | Fine/offset layers |
| # Teeth | 8 | 17 |
| Diameter of blade | 1530 | 1494 |
| Top Protrusion | 230 | 278 |
| Bottom Protrusion | 0 | 118 |

Design 5
Fine Blades
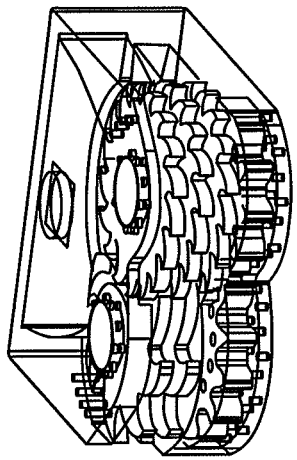
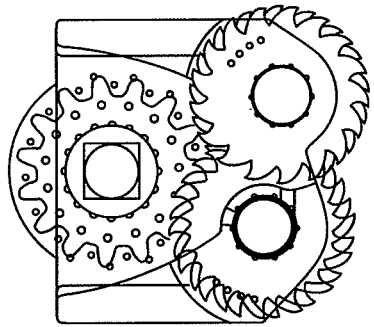
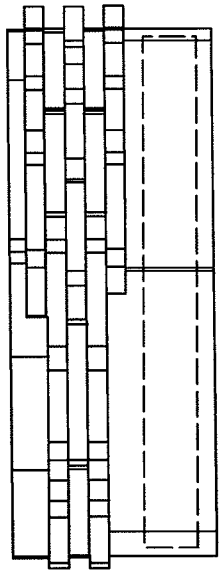
|  | Left | Right |
|---|---|---|
| Rings | Yes | |
| Gap between blades | 30 | 30 |
| Axle diameter | 458 | 458 |
| Blade type | Fine | Fine |
| # Teeth | 15 | 17 |
| Diameter of blade | 1522 | 1473 |
| Top Protrusion | 230 | 268 |
| Bottom Protrusion | 10 | 108 |
FIG. 66E

Design 6
Bidrectional Saw Cut
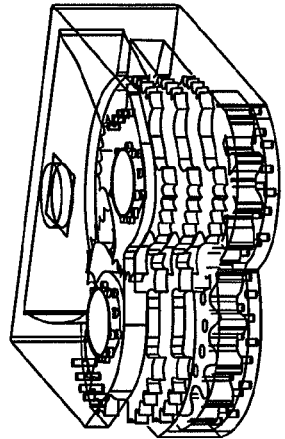
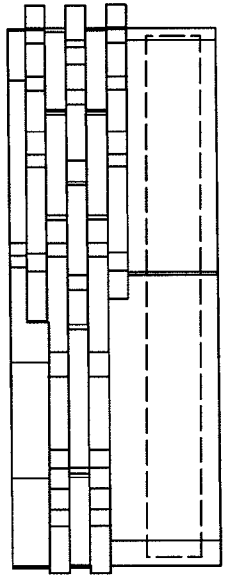
|  | Left | No | Right |
|---|---|---|---|
| Rings | | 30 | |
| Gap between blades | 30 | | 30 |
| Axle diameter | 458 | | 458 |
| Blade type | Bi-dir saw | | Bi-dir saw |
| # Teeth | 4 | | 4 |
| Diameter of blade | 1660 | | 1450 |
| Top Protrusion | 292 | | 248 |
| Bottom Protrusion | 54 | | 92 |
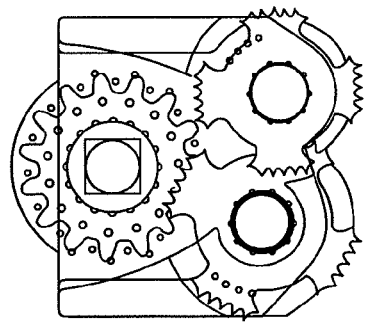
FIG. 66F

Design 7
Bidrectional
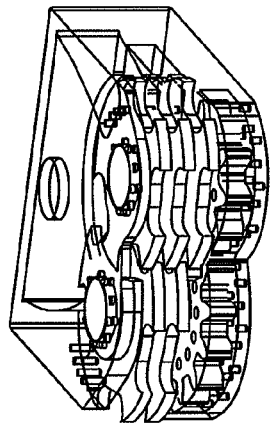
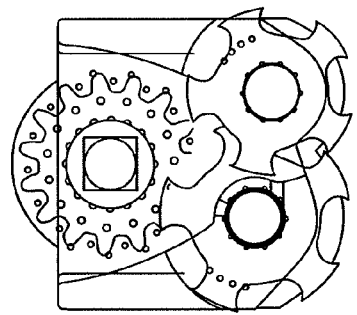
|  | Left | Right |
|---|---|---|
| Rings | No | |
| Gap between blades | 30 | 30 |
| Axle diameter | 458 | 458 |
| Blade type | Bi-Dir | Bi-Dir |
| # Teeth | 5 | 5 |
| Diameter of blade | 1660 | 1450 |
| Top Protrusion | 294 | 237 |
| Bottom Protrusion | 54 | 87 |
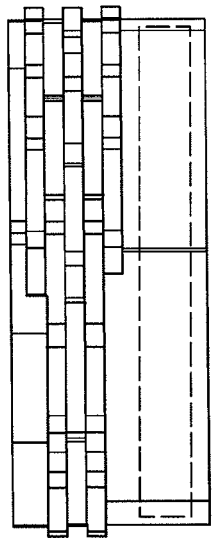
FIG. 66G

Design 8
Hybrid Blades
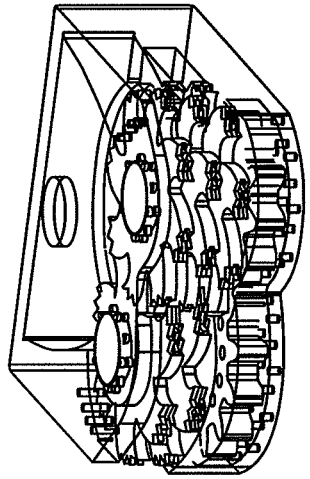
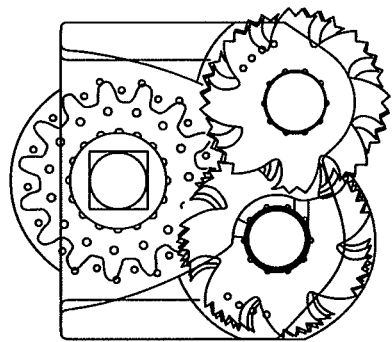
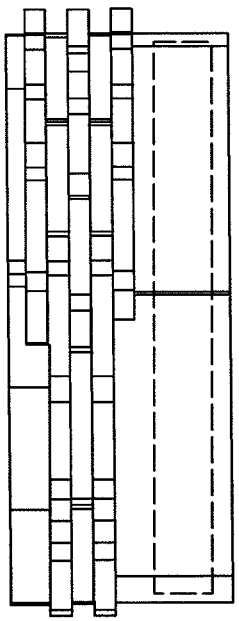
| Rings | Left | Right |
|---|---|---|
| | Yes | |
| Gap between blades | 25 | 25 |
| Axle diameter | 458 | 458 |
| Blade type | Coarse-Saw | Coarse-Saw |
| # Teeth | 7 | 8 |
| Diameter of blade | 1523 | 1500 |
| Top Protrusion | 214 | 238 |
| Bottom Protrusion | 0 | 118 |
FIG. 66H

Design 9
Large Blade; 4Gear offset
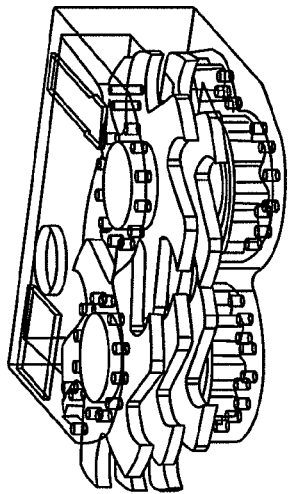
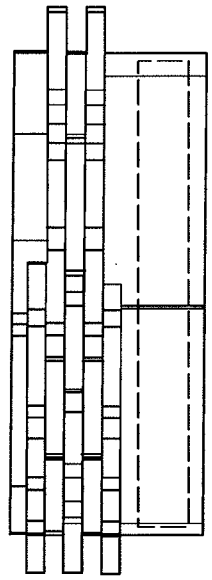
| | Left | Right |
|---|---|---|
| Rings | No | |
| Gap between blades | 40 | 40 |
| Axle diameter | 578 | 578 |
| Blade type | Coarse | Coarse |
| # Teeth | 6 | 6 |
| Diameter of blade | 1735 | 1735 |
| Top Protrusion | 320 | 320 |
| Bottom Protrusion | 320 | 320 |
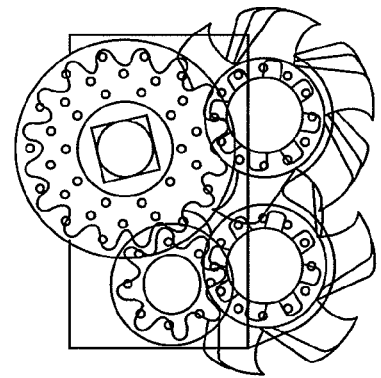
FIG. 66I

Design 10
Blades on Driving Gear
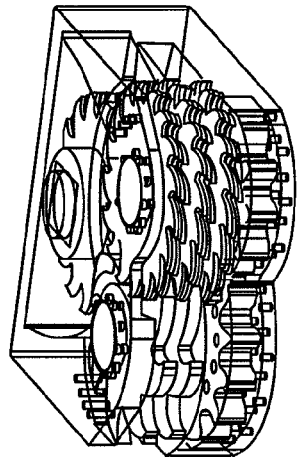
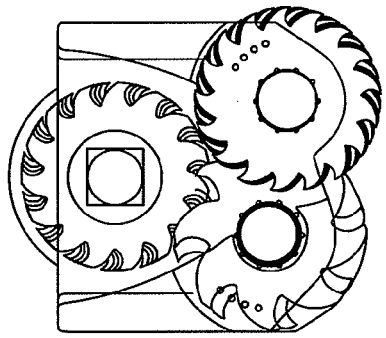
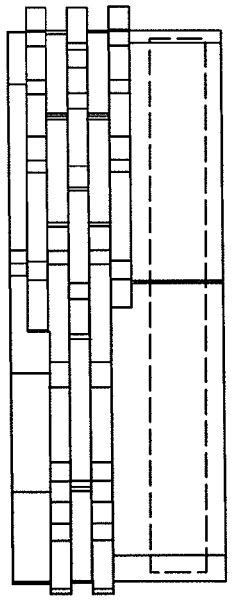
|  | Left | Right |
|---|---|---|
| Rings | No | |
| Gap between blades | 130 | 110 |
| Axle diameter | 458 | 458 |
| Blade type | Coarse | Fine |
| # Teeth | 8 | 17 |
| Diameter of blade | 1530 | 1494 |
| Top Protrusion | 230 | 278 |
| Bottom Protrusion | 0 | 118 |
FIG. 66J

Design 11
Bidir-Double-Cut
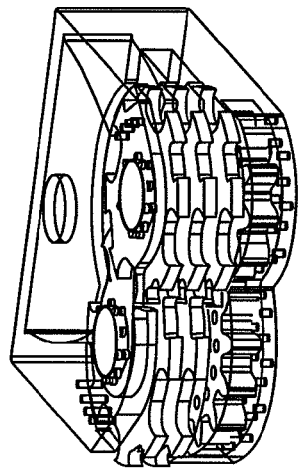
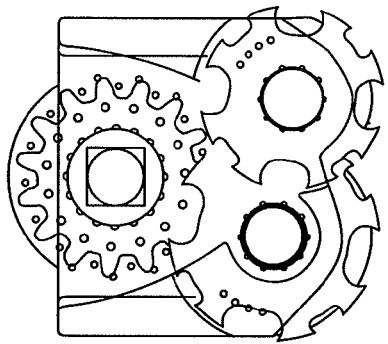
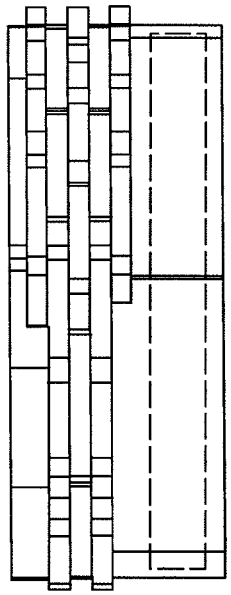
|  | Left | Right |
|---|---|---|
| Rings | Yes | |
| Gap between blades | 30 | 30 |
| Axle diameter | 458 | 458 |
| Blade type | Dual Bi-Dir | Dual Bi-Dir |
| # Teeth | 4 | 4 |
| Diameter of blade | 1660 | 1450 |
| Top Protrusion | 295 | 250 |
| Bottom Protrusion | 54 | 90 |
FIG. 66K

Design 12
4 Gear Centered
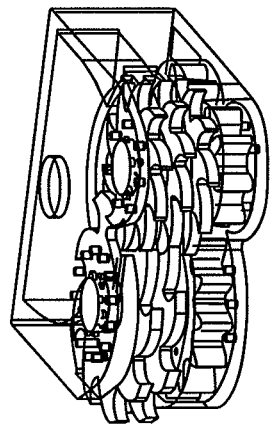
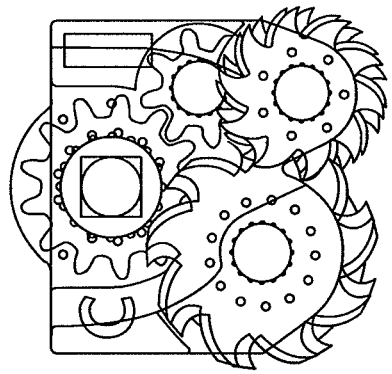
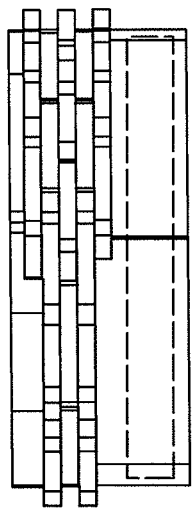
|  | Left | Right |
|---|---|---|
| Rings |  | Yes |
| Gap between blades | 263 | 36 |
| Axle diameter | 400 | 400 |
| Blade type | Coarse | Fine |
| # Teeth | 9 | 10 |
| Diameter of blade | 1750 | 1300 |
| Top Protrusion | 260 | 228 |
| Bottom Protrusion | 100 | 113 |
FIG. 66L

Design 13
3 Gear Larger Blade
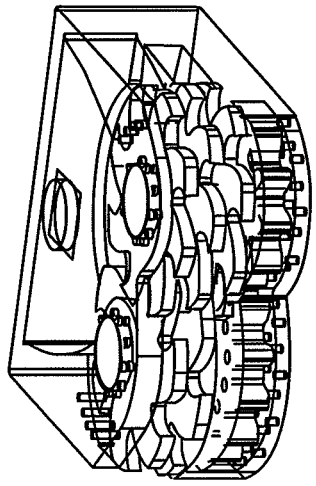
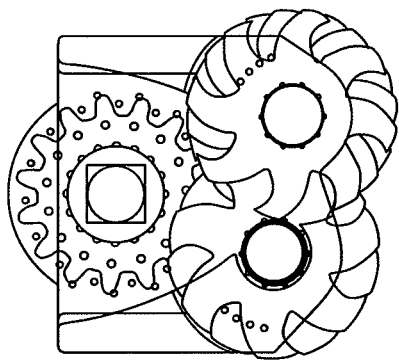
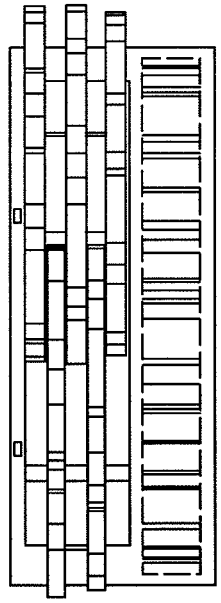
| | Left | Right |
|---|---|---|
| Rings | No | No |
| Gap between blades | 30 | 30 |
| Axle diameter | 458 | 458 |
| Blade type | Coarse | Coarse |
| # Teeth | 7 | 8 |
| Diameter of blade | 1644 | 1626 |
| Top Protrusion | 279 | 341 |
| Bottom Protrusion | 39 | 181 |
FIG. 66M

SELECTIVE TISSUE REMOVAL TOOL FOR USE IN MEDICAL APPLICATIONS AND METHODS FOR MAKING AND USING

CROSS REFERENCE TO RELATED APPLICATIONS

This application is a Continuation of U.S. application Ser. No. 13/007,578 filed Jan. 14, 2011 which is a Continuation in Part of U.S. application Ser. No. 12/490,295 filed Jun. 23, 2009 which claims priority to: U.S. Provisional Application No. 61/075,006 filed Jun. 23, 2008; U.S. Provisional Application No. 61/164,864 filed Mar. 30, 2009; and U.S. Provisional Application No. 61/164,883 filed Mar. 30, 2009. This application is a Continuation of U.S. application Ser. No. 13/007,578 filed Jan. 14, 2011 which is also a Continuation in Part of U.S. application Ser. No. 12/490,301 filed Jun. 23, 2009 which claims priority to: U.S. Provisional Application No. 61/075,006 filed Jun. 23, 2008; U.S. Provisional Application No. 61/164,864 filed Mar. 30, 2009; and U.S. Provisional Application No. 61/164,883 filed Mar. 30, 2009. In addition, this application is a Continuation of U.S. application Ser. No. 13/007,578 filed Jan. 14, 2011 which claims priority to U.S. Provisional Application No. 61/408,558 filed Oct. 29, 2010. Each of these applications is incorporated herein by reference as if set forth in full herein.

GOVERNMENT RIGHTS

This invention was made with government support under Grant No. R01 HL087797 awarded by the National Institutes of Health. The government has certain rights in the invention.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

Embodiments of the present invention relate to micro-scale and millimeter-scale shredding devices that may, for example, be used to remove unwanted tissue or other material from selected locations within a body of a patient during a minimally invasive or other medical procedures and in particular embodiments multi-layer, multi-material electrochemical fabrication methods are used to, in whole or in part, form such devices.

BACKGROUND OF THE INVENTION

An electrochemical fabrication technique for forming three-dimensional structures from a plurality of adhered layers is being commercially pursued by Microfabrica® Inc. (formerly MEMGen Corporation) of Van Nuys, Calif. under the name EFAB®.

Various electrochemical fabrication techniques were described in U.S. Pat. No. 6,027,630, issued on Feb. 22, 2000 to Adam Cohen. Some embodiments of this electrochemical fabrication technique allow the selective deposition of a material using a mask that includes a patterned conformable material on a support structure that is independent of the substrate onto which plating will occur. When desiring to perform an electrodeposition using the mask, the conformable portion of the mask is brought into contact with a substrate, but not adhered or bonded to the substrate, while in the presence of a plating solution such that the contact of the conformable portion of the mask to the substrate inhibits deposition at selected locations. For convenience, these masks might be generically called conformable contact masks; the masking technique may be generically called a conformable contact mask plating process. More specifically, in the terminology of Microfabrica Inc. such masks have come to be known as INSTANT MASKS™ and the process known as INSTANT MASKING™ or INSTANT MASK™ plating. Selective depositions using conformable contact mask plating may be used to form single selective deposits of material or may be used in a process to form multi-layer structures. The teachings of the '630 patent are hereby incorporated herein by reference as if set forth in full herein. Since the filing of the patent application that led to the above noted patent, various papers about conformable contact mask plating (i.e., INSTANT MASKING) and electrochemical fabrication have been published:

(1) A. Cohen, G. Zhang, F. Tseng, F. Mansfeld, U. Frodis and P. Will, "EFAB Batch production of functional, fully-dense metal parts with micro-scale features", Proc. 9th Solid Freeform Fabrication, The University of Texas at Austin, p 161, August 1998.

(2) A. Cohen, G. Zhang, F. Tseng, F. Mansfeld, U. Frodis and P. Will, "EFAB: Rapid, Low-Cost Desktop Micromachining of High Aspect Ratio True 3-D MEMS", Proc. 12th IEEE Micro Electro Mechanical Systems Workshop, IEEE, p 244, January 1999.

(3) A. Cohen, "3-D Micromachining by Electrochemical Fabrication", Micromachine Devices, March 1999.

(4) G. Zhang, A. Cohen, U. Frodis, F. Tseng, F. Mansfeld, and P. Will, "EFAB: Rapid Desktop Manufacturing of True 3-D Microstructures", Proc. 2nd International Conference on Integrated MicroNanotechnology for Space Applications, The Aerospace Co., April 1999.

(5) F. Tseng, U. Frodis, G. Zhang, A. Cohen, F. Mansfeld, and P. Will, "EFAB: High Aspect Ratio, Arbitrary 3-D Metal Microstructures using a Low-Cost Automated Batch Process", 3rd International Workshop on High Aspect Ratio MicroStructure Technology (HARMST'99), June 1999.

(6) A. Cohen, U. Frodis, F. Tseng, G. Zhang, F. Mansfeld, and P. Will, "EFAB: Low-Cost, Automated Electrochemical Batch Fabrication of Arbitrary 3-D Microstructures", Micromachining and Microfabrication Process Technology, SPIE 1999 Symposium on Micromachining and Microfabrication, September 1999.

(7) F. Tseng, G. Zhang, U. Frodis, A. Cohen, F. Mansfeld, and P. Will, "EFAB: High Aspect Ratio, Arbitrary 3-D Metal Microstructures using a Low-Cost Automated Batch Process", MEMS Symposium, ASME 1999 International Mechanical Engineering Congress and Exposition, November, 1999.

(8) A. Cohen, "Electrochemical Fabrication (EFAB™)", Chapter 19 of The MEMS Handbook, edited by Mohamed Gad-El-Hak, CRC Press, 2002.

(9) Microfabrication—Rapid Prototyping's Killer Application", pages 1-5 of the Rapid Prototyping Report, CAD/CAM Publishing, Inc., June 1999.

An electrochemical deposition for forming multilayer structures may be carried out in a number of different ways as set forth in the above patent and publications. In one form, this process involves the execution of three separate operations during the formation of each layer of the structure that is to be formed:

1. Selectively depositing at least one material by electrodeposition upon one or more desired regions of a substrate. Typically this material is either a structural material or a sacrificial material.
2. Then, blanket depositing at least one additional material by electrodeposition so that the additional deposit covers both the regions that were previously selectively deposited onto, and the regions of the substrate that did not receive any previously applied selective depositions. Typically this material is the other of a structural material or a sacrificial material.
3. Finally, planarizing the materials deposited during the first and second operations to produce a smoothed surface of a first layer of desired thickness having at least one region containing the at least one material and at least one region containing at least the one additional material.

After formation of the first layer, one or more additional layers may be formed adjacent to an immediately preceding layer and adhered to the smoothed surface of that preceding layer. These additional layers are formed by repeating the first through third operations one or more times wherein the formation of each subsequent layer treats the previously formed layers and the initial substrate as a new and thickening substrate.

Once the formation of all layers has been completed, at least a portion of at least one of the materials deposited is generally removed by an etching process to expose or release the three-dimensional structure that was intended to be formed. The removed material is a sacrificial material while the material that forms part of the desired structure is a structural material.

The preferred method of performing the selective electrodeposition involved in the first operation is by conformable contact mask plating. In this type of plating, one or more conformable contact (CC) masks are first formed. The CC masks include a support structure onto which a patterned conformable dielectric material is adhered or formed. The conformable material for each mask is shaped in accordance with a particular cross-section of material to be plated (the pattern of conformable material is complementary to the pattern of material to be deposited). At least one CC mask is used for each unique cross-sectional pattern that is to be plated.

The support for a CC mask is typically a plate-like structure formed of a metal that is to be selectively electroplated and from which material to be plated will be dissolved. In this typical approach, the support will act as an anode in an electroplating process. In an alternative approach, the support may instead be a porous or otherwise perforated material through which deposition material will pass during an electroplating operation on its way from a distal anode to a deposition surface. In either approach, it is possible for multiple CC masks to share a common support, i.e. the patterns of conformable dielectric material for plating multiple layers of material may be located in different areas of a single support structure. When a single support structure contains multiple plating patterns, the entire structure is referred to as the CC mask while the individual plating masks may be referred to as "submasks". In the present application such a distinction will be made only when relevant to a specific point being made.

In preparation for performing the selective deposition of the first operation, the conformable portion of the CC mask is placed in registration with and pressed against a selected portion of (1) the substrate, (2) a previously formed layer, or (3) a previously deposited portion of a layer on which deposition is to occur. The pressing together of the CC mask and relevant substrate occur in such a way that all openings, in the conformable portions of the CC mask contain plating solution. The conformable material of the CC mask that contacts the substrate acts as a barrier to electrodeposition while the openings in the CC mask that are filled with electroplating solution act as pathways for transferring material from an anode (e.g. the CC mask support) to the non-contacted portions of the substrate (which act as a cathode during the plating operation) when an appropriate potential and/or current are supplied.

An example of a CC mask and CC mask plating are shown in FIGS. 1A-1C. FIG. 1A shows a side view of a CC mask 8 consisting of a conformable or deformable (e.g. elastomeric) insulator 10 patterned on an anode 12. The anode has two functions. One is as a supporting material for the patterned insulator 10 to maintain its integrity and alignment since the pattern may be topologically complex (e.g., involving isolated "islands" of insulator material). The other function is as an anode for the electroplating operation. FIG. 1A also depicts a substrate 6, separated from mask 8, onto which material will be deposited during the process of forming a layer. CC mask plating selectively deposits material 22 onto substrate 6 by simply pressing the insulator against the substrate then electrodepositing material through apertures 26a and 26b in the insulator as shown in FIG. 1B. After deposition, the CC mask is separated, preferably non-destructively, from the substrate 6 as shown in FIG. 1C.

The CC mask plating process is distinct from a "through-mask" plating process in that in a through-mask plating process the separation of the masking material from the substrate would occur destructively. Furthermore in a through mask plating process, opening in the masking material are typically formed while the masking material is in contact with and adhered to the substrate. As with through-mask plating, CC mask plating deposits material selectively and simultaneously over the entire layer. The plated region may consist of one or more isolated plating regions where these isolated plating regions may belong to a single structure that is being formed or may belong to multiple structures that are being formed simultaneously. In CC mask plating as individual masks are not intentionally destroyed in the removal process, they may be usable in multiple plating operations.

Another example of a CC mask and CC mask plating is shown in FIGS. 1D-1G. FIG. 1D shows an anode 12' separated from a mask 8' that includes a patterned conformable material 10' and a support structure 20. FIG. 1D also depicts substrate 6 separated from the mask 8'. FIG. 1E illustrates the mask 8' being brought into contact with the substrate 6. FIG. 1F illustrates the deposit 22' that results from conducting a current from the anode 12' to the substrate 6. FIG. 1G illustrates the deposit 22' on substrate 6 after separation from mask 8'. In this example, an appropriate electrolyte is located between the substrate 6 and the anode 12' and a current of ions coming from one or both of the solution and the anode are conducted through the opening in the mask to the substrate where material is deposited. This type of mask may be referred to as an anodeless INSTANT MASK™ (AIM) or as an anodeless conformable contact (ACC) mask.

Unlike through-mask plating, CC mask plating allows CC masks to be formed completely separate from the substrate on which plating is to occur (e.g. separate from a three-dimensional (3D) structure that is being formed). CC masks may be formed in a variety of ways, for example, using a photolithographic process. All masks can be generated simultaneously, e.g. prior to structure fabrication rather than during it. This separation makes possible a simple, low-cost, automated, self-contained, and internally-clean "desktop factory" that can be installed almost anywhere to fabricate 3D structures, leaving any required clean room processes, such as photolithography to be performed by service bureaus or the like.

An example of the electrochemical fabrication process discussed above is illustrated in FIGS. 2A-2F. These figures show that the process involves deposition of a first material 2 which is a sacrificial material and a second material 4 which is a structural material. The CC mask 8, in this example, includes a patterned conformable material (e.g. an elastomeric dielectric material) 10 and a support 12 which is made from deposition material 2. The conformal portion of the CC mask is pressed against substrate 6 with a plating solution 14 located within the openings 16 in the conformable material 10. An electric current, from power supply 18, is then passed through the plating solution 14 via (a) support 12 which doubles as an anode and (b) substrate 6 which doubles as a cathode. FIG. 2A illustrates that the passing of current causes material 2 within the plating solution and material 2 from the anode 12 to be selectively transferred to and plated on the substrate 6. After electroplating the first deposition material 2 onto the substrate 6 using CC mask 8, the CC mask 8 is removed as shown in FIG. 2B. FIG. 2C depicts the second deposition material 4 as having been blanket-deposited (i.e. non-selectively deposited) over the previously deposited first deposition material 2 as well as over the other portions of the substrate 6. The blanket deposition occurs by electroplating from an anode (not shown), composed of the second material, through an appropriate plating solution (not shown), and to the cathode; substrate 6. The entire two-material layer is then planarized to achieve precise thickness and flatness as shown in FIG. 2D. After repetition of this process for all layers, the multi-layer structure 20 formed of the second material 4 (i.e. structural material) is embedded in first material 2 (i.e. sacrificial material) as shown in FIG. 2E. The embedded structure is etched to yield the desired device, i.e. structure 20, as shown in FIG. 2F.

Various components of an exemplary manual electrochemical fabrication system 32 are shown in FIGS. 3A-3C. The system 32 consists of several subsystems 34, 36, 38, and 40. The substrate holding subsystem 34 is depicted in the upper portions of each of FIGS. 3A-3C and includes several components: (1) a carrier 48, (2) a metal substrate 6 onto which the layers are deposited, and (3) a linear slide 42 capable of moving the substrate 6 up and down relative to the carrier 48 in response to drive force from actuator 44. Subsystem 34 also includes an indicator 46 for measuring differences in vertical position of the substrate which may be used in setting or determining layer thicknesses and/or deposition thicknesses. The subsystem 34 further includes feet 68 for carrier 48 which can be precisely mounted on subsystem 36.

The CC mask subsystem 36 shown in the lower portion of FIG. 3A includes several components: (1) a CC mask 8 that is actually made up of a number of CC masks (i.e. submasks) that share a common support/anode 12, (2) precision X-stage 54, (3) precision Y-stage 56, (4) frame 72 on which the feet 68 of subsystem 34 can mount, and (5) a tank 58 for containing the electrolyte 16. Subsystems 34 and 36 also include appropriate electrical connections (not shown) for connecting to an appropriate power source (not shown) for driving the CC masking process.

The blanket deposition subsystem 38 is shown in the lower portion of FIG. 3B and includes several components: (1) an anode 62, (2) an electrolyte tank 64 for holding plating solution 66, and (3) frame 74 on which feet 68 of subsystem 34 may sit. Subsystem 38 also includes appropriate electrical connections (not shown) for connecting the anode to an appropriate power supply (not shown) for driving the blanket deposition process.

The planarization subsystem 40 is shown in the lower portion of FIG. 3C and includes a lapping plate 52 and associated motion and control systems (not shown) for planarizing the depositions.

In addition to teaching the use of CC masks for electrodeposition purposes, the '630 patent also teaches that the CC masks may be placed against a substrate with the polarity of the voltage reversed and material may thereby be selectively removed from the substrate. It indicates that such removal processes can be used to selectively etch, engrave, and polish a substrate, e.g., a plaque.

The '630 patent further indicates that the electroplating methods and articles disclosed therein allow fabrication of devices from thin layers of materials such as, e.g., metals, polymers, ceramics, and semiconductor materials. It further indicates that although the electroplating embodiments described therein have been described with respect to the use of two metals, a variety of materials, e.g., polymers, ceramics and semiconductor materials, and any number of metals can be deposited either by the electroplating methods therein, or in separate processes that occur throughout the electroplating method. It indicates that a thin plating base can be deposited, e.g., by sputtering, over a deposit that is insufficiently conductive (e.g., an insulating layer) so as to enable subsequent electroplating. It also indicates that multiple support materials (i.e. sacrificial materials) can be included in the electroplated element allowing selective removal of the support materials.

The '630 patent additionally teaches that the electroplating methods disclosed therein can be used to manufacture elements having complex microstructure and close tolerances between parts. An example is given with the aid of FIGS. 14A-14E of that patent. In the example, elements having parts that fit with close tolerances, e.g., having gaps between about 1-5 um, including electroplating the parts of the device in an unassembled, preferably pre-aligned, state and once fabricated. In such embodiments, the individual parts can be moved into operational relation with each other or they can simply fall together. Once together the separate parts may be retained by clips or the like.

Another method for forming microstructures from electroplated metals (i.e. using electrochemical fabrication techniques) is taught in U.S. Pat. No. 5,190,637 to Henry Guckel, entitled "Formation of Microstructures by Multiple Level Deep X-ray Lithography with Sacrificial Metal layers". This patent teaches the formation of metal structure utilizing through mask exposures. A first layer of a primary metal is electroplated onto an exposed plating base to fill a void in a photoresist (the photoresist forming a through mask having a desired pattern of openings), the photoresist is then removed and a secondary metal is electroplated over the first layer and over the plating base. The exposed surface of the secondary metal is then machined down to a height which exposes the first metal to produce a flat uniform surface extending across both the primary and secondary metals. Formation of a second layer may then begin by applying a photoresist over the first layer and patterning it (i.e. to form a second through mask) and then repeating the process that was used to produce the first layer to produce a second layer of desired configuration. The process is repeated until the entire structure is formed and the secondary metal is removed by etching. The photoresist is formed over the plating base or previous layer by casting and patterning of the photoresist (i.e. voids formed in the photoresist) are formed by exposure of the photoresist through a patterned mask via X-rays or UV radiation and development of the exposed or unexposed areas.

The '637 patent teaches the locating of a plating base onto a substrate in preparation for electroplating materials onto the substrate. The plating base is indicated as typically involving the use of a sputtered film of an adhesive metal, such as chromium or titanium, and then a sputtered film of the metal that is to be plated. It is also taught that the plating base may be applied over an initial layer of sacrificial material (i,e. a layer or coating of a single material) on the substrate so that the structure and substrate may be detached if desired. In such cases after formation of the structure the sacrificial material forming part of each layer of the structure may be removed along the initial sacrificial layer to free the structure. Substrate materials mentioned in the '637 patent include silicon, glass, metals, and silicon with protected semiconductor devices. A specific example of a plating base includes about 150 angstroms of titanium and about 300 angstroms of nickel, both of which are sputtered at a temperature of 160° C. In another example it is indicated that the plating base may consist of 150 angstroms of titanium and 150 angstroms of nickel where both are applied by sputtering.

Electrochemical Fabrication provides the ability to form prototypes and commercial quantities of miniature objects, parts, structures, devices, and the like at reasonable costs and in reasonable times. In fact, Electrochemical Fabrication is an enabler for the formation of many structures that were hitherto impossible to produce. Electrochemical Fabrication opens the spectrum for new designs and products in many industrial fields. Even though Electrochemical Fabrication offers this new capability and it is understood that Electrochemical Fabrication techniques can be combined with designs and structures known within various fields to produce new structures, certain uses for Electrochemical Fabrication provide designs, structures, capabilities and/or features not known or obvious in view of the state of the art.

A need exists in various fields for miniature devices having improved characteristics, reduced fabrication times, reduced fabrication costs, simplified fabrication processes, greater versatility in device design, improved selection of materials, improved material properties, more cost effective and less risky production of such devices, and/or more independence between geometric configuration and the selected fabrication process.

The medical device field is one area which can benefit from the ability to produce a device (e.g., implantable devices, tools used in medical procedures, including surgical procedures and minimally invasive procedures, etc.), or certain parts of the device, with very small dimensions, or from the ability to produce devices or parts of the device with small dimensions, but with improved performance over existing products and procedures. Some medical procedures include, or consist primarily of the removal of tissue from a subject. The tissue can be native to the subject or tissue which may be considered to be foreign tissue (e.g. tumor mass).

Some devices with relatively large dimensions risk removing unintended tissue from the subject, or damaging the unintended tissue. There is a need for tissue removal devices which have small dimensions and improved functionality which allow them to more safely remove only the desired tissue from the patient. There is also a need for tissue removal devices which have small dimensions and improved functionality over existing products and procedures which allow them to more efficiently remove tissue from the patient.

One portion of the body in which tissue can be removed to treat a variety of conditions is the spine area. Tissue removal devices for the spine are needed that can produced with sufficiently small dimension and/or that have increased performance over existing techniques. For example, a herniated disc or bulging disc can be treated by performing a discectomy, e.g. by removing all or part of the nucleus pulposus of the damaged disc. Such procedures may also involve a laminotomy or laminectomy wherein a portion or all of a lamina may be removed to allow access to the herniated disc. Artificial disc replacement (total or partial) is another example of a procedure which requires the removal of all or a portion of the disc, which is replaced with an artificial device or material.

Prior art tissue removal devices often remove tissue in large pieces, having dimensions well over 2 mm. The tissue pieces are removed through an aspiration lumen typically 3.5 to 5 mm in diameter. Since the tissue pieces being removed commonly have dimensions that are 1 to 2 lumen diameters in length, the tissue pieces can often clog the tissue removal lumen.

Tissue removal devices are needed which can be produced with sufficient mechanical complexity and a small size so that they can both safely and more efficiently remove tissue from a subject, and/or remove tissue in a less invasive procedure and/or with less damage to adjacent tissue such that risks are lowered and recovery time is improved. Additionally, tissue removal devices are needed which can aid a surgeon by automatically selecting between target tissue to be removed and non-target tissue that is to be left intact.

SUMMARY OF THE DISCLOSURE

According to some aspects of the disclosure, methods of selectively removing tissue are provided. One exemplary method includes the steps of providing a tissue cutting instrument capable of distinguishing between target tissue to be removed and non-target tissue, urging the instrument against the target tissue and the non-target tissue, and allowing the instrument to cut the target tissue while automatically avoiding cutting of non-target tissue.

According to some aspects of the disclosure, debridement instruments are provided. One exemplary instrument includes an elongated introducer having a proximal end and a distal end, and a cutter housing located near the distal end of the introducer. In this embodiment, at least one cutter element is rotably mounted to the cutter housing. The cutter element is configured to remove portions of soft tissue from a body. The instrument also includes a tissue removal lumen extending along the introducer and having an inlet within the cutter housing. The lumen is configured to remove the tissue portions cut by the cutter element. The instrument is configured to ensure that the portions of removed tissue have a maximum dimension less than about 2 mm across before they pass through the tissue removal lumen inlet. In some embodiments having larger instruments, the maximum tissue dimension is larger than about 2 mm.

According to some aspects of the disclosure, a method of selectively removing soft target tissue from a body includes providing an instrument comprising an elongated introducer, a cutter housing located near a distal end of the introducer, and at least one cutter element rotably mounted to the cutter housing. The cutter element is rotated, and the cutter element and soft target tissue are caused to come into contact with one another such that the rotating cutter element cuts off portions of the soft target tissue. The instrument is configured to cut the tissue in portions having a maximum dimension less than 2 mm across. The cut tissue portions are removed through a tissue removal lumen extending from adjacent the cutter element and along the introducer.

Other aspects of the disclosure will be apparent to those of skill in the art upon review of the teachings herein. The various embodiments of the disclosure, set forth explicitly herein or otherwise ascertained from the teachings herein, may address one or more of the above needs that are not met by the prior art, alone or in combination, or alternatively may address some other need ascertained from the teachings herein. It is not necessarily intended that all needs be addressed by any single aspect of the disclosure even though that may be the case with regard to some aspects.

The disclosure of the present invention provides to number of device embodiments which may be fabricated, but are not necessarily fabricated, from a plurality of formed and adhered layers with each successive layer including at least two materials, one of which is a structural material and the other of which is a sacrificial material, and wherein each successive layer defines a successive cross-section of the three-dimensional structure, and wherein the forming of each of the plurality of successive layers includes: (i) depositing a first of the at least two materials; (ii) depositing a second of the at least two materials; and (B) after the forming of the plurality of successive layers, separating at least a portion of the sacrificial material from the structural material to reveal the three-dimensional structure. In some embodiments, the device may include a plurality of components movable relative to one another which contain etching holes which may be aligned during fabrication and during release from at least a portion of the sacrificial material.

Other aspects of the disclosure will be understood by those of skill in the art upon review of the teachings herein. Other aspects of the disclosure may involve combinations of the above noted aspects of the disclosure. These other aspects of the disclosure may provide various combinations of the aspects presented above as well as provide other configurations, structures, functional relationships, and processes that have not been specifically set forth above.

BRIEF DESCRIPTION OF THE DRAWINGS

FIGS. 1A-1C schematically depict side views of various stages of a CC mask plating process, while FIGS. 1D-G schematically depict a side views of various stages of a CC mask plating process using a different type of CC mask.

FIG. 34A-34F illustrate an exemplary procedure for treating a herniated disc by removing nucleus tissue using a tissue removal device as described herein.

FIG. 35 illustrates an exemplary embodiment wherein the axes of rotation of the rotors for a set of blades are substantially orthogonal to the longitudinal axis of at least the working end.

FIG. 36 shows a distal end of a working end including a single rotor and stator wherein the stator includes fingers or other elements that work with the rotor to cause shredding or other disruption of the tissue into small pieces that may be removed via the device from the body of a patient.

FIGS. 40A (perspective view) and 40B (top view) illustrate an alternative embodiment of a working end in which tissue is captured and processed in multiple steps.

FIGS. 47A-47C illustrate an exemplary embodiment of a working end including a gear train and two shredder rotors.

FIGS. 51A and 51B provide closed (compacted) and open (expanded) views of a sample device according to a procedural embodiment of the disclosure.

FIGS. 52A-52F illustrate the use of the devices of FIGS. 50A-50B and 51A-51B in a thrombectomy application.

FIGS. 66A-66M show views of 13 more examples of cutter heads constructed according to aspects of the present invention.

DETAILED DESCRIPTION

Electrochemical Fabrication in General

FIGS. 1A-1G, 2A-2F, and 3A-3C illustrate various features of one form of electrochemical fabrication. Other electrochemical fabrication techniques are set forth in the '630 patent referenced above, in the various previously incorporated publications, in various other patents and patent applications incorporated herein by reference. Still others may be derived from combinations of various approaches described in these publications, patents, and applications, or are otherwise known or ascertainable by those of skill in the art from the teachings set forth herein. All of these techniques may be combined with those of the various embodiments of various aspects of the disclosure to yield enhanced embodiments. Still other embodiments may be derived from combinations of the various embodiments explicitly set forth herein.

Figure 2A:
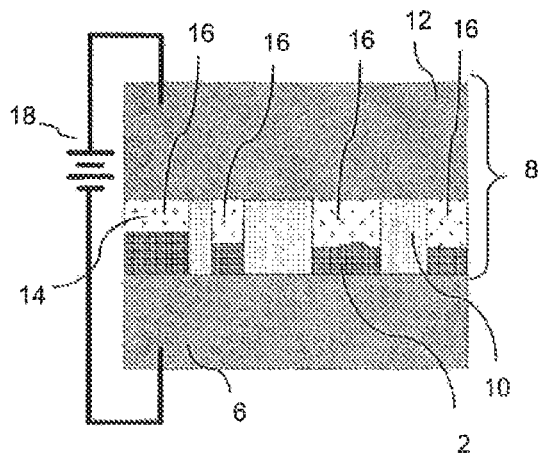
FIGS. 2A-2F schematically depict side views of various stages of an electrochemical fabrication process as applied to the formation of a particular structure where a sacrificial material is selectively deposited while a structural material is blanket deposited.
Figure 2B:
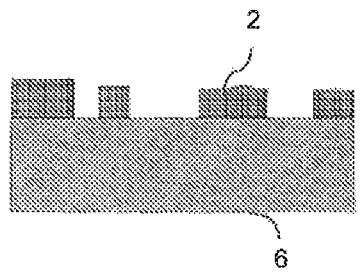
Figure 2C:
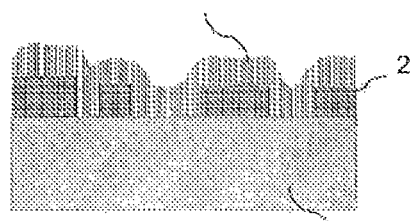
Figure 2D:
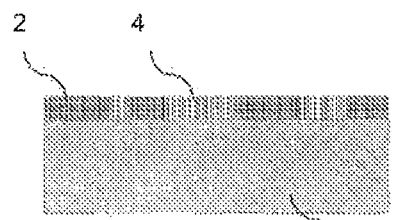
Figure 2E:
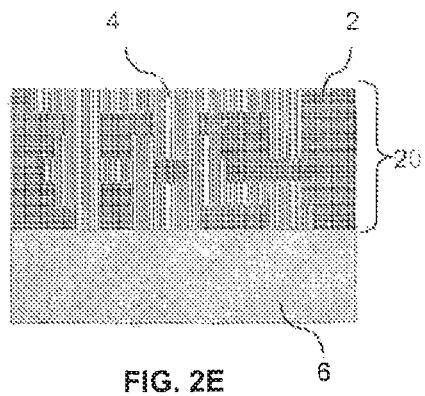
Figure 2F:
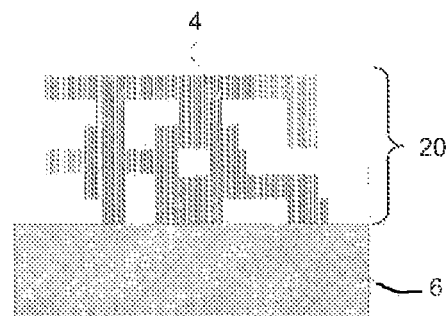
Figures 3A, 3B, 3C:
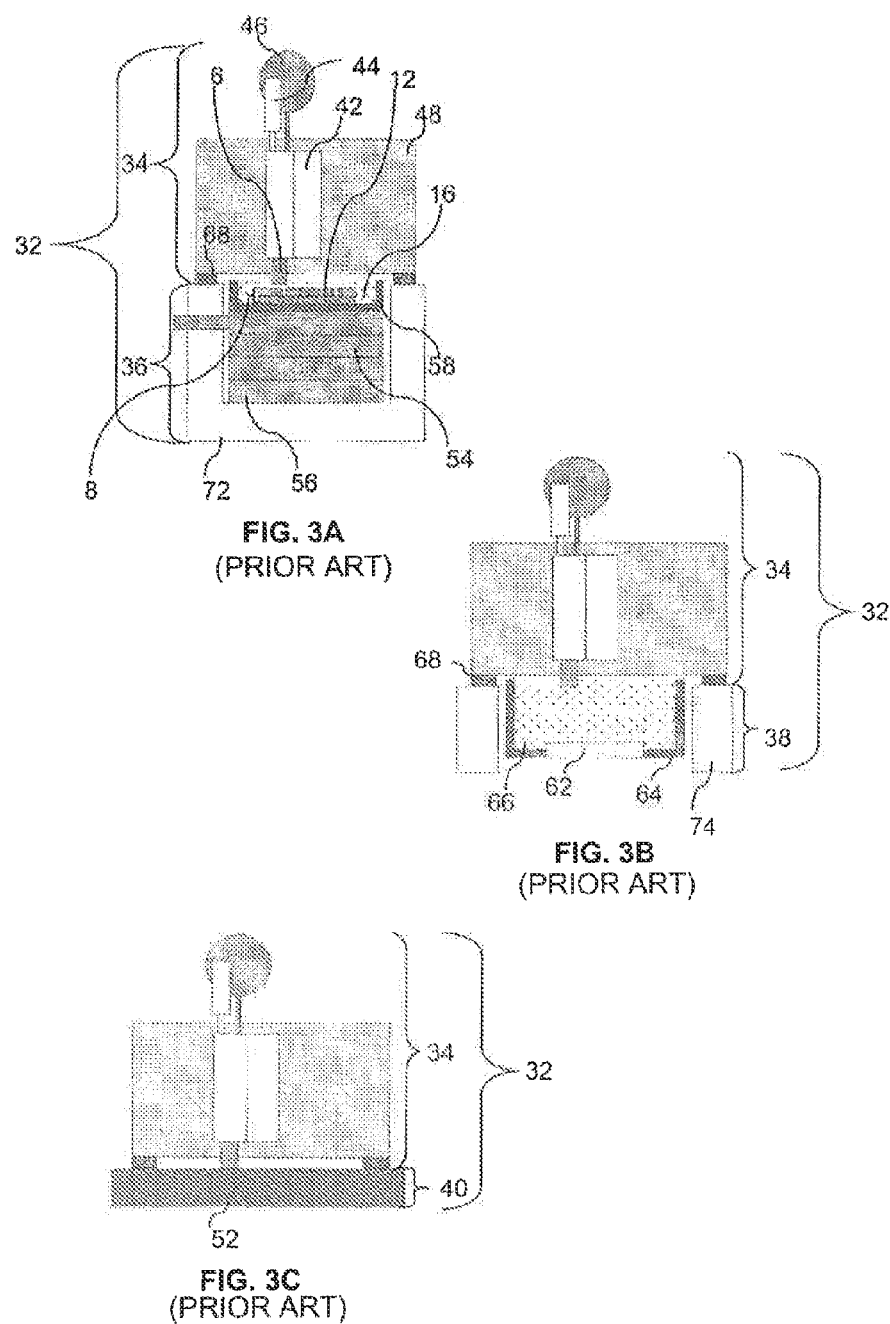
FIGS. 3A-3C schematically depict side views of various example subassemblies that may be used in manually implementing the electrochemical fabrication method depicted in FIGS. 2A-2F.
Figure 4A:
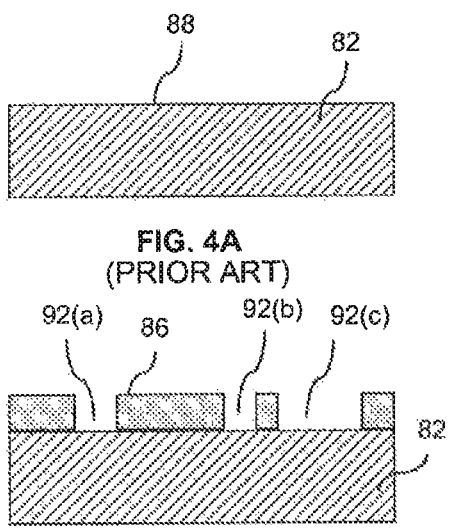
FIGS. 4A-4F schematically depict the formation of a first layer of a structure using adhered mask plating where the blanket deposition of a second material overlays both the openings between deposition locations of a first material and the first material itself
Figure 4B:
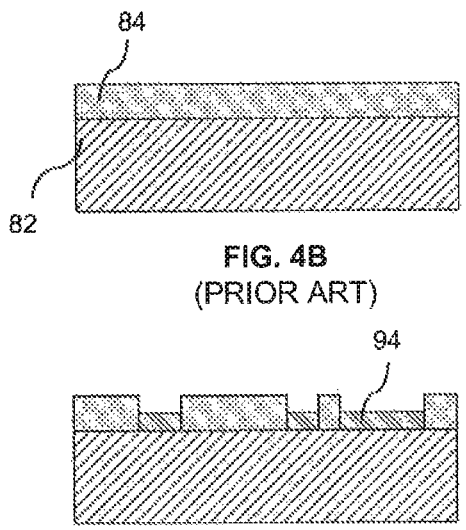
Figure 4C:
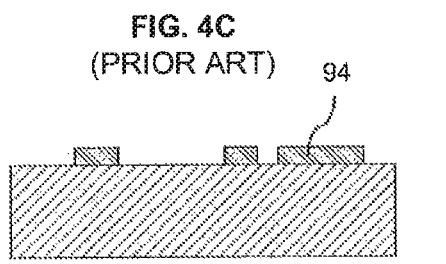
Figure 4D:
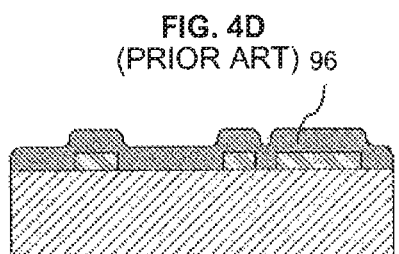
Figure 4E:
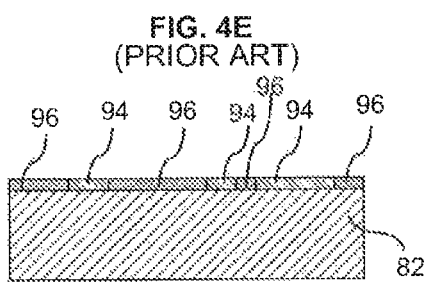
Figure 4F:
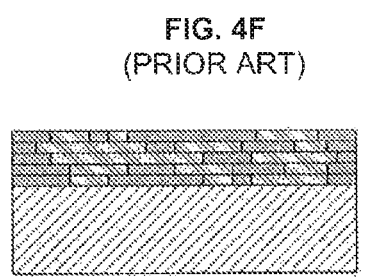
Figure 4G:
FIG. 4G depicts the completion of formation of the first layer resulting from planarizing the deposited materials to a desired level.
Figure 4H:
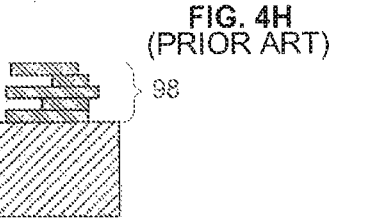
FIGS. 4H and 4I respectively depict the state of the process after formation of the multiple layers of the structure and after release of the structure from the sacrificial material.
Figure 4I:
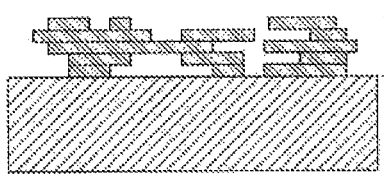

FIGS. 4A-4I illustrate various stages in the formation of a single layer of a multi-layer fabrication process where a second metal is deposited on a first metal as well as in openings in the first metal so that the first and second metal form part of the layer. In FIG. 4A a side view of a substrate 82 is shown, onto which patternable photoresist 84 is cast as shown in FIG. 4B. In FIG. 4C, a pattern of resist is shown that results from the curing, exposing, and developing of the resist. The patterning of the photoresist 84 results in openings or apertures 92(a)-92(c) extending from a surface 86 of the photoresist through the thickness of the photoresist to surface 88 of the substrate 82. In FIG. 4D a metal 94 (e.g. nickel) is shown as having been electroplated into the openings 92(a)-92(c). In FIG. 4E the photoresist has been removed (i.e. chemically stripped) from the substrate to expose regions of the substrate 82 which are not covered with the first metal 94. In FIG. 4F a second metal 96 (e.g. silver) is shown as having been blanket electroplated over the entire exposed portions of the substrate 82 (which is conductive) and over the first metal 94 (which is also conductive). FIG. 4G depicts the completed first layer of the structure which has resulted from the planarization of the first and second metals down to a height that exposes the first metal and sets a thickness for the first layer. In FIG. 4H the result of repeating the process steps shown in FIGS. 4B-4G several times to form a multi-layer structure are shown where each layer consists of two materials. For most applications, one of these materials is removed as shown in FIG. 4I to yield a desired 3-D structure 98 (e.g. component or device).

Various embodiments of various aspects of the disclosure are directed to formation of three-dimensional structures from materials some of which may be electrodeposited or electroless deposited. Some of these structures may be formed form a single build level formed from one or more deposited materials while others are formed from a plurality of build layers each including at least two materials (e.g. two or more layers, more preferably five or more layers, and most preferably ten or more layers). In some embodiments, layer thicknesses may be as small as one micron or as large as fifty microns. In other embodiments, thinner layers may be used while in other embodiments, thicker layers may be used. In some embodiments structures having features positioned with micron level precision and minimum features size on the order of tens of microns are to be formed. In other embodiments structures with less precise feature placement and/or larger minimum features may be formed. In still other embodiments, higher precision and smaller minimum feature sizes may be desirable. In the present application meso-scale and millimeter scale have the same meaning and refer to devices that may have one or more dimensions extending into the 0.5-20 millimeter range, or somewhat larger and with features positioned with precision in the 10-100 micron range and with minimum features sizes on the order of 100 microns.

The various embodiments, alternatives, and techniques disclosed herein may form multi-layer structures using a single patterning technique on all layers or using different patterning techniques on different layers. For example, various embodiments of the disclosure may perform selective patterning operations using conformable contact masks and masking operations (i.e. operations that use masks which are contacted to but not adhered to a substrate), proximity masks and masking operations (i,e. operations that use masks that at least partially selectively shield a substrate by their proximity to the substrate even if contact is not made), non-conformable masks and masking operations (i.e. masks and operations based on masks whose contact surfaces are not significantly conformable), and/or adhered masks and masking operations (masks and operations that use masks that are adhered to a substrate onto which selective deposition or etching is to occur as opposed to only being contacted to it). Conformable contact masks, proximity masks, and non-conformable contact masks share the property that they are preformed and brought to, or in proximity to, a surface which is to be treated (i.e. the exposed portions of the surface are to be treated). These masks can generally be removed without damaging the mask or the surface that received treatment to which they were contacted, or located in proximity to. Adhered masks are generally formed on the surface to be treated (i.e. the portion of that surface that is to be masked) and bonded to that surface such that they cannot be separated from that surface without being completely destroyed damaged beyond any point of reuse. Adhered masks may be formed in a number of ways including (1) by application of a photoresist, selective exposure of the photoresist, and then development of the photoresist, (2) selective transfer of pre-patterned masking material, and/or (3) direct formation of masks from computer controlled depositions of material.

Patterning operations may be used in selectively depositing material and/or may be used in the selective etching of material. Selectively etched regions may be selectively filled in or filled in via blanket deposition, or the like, with a different desired material. In some embodiments, the layer-by-layer build up may involve the simultaneous formation of portions of multiple layers. In some embodiments, depositions made in association with some layer levels may result in depositions to regions associated with other layer levels (i.e. regions that lie within the top and bottom boundary levels that define a different layer's geometric configuration). Such use of selective etching and interlaced material deposition in association with multiple layers is described in U.S. patent application Ser. No. 10/434,519, by Smalley, now U.S. Pat. No. 7,252,861, and entitled "Methods of and Apparatus for Electrochemically Fabricating Structures Via Interlaced Layers or Via Selective Etching and Filling of Voids layer elements" which is hereby incorporated herein by reference as if set forth in full.

Temporary substrates on which structures may be formed may be of the sacrificial-type (i.e., destroyed or damaged during separation of deposited materials to the extent they cannot be reused), non-sacrificial-type (i.e. not destroyed or excessively damaged, i.e. not damaged to the extent they may not be reused, e.g. with a sacrificial or release layer located between the substrate and the initial layers of a structure that is formed). Non-sacrificial substrates may be considered reusable, with little or no rework (e.g. replanarizing one or more selected surfaces or applying a release layer, and the like) though they may or may not be reused for a variety of reasons.

Definitions

This section of the specification is intended to set forth definitions for a number of specific terms that may be useful in describing the subject matter of the various embodiments of the disclosure described herein. It is believed that the meanings of most if not all of these terms is clear from their general use in the specification but they are set forth hereinafter to remove any ambiguity that may exist It is intended that these definitions be used in understanding the scope and limits of any claims that use these specific terms. As far as interpretation of the claims of this patent disclosure are concerned, it is intended that these definitions take precedence over any contradictory definitions or allusions found in any materials which are incorporated herein by reference.

"Build" as used herein refers, as a verb, to the process of building a desired structure or plurality of structures from a plurality of applied or deposited materials which are stacked and adhered upon application or deposition or, as a noun, to the physical structure or structures formed from such a process. Depending on the context in which the term is used, such physical structures may include a desired structure embedded within a sacrificial material or may include only desired physical structures which may be separated from one another or may require dicing and/or slicing to cause separation.

"Build axis" or "build orientation" is the axis or orientation that is substantially perpendicular to substantially planar levels of deposited or applied materials that are used in building up a structure. The planar levels of deposited or applied materials may be or may not be completely planar but are substantially so in that the overall extent of their cross-sectional dimensions are significantly greater than the height of any individual deposit or application of material (e.g. 100, 500, 1000, 5000, or more times greater). The planar nature of the deposited or applied materials may come about from use of a process that leads to planar deposits or it may result from a planarization process (e.g. a process that includes mechanical abrasion, e.g. lapping, fly cutting, grinding, or the like) that is used to remove material regions of excess height. Unless explicitly noted otherwise, "vertical" as used herein refers to the build axis or nominal build axis (if the layers are not stacking with perfect registration) while "horizontal" refers to a direction within the plane of the layers (i.e. the plane that is substantially perpendicular to the build axis).

"Build layer" or "layer of structure" as used herein does not refer to a deposit of a specific material but instead refers to a region of a build located between a lower boundary level and an upper boundary level which generally defines a single cross-section of a structure being formed or structures which are being formed in parallel. Depending on the details of the actual process used to form the structure, build layers are generally formed on and adhered to previously formed build layers. In some processes the boundaries between build layers are defined by planarization operations which result in successive build layers being formed on substantially planar upper surfaces of previously formed build layers. In some embodiments, the substantially planar upper surface of the preceding build layer may be textured to improve adhesion between the layers. In other build processes, openings may exist in or be formed in the upper surface of a previous but only partially formed build layers such that the openings in the previous build layers are filled with materials deposited in association with current build layers which will cause interlacing of build layers and material deposits. Such interlacing is described in U.S. patent application Ser. No. 10/434,519, now U.S. Pat. No. 7,252,861. This referenced application is incorporated herein by reference as if set forth in full. In most embodiments, a build layer includes at least one primary structural material and at least one primary sacrificial material. However, in some embodiments, two or more primary structural materials may be used without a primary sacrificial material (e.g. when one primary structural material is a dielectric and the other is a conductive material). In some embodiments, build layers are distinguishable from each other by the source of the data that is used to yield patterns of the deposits, applications, and/or etchings of material that form the respective build layers. For example, data descriptive of a structure to be formed which is derived from data extracted from different vertical levels of a data representation of the structure define different build layers of the structure. The vertical separation of successive pairs of such descriptive data may define the thickness of build layers associated with the data. As used herein, at times, "build layer" may be loosely referred simply as "layer". In many embodiments, deposition thickness of primary structural or sacrificial materials (i.e. the thickness of any particular material after it is deposited) is generally greater than the layer thickness and a net deposit thickness is set via one or more planarization processes which may include, for example, mechanical abrasion (e.g. lapping, fly cutting, polishing, and the like) and/or chemical etching (e.g. using selective or non-selective etchants). The lower boundary and upper boundary for a build layer may be set and defined in different ways. From a design point of view they may be set based on a desired vertical resolution of the structure (which may vary with height). From a data manipulation point of view, the vertical layer boundaries may be defined as the vertical levels at which data descriptive of the structure is processed or the layer thickness may be defined as the height separating successive levels of cross-sectional data that dictate how the structure will be formed. From a fabrication point of view, depending on the exact fabrication process used, the upper and lower layer boundaries may be defined in a variety of different ways. For example by planarization levels or effective planarization levels (e.g. lapping levels, fly cutting levels, chemical mechanical polishing levels, mechanical polishing levels, vertical positions of structural and/or sacrificial materials after relatively uniform etch back following a mechanical or chemical mechanical planarization process). For example, by levels at which process steps or operations are repeated. At levels at which, at least theoretically, lateral extends of structural material can be changed to define new cross-sectional features of a structure.

"Layer thickness" is the height along the build axis between a lower boundary of a build layer and an upper boundary of that build layer.

"Planarization" is a process that tends to remove materials, above a desired plane, in a substantially non-selective manner such that all deposited materials are brought to a substantially common height or desired level (e.g. within 20%, 10%, 5%, or even 1% of a desired layer boundary level). For example, lapping removes material in a substantially non-selective manner though some amount of recession one material or another may occur (e.g. copper may recess relative to nickel). Planarization may occur primarily via mechanical means, e.g. lapping, grinding, fly cutting, milling, sanding, abrasive polishing, frictionally induced melting, other machining operations, or the like (i.e. mechanical planarization). Mechanical planarization maybe followed or proceeded by thermally induced planarization (e.g. melting) or chemically induced planarization (e.g. etching). Planarization may occur primarily via a chemical and/or electrical means (e.g. chemical etching, electrochemical etching, or the like). Planarization may occur via a simultaneous combination of mechanical and chemical etching (e.g. chemical mechanical polishing (CMP)).

"Structural material" as used herein refers to a material that remains part of the structure when put into use.

"Supplemental structural material" as used herein refers to a material that forms part of the structure when the structure is put to use but is not added as part of the build layers but instead is added to a plurality of layers simultaneously (e.g. via one or more coating operations that applies the material, selectively or in a blanket fashion, to a one or more surfaces of a desired build structure that has been released from a sacrificial material.

"Primary structural material" as used herein is a structural material that forms part of a given build layer and which is typically deposited or applied during the formation of that build layer and which makes up more than 20% of the structural material volume of the given build layer. In some embodiments, the primary structural material may be the same on each of a plurality of build layers or it may be different on different build layers. In some embodiments, a given primary structural material may be formed from two or more materials by the alloying or diffusion of two or more materials to form a single material.

"Secondary structural material" as used herein is a structural material that forms part of a given build layer and is typically deposited or applied during the formation of the given build layer but is not a primary structural material as it individually accounts for only a small volume of the structural material associated with the given layer. A secondary structural material will account for less than 20% of the volume of the structural material associated with the given layer. In some preferred embodiments, each secondary structural material may account for less than 10%, 5%, or even 2% of the volume of the structural material associated with the given layer. Examples of secondary structural materials may include seed layer materials, adhesion layer materials, harrier layer materials (e.g. diffusion barrier material), and the like. These secondary structural materials are typically applied to form coatings having thicknesses less than 2 microns, 1 micron, 0.5 microns, or even 0.2 microns). The coatings may he applied in a conformal or directional manner (e.g. via CND, PVD, electroless deposition, or the like). Such coatings may be applied in a blanket manner or in a selective manner. Such coatings may be applied in a planar manner (e.g. over previously planarized layers of material) as taught in U.S. patent application Ser. No. 10/607,931. in other embodiments, such coatings may be applied in a non-planar manner, for example, in openings in and over a patterned masking material that has been applied to previously planarized layers of material as taught in U.S. patent application Ser. No. 10/841,383. These referenced applications are incorporated herein by reference as if set forth in full herein.

"Functional structural material" as used herein is a structural material that would have been removed as a sacrificial material but for its actual or effective encapsulation by other structural materials. Effective encapsulation refers, for example, to the inability of an etchant to attack the functional structural material due to inaccessibility that results from a very small area of exposure and/or due to an elongated or tortuous exposure path. For example, large (10,000 µm²) but thin (e.g. less than 0.5 microns) regions of sacrificial copper sandwiched between deposits of nickel may define regions of functional structural material depending on ability of a release etchant to remove the sandwiched copper.

"Sacrificial material" is material that forms part of a build layer but is not a structural material. Sacrificial material on a given build layer is separated from structural material on that build layer after formation of that build layer is completed and more generally is removed from a plurality of layers after completion of the formation of the plurality of layers during a "release" process that removes the bulk of the sacrificial material or materials. In general sacrificial material is located on a build layer during the formation of one, two, or more subsequent build layers and is thereafter removed in a manner that does not lead to a planarized surface. Materials that are applied primarily for masking purposes, i.e. to allow subsequent selective deposition or etching of a material, e.g. photoresist that is used in forming a build layer but does not form part of the build layer) or that exist as part of a build for less than one or two complete build layer formation cycles are not considered sacrificial materials as the term is used herein but instead shall be referred as masking materials or as temporary materials. These separation processes are sometimes referred to as a release process and may or may not involve the separation of structural material from a build substrate. In many embodiments, sacrificial material within a given build layer is not removed until all build layers making up the three-dimensional structure have been formed. Of course sacrificial material may be, and typically is, removed from above the upper level of a current build layer during planarization operations during the formation of the current build layer. Sacrificial material is typically removed via a chemical etching operation but in some embodiments may be removed via a melting operation or electrochemical etching operation. In typical structures, the removal of the sacrificial material (i.e. release of the structural material from the sacrificial material) does not result in planarized surfaces but instead results in surfaces that are dictated by the boundaries of structural materials located on each build layer. Sacrificial materials are typically distinct from structural materials by having different properties there from (e.g. chemical etchability, hardness, melting point, etc.) but in some cases, as noted previously, what would have been a sacrificial material may become a structural material by its actual or effective encapsulation by other structural materials. Similarly, structural materials may be used to form sacrificial structures that are separated from a desired structure during a release process via the sacrificial structures being only attached to sacrificial material or potentially by dissolution of the sacrificial structures themselves using a process that is insufficient to reach structural material that is intended to form part of a desired structure. It should be understood that in some embodiments, small amounts of structural material may be removed, after or during release of sacrificial material. Such small amounts of structural material may have been inadvertently formed due to imperfections in the fabrication process or may result from the proper application of the process but may result in features that are less than optimal (e.g. layers with stairs steps in regions where smooth sloped surfaces are desired. In such cases the volume of structural material removed is typically minuscule compared to the amount that is retained and thus such removal is ignored when labeling materials as sacrificial or structural.

Sacrificial materials are typically removed by a dissolution process, or the like, that destroys the geometric configuration of the sacrificial material as it existed on the build layers. In many embodiments, the sacrificial material is a conductive material such as a metal. As will be discussed hereafter, masking materials though typically sacrificial in nature are not termed sacrificial materials herein unless they meet the required definition of sacrificial material.

"Supplemental sacrificial material" as used herein refers to a material that does not form part of the structure when the structure is put to use and is not added as part of the build layers but instead is added to a plurality of layers simultaneously (e.g. via one or more coating operations that applies the material, selectively or in a blanket fashion, to a one or more surfaces of a desired build structure that has been released from an initial sacrificial material. This supplemental sacrificial material will remain in place for a period of time and/or during the performance of certain post layer formation operations, e.g. to protect the structure that was released from a primary sacrificial material, but will be removed prior to putting the structure to use.

"Primary sacrificial material" as used herein is a sacrificial material that is located on a given build layer and which is typically deposited or applied during the formation of that build layer and which makes up more than 20% of the sacrificial material volume of the given build layer. In some embodiments, the primary sacrificial material may be the same on each of a plurality of build layers or may be different on different build layers. In some embodiments, a given primary sacrificial material may be formed from two or more materials by the alloying or diffusion of two or more materials to form a single material.

"Secondary sacrificial material" as used herein is a sacrificial material that is located on a given build layer and is typically deposited or applied during the formation of the build layer but is not a primary sacrificial materials as it individually accounts for only a small volume of the sacrificial material associated with the given layer. A secondary sacrificial material will account for less than 2.0% of the volume of the sacrificial material associated with the given layer. In some preferred embodiments, each secondary sacrificial material may account for less than 10%, 5%, or even 2% of the volume of the sacrificial material associated with the given layer. Examples of secondary structural materials may include seed layer materials, adhesion layer materials, barrier layer materials (e.g. diffusion barrier material), and the like. These secondary sacrificial materials are typically applied to form coatings having thicknesses less than 2 microns, 1 micron, 0.5 microns, or even 0.2 microns). The coatings may be applied in a conformal or directional manner (e.g. via CVD, PVD, electroless deposition, or the like). Such coatings may be applied in a blanket manner or in a selective manner. Such coatings may be applied in a planar manner (e.g. over previously planarized layers of material) as taught in U.S. patent application Ser. No. 10/607,931, now U.S. Pat. No. 7,239,219. In other embodiments, such coatings may be applied in a non-planar manner, for example, in openings in and over a patterned masking material that has been applied to previously planarized layers of material as taught in U.S. patent application Ser. No. 10/841,383, now U.S. Pat. No. 7,195,989. These referenced applications are incorporated herein by reference as if set forth in full herein.

"Adhesion layer", "seed layer", "barrier layer", and the like refer to coatings of material that are thin in comparison to the layer thickness and thus generally form secondary structural material portions or sacrificial material portions of some layers. Such coatings may be applied uniformly over a previously formed build layer, they may be applied over a portion of a previously formed build layer and over patterned structural or sacrificial material existing on a current (i.e. partially formed) build layer so that a non-planar seed layer results, or they may be selectively applied to only certain locations on a previously formed build layer. In the event such coatings are non-selectively applied, selected portions may be removed (1) prior to depositing either a sacrificial material or structural material as part of a current layer or (2) prior to beginning formation of the next layer or they may remain in place through the layer build up process and then etched away after formation of a plurality of build layers.

"Masking material" is a material that may be used as a tool in the process of forming a build layer but does not form part of that build layer. Masking material is typically a photopolymer or photoresist material or other material that may be readily patterned. Masking material is typically a dielectric. Masking material, though typically sacrificial in nature, is not a sacrificial material as the term is used herein. Masking material is typically applied to a surface during the formation of a build layer for the purpose of allowing selective deposition, etching, or other treatment and is removed either during the process of forming that build layer or immediately after the formation of that build layer.

"Multilayer structures" are structures formed from multiple build layers of deposited or applied materials.

"Multilayer three-dimensional (or 3D or 3-D) structures" are Multilayer Structures that meet at least one of two criteria: (1) the structural material portion of at least two layers of which one has structural material portions that do not overlap structural material portions of the other.

"Complex multilayer three-dimensional (or 3D or 3-D) structures" are multilayer three-dimensional structures formed from at least three layers where a line may be defined that hypothetically extends vertically through at least some portion of the build layers of the structure will extend from structural material through sacrificial material and back through structural material or will extend from sacrificial material through structural material and back through sacrificial material (these might be termed vertically complex multilayer three-dimensional structures). Alternatively, complex multilayer three-dimensional structures may be defined as multilayer three-dimensional structures formed from at least two layers where a line may be defined that hypothetically extends horizontally through at least some portion of a build layer of the structure that will extend from structural material through sacrificial material and back through structural material or will extend from sacrificial material through structural material and back through sacrificial material (these might be termed horizontally complex multilayer three-dimensional structures). Worded another way, in complex multilayer three-dimensional structures, a vertically or horizontally extending hypothetical line will extend from one or structural material or void (when the sacrificial material is removed) to the other of void or structural material and then back to structural material or void as the line is traversed along at least a portion of the line.

"Moderately complex multilayer three-dimensional (or 3D or 3-D) structures are complex multilayer 3D structures for which the alternating of void and structure or structure and void not only exists along one of a vertically or horizontally extending line but along lines extending both vertically and horizontally.

"Highly complex multilayer (or 3D or 3-D) structures are complex multilayer 3D structures for which the structure-to-void-to-structure or void-to-structure-to-void alternating occurs once along the line but occurs a plurality of times along a definable horizontally or vertically extending line.

"Up-facing feature" is an element dictated by the cross-sectional data for a given build layer "n" and a next build layer "n+1" that is to be formed from a given material that exists on the build layer "n" but does not exist on the immediately succeeding build layer "n+1". For convenience the term "up-facing feature" will apply to such features regardless of the build orientation.

"Down-facing feature" is an element dictated by the cross-sectional data for a given build layer "n" and a preceding build layer "n−1" that is to be formed from a given material that exists on build layer "n" but does not exist on the immediately preceding build layer "n−1". As with up-facing features, the term "down-facing feature" shall apply to such features regardless of the actual build orientation.

"Continuing region" is the portion of a given build layer "n" that is dictated by the cross-sectional data for the given build layer "n", a next build layer "n+1" and a preceding build layer "n−1" that is neither up-facing nor down-facing for the build layer "n".

"Minimum feature size" refers to a necessary or desirable spacing between structural material elements on a given layer that are to remain distinct in the final device configuration. If the minimum feature size is not maintained on a given layer, the fabrication process may result in structural material inadvertently bridging the two structural elements due to masking material failure or failure to appropriately fill voids with sacrificial material during formation of the given layer such that during formation of a subsequent layer structural material inadvertently fills the void. More care during fabrication can lead to a reduction in minimum feature size or a willingness to accept greater losses in productivity can result in a decrease in the minimum feature size. However, during fabrication for a given set of process parameters, inspection diligence, and yield (successful level of production) a minimum design feature size is set in one way or another. The above described minimum feature size may more appropriately be termed minimum feature size of sacrificial material regions. Conversely a minimum feature size for structure material regions (minimum width or length of structural material elements) may be specified. Depending on the fabrication method and order of deposition of structural material and sacrificial material, the two types of minimum feature sizes may be different. In practice, for example, using electrochemical fabrication methods and described herein, the minimum features size on a given layer may be roughly set to a value that approximates the layer thickness used to form the layer and it may be considered the same for both structural and sacrificial material widths and lengths. In some more rigorously implemented processes, examination regiments, and rework requirements, it may be set to an amount that is 80%, 50%, or even 30% of the layer thickness. Other values or methods of setting minimum feature sizes may be set.

"Sublayer" as used herein refers to a portion of a build layer that typically includes the full lateral extents of that build layer but only a portion of its height. A sublayer is usually a vertical portion of build layer that undergoes independent processing compared to another sublayer of that build layer.

Tissue Shredding Devices, Methods for Making and Methods for Using

Figure 5:
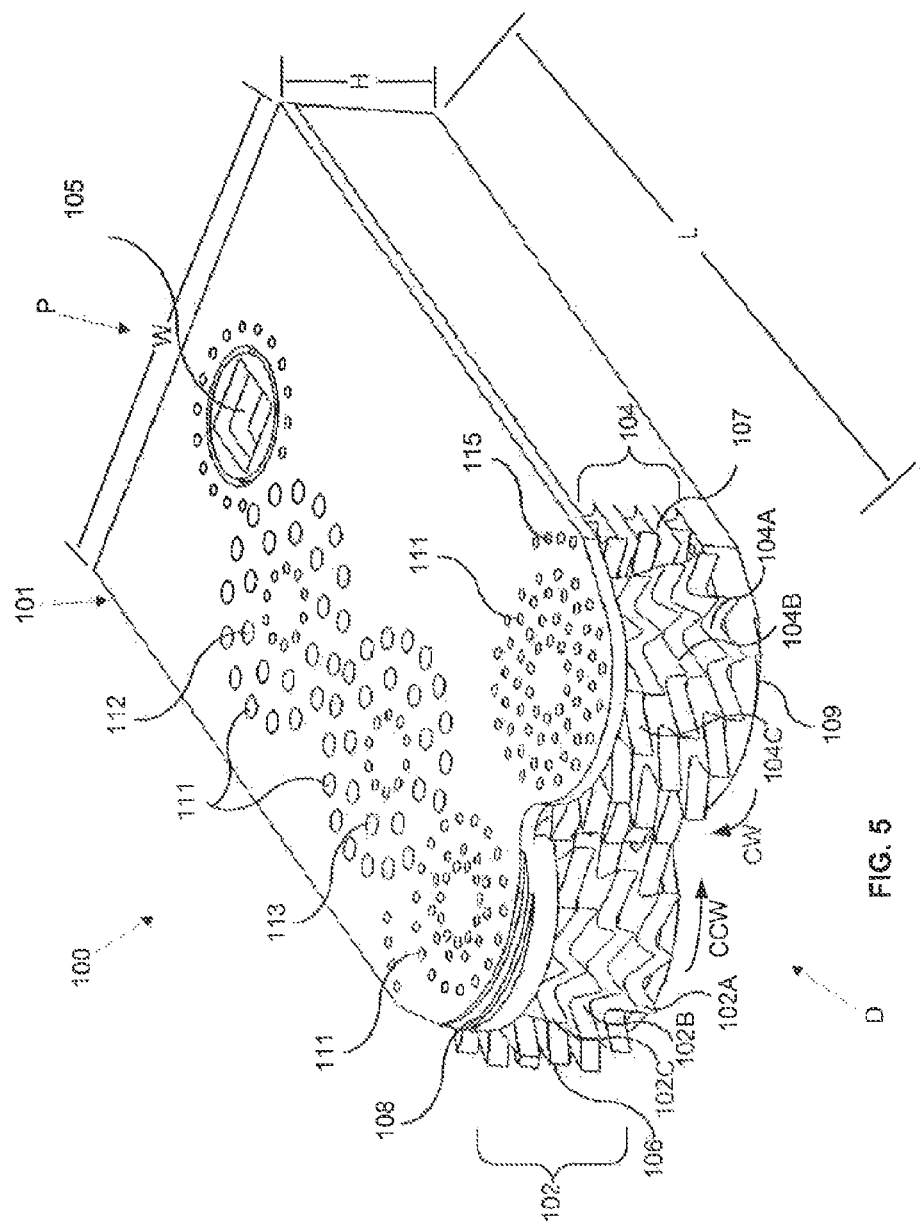
FIGS. 5-7 illustrate an exemplary embodiment of a working end of a tissue removal device which can be fabricated wholly or in part by electrochemical fabrication techniques, such as those described or referenced herein.
Figure 6:
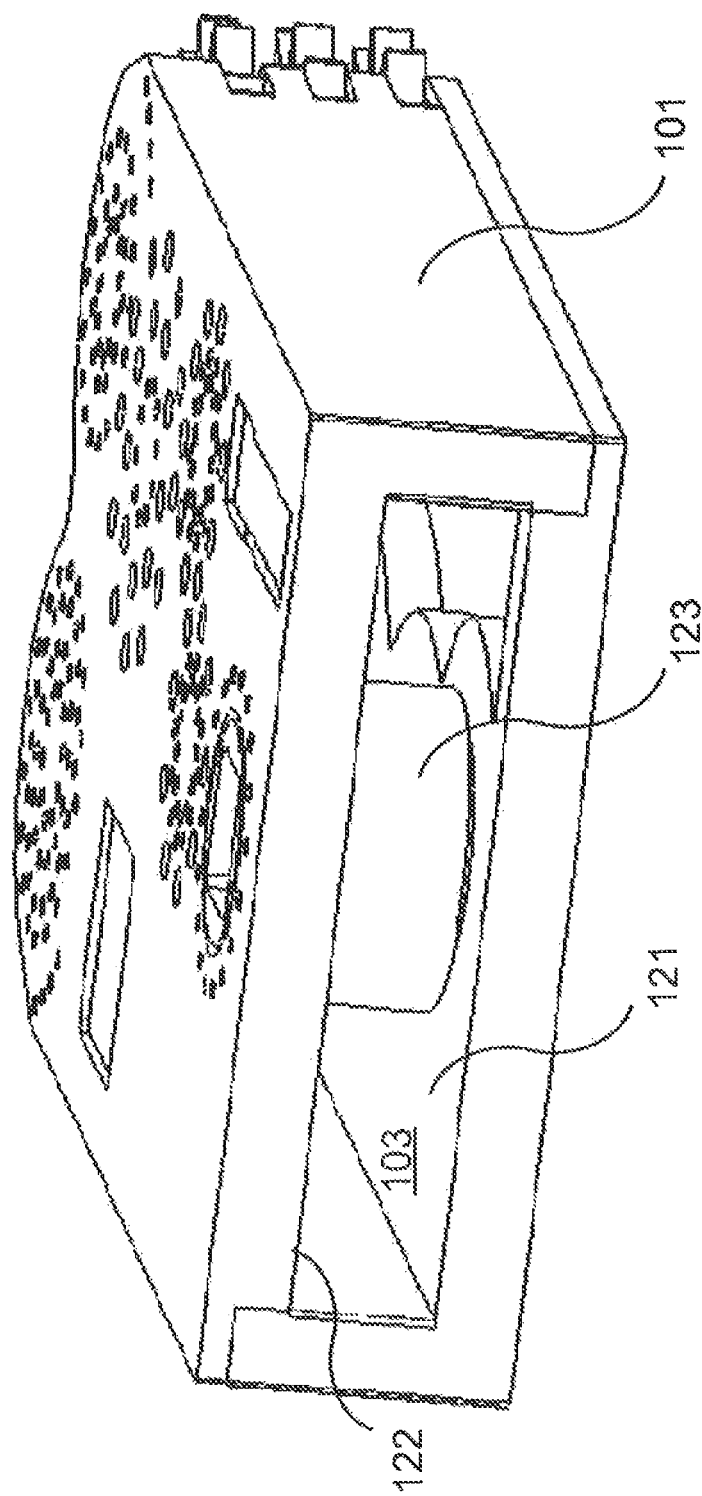
Figure 7:
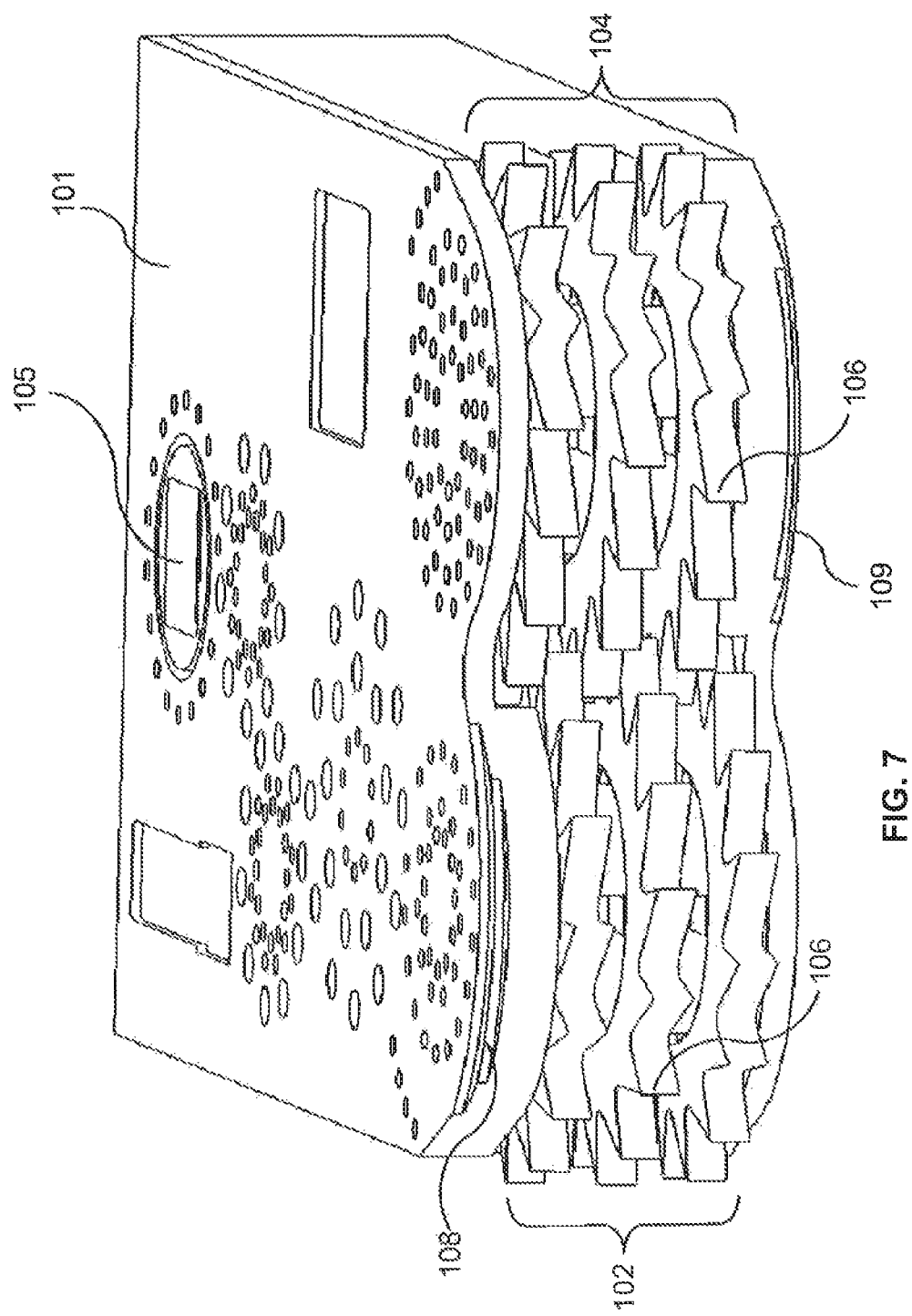

FIGS. 5-7 illustrate an exemplary embodiment of a working end of a tissue removal device which can be fabricated wholly or in part by electrochemical fabrication techniques, such as those described or referenced herein. Tissue removal device working end 100 has a distal region "D" and proximal region "P," and includes housing 101 and blade stacks 102 and 104. Blade stacks 102 and 104 include a plurality of blades 102A-102C and 104A-104C, respectively. Three blades are shown in each stack, although the blade stacks can have one or more blades. Each of the blades includes a plurality of teeth 106 (see FIG. 7), some of which are shown projecting from housing 101 and configured to engage and process tissue. Processing tissue as used herein includes any of cutting tissue, shredding tissue, capturing tissue, any other manipulation of tissue as described herein, or any combination thereof. The working end of the device generally has a length L, height H, and width W. Housing 101 can have a variety of shapes or configurations, including a generally cylindrical shape.

In this embodiment both blade stacks are configured to rotate. The blades in blade stack 102 are configured to rotate in a direction opposite that of the blades in blade stack 104, as designated by the counterclockwise "CCW" and clockwise "CW" directions in FIG. 5. The oppositely rotating blades direct material, such as tissue, into an interior region of housing 101 (described in more detail below). In some embodiments, the blades can be made to rotated in directions opposite to those indicated, e.g. to disengage from tissue if a jam occurs or to cause the device to be pulled distally into a body of tissue when given appropriate back side teeth configurations.

Housing 101 also includes a drive mechanism coupler 105, shown as a square hole or bore, which couples a drive train disposed in the housing to a drive mechanism disposed external to the housing. The drive mechanism, described in more detail below, drives the rotation of the drive train, which drives the rotation of the blades. The drive train disposed in the housing can also be considered part of the drive mechanism when viewed from the perspective of the blades. Drive mechanism coupler 105 translates a rotational force applied to the coupler by the drive mechanism (not shown) to the drive train disposed within housing 101.

FIG. 5 also shows release holes 111-115 which allow for removal of sacrificed material during formation of the working end.

FIG. 6 shows a perspective view of the proximal end of tissue removal device working end 100. Material directed into housing 101 by the rotating blades is directed into chamber 103, wherein it can be stored temporarily or directed further proximally, as described below. A first gear train cover 121 provides for a first surface of chamber 103, while a second gear train cover 122 provides a second surface of chamber 103. FIG. 6 also shows drive mechanism coupler cover 123.

In some embodiments in which the working end 100 includes a storage chamber, the chamber may remain open while in other embodiments it may be closed while in still other embodiments it may include a filter that only allows passage of items of a sufficiently small size to exit.

FIG. 7 shows a perspective view of the distal end of the working end 100. In this embodiment the blades in stack 102 are interdigitated with the blades in stack 104 (i.e. the blade ends are offset vertically along dimension H and over have maximum radial extensions that overlap laterally along the width dimension W. The blades can be formed to be interdigitated by, e.g. if formed using a multi-layer, multi-material electrochemical fabrication technique, forming each blade in stack 102 in a different layer than each blade in stack 104. If during formation portions of separately moveable blade components overlap laterally the overlapping blade must not just be formed on different layers but formed such an intermediate layer defined a vertical gap between them. For example, the bottom blade in stack 102 is shown formed in a layer beneath the layer in which the bottom blade in stack 104 is formed.

Figure 8:
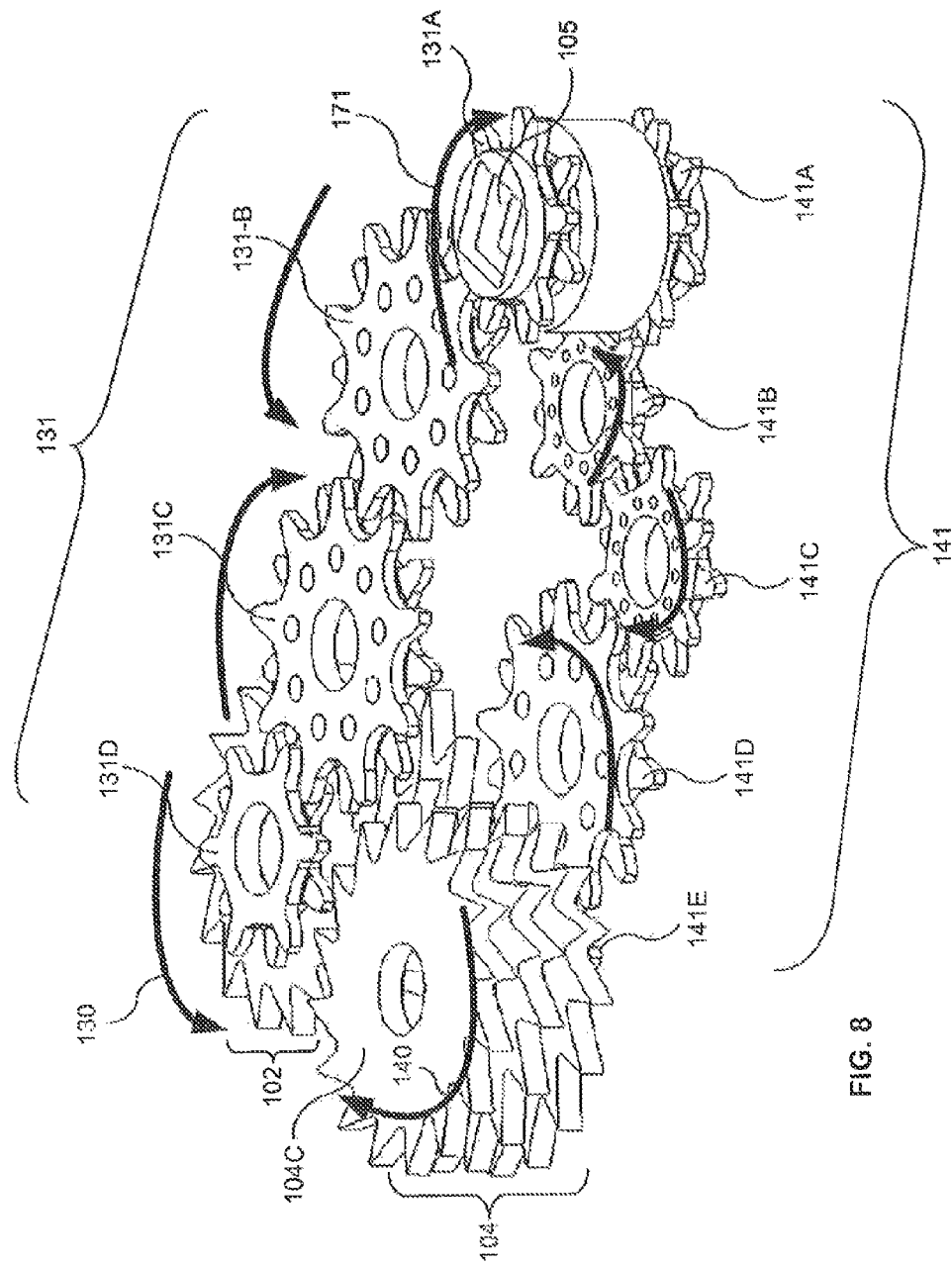
FIG. 8 illustrates a perspective view of an exemplary gear train system which can be included in any suitable working end described herein to drive the rotation of the blades.

FIG. 8 illustrates a perspective view of an exemplary gear train system which can be included in any suitable working end described herein to drive the rotation of the blades (such as the embodiment of the working end shown in FIGS. 5-7). The gear train system includes drive mechanism coupler 105 at a first end of the gear train which is coupled to gear 131A in first gear train 131, and is coupled to gear 141A in gear train 141. Coupler 105, in response to a rotational force applied via a rotating pin (not shown) which may be considered part of the drive mechanism or a separate component of the device, drives the gears in first gear train 131 and the gears in the second gear train 141, which drives the respectively coupled blade stacks to rotate in opposite directions. Gears 131D and 141E are coupled to blade stack shafts, which allow the gear trains to drive the rotation of the blades. Gear trains 131 and 141 include gears 131A-131D and 141A-141E, respectively. By having an odd number of gears in one gear train and an even number of gears in the other gear train, the blades will rotate in opposite directions. The arrows in FIG. 8 show the direction of forward rotation of the gears and the blades.

Figure 9:
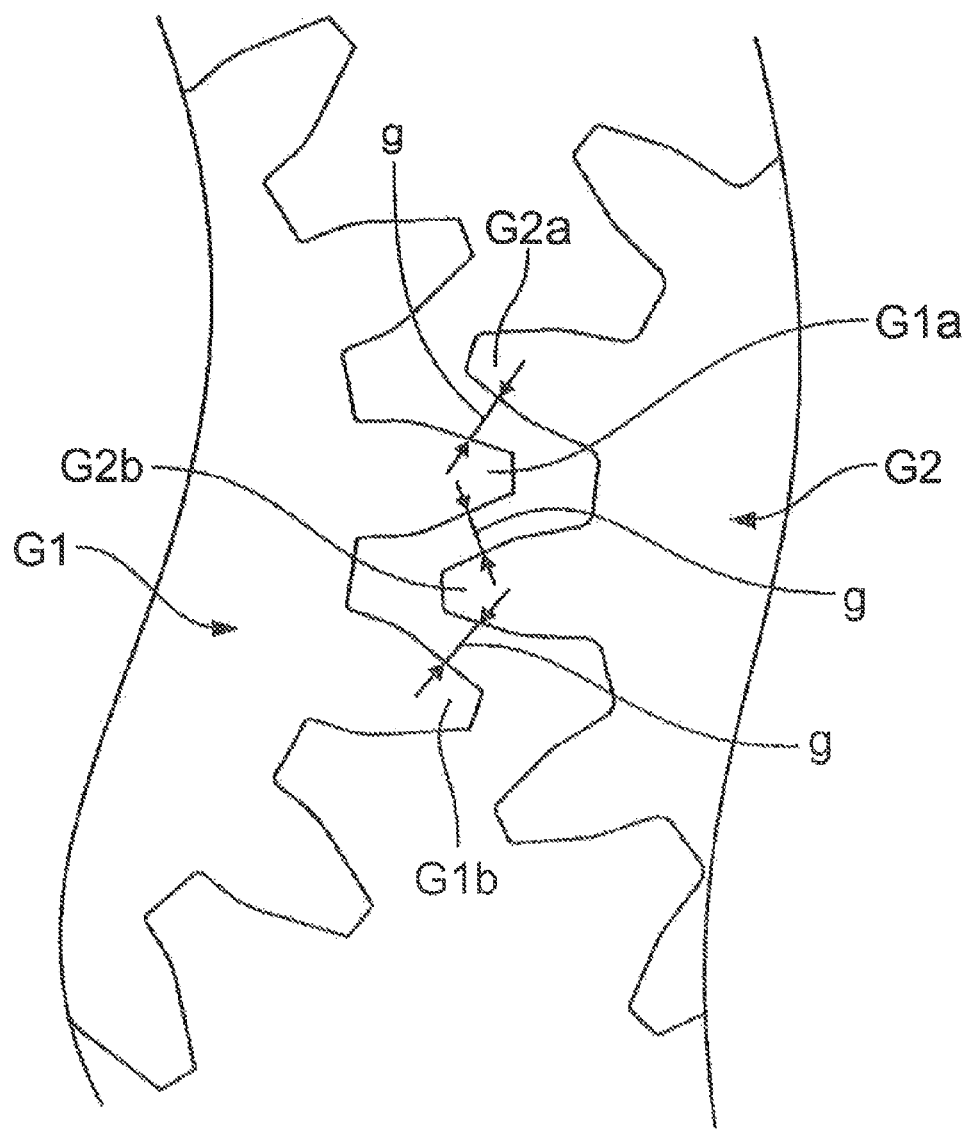
FIG. 9 shows a portion of two adjacent gears formed from a multi-layer, multi-material electrochemical fabrication process.

A potential challenge when fabricating parts or components of a device using a multi-layer multi-material electrochemical fabrication process or other similar process can be creating very small gaps, or spaces, between components of the device. Potential challenges are described above in the "Minimum feature size" definition section. In some embodiments the gears are formed using an electrochemical fabrication process or other similar process and are formed in a single multi-material layer. One challenge in forming microgears in this manner can be making sure the gaps between teeth on adjacent gears (i.e. meshing gears) can be formed consistently and with appropriate dimensions. For example, FIG. 9 shows a portion of two adjacent gears G1 and G2 formed from a multi-layer, multi-material electrochemical fabrication process. The gears are formed in this configuration, such that at least one tooth on one of the gears is formed "in-between" two teeth on the adjacent gear. Gear G1 includes teeth G1a and G1b and gear G2 includes teeth G2a and G2b. During the fabrication process, gaps "g," formed between structural material depositions of the teeth of gear G1 and gear G2 must be large enough to meet an associated minimum feature size while still providing a desired engagement with teeth of the adjacent gear so that a backlash is not excessive and so that binding of the gears does not occur due to either lateral shifting of gears as a result of lateral shifting of their axles within their engagement holes or canting or tilting of the gears relative to one another as a result of out of movement that may be allowed by the spacing between the gear shafts and their guide holes.

Figure 10:
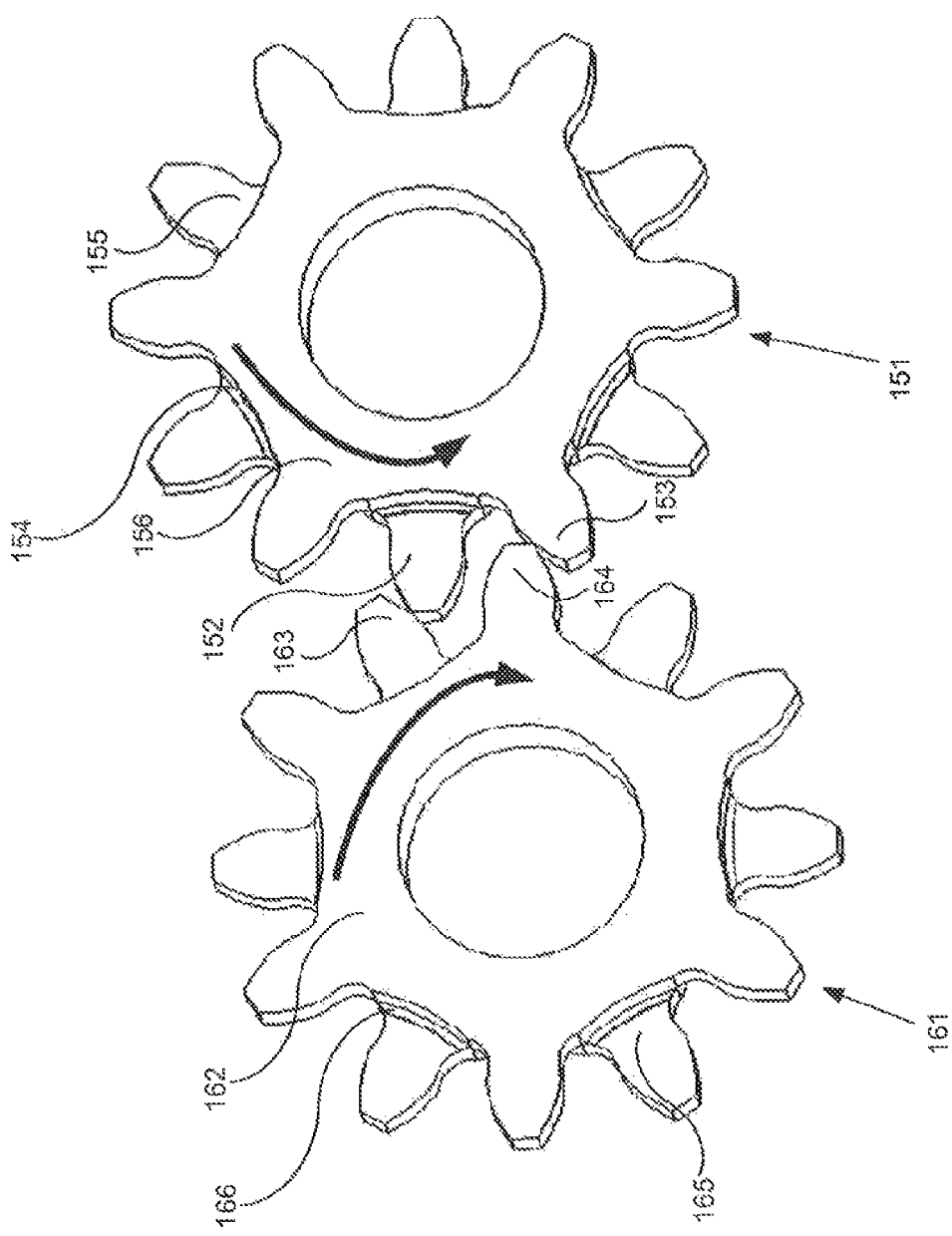
FIG. 10 illustrates an exemplary embodiment of a first gear configuration for assembled fabrication which allows for minimizing backlash while still meeting minimum feature size limitations in both gear tooth spacing as well as axle shaft and guide hole, bearing or bushing spacing.

FIG. 10 illustrates an exemplary embodiment of a first gear configuration for assembled fabrication which allows for minimizing backlash while still meeting minimum feature size limitations in both gear tooth spacing as well as axle shaft and guide hole, bearing or bushing spacing. Each gear is formed from more than one layer of material rather than one layer of material. Each gear "layer" may be referred herein as a "tier." Driving gear 161 includes upper tier 162, lower tier 165, and intermediate tier 166. Intermediate tier is formed as a separate layer and is between upper tier 162 and lower tier 165. Upper tier 162 includes tooth 164 and lower tier 165 includes tooth 163. Six teeth are shown on the upper and lower tiers, while there are no teeth on the intermediate tier. Driven gear 151 is formed in the same manner as driving gear 161 and includes upper tier 156 including tooth 153, lower tier 155 including tooth 152, and intermediate tier 154. Six teeth are shown on the upper and lower tiers in driven gear 151, while there are no teeth on intermediate tier 153.

The teeth on gears 161 and 151 mesh properly and behave may behave, for example, as an involute spur gears. In operation, tooth 164 of upper tier 162 of driving gear 161 contacts and drives tooth 153 on the upper tier 156 of driven gear 151. Tooth 163 on lower tier 165 of driving gear 161 contacts and drives tooth 152 on lower tier 155 of driven gear 151.

In some embodiments, the teeth are formed such that as the gears turn there are always two consecutive teeth on the driving gear on different tiers (e.g., tooth 164 and tooth 163 of driving gear 161) that are in contact with two consecutive teeth on the driven gear (e.g. tooth 153 and tooth 152 on driven gear 151). The gears can be fabricated such that the distance, or gap dimension, between consecutive teeth on a single tier is maximized, which may be beneficial if the gap size would have been too small for fabrication if all gear teeth were on a single tier instead of split between different tears.

It is possible to drive the gear train in both directions. In some embodiments, additional tiers with teeth may be incorporated into the gears so that gear interfaces (i.e., contact between teeth on adjacent gears) do not occur on merely two levels but rather occur on three or more levels.

Figure 11:
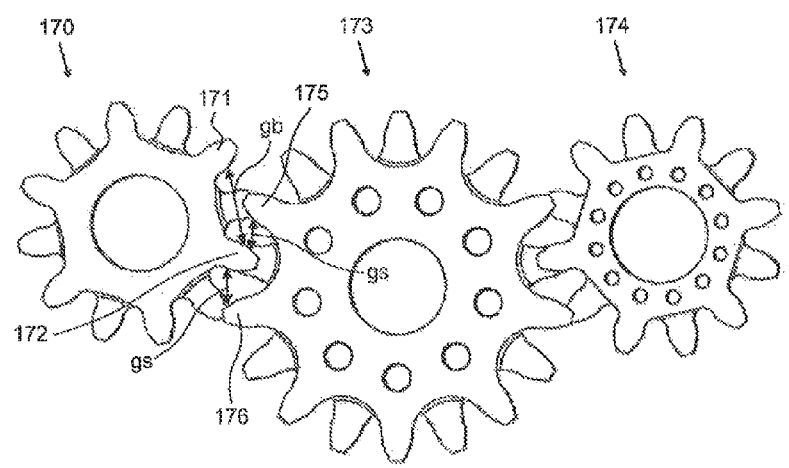
FIGS. 11 and 12 show three gears in an "as fabricated" configuration.
Figure 12:
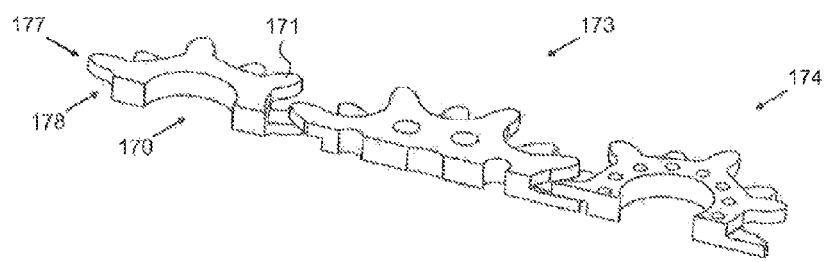

FIGS. 11 and 12 show three gears in an "as fabricated" configuration. FIG. 11 is a top view of gear 170, gear 173, and gear 174. Gear 170 includes tooth 171 and tooth 172 on its upper tier, separated by distance, or gap, "gb." Gear 173 includes tooth 175 and 176 on its upper tier. Teeth 175 and 176 are fabricated separated on either side of tooth 172 of gear 170 by a distance, or gap, "gs." By using a multi-tiered gear, the distance gs between the teeth on adjacent gears is larger than if the teeth on gears 170 and 173 were on a single tier. FIG. 12 shows a cross-sectional perspective view of the three gears from FIG. 11, illustrating upper tier 177 and lower tier 178 which are separated by an intermediate tier 179 without teeth that may be relatively thin (e.g. ½, ⅕, 1/10, or even 1/20 or less of the thickness of the upper and lower tiers). These intermediate tiers allow a lower tiered tooth on one gear to be fabricated under an upper tier tooth such that they partially or completely laterally (i.e. within the dimensions the layers, e.g. XY dimensions, relative to the axis of stacking of the layers, e.g. the Z dimension) overlap without causing layer-to-layer adhesion of the teeth due to the presence of an intermediate volume of sacrificial material located vertically between them. Forming gears with multiple tiers, allows for intra-layer gaps between teeth of adjacent gears (i.e, engaging gears) to remain above a minimum feature size while allowing effective gaps between engaging gears as a Whole to have a much smaller tooth gap or tighter tooth pitch. In some embodiments, the existence of intermediate non-toothed tiers allows tighter teeth spacing and/or wider teeth dimensions without needing to resort to gears with more than two toothed tiers. Multi-tier gears as set forth in the example, provide an engage method and components for forming tightly-meshed teeth while allowing necessary gaps to be reliably formed between teeth on adjacent gears. In some embodiments, each tier may be formed from a single multi-material layer, while in other embodiments each tier may be formed from a plurality of multi-material layers.

In embodiments in which a gear has more than one tier, and it may be possible to remove one or more of the immediate tiers (i.e, those that do not have gear teeth) as it may be possible to form gear teeth on multiple levels without any two consecutive levels having teeth that overlap in the X-Y plane in the as formed position.

Figure 13:
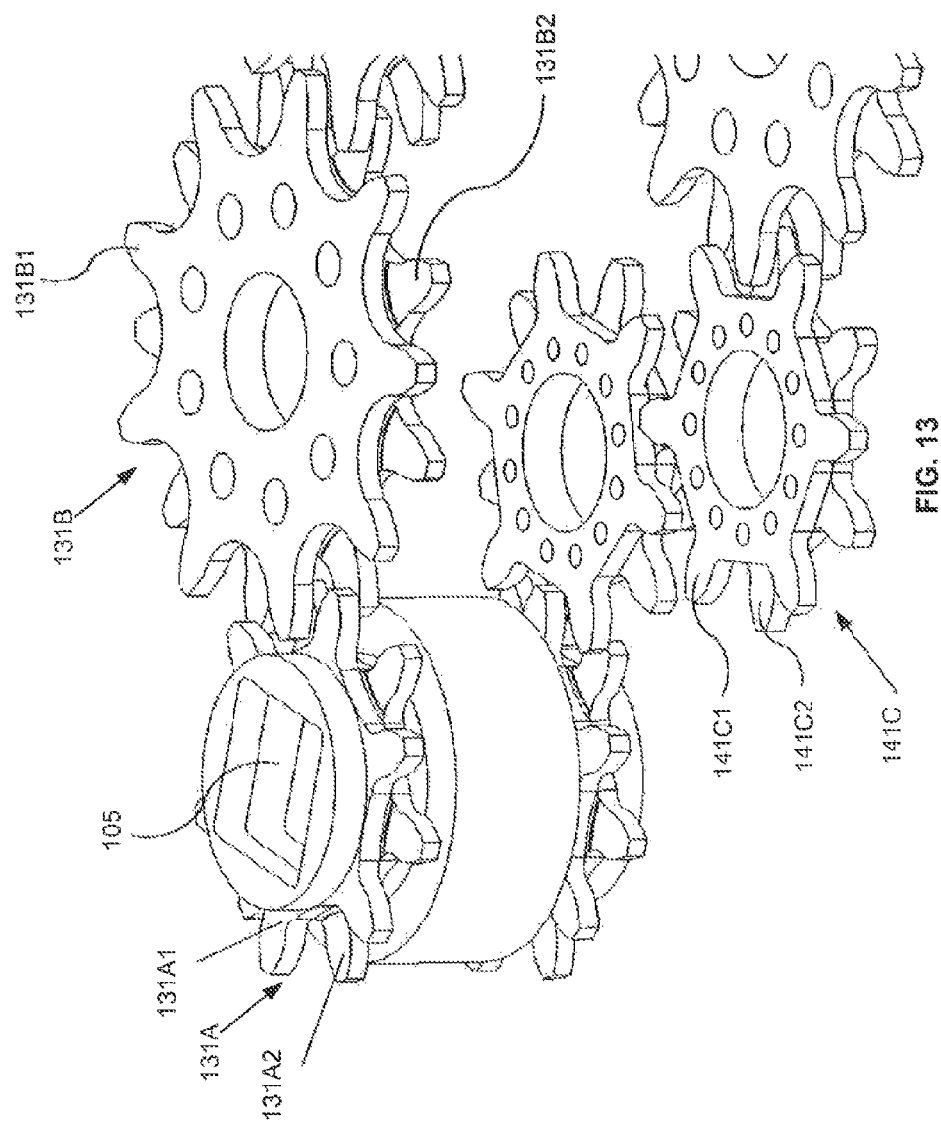
FIGS. 13 and 14 highlight the proximal end and distal end, respectively, of the gear trains shown in FIG. 8, which incorporate a multi-tiered gear design.
Figure 14:
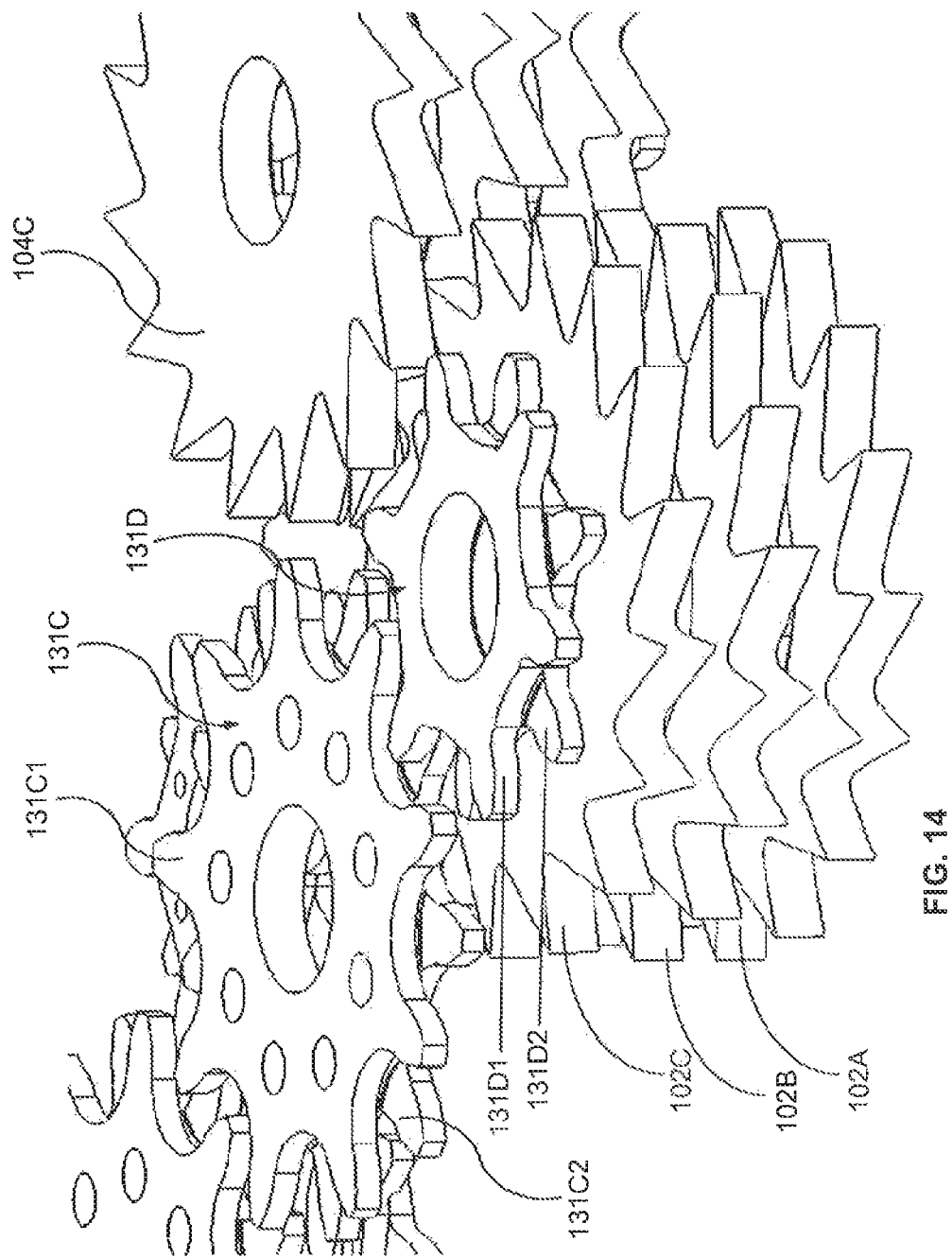

FIGS. 13 and 14 highlight the proximal end and distal end, respectively, of the gear trains shown in FIG. 8, which incorporate a multi-tiered gear design. Gear 131A is comprised of a first tier 131A1 and a second tier 131A2, each having six teeth. Rotation of gear 131A due to rotational threes on the drive mechanism coupler 105 causes the teeth on tier 131A1 to contact and drive the teeth on tier 131B1 of gear 131B, while teeth on tier 131A2 engage teeth on tier 131B2. The gears in gear train 141 also include multi-tiered or multi-layered gears and function in the same way. FIG. 14 illustrates the distal end of the gear train, illustrating gear 131C comprising tier 131C1, which is configured to rotate and engage with tier 131D1 of gear 131D, and tier 131C2, which is configured to rotate and engage with tier 131D2 of gear 131D. Rotation of gear 131D rotates the blades in blade stack 102 about a blade shaft (not shown).

Figure 15:
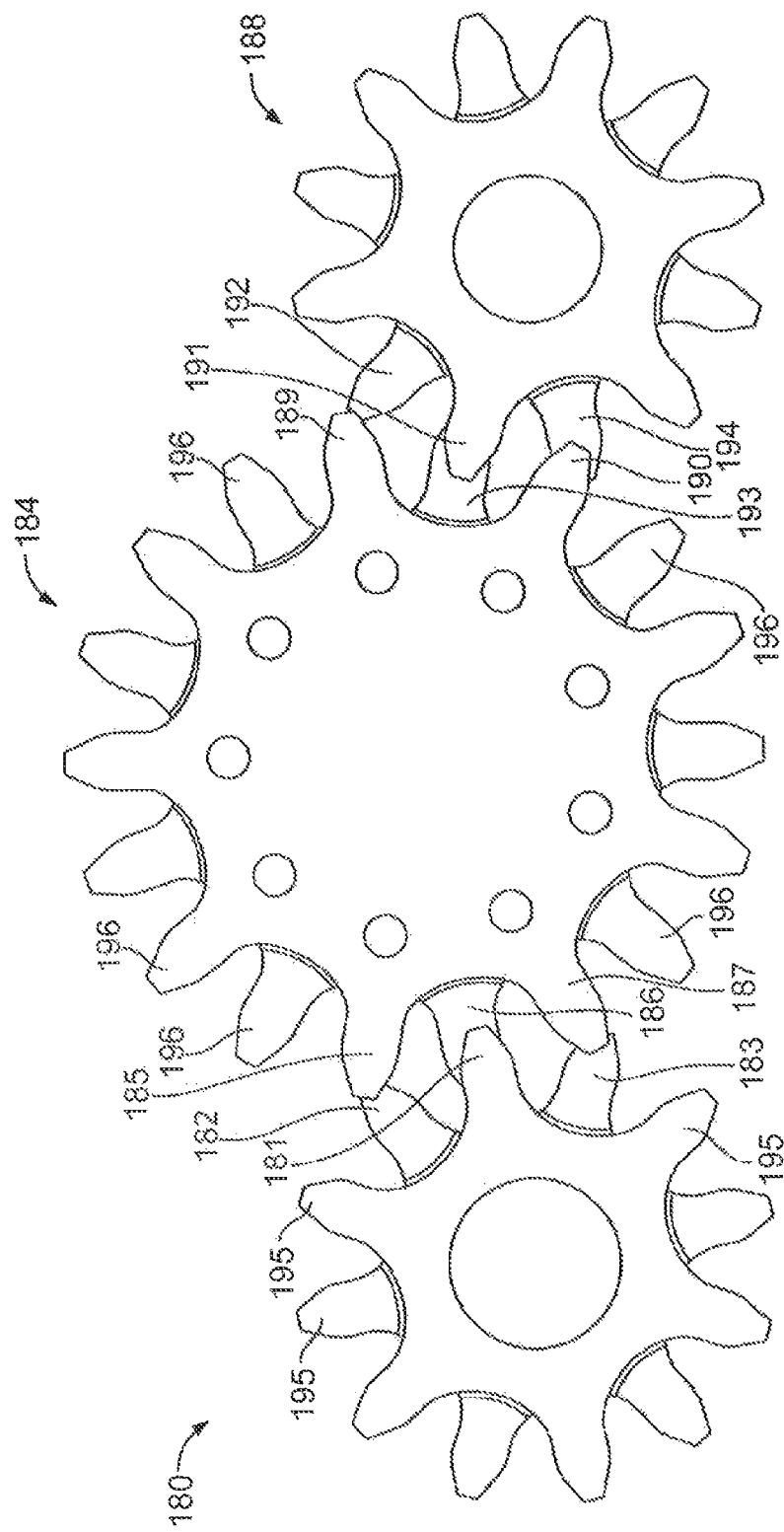
FIG. 15 illustrates an alternative embodiment of a gear formation that can be used in any of the tissue removal devices herein.

FIG. 15 illustrates an alternative embodiment of a gear formation that can be used in any of the tissue removal devices herein. The drive train includes driving gear 180, gear 184, and gear 188 formed by an EFAB process in the configuration shown. In this embodiment the gears are comprised of multiple tiers, but not all of the teeth alternate amongst tiers as in the embodiment in FIGS. 8-14. In this embodiment only the teeth that are near teeth on an adjacent gear in the "as-fabricated" configuration are formed in only one tier, while the remaining teeth on the gears are formed in all tier layers. In terms of teeth height, the teeth that are near teeth on an adjacent gear during formation have a shorter height (with height being measured in the layer stacking direction and the gears being formed with their planes lying in the planes of the layers) than the other teeth on the gear. In reference to FIG. 15, driving gear 180 includes an upper tier and a lower tier, wherein the nine teeth 195 (only three of which are labeled) are three layers (or tiers) thick (i,e. upper, lower, and intermediate tiers). Teeth 181, 182, and 183 are each only one layer thick, with teeth 182 and 183 formed only in the lower tier, and tooth 181 is formed only in the upper tier. Gear 184 is formed in a similar manner, with all of the teeth except for teeth 185, 186, 187, 189, 190, and 193 formed in both the upper and lower tiers. Teeth 185, 187, 189, and 190 are formed only in the upper tier, and teeth 186 and 193 are formed only in the lower tier. Gear 188 is formed in the same manner as 180. In use, when driving gear 180 is rotated (e.g., in a clockwise direction), tooth 182 contacts tooth 186 on gear 184, and the first tooth 195 on gear 180 contacts tooth 185 on gear 184. As gear 180 continues to rotate after almost a full revolution, lower tier tooth 183 on gear 180 contacts lower tier tooth 193 on gear 184, and upper tier tooth 181 contacts upper tier tooth 190 on gear 184.

Because teeth 195 and 196 on gears 180 and 184, respectively, are formed on multiple layers and therefore have a greater height than a tooth formed on a single layer, they may be better able to make solid contact with one another and more effectively turn the gear. It may be beneficial to fabricate the teeth in such a manner if forming the teeth on only one tier prevents the gear from turning effectively because the height of teeth formed from a single layer of material is too small, and adequate contact is not being made between the teeth as the gears rotate. An exemplary advantage of this design can allow for gaps to be created that are of a large enough size while providing for better contact between gear teeth.

Figure 16:
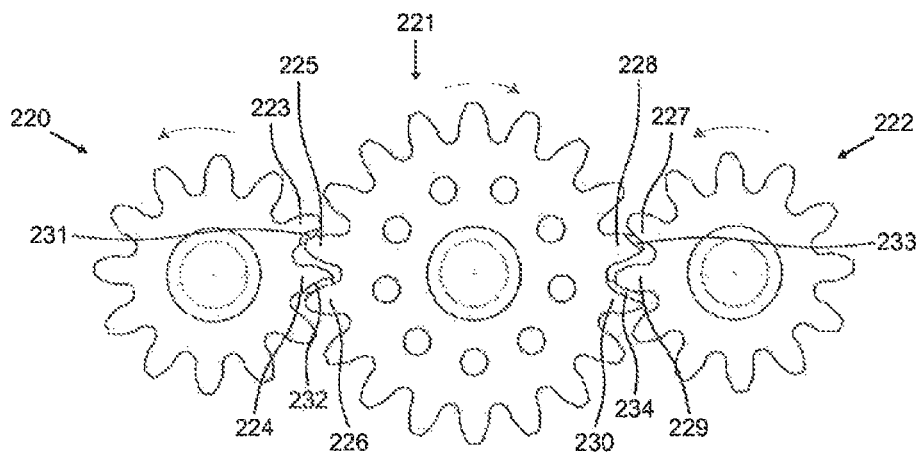
FIGS. 16-19 illustrate yet another alternative gear train design which may allow meeting minimum feature size requirements while providing more robust gears along with back lash not being excessively large.
Figure 17:
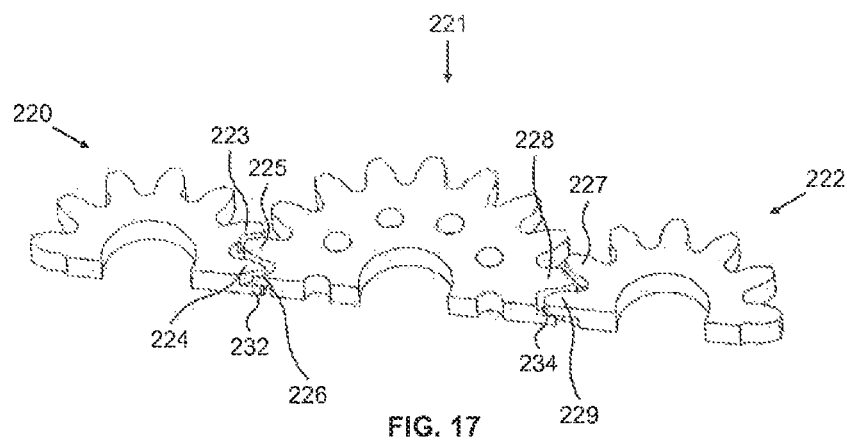

FIGS. 16-19 illustrate yet another alternative gear train design which may allow meeting minimum feature size requirements while providing more robust gears along with back lash not being excessively large. FIG. 16 shows driving gears 220, 221, and 222 in their as-formed configuration. Teeth 223 and 224 on gear 220, teeth 225, 226, 228 and 230 on gear 221, and teeth 227 and 229 on gear 222, are formed such that each tooth is notched (i.e. a segment of each tooth is removed from one of the upper or lower tier and from the intermediate tier. Each of these teeth have a portion that is sacrificed to allow assembled formation of the all of the components (gears 220, 221, and 222) during the formation process. Sacrificing a portion of the each of these teeth allows for an intra-layer gap to be created between teeth (i.e., between teeth 223 and 225, 224 and 226, 227 and 228, and 229 and 230) to be larger than the minimum feature size while allowing a tighter gear engagement with each tooth being stronger and significantly more rigid that it was in either of the previous two embodiments. One method of sacrificing a portion of the tooth is to create each gear from three tiers (e.g. layers) of material, and forming the tooth so that the notched portion of selected gears is formed as a single tier thickness (e.g. a single layer thickness). All of most of the teeth are three tiers thick while only a small portion of the notched teeth are not three tiers. As noted above tooth 223 includes portion 231, however, that is only 1 tier thick. Teeth 224, 225, 226, 227, 228, 229, and 230 also each have a portion that is only 1 layer thick. Teeth 225, 226, 227, and 229 have portions sacrificed that cannot be seen in FIG. 16, but have positions on the teeth that allow formation of the underling teeth from the mating gears to be formed without causing inadvertent gear bonding or welding. By creating a portion of a tooth that is only 1 tier thick, more intralayer space can be created between the teeth, which can be beneficial in the fabrication process. FIG. 17 illustrates a partial perspective view of the three gears from FIG. 16 in their "as fabricated" configuration.

Figure 18:
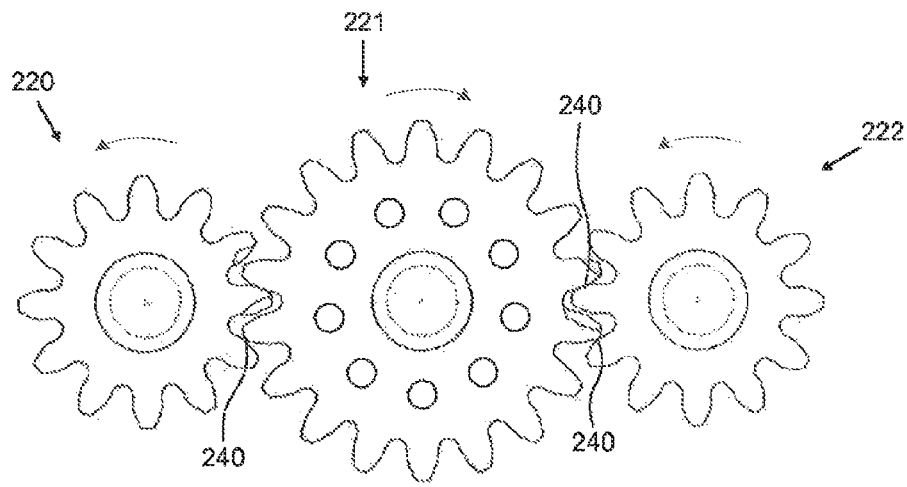
Figure 19:
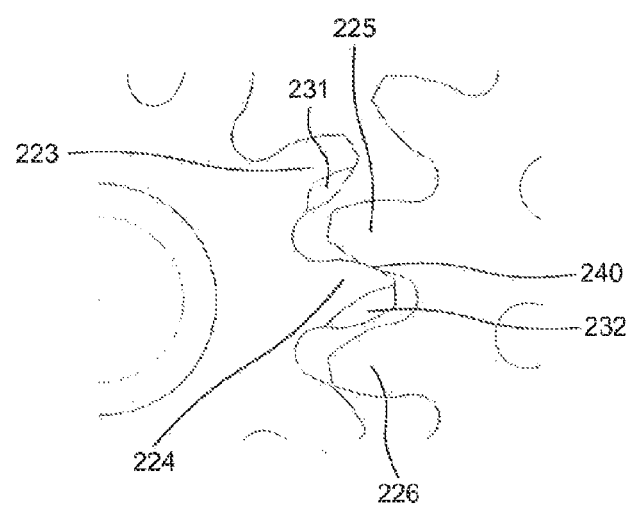

FIG. 18 shows the gears from FIGS. 16 and 17 showing the direction of rotation as illustrated by the arrows where gear 220 is the driving gear and gears 221 and 222 are being driven. FIG. 18 also shows contacts points 240 between the teeth. FIG. 19 shows a magnified view of contact points 240 between the driving and driven teeth. As shown, the portion of the tooth that is sacrificed is preferably on edge of the gear that is opposite the side of the gears that do the driving or are being driven during the forward or high torque operation of the gear train.

The gear trains described above allow a drive mechanism, examples of which are described above and below, to be at a distance from the blades such that the distal end of the working end can be advanced into contact with tissue in an unobstructed manner.

In some alternative embodiments the all or portions of the gear train(s) can be replaced with one or more sprockets and one or more chains to drive the blades, one or more pulley and belts, one or more fluid flow paths and turbine blades, or the like.

When manufacturing tissue removal devices of the various embodiments set forth herein using a multi-layer multi-material electrochemical fabrication process, it is generally beneficial if not necessary to maintain horizontal spacing of component features and widths of component dimensions remain above the minimum feature size. It is important that vertical gaps of appropriate size be formed between separately movable components that overlap in X-Y space (assuming the layers during formation are being stacked along the Z axis) so that they do not inadvertently bond together and to ensure that adequate pathways are provided to allow etching of sacrificial material to occur. For example, it is generally important that gaps exist between a gear element (e.g. a tooth) in a first gear tier and a second gear tier so that the overlapping teeth of adjacent gears do not bond together. It is also generally important to form gaps between components that move relative to one another (e.g., gears and gear covers 121 and 122 (see FIG. 20), between blades and housing 101, etc.). In some embodiments the gaps formed between moving layers is between about 2 um and about 8 um.

Figure 20:
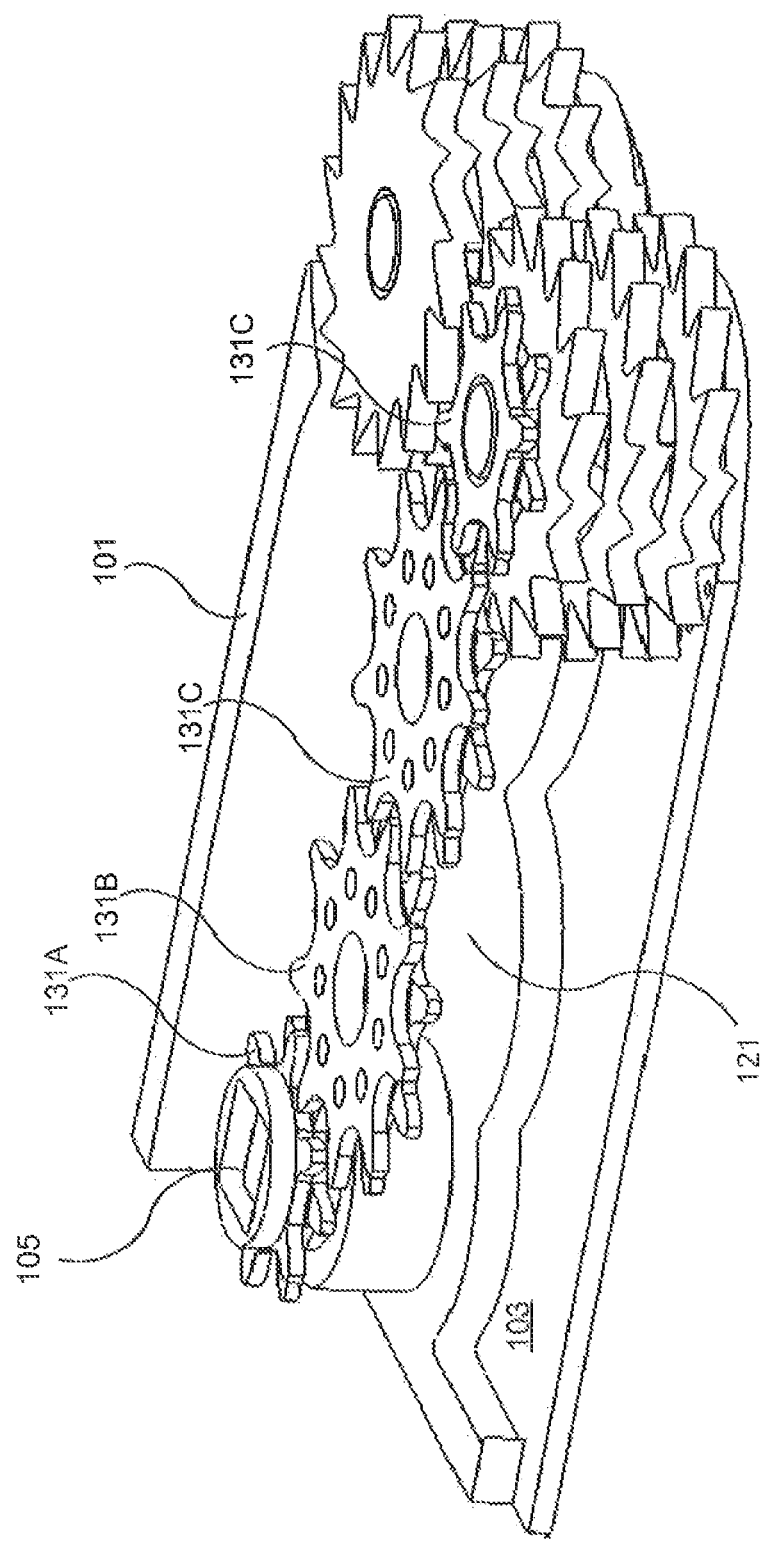
FIG. 20 illustrates a partial view of the working end of tissue removal device in which the top portion and one side wall of housing have been removed to show one of the exemplary gear trains from FIG. 8 disposed in housing.
Figure 21:
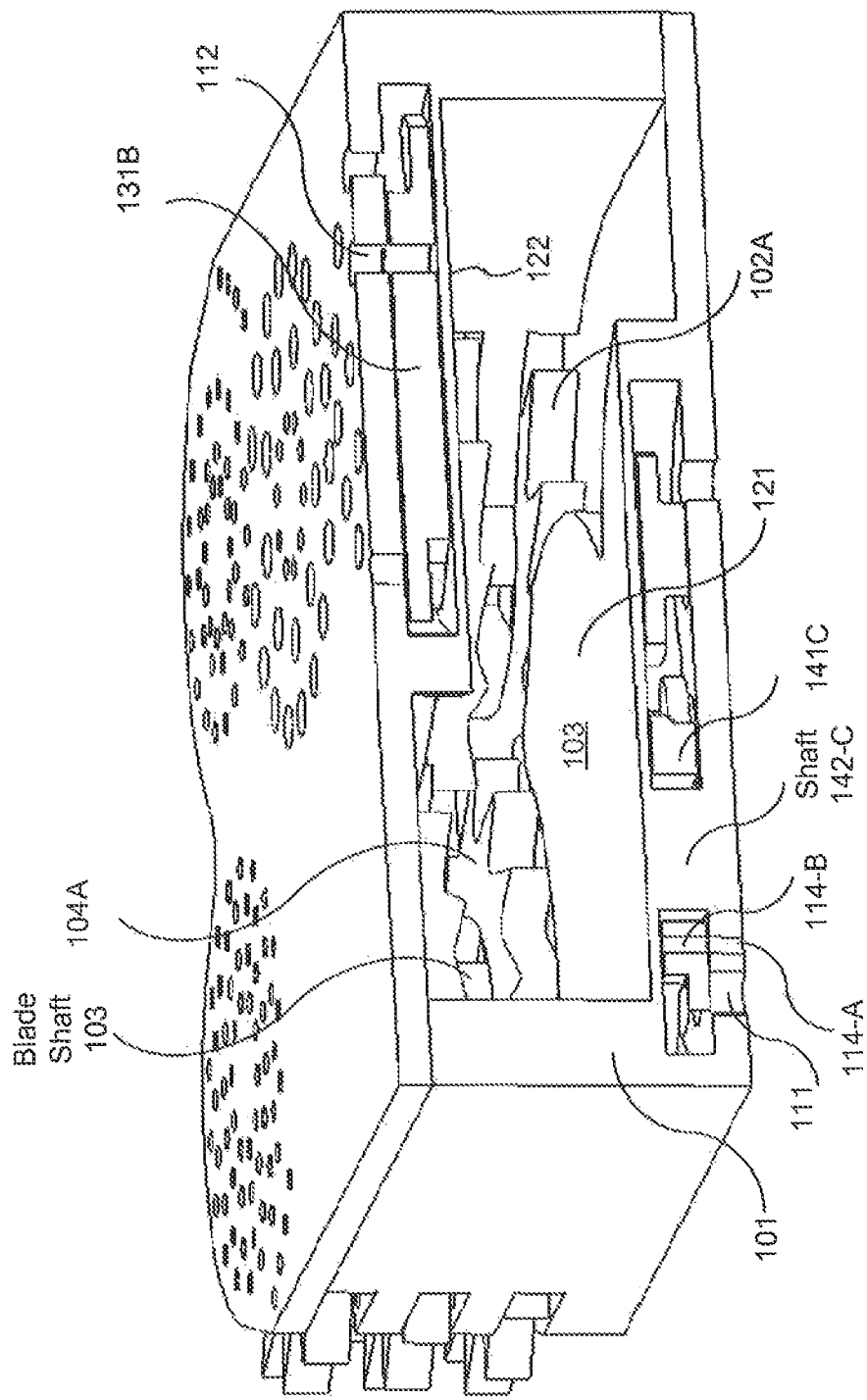
FIG. 21 provides a perspective cross-sectional view of the rear portion of a working end of a device according to an embodiment of the disclosure with the back shielding and a portion of the gears cut away so that the relationship between the gears, the upper and lower gear enclosures, and outer housing of the device can be seen.

FIG. 20 illustrates a partial view of the working end of tissue removal device in which the top portion and one side wall of housing 101 have been removed to show one of the exemplary gear trains from FIG. 8 disposed in housing 101. Gear enclosure or cover 121 encloses the first gear train 141 (not shown) and provides a lower surface, in combination with the inside of housing 101, for chamber 103. FIG. 21 shows a perspective cross-sectional view of the device of FIG. 20, including second gear train cover 122 wherein the cross-sectional cut sections gears 131B and 141C each in their as fabricated positions wherein gaps formed from sacrificial material laterally located on intervening layers exist between upper and lower surfaces of these gears and the corresponding lower surfaces of covers 122 and 121 and upper surfaces of the lower portions of housing 101. The gear train covers 121 and 122 extend from the proximal end of the device to a point just proximal to the blades, and have distal ends which are rounded to accommodate the rotation of the blades while preventing as much tissue as possible from entering the gear train assembly. An exemplary function of gear covers 121 and 122 is to prevent material which is directed into chamber 103 from getting caught in the gears and preventing continued rotation of the blades. FIG. 21 also illustrates the section of gear 141-C exposes shaft 142-C around which gear 141-C rotates via a circular gaps (e.g. having an intralayer radial width greater than the minimum feature size). Also FIG. 21 illustrates that when gears 131B and 141C are in their as formed positions, they have etching holes 112-B and 114-B respectively that are aligned with etching holes 112-A and 114-A in housing 101 that allow more direct entry of etchant into the gear movement cavities defined by covers 122 and 121 in conjunction with housing 101 so that post-layer formation etching of sacrificial material can more readily occur from these cavities. In some embodiments partial alignment would be better than no alignment and offset of etching holes by no more than 2 mm or even 5 mm would be beneficial as compared to offsets which are significantly greater. FIG. 21 also shows a portion of blade shaft 103 around which blade stack 104 rotates. FIG. 21 along with FIG. 5 also shows interdigitated fingers 107 which are located between successive blade levels to inhibit the outflow of tissue drawing into cavity 103 as the blades tips rotate out of and then back into the housing. Such fingers, vacuum (i.e. suction applied to the proximal end of the working end), irrigation directed onto the blades within the housing (e.g. vertically downward or downward and proximally), or a combination of two or more of these elements may be useful in removing tissue from the blade and inhibiting its distal exit from the working end back into working area within the body of a patient. In some embodiments, it is desired to define a Shearing thickness as the gap between elements has they move past one another. Such gaps may be defined by layer thickness increments or multiple such increment or by the intralayer spacing of elements as they move past one another. In some embodiments, shearing thickness of blades passing blades or blades moving past interdigitated fingers, or the like may be optimally set in the range of 2-100 microns or some other amount depending on the viscosity or other parameters of the materials being encounter and what the interaction is to be (e.g. tearing, shredding, transporting, or the like). For example for shredding or tearing the gap may be in the range of 2-10 microns and more preferably in the range of 4-6 microns.

Figure 22:
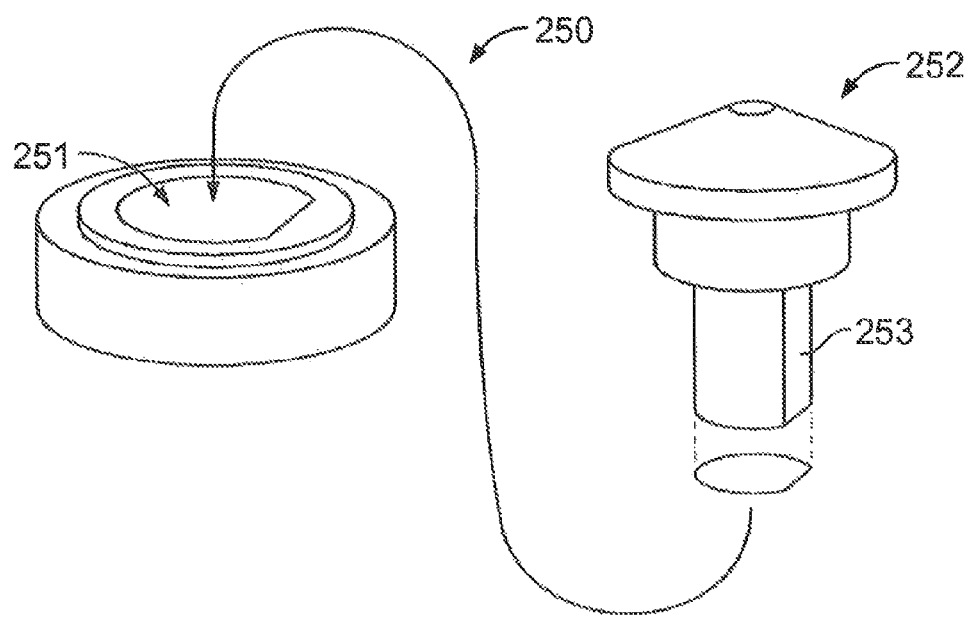
FIG. 22 illustrates an alternative drive mechanism coupler having a D-shaped hole or bore.

As described in the embodiments above, the working end includes a drive mechanism coupler 105 that is configured to be coupled to a drive mechanism which translates a rotational force to rotation of the first set of gears in each of the gear trains. For example, as shown in FIG. 5, drive mechanism coupler 105 has a square configuration and is adapted to receive a square drive pin (not shown), wherein the pin is part of a drive mechanism which translates a rotational force to rotation of the gears in the train. FIG. 22 illustrates an alternative drive mechanism coupler 250 with a D-shaped hole, or bore, 251, which is adapted to receive D-shaped element 253 which can be engaged with a chain, a belt, a fluid flow, an electrical motor, a flexible drive shaft, bevel gear, crown gear, a spur gear, linear gear, or the like which can undergo a motive force to cause a desired rotation of the drive chain and blades to power the device. The shaped element may be part of a pin or other element which allows appropriate engagement. The cross sectional shape of the drive bore and pin can also be almost any other cross-sectional shape which can drive the gear train, for example, a hexagonal shape, oval, elliptical, etc.

FIGS. 23A-27C illustrate alternative exemplary embodiments of drive mechanisms which can power the drive trains in the working end, any of which may be adapted to be included in any suitable tissue removal device, such as those described herein. To position the working end at a desired location in the patient, the working end can be advanced to the target site within a delivery member (e.g., cannula, catheter, sheath, etc.). A portion of the device, e.g. the working end or the working end in combination with a single or multi-port catheter can also be adapted to be advanced over a guide wire. In some embodiments, the tissue removal device is coupled to an elongate introducer which is used to advance the working end of the tissue removal device to the target tissue site through a delivery member. In some embodiments, the drive mechanism, or at least a portion thereof, is disposed within the introducer. An example delivery systems are described in more detail below.

Figure 23C:
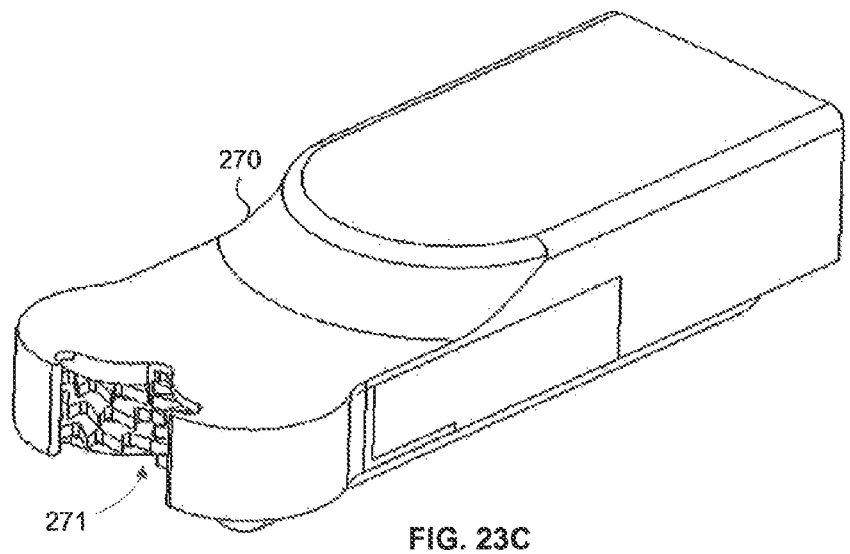
FIGS. 23A-27C illustrate alternative exemplary embodiments of drive mechanisms which can power the drive trains in the working end, any of which may be adapted to be included in any suitable tissue removal device, such as those described herein.
Figure 23D:
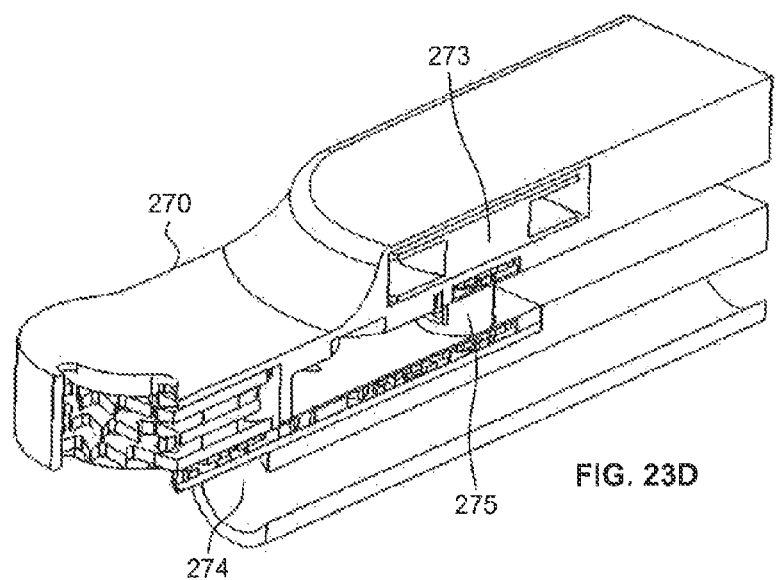

FIGS. 23A-23D illustrate a first embodiment of the working end and drive system of a device in which the drive mechanism includes a belt and pulley. FIG. 23A shows a portion of housing 270, tissue processing elements 271, a portion of gear train 276, belt 272, and pulley 273. FIG. 23B shows a sectional view including belt 272 and a portion of pulley 273 disposed in housing 270. FIG. 23C shows the housing 270 without the belt. FIG. 23D shows a sectional view of housing 270 including a portion of pulley 273, drive mechanism coupler 275, and optional guide wire lumen 274 disposed on the bottom of housing 270. Actuating the belt as shown by the arrows in FIGS. 23A and 23B causes pulley 273 to rotate due to frictional forces between the belt and pulley. The pulley includes a protruding pin (not shown) which couples with drive mechanism coupler 275 to drive the gear train. Rotation of the pulley 273 drives the gear trains which activates the tissue processing elements 271. In some embodiments the belt is a nitinol wire but can be any other suitable material. In other embodiments, the smooth belt and pulley may be replaced with a chain and sprocket or with a miniature toothed pulley and toothed belt. In some embodiments, the pulley and belt he controlled, at times, to drive the tissue processing elements in the opposite direction to that indicated.

Figure 24A:
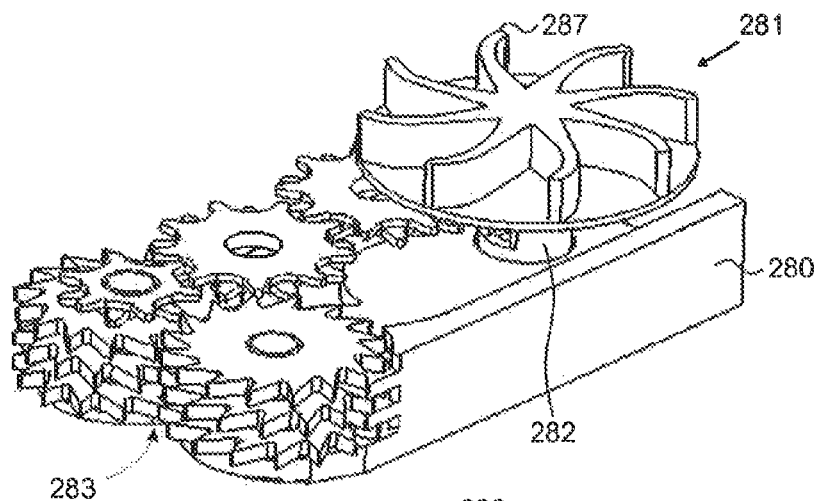
Figure 24B:
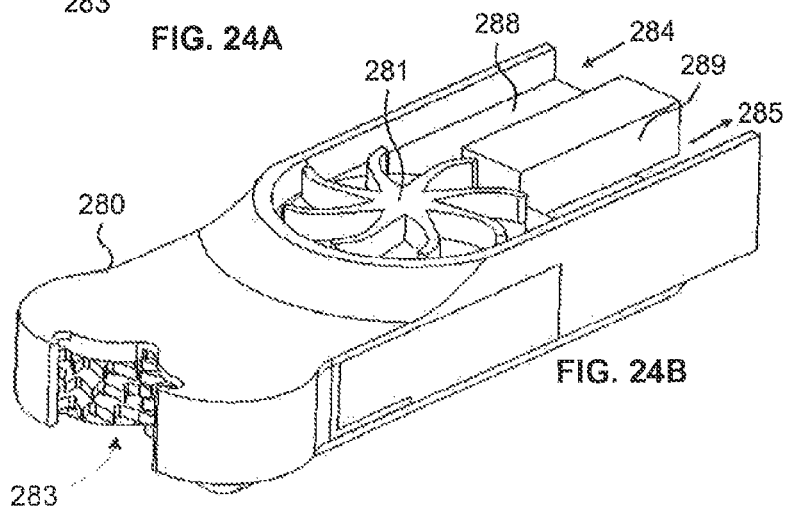
Figure 24C:
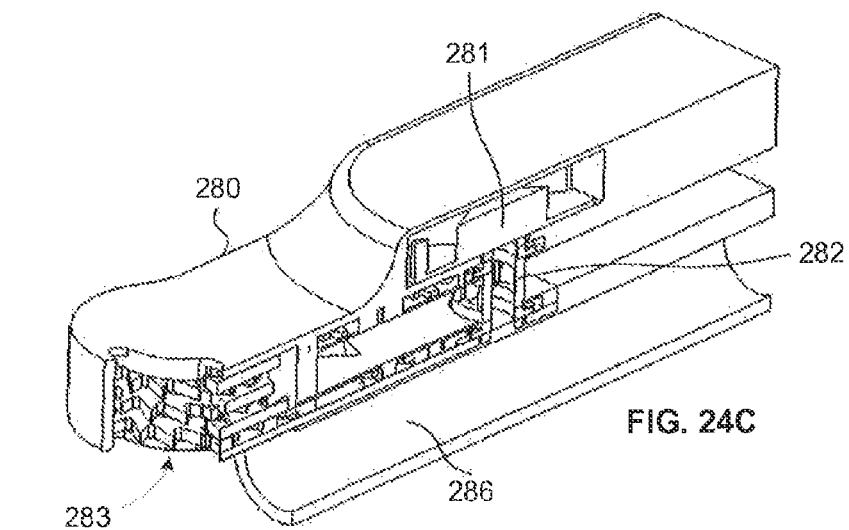

FIGS. 24A-C illustrate a second embodiment of the working end and drive system of a device in which the drive mechanism is a hydraulic drive mechanism. FIG. 24A shows a portion of the device including a portion of housing 280, tissue processing elements 283, turbine 281 with a plurality of blades 287 coupled to a driving pin (not shown in FIG. 24A), wherein turbine 281 is coupled to drive mechanism coupler 282 via the pin. FIG. 24B is a sectional view of housing 280 in which turbine 281 is disposed. Housing 280 includes fluid channel 288 through which fluid (e.g., liquid or gas) flows in the direction of arrow 284, rotating turbine 281. The fluid exits the housing in the direction of arrow 285 through fluid channel 289. The fluid rotates the blades 287 of turbine 281, which drives the gear train, which activates the tissue processing elements 283. A pump disposed proximal to the housing (e.g. outside the body of the patient and connected to the working end by lumens within a multi-port catheter) and can be used to control the flow of fluid into the housing. In some embodiments, the pump and other elements in the fluid flow path may be configured to allow reversed operation of the device when desired.

In the embodiments above the tissue removal, or processing, elements and the housing of the working end are configured such that the tissue removal elements can remove tissue which is located distal to the working end. The tissue removal elements can also be, however, disposed at other locations within the working end. In some embodiments they are disposed so that they can remove tissue along one or more sides of the housing. In some uses the device may be advanced in a distal direction, yet the tissue which is to be removed is located along the sides of the device. As will be described in more detail below, it may be advantageous to protect certain tissue from being damaged while removing other tissue. Positioning the blades in the working end in specific locations can be one way to do this.

Figure 25A:
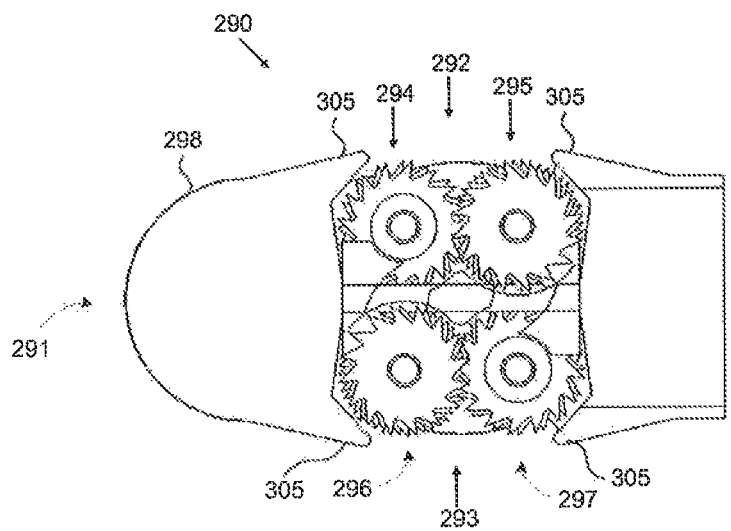
Figure 25B:
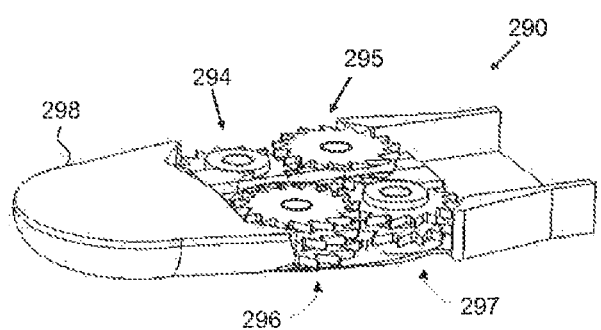
Figure 25C:
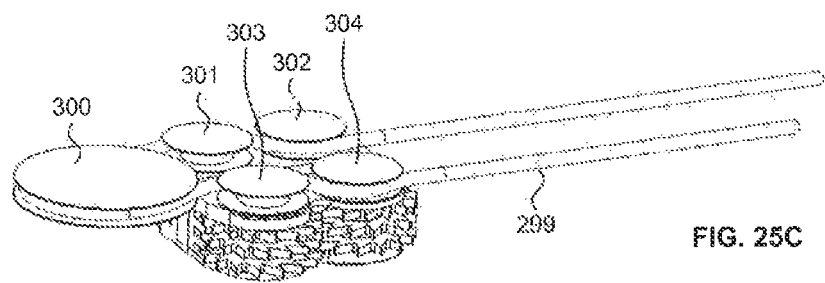
Figure 25D:
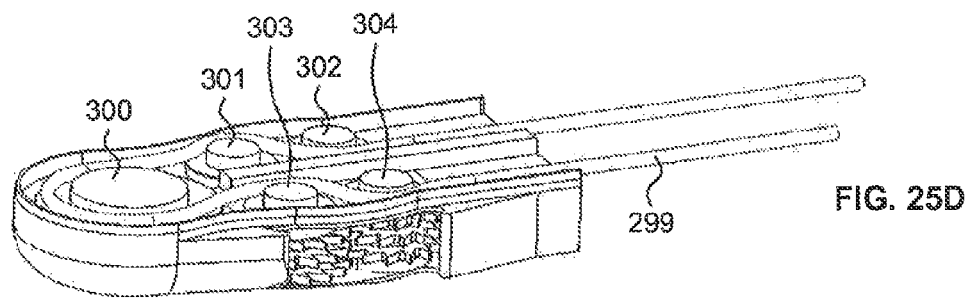
Figure 25E:
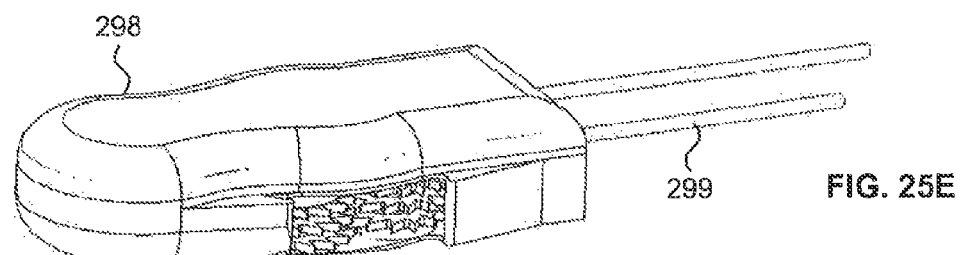
Figure 25F:
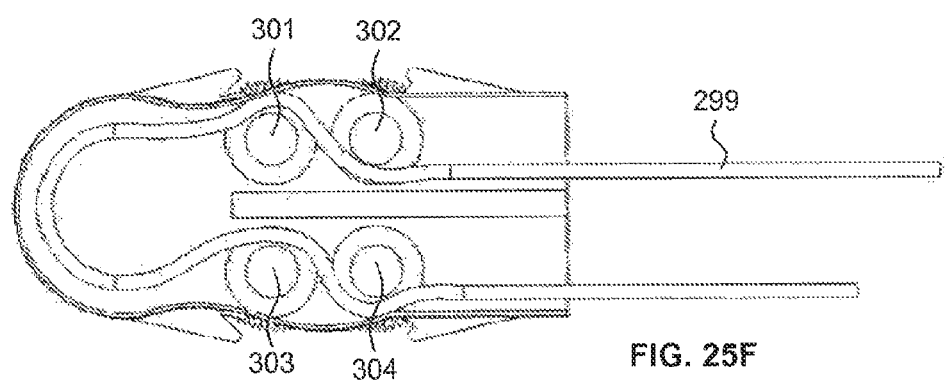
Figure 25G:
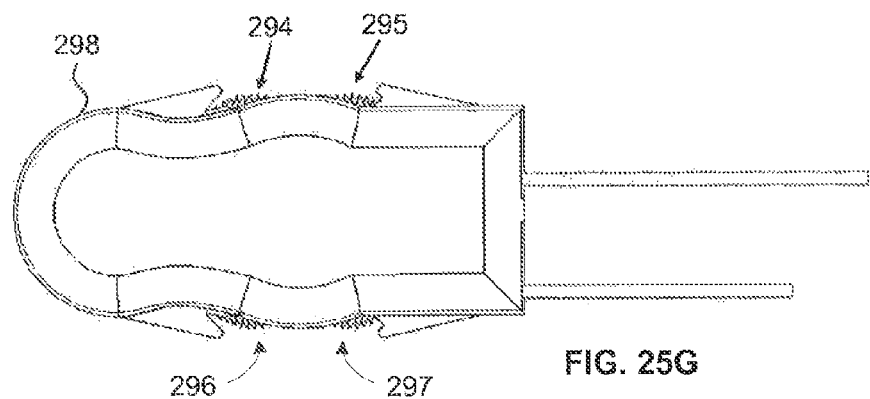

FIGS. 25A-25G illustrate an example a of a side tissue removal working end. FIG. 25A is a top sectional view with a top portion of the housing removed, which shows working end 290 comprising housing 298 and four tissue removal elements 294-297, which are shown as blade stacks. Blade stacks 294 and 295 process tissue along one side of the housing by directing tissue in the direction of arrow 292. Blade stacks 296 and 297 process tissue along a second side of the housing by directing tissue in the direction of arrow 293. As shown in FIGS. 25A-B, blade stacks 294 and 297 each have two blades, while blade stacks 295 and 296 each have three blades. FIG. 25C shows a perspective view without housing 298 illustrating the drive mechanism for the side tissue removal device 290. The drive mechanism includes belt 299, distal pulley 300, and side pulleys 301-304. The side pulleys are coupled to the blade stacks and rotation of the side pulleys rotates the blade stacks. The belt is disposed through side pulleys 301 and 302 and around distal pulley 300 before returning through side pulleys 303 and 304. Actuating of belt 299 therefore activates all four blade stacks. In some embodiments the belt is a nitinol wire, but can be any other suitable material. FIG. 25D is a view with the top portion of the housing removed to show the internal drive mechanism. FIG. 25E shows the same view with the top on the housing. FIGS. 25F and 25G show top views of the working end shown in FIGS. 25D and 25E, respectively. In still embodiment, as well as in the other embodiments, set forth herein, vacuum, irrigation, or a combination of the two may be used to send extracted tissue from the interior of the working end, proximally to a storage reservoir (e.g. within the working end or located outside the body of the patient on which a procedure is being performed).

Figure 26E:
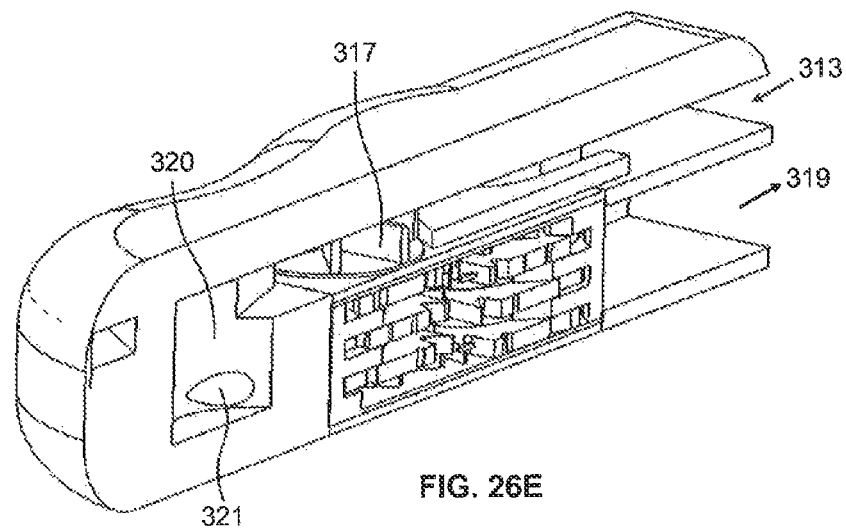
Figure 26F:
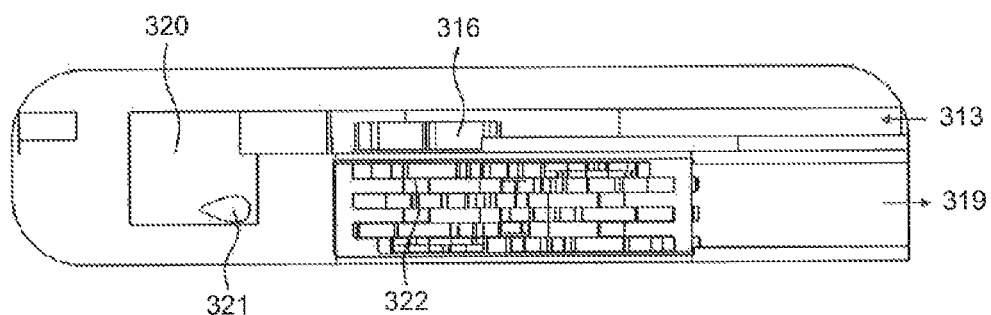

FIGS. 26A-26F illustrate an alternative hydraulic or pneumatic drive mechanism for a side tissue removal working end. FIG. 26A shows the device 310 including housing 311 and tissue removal elements on a first side 312 of device 310. FIG. 26B illustrates housing 311 with a top portion removed to reveal inside the housing. The housing includes fluid channels which allows fluid to flow into the housing in the direction of arrows 313 and 314. The fluid turns the blades of turbines 316 and 318, which rotates the turbines shafts, which are coupled to the tissue removal elements. Guides 315 helps direct the flow of fluid to ensure the blades of the turbines rotate in the proper direction to cause the tissue removal elements to rotate inward. The fluid continues past the turbines and drops through opening 320. The fluid exits through hole 321 (see FIG. 26E) and out of housing in the direction of arrow 319. The exiting fluid can also help direct tissue in the proximal direction away from the working end. FIG. 26C shows a top view of the device shown in FIG. 26B. FIG. 26D shows the turbines each coupled to one blade stack. FIG. 26E is a sectional perspective view, showing fluid inlet 313, blades 317 of the turbine and a portion of the tissue removal elements. FIG. 26F shows a side sectional view of the view shown in FIG. 26E, including blade shaft 322.

Figure 27A:
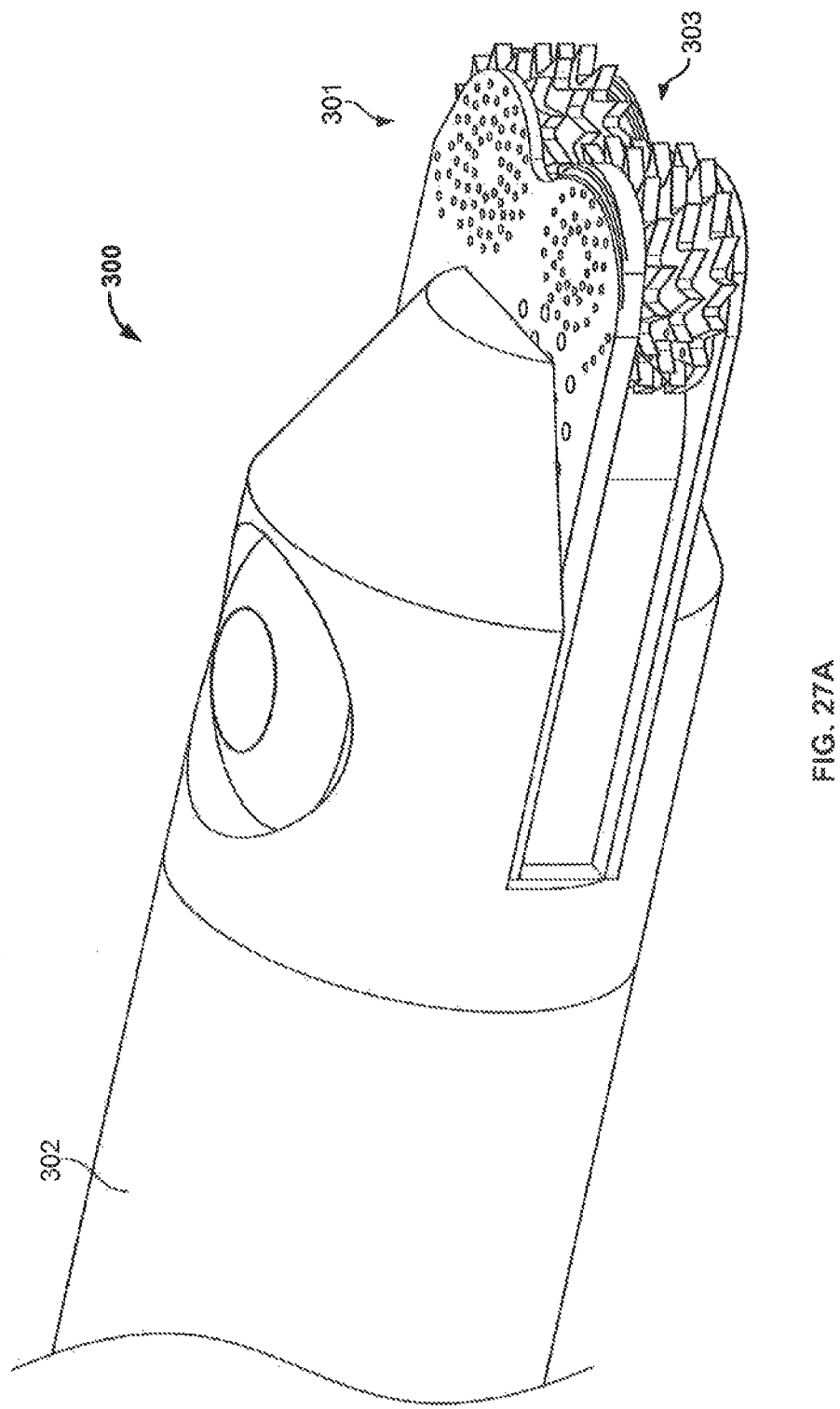
Figure 27B:
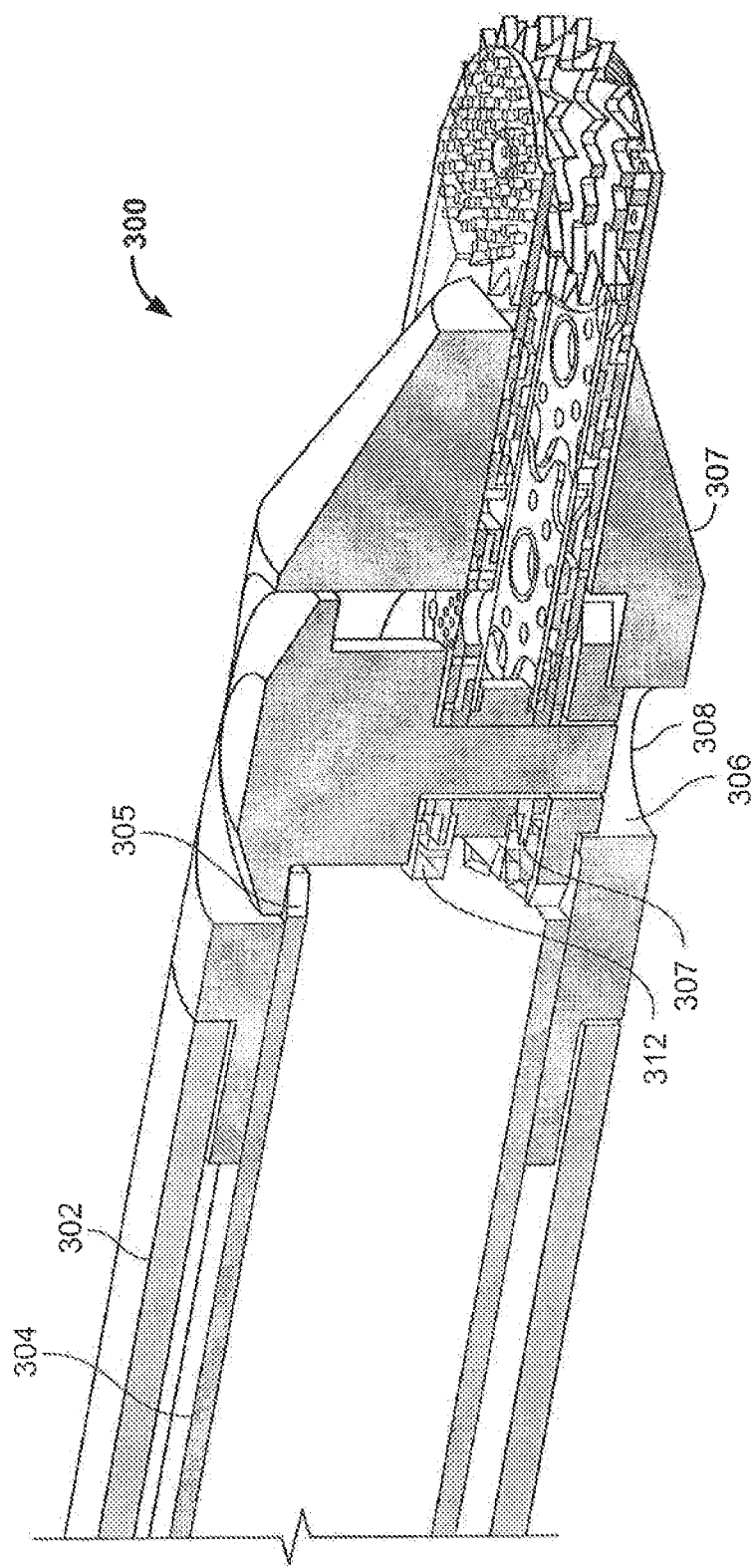
Figure 27C:
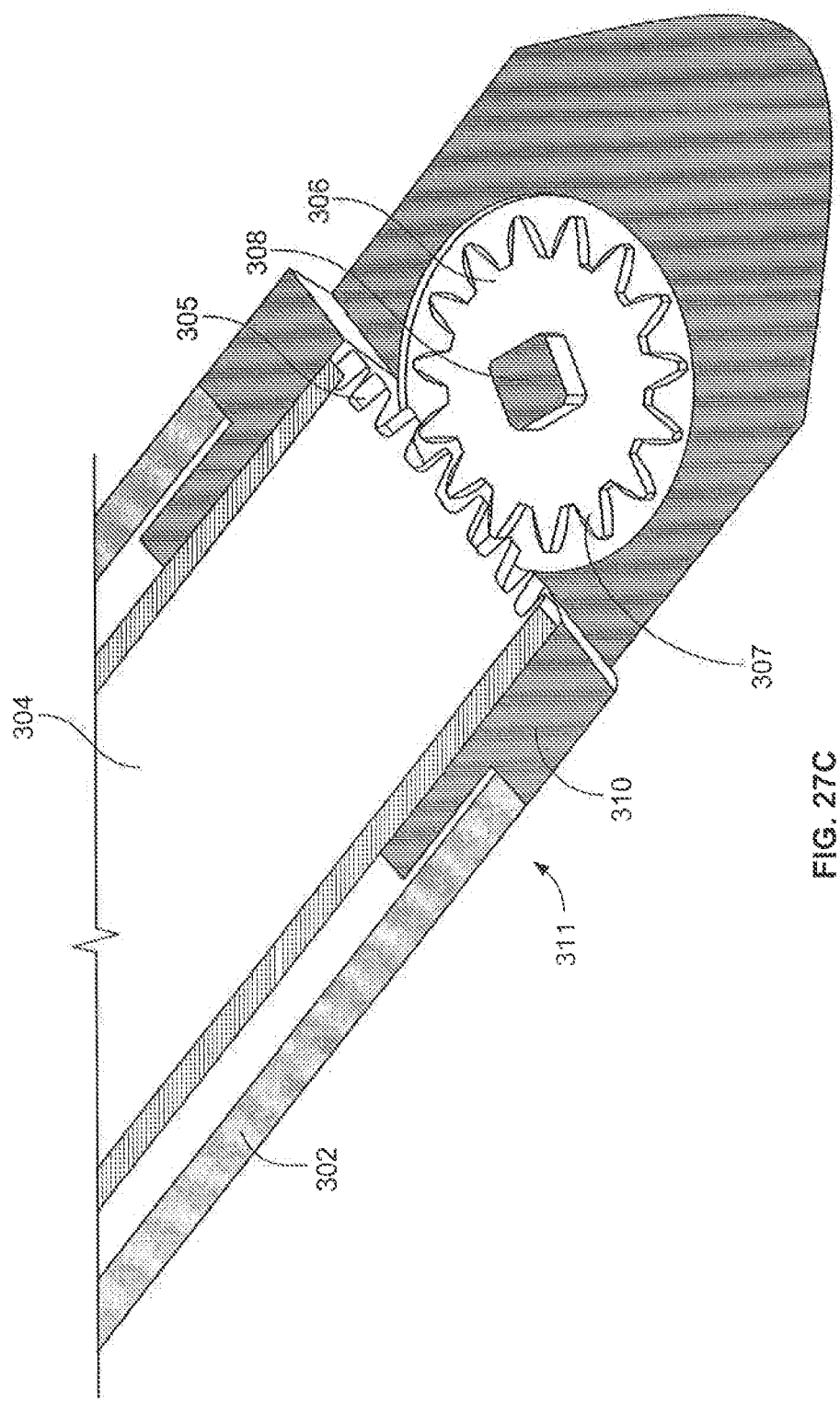

FIGS. 27A-27C illustrate an alternative drive mechanism. FIG. 27A illustrates tissue removal device 300 including working end 301 and introducer 302. Working end 301 includes distally facing tissue shredder elements 303. FIG. 27B and 27C illustrate the drive mechanism with a sectional perspective view and a partial top view. The drive mechanism includes tube 304 (disposed within introducer 302) with gear teeth 305 cut circumferentially, which can be seen more clearly in FIG. 27C. When rotated, the teeth 305 on tube 304 contact and drive teeth 307 on gear 306, the axis of rotation of which is substantially orthogonal to the axis of rotation of tube 304. Pin 308 (shown with a square cross sectional shape) is engaged with a square hole in gear 306 and with a square hole in drive mechanism coupler 312 in the working end. Rotation of gear 306 therefore rotates pin 308, which rotates the drive mechanism coupler 312, which drives the gear trains (which can be partially seen in FIG. 12) within the working end. FIG. 27C also shows an exemplary coupling 311 between a distal end of introducer 302 and housing 310 of working end 301.

The tissue removal device as shown in FIGS. 27A-C can also provide irrigation to the working end to provide for maximum suction by a vacuum, which is used to remove tissue from the working end. Irrigation fluid can be delivered between inner tube 304 and the inner diameter of introducer tube 302. The irrigation as well as debris is then pulled proximally by suction through the lumen of inner tube 304 in the direction of the arrow shown in the figure. Irrigating helps maximize the suction by ensuring that the volume on the inner tube 304 is full of both tissue and irrigating fluid. The irrigating fluid forced distally between the introducer and inner tube 304 can also be directed into the working end to provide irrigation to the working end.

In variations of the above noted embodiments the drive mechanism can be configured to include one or more sprockets and one or more chains.

In some alternative embodiments the drive mechanism which extends through an introducer may extend a significant distant from the drive mechanism coupler (e.g. perpendicular to the plane of the upper or lower faces of the housing, i.e. in the Z-direction or vertical direction relative to the planes of the layers (e.g. horizontal planes) used in forming the device via multi-layer, multi-material electrochemical fabrication methods. In other alternative embodiments the drive mechanism may be coupled to a secondary shaft or flexible lead which extends in a direction parallel to the planes of the faces of the housing (e.g. proximally along the longitudinal axis of the device or radially relative to the longitudinal axis of the device).

In some embodiments the drive mechanism includes universal joints, crown gears, or bevel gears coupled to drive gears and oriented so the drive train axis may be rotated to become parallel to the longitudinal axis of the device, or to otherwise lie perpendicular to the height of the device. In some embodiments some gears in a gear train may be formed in the same orientation as other gears in the train, but then rotated on bendable supports or pivotable supports to take on a desired orientation.

The working ends of the tissue removal devices described herein can be used to remove tissue from a subject. The tissue to be removed is generally referred to herein as "target tissue", and the general location at which the working end is positioned to remove the target tissue is generally referred to herein as the target tissue "site." The working end can be configured for use in a variety of types of medical procedures. For example without limitation, the working end can be configured for use in traditional open surgical procedures or minimally invasive procedures (i.e., any procedure less invasive than open surgery, such as percutaneous procedures).

Figure 28:
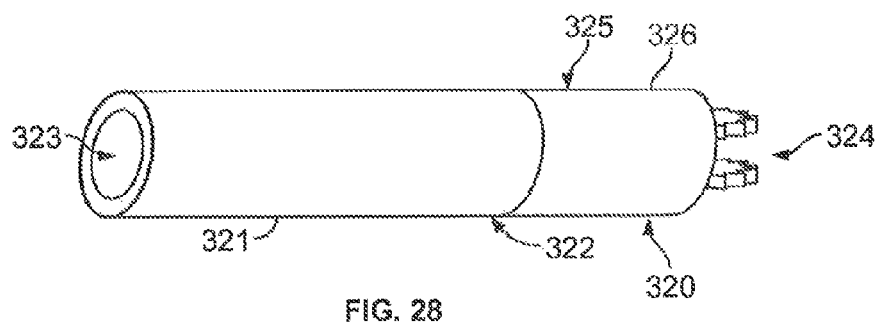
FIG. 28 illustrates an exemplary coupling between an introducer and a working end, wherein the introducer is adapted to introduce, or position, the working end at the target tissue site.
Figure 29:
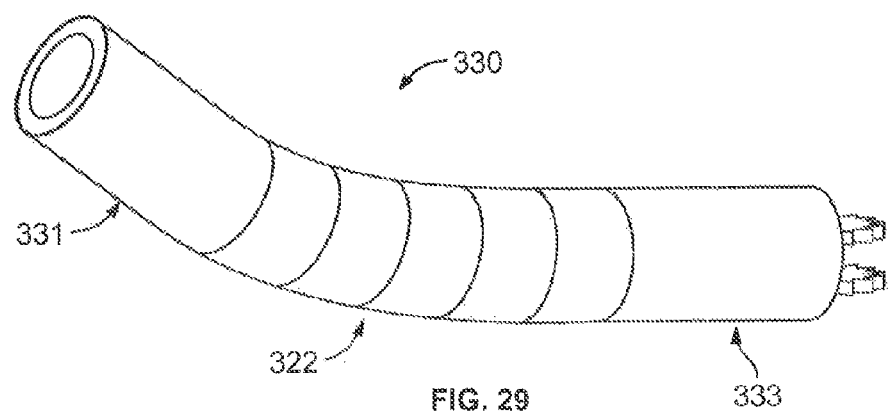
FIG. 29 illustrates an exemplary articulatable introducer including non-articulating portion and articulating portion, wherein the introducer is coupled to working end.

When the working end is used in some minimally invasive procedures, it is coupled to a elongate member of a delivery system so that the working end can be positioned at the target tissue site. FIG. 28 illustrates an exemplary coupling 322 between introducer 321 and working end 320, wherein the introducer is adapted to introduce, or position, the working end at the target tissue site. As shown, introducer 321 is coupled to the proximal end of the working end 320, but the introducer need not necessarily be coupled to the proximal end of the working end 320, but can be coupled to a general proximal region of working end 320. In some embodiments the coupling between introducer 321 and working end 320 is performed after the fabrication of working end 320, or after partial fabrication of working 320. Coupling 322 can take on a variety of forms, such as, without limitation, a lap joint, as is the exemplary coupling 311 shown in FIG. 27C. Introducer 321 can have one or more lumens 323 (only one shown) which are in communication with the chamber within the working end (not shown). The lumen(s) of the introducer can house any or all of the drive mechanism components, irrigation system, aspiration system, etc. As shown in FIG. 28, the proximal end 325 of housing 326 and the distal end of introducer 321 have substantially similar cross-sectional shapes (shown as generally circular), which may make it easier to couple the working end to an introducer. The introducer generally extends proximally from the working end and may have a proximal end adapted to be disposed external to the subject. In some embodiments the introducer is a stiff rigid element, while in some embodiments it is a torsionally stiff and flexible element. FIG. 29 illustrates an exemplary articulatable introducer 330 including non-articulating portion 331 and articulating portion 332, wherein the introducer is coupled to working end 333. The entire introducer may also be articulatable, or there may be alternating portions of articulatable and non-articulatable portions of the introducer. For some procedures it may be known where the introducer is likely to need to bend or articulate, and only this portion of the introducer may be configured to articulate. The articulating segments can be articulated with delivery system actuators as described below.

Figure 30:
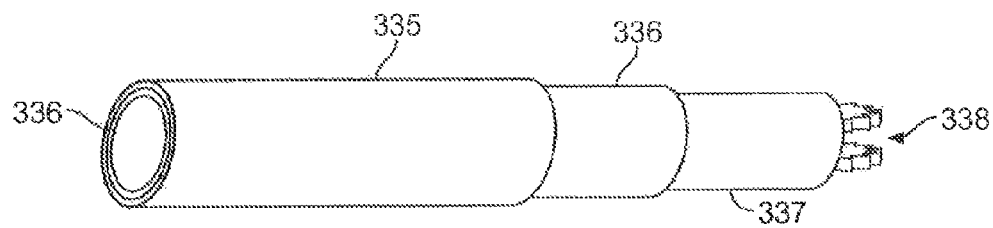
FIG. 30 shows an introducer and a working end, including shredders, coupled together, with a portion of introducer disposed within a delivery member.

Depending on the medical procedure, the introducer can be coupled to the working end to advance the working end to the target tissue site through a delivery member such as, without limitation, a cannula, trocar, catheter, sheath, etc. FIG. 30 shows introducer 336 and working end 337, including shredders 338, coupled together, with a portion of introducer disposed within delivery member 335. The introducer/working end assembly can be moved axially relative to the delivery member by distally advancing the introducer and/or proximally withdrawing the delivery member.

Figure 31A:
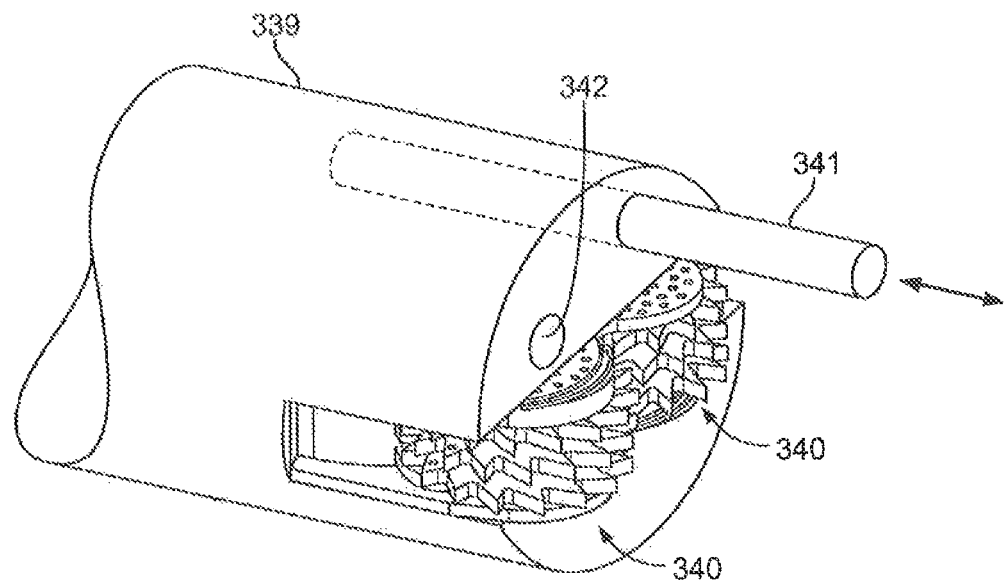
FIG. 31A illustrates a portion of a housing of a working end, including fixed tissue removal elements, an optional irrigation port, and a slidable element disposed within a bore in a housing.

The working end of the device may be adapted with a lumen or bore to incorporate additional delivery system components that can be moved axially relative to the fixed shredders within the working end. FIG. 31A illustrates a portion of housing 339 of the working end, including fixed tissue removal elements 340, optional irrigation port 342, and slidable element 341 disposed within a bore in housing 339. The slidable element 341 can be actuated axially (i.e., distally or proximally) as shown by the directions of the arrows using an actuator in the delivery hand-piece or other mechanism that allows for user control. In some embodiments the introducer can have a separate lumen for the slidable element which is aligned with the slidable element bore or lumen in the working end.

In some embodiments the working end housing is configured with more than one bore (the introducer can similarly have one or more lumens) to enable it to receive more than one axially movable element, which can enable more delivery tools to access the target tissue site more quickly. In some embodiments the slidable, or axially movable, elements, can be visualization tools such as a camera or an illumination tool. Focus on the target tissue can be maintained before and during the procedure by being able to move visualization tools in this manner. In some embodiments irrigation and/or suction tools are slidable elements. In use, a slidable element may also be configured to be retracted completely from the introducer/working end assembly to allow for a different element to be advanced to the distal end of the housing.

Figure 31B:
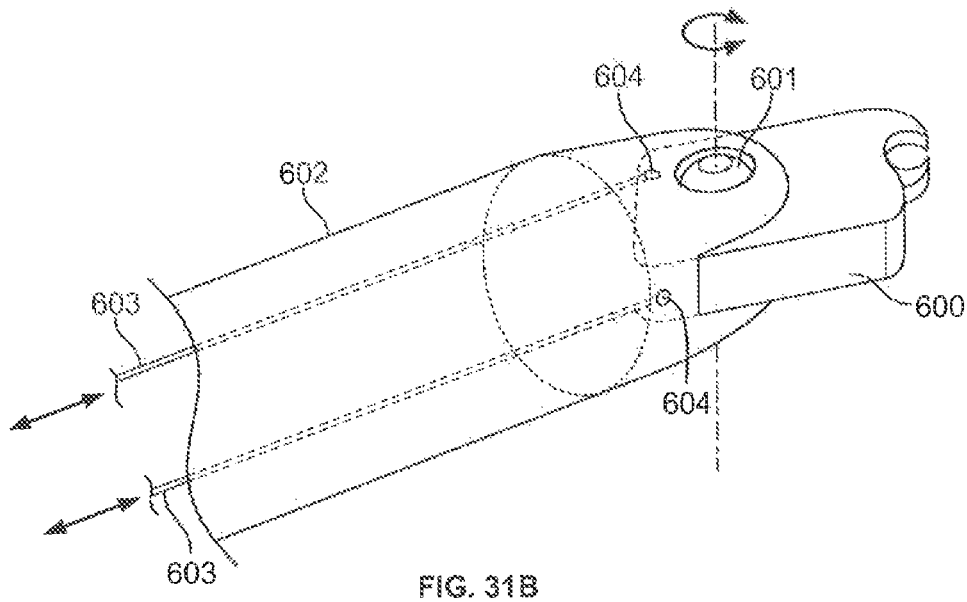
FIG. 31B shows an exemplary embodiment of a working end that is adapted to be actuated to rotate a working end relative to an introducer.

FIG. 31B shows an exemplary embodiment of working end 600 that is adapted to be actuated to rotate working end 600 relative to introducer 602. Working end 600 pivots through drive pin 601, and actuation wires 603 are coupled to working end 600 at attachment points 604. Actuation of wires 603 causes rotation of working end 600 relative to introducer 602.

Figure 32A:
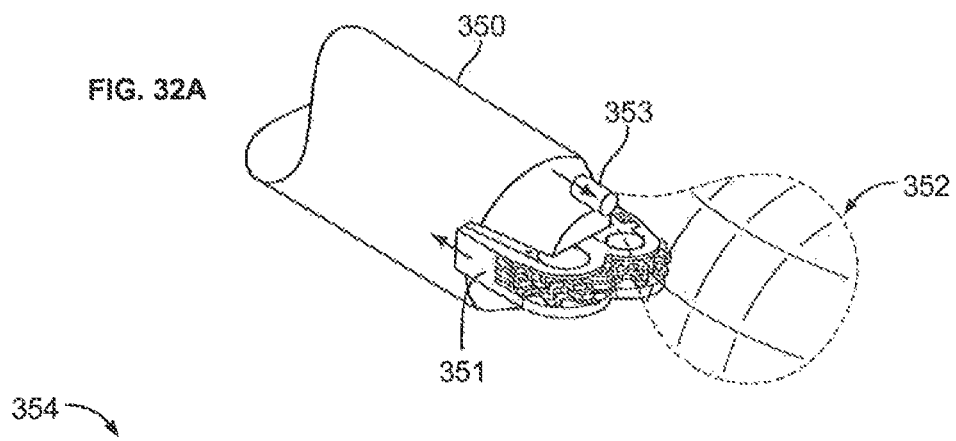
FIGS. 32A-32C illustrate a device and methods for providing a space for visualization of the target site, and/or target tissue.
Figure 32B:
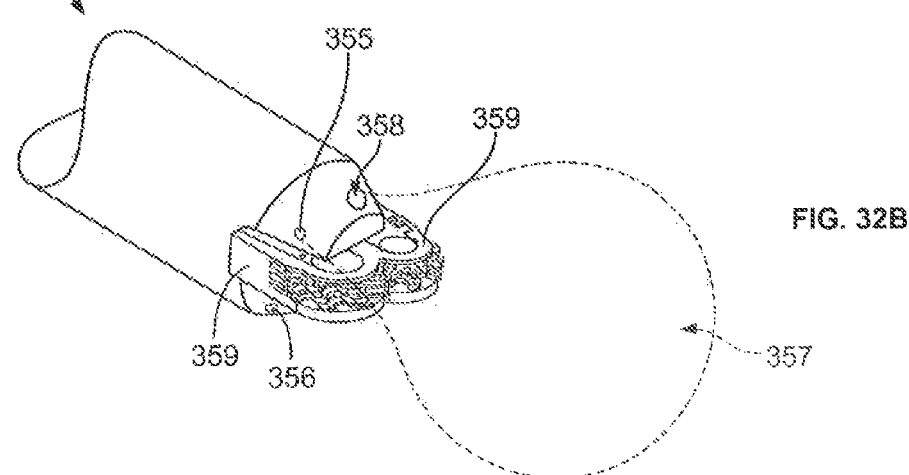
Figure 32C:
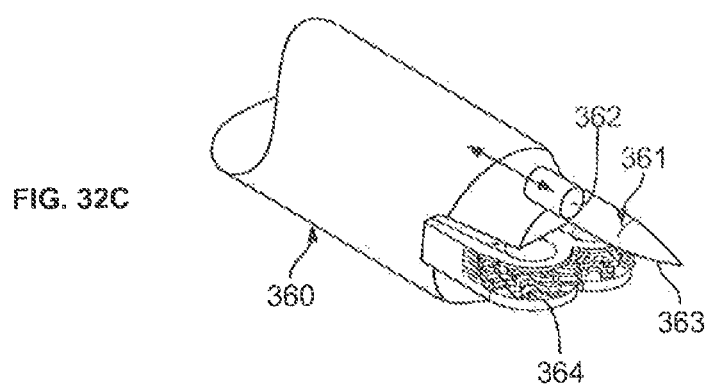

FIGS. 32A-32C illustrate a device and methods for providing a space for visualization of the target site, and/or target tissue. Creating a space in front of the tissue removal elements allows for visualization of the working area during and after tissue removal. FIG. 32A illustrates a first embodiment in which working end 350 includes retractable shredders 351. Inflated balloon 352 is inflated in the direction of tissue that is to be removed to create a space for visualization. In one embodiment the inflatable balloon is disposed at the distal end of an axially slidable element which is advanced to the working area through the working end of the device. An inflation fluid (e.g., gas, liquid) is then pumped through the lumen of the slidable element into the balloon to expand the balloon. The working end also includes an optical device 353 (e.g., a camera) which can be a separate slidable element, which is distally advanced towards the working area to visualize the working area. The balloon can then be deflated and retracted back into the working end. The camera is similarly retracted into the working end. The tissue removal elements can be retractable to avoid puncturing the balloon with the tissue removal elements.

FIG. 32B illustrates an alternative embodiment in which working end 354 includes irrigation port 355, suction port 356, and camera 358. Fluid 357 can be flooded into the working area in front of tissue shredders 359 to provide for visualization of the working area with camera 358. The fluid can be aspirated from the working area through suction port 356.

FIG. 32C illustrates an alternative embodiment in which working end 360 includes an axially slidable element 361 which includes a tapered optical cone 363 at its distal end and a camera 362 proximal to the distal end of cone 363. The optical cone can be advanced distally in front of shredders 364 to provide a space for visualization of the working area with camera 362. The optical cone can be retracted within working end 360 when not in use.

Figure 33A:
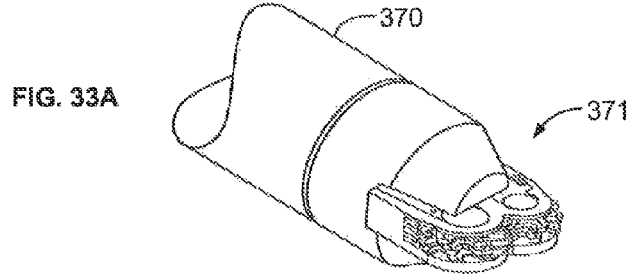
FIGS. 33A-33C illustrate an alternative arrangement of the delivery system for visualizing the working area.
Figure 33B:
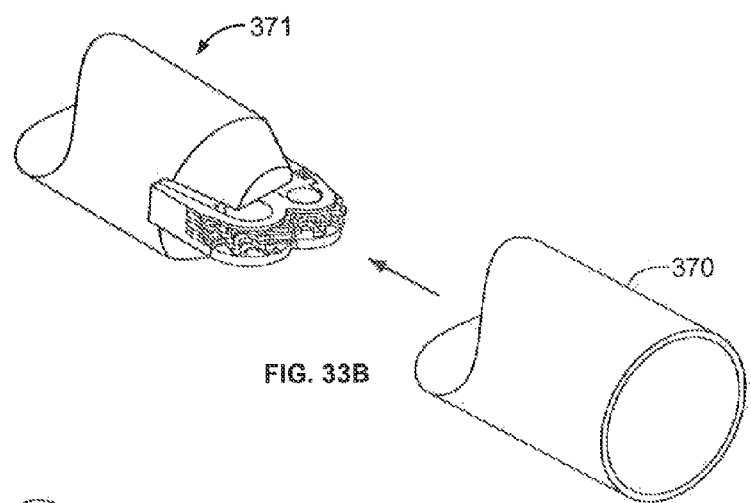
Figure 33C:
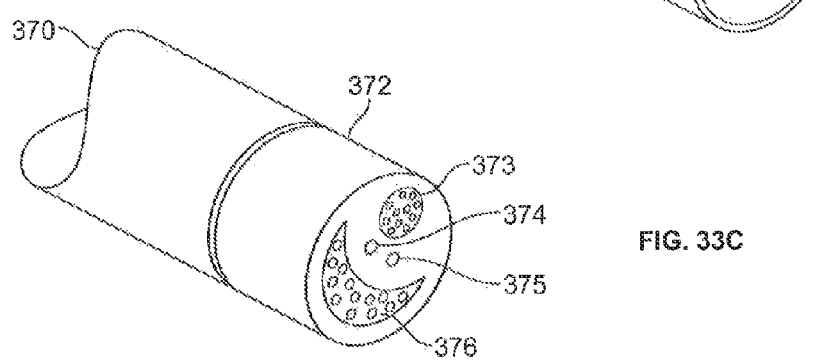

FIGS. 33A-33C illustrate an alternative arrangement of the delivery system for visualizing the working area. FIG. 33A illustrates working end 371 extending from delivery member 370 (an introducer is coupled to the working end but is within delivery member 370). In this configuration the shredders can remove tissue. The introducer and working end are then retracted proximally as shown in FIG. 33B and removed completely from the delivery member 370 (whose proximal end is positioned external to the patient). A separate scope 372 is then advanced through delivery member 370 to the working area, as shown in FIG. 33C. The scope includes camera or image bundle 373, irrigation port 374, suction port 375, and illumination bundle or LED 376. In use, tissue is removed with the shredders, then the working end is removed, the scope is then advanced to visualize the working area to determine the progress of the procedure, and the scope is then removed. These steps are repeated until the desired amount of tissue has been removed.

FIG. 34, steps A-E, illustrate an exemplary procedure for treating a herniated disc by removing nucleus tissue using a tissue removal device as described herein. As used herein, "disc tissue" can refer to the nucleus, annulus, and endplates. The following procedure can be used to remove nucleus tissue in the cervical, thoracic, or lumbar spine. FIG. 34A shows disc 370 (vertebrae not shown for clarity) including annulus 371 and nucleus 372. Using an imaging technique such as fluoroscopy or a CT scan, delivery member 373 (e.g., a delivery cannula) and dilator 374, which is shown with a "bullet" tip, are advanced towards disc 370 in either a posterior or anterior approach. Dilator 374 and delivery member 373 are then advanced through the annulus, as shown in FIG. 34B. The dilator's bullet tip shape separates and expands the fibers of the annulus and does not cut or tear them. Once the distal end of delivery member 373 is positioned at the desired location, dilator 374 is completely withdrawn from delivery member 373, as shown in FIG. 34C. Tissue removal device 375 is then advanced through delivery member 373, positioning the working end at the target tissue site, as shown in FIG. 34D. The tissue removal elements are then activated by a physician via a handpiece portion of the delivery system (not shown) to remove disc tissue to repair a herniated disc, as shown in FIG. 34E. In this embodiment delivery member 373 protects the annulus from the tissue shredders.

In an alternative method, rather than positioning delivery member 373 under fluoroscopy or CT scan, dilator 374 incorporates an visualization tool such as a camera which can be used to position delivery device 373.

An exemplary advantage of using a tissue removal device as described herein to remove nucleus tissue is that the tissue can be removed with minimal damage to the annulus and endplates. The tissue processing elements can he manufactured to have dimensions that allows for safe and efficient removal of nucleus tissue. Additionally, by using small tissue processing elements, it is less likely that endplate or annulus tissue will be damaged or unintentionally removed from the patient.

In other procedures the tissue removal device can specifically be used to remove annulus tissue as well. For example, in complete disc removal procedures, the tissue removal devices herein can be used to remove the entire disc.

The tissue removal devices herein can also be used to treat spinal stenosis. The tissue removal devices herein can be used to remove blood clots in a thrombectomy, or to remove plaque in an atherectomy. These are merely examples of procedures that can be performed with the tissue removal devices herein to remove tissue from a subject, and the devices herein can be adapted to be used in other procedures. As necessary, they can be adapted to be coupled to additional delivery system components to better adapt them for certain procedures.

In embodiments in which the blades are disposed at the distal end of the working end, the working end can be advanced distally to engage and remove tissue. It may need to be retracted and advanced several times to remove the target tissue. It may also be necessary to change the direction in which the working end is advanced each time to ensure that tissue is continuously and efficiently removed. In embodiments in which the blades are disposed on a side or sides of the working end, it may be necessary to laterally move the working end in a sweeping motion to remove the tissue. The working end may also be rotated during use (e.g. via rotation of the introducer).

In use, the tissue removal device may be used in combination with expanders and/or distal protection devices. The tissue removal devices herein may also be used in combination with forceps or claws to pull or push tissue toward the blades.

The tissue removal devices as described herein may include a user actuation member, such as a hand-piece or other external control mechanism for controlling and actuating the tissue removal device. The actuation member generally includes an actuator adapted to turn the processing blades on and off, such as via a motor. The same actuator or a different actuator(s) can be adapted to control an irrigation/suction system, such as by activating a pump to force a fluid distally through an irrigation tube, while activating a vacuum to apply suction to pull tissue and irrigation fluid back proximally through the introducer. Any other actuators can be incorporated into an external control mechanism to control the operation of the working end, drive mechanism, irrigation/suction system, etc.

According to some embodiments of the disclosure the drive mechanism may he powered by an electric motor located in proximity to the device, an electric motor located at the end of a flexible shaft drive wherein the motor is remote from the device (e.g. outside the body when the device is used at the end a catheter or other delivery lumen in a minimally invasive procedure.

The tissue removal devices described herein are generally configured to remove target tissue from a subject. "Removing," or the "removal" of tissue from a subject as used herein include any and all of the steps involved in removing tissue at least from the target tissue area, and in some embodiments removing the tissue completely from the subject's body. The working end of the device comprises blades which initiate the tissue processing step. Processing tissue as used herein includes cutting tissue, directing tissue from a location in the patient to a different location, and capturing, or entraining tissue, as well as directing tissue proximally through the delivery system to a location external to the patient. While "blades" as used herein may imply a cutting or shredding motion, the working end can includes many different types of blades, not all of which cut, shred, or tear tissue; some may merely be involved in directing the tissue from one location to another (whether from external to the device to a location internal to the device, or from a location internal to the device to a second location internal to the device). In some cases in which a blade is described as merely directing tissue from one location to another, there may of course be some incidentally tearing, cutting, and/or shredding. Additionally, the tissue which is removed from the target tissue area may be stored at least temporarily within the tissue removal device (e.g., in a tissue storage chamber), or the tissue may immediately be directed from the target tissue area to a location external to the tissue removal device (e.g., through a suction lumen). In either case, the tissue can be moved within the tissue removal device by, for example without limitation, a vacuum or other extraction mechanism such as an Archimedes screw or other mechanical conveyor.

The blades of the tissue removal devices may be configured to optimize one or more of the above functions, and in some embodiments the blades shape and function to be performed are influenced by the type of tissue that is being removed.

FIG. 35 illustrates an exemplary embodiment wherein the axes of rotation 384 of the rotors for blades 382 are substantially orthogonal to the longitudinal axis 383 of at least the working end 381. As used herein, "substantially orthogonal" includes angles that are +/− about 30 degrees to the right angle. That is, angles between the two axes that are about 60 degrees to about 120 degrees are considered substantially orthogonal. In some embodiments the rotors are not fixed relative to the working end, but instead can be articulated in one or more directions. In these embodiments the rotor axis is considered orthogonal if it can be rotated +/− about 30 degrees. In embodiments described above in which the blades are oriented along a side of the working end, the axes of rotation of the blade rotors are also substantially orthogonal to the longitudinal axis of at least the working end.

In generally, the tissue removal device includes at least one orthogonal rotor. FIG. 36 shows a distal end of a working end including a single rotor 391 and stator 392 wherein the stator includes fingers or other elements that work with the rotor to cause shredding or other disruption of the tissue into small pieces that may be removed via the device from the body of the patient. In some embodiments the single rotor may include a plurality of blade elements located in parallel with one another to allow wider contact with tissue to be removed.

Figure 37:
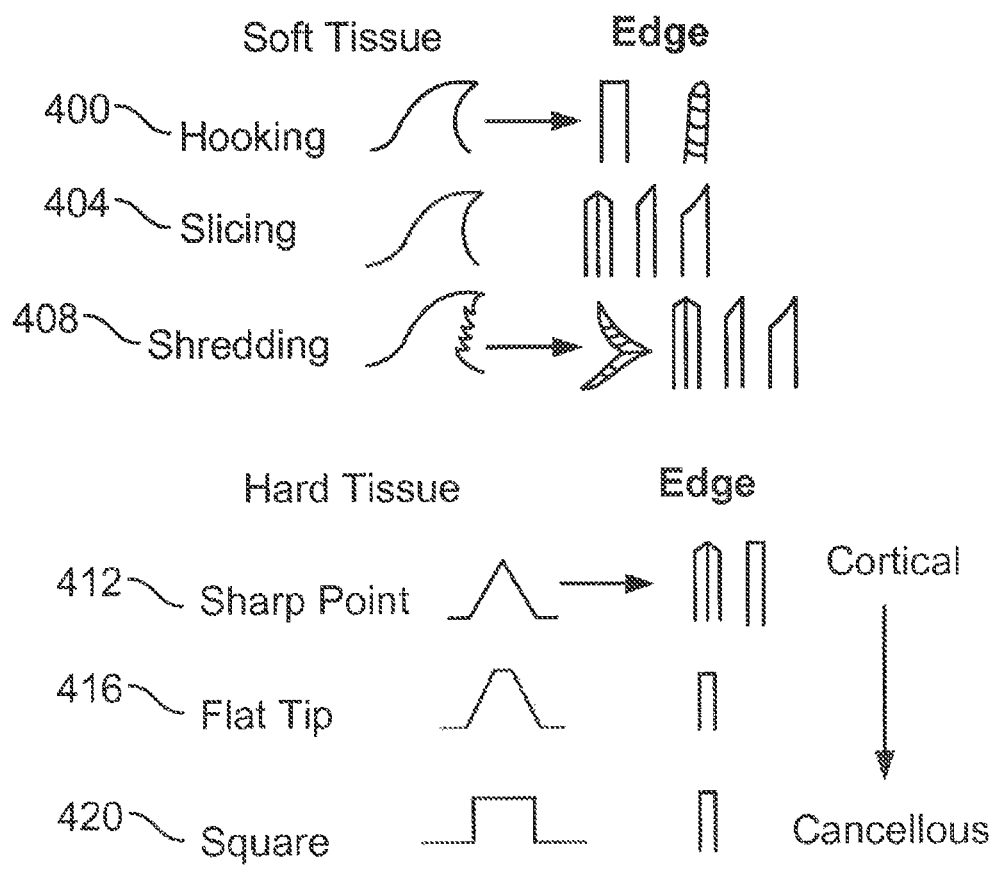
FIG. 37 shows exemplary blade profiles for removing soft tissue.

FIG. 37 shows exemplary blade profiles, wherein profiles 400, 404, and 408 would be most beneficial in removing soft tissue. Blade profiles 412, 416, and 420 would be most beneficial in removing bone. Profile 400 shows a blade shape for "hooking" which has a non-sharpened or dull edge. Profile 404 shows a blade for slicing, which is hooked-shaped with a sharp edge. Blade profile 408 can be used for shredding, and is hooked-shaped with serrations. The blade profiles for cutting bone are generally not hooked shaped and are more symmetrical. The shapes produce a more robust blade for contacting hard materials. Blade profile 412 has a sharp point and creates high pressure when cutting through cortical bone. Blade profiles 416 and 420 have a flat tip and square tip, respectively, and these blunt tips can be used for cortical bone but may be more suited for cancellous bone.

Figure 38:
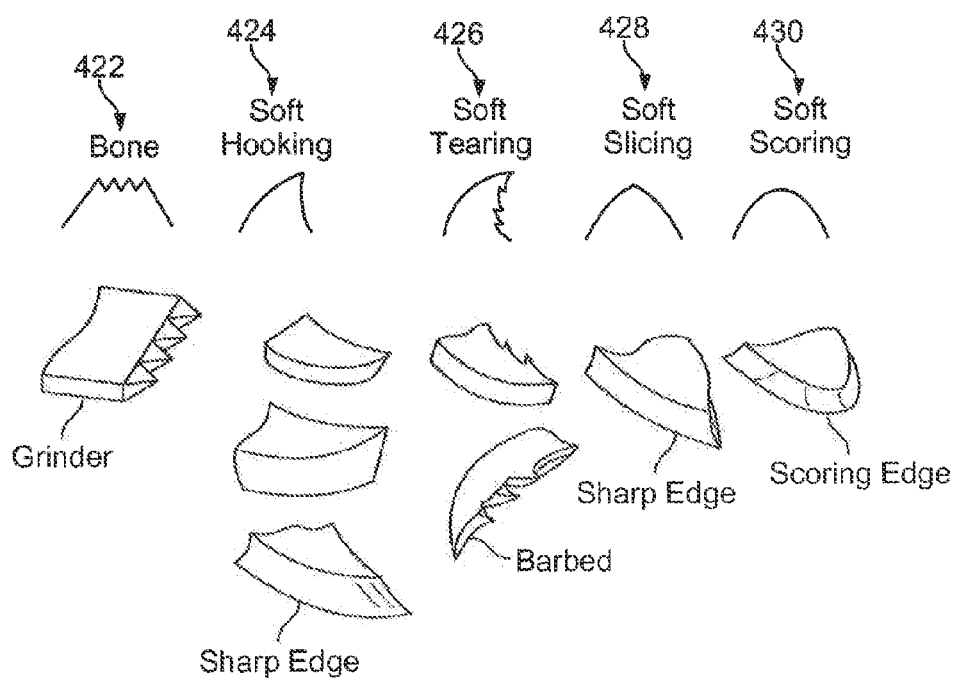
FIG. 38 shows some additional exemplary blade types, supplementing some of the blade types shown in FIG. 37.

FIG. 38 shows some additional exemplary blade types, supplementing some of the blade types shown in FIG. 37. Blades 422*a* and 422*b* illustrate a bone grinder with a serrated tip. Blade 424A-434*d* have a hooking shaft which can be used to remove soft tissue. The hooking shape can also have a sham edge as shown in 424*d*. Blades 426A-436C can be used to tear through soft tissue, and can have a barbed edge as shown in FIG. 426C. Blade 428E-428B can be used for slicing soft tissue, and can have a sharp edge as shown in 428B. Blade 430A-430C can be used for scoring soft tissue, and can have a scoring edge as shown in 430*b*.

Figure 39A:
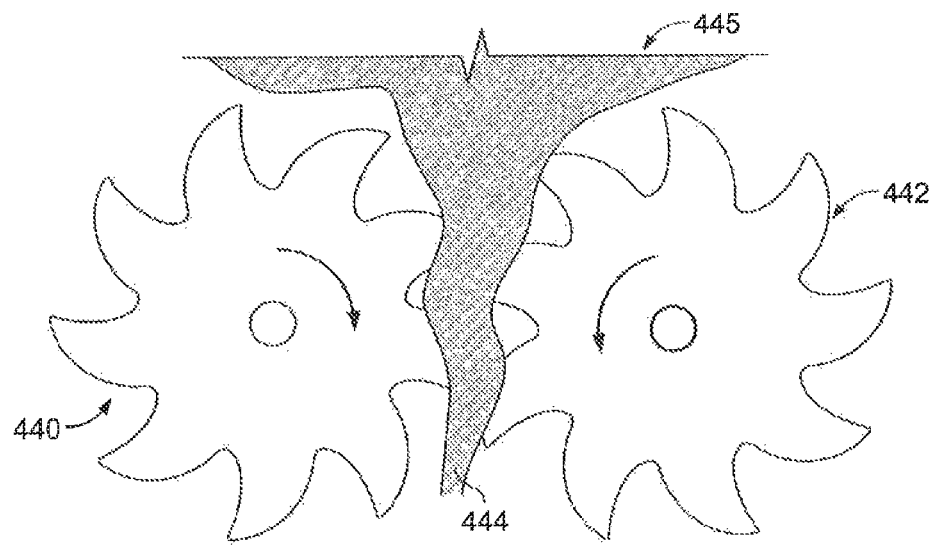
FIGS. 39A-39C illustrate exemplary embodiments of double rotor blade designs.
Figure 39B:
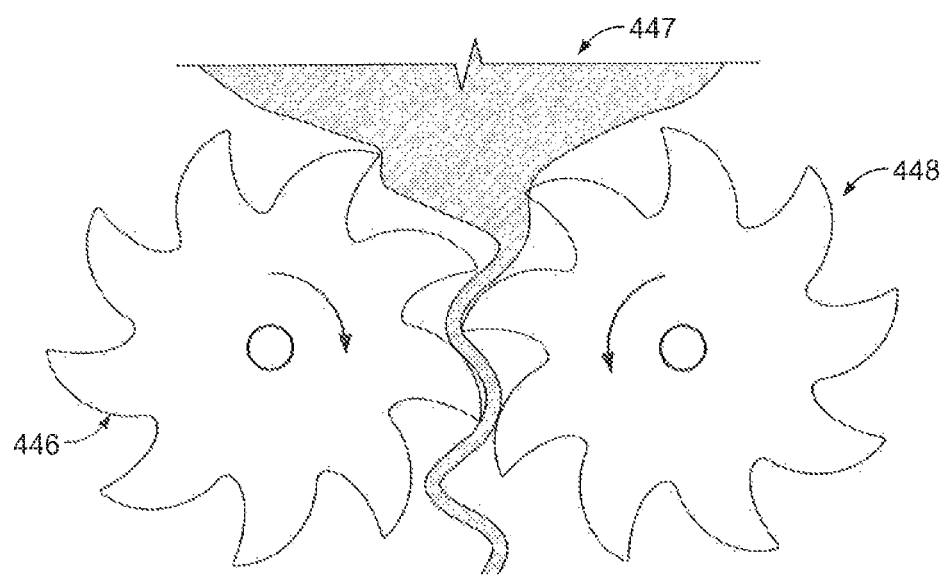
Figure 39C:
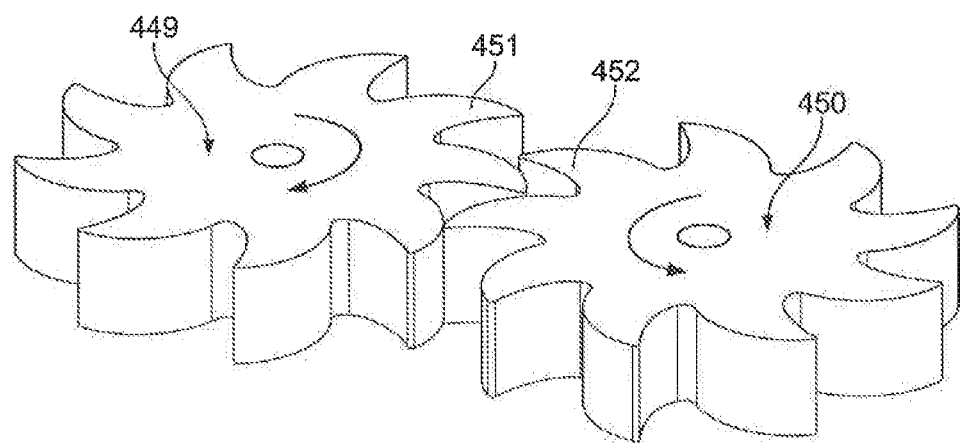

FIGS. 39A-39C illustrate exemplary embodiments of double rotor blade designs. FIG. 39A shows a first rotor 440A and a second rotor 442 in an overlapping, or interdigitated, configuration, with overlapping region 444. Tissue 445 is being pulled centrally inward as the two rotors rotate in opposite directions. This is the configuration of the blades in the blade stacks shown in, for example, FIG. 7. FIG. 39B shows non-overlapping, or non-interdigitated, rotors 446 and 448 pulling tissue 447 into the working end of the device. The left portion of FIG. 39C provides a schematic illustration of a blade element of extended height (e.g. numerous layers) which may be used for transporting material as opposed to tearing or shredding it. While the right most side of FIG. 39C shows how the teeth of such blades may meshed but not contacting so as to cause transportation of intervening material as rotation occurs. On the right of FIG. 39C, rotor 449 and rotor 450 have meshed teeth (e.g., 451 and 452) like a gear which have tall profiles as shown. Rotors 449 and 450 can effectively work like a gear pump as a pressure differential is created when the rotors begin to rotate, which can draw high viscosity gelatinous material (e.g., nucleus material from a spinal disc, blood clots, etc.) into the working end of the device. Unlike the blade stacks 102 and 104 as shown in FIG. 7, rotors 449 and 450 can be fabricated from one solid extrusion, which gives the blades a taller profile.

FIGS. 40A (perspective view) and 40B (top view) illustrate an alternative embodiment of working end 500 in which tissue is captured and processed in multiple steps. The rotating elements at the most distal end (rotor 504) are not sharp and merely pull tissue into the housing, while secondary blades (503 and 502) process the captured tissue into smaller segments. Driving gear (left gear) and blade 502 is shown with a bore which is adapted to receive a driving pin (not shown) as described above. A drive mechanism (such as those described herein) can be activated to rotate the pin and thus drive gears 506, which rotates rotors 502, 503, and 504 in the directions shown by the arrows. Working end 500 includes stator 501. Rotor 504 includes hooked-shaped grasper teeth 517 and 518 which when rotating pull tissue (not shown) into the device in the direction of arrow 509, but do not necessarily rip the tissue. Graspers 517 and 518 rotate and pull the tissue towards fixed hooked-shape blade 508 which is fixed to the inside of side of the housing. Blade 508 is formed in the housing to fit between graspers 517 and 518 as graspers 517 and 518 rotate past blade 508. As shown in FIG. 40B, the tissue is compressed between the rotor and the wall of the housing and is sheared by fixed blade 508 and graspers 517 and 518. As rotor 504 continues to rotate, graspers 517 and 518, in combination with solid wall guide wall 510, pull the tissue into a first area between the rotors where it is allowed to expand, as illustrated in FIG. 40B. Stripper 511 extends from the housing wall and is formed in between the planes of grasper 517 and 518. Stripper 511 may extend between graspers 517 and 518 to a location that provides near contact with a central rotating shall of rotor 501 so as to inhibit passage of material from the interior of the working end to a position outside the working end. Stripper 511 preferably also has a configuration, e.g. slope or the like, which helps remove material from graspers or blades 517 thereby helping prevent the material from exiting the housing.

Grasper 520 on rotor 503 then grasps and pulls tissue towards the second fixed blade 512, which is fixed to a second wall of the housing. The process that occurred at the first fixed blade 508 is repeated again, and once again the tissue is then directed towards a third fixed blade 515. Shredded material is directed proximally in the direction of arrow 516, when it is extricated by a vacuum. In most the most preferred implementation of the devices of the type exemplified in FIGS. 40A and 40B, rotators that at located more proximally relative to the distal end of the working end preferably rotate at a faster rate than the next for distal rotor and/or have more blade elements that can be used to extract material from the grip of more distal blades and thus drive the material deeper into the working end and the sonic blade to further aid in reducing the size of the entrained material.

In variations of the embodiment of the FIGS. 40A and 40B, multiple rotors "n" may be located in parallel so that multiple rotors are used to transport and breakdown material. The details of how this system of rotors in series works is listed below.

The devices of the type of FIGS. 40A and 40B preferable include gripping blades shearing blades, externals stators internal stators of varying thickness and spacing directing elements which are digitated or not along with stripping element which are preferably digitated. The devices also include expansion areas which allow soft tissue to decompress or de-stretch while waiting for pick up or breakdown by a next series of elements. In some embodiments, the fixed stators may be replace by moving rotor elements. Internal stators may be used to shred incoming tissue at different levels of fineness. Progressive shredding maybe accomplished by increasing the number of blade planes and stators for each stage after the intake rotor or rotors. Progressive shredding and outflow inhibition may also be accomplished by running the internal rotors at higher rates than that of the intake rotor and even that of the next more distal rotors. As illustrated in FIGS. 40A and 40B, directors 510, 511, 513, and 514 direct the material into the expansion areas where it will be ripped and pulled into the next set of rotors. Any excess material that is caught between the rotor blades of the first shredder will be stripped and directed by be a stripper that is interleaved with the blades rotor. The strippers 511 and 514 may act as a stators that void additional shearing. Directors 510, 511, 513 and 514 are generally not interleaved with rotors but may be in some embodiments.

In the device of FIGS. 40A and 40B, tissue is pulled into the device by intake rotor, e.g. this may be defined as step 1. A second set of stators 508 internal to the housing may provide tissue shredding. As intake Rotor A continues around for the next exterior swath cut of tissue, potential tissue located in between the blades may be stripped away by stripper 511 or by movement of blades 520. Tissue is directed into an expansion region between rotors 504 and 503 and may be allowed to expand before being compacted and hooked by the next rotor 503. Tissue is cut or shredded from rotor 501A by the motion of rotor 503, which may be defined as step 2. As noted above rotor 503 may he rotating at a higher rate than rotor 504. Next the tissue is directed into the gap between rotors 503 and 502 and may be allowed to expand before being compacted and hooked by the next rotor 502. Tissue is sliced again by a higher density blade on rotor 502, which may be defined as shredding step 3. Rotor 502 may be rotating at a higher rate than rotor 503. The process of progressive, i.e. stepped, shredding may be continue through n number of stages until tissue has reached a desired size and then the individual particles of tissue may be extricated through the device by vacuum and or via irrigation.

While FIGS. 40A and 40B show three rotary devices in series, in some embodiments there are more or less than three rotary devices. In some embodiments there is more than one rotor at each stage. For example, there can he two sets of three rotors in series, with the two sets adjacent one another in the housing. This can potentially increase the rate of tissue processing as well as provide more efficient shearing of tissue.

While gear 502 in FIG. 40 is the driving rotor, any of the rotors can be the driving rotor, such as rotor 503. In some embodiments the rates of rotor rotation is not 1:1. In some embodiments the most distal rotor (i.e., rotor 504 in FIG. 40) rotates faster than the other rotors. For example, rotor 503 can rotate at 10 times the speed of rotor 504, which can increase the speed with which the tissue is processed in the housing. In embodiments in which the rotors rotate at different speeds, the gears which rotate the rotors may not he in the same train or may be in the same train with different diameters and teeth counts, alternatively multiple drive trains can exist.

Figure 41:
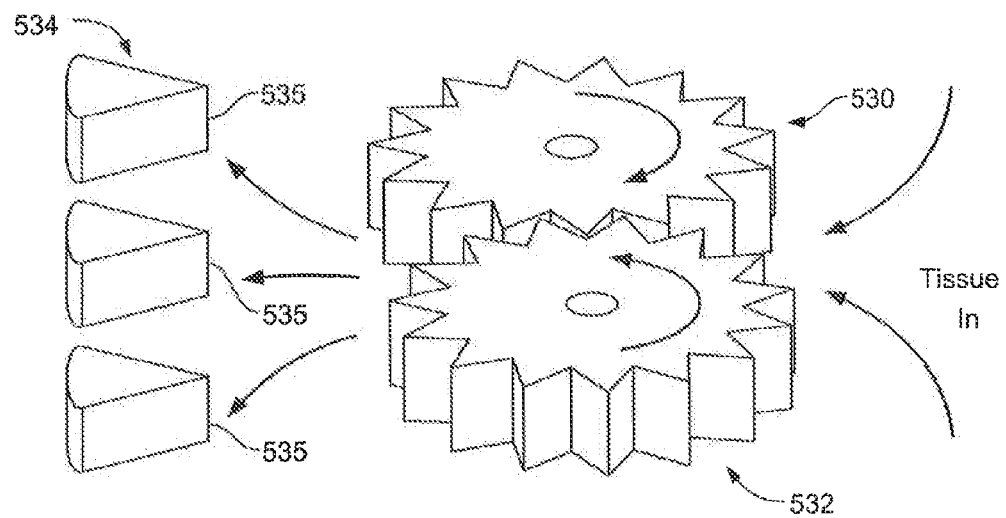
FIG. 41 illustrates an alternative design in which a plurality of blade rotors directs tissue (not shown) towards a set of vertical cutters which are fixed in place.

FIG. 41 illustrates an alternative design in which a plurality of blade rotors 530 and 532 direct tissue (not shown) towards vertical cutters 534 which are fixed in place (e.g., fixed to a housing in a working end of the device). Vertical cutters have sharp edges 535. After passing through vertical cutters, the tissue can be rotary sliced or passed again through a second set of vertical column cutters or rotating cutters.

Figure 42:
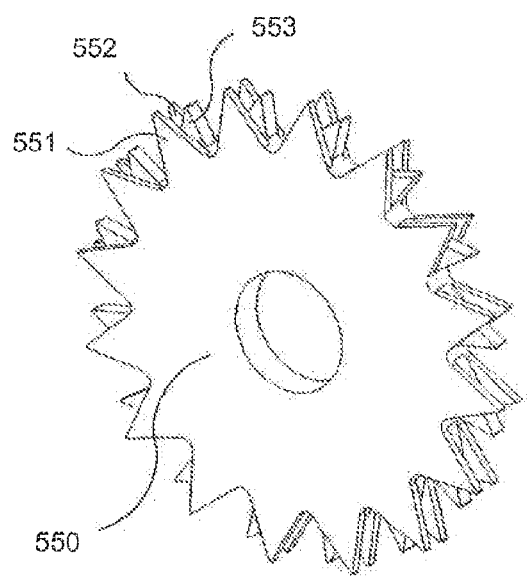
FIG. 42 shows an alternative embodiment of a 'hybrid' blade with teeth that are capable of both piercing and cutting into tissue to entrain it.

FIG. 42 shows an alternative embodiment of a 'hybrid' blade with teeth that are capable of both piercing, or cutting, into tissue to entrain it. The outer portions of the teeth 552 and 551 are intended to cut the tissue, while the inner portion 553 is intended to entrain the cut tissue and convey it into the instrument. In some embodiments, the outer portions are thinner (e.g., formed from a single relative thin multi-material layer) and the inner portion is thicker (e.g., formed from one or more multi-material layers). In some alternative embodiments the blade may have a non-symmetric shape based on the intended directions of motion and use.

Figure 43:
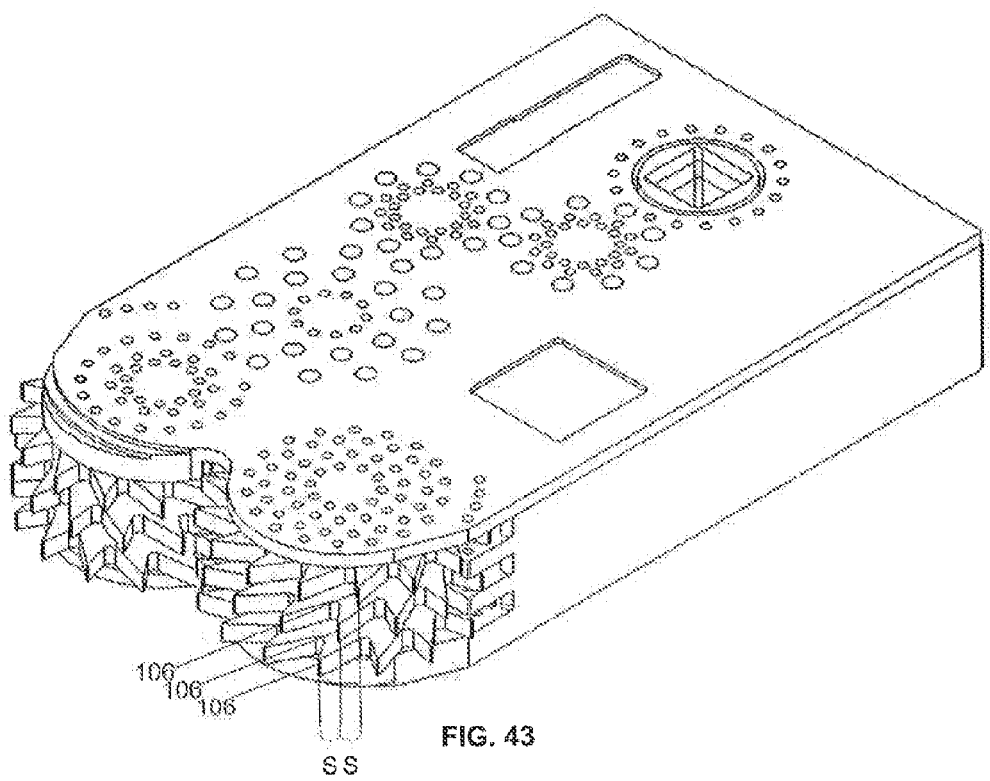
FIG. 43 illustrates an optional blade stagger design in which the tips of teeth are staggered from one another as measured circumferentially or in an offset angular increment relative to adjacent blade tips.

FIG. 43 illustrates an optional blade stagger design in which the tips of teeth 106 are staggered a distance "S" from one another measured circumferentially or in an offset angular increment relative to adjacent blade tips. When more than two blades are used in a blade stack, the distance S for a pair of blades can be the same or can be different than the distance S for a different pair of blades.

In some embodiments the distal end of the working end can include more than two blade rotors sets. In some embodiments blade stacks may be stacked on one another. For example, two blade stacks can be stacked on the top of two other blade stacks for form a four rotor blade system. Additionally, the axis of rotation of the blade stacks are not necessarily parallel to one another. For example, a working end can have 4 blade stacks pointing in the distal axial direction but rotated with respect to each other for example to having rotation axes rotating about shaft positioned on the hour hand of a clock located at "12 o'clock,"3 o'clock, 6 o'clock, and 9 o'clock positions. Wherein the axes of rotation of the 12 o'clock and 6 o'clock rotors are parallel, and the axes of the 3 o'clock and 9 o'clock rotors are parallel. One set of axes is perpendicular to the other set of axes. All four rotor sets may be directing the tissue centrally inward. In an alternative embodiment, there are three blade stacks and each is 120 degrees from each of the other blade stacks, and their axes of rotation form an equilateral triangle at their points of intersection (e.g. 2 o'clock, 10 o'clock, and 6 o'clock).

In some embodiments blade tips, gear pins and other high wear surfaces may be formed from a wear resistant material (e.g. rhodium or diamond) while other portions of the device may be formed from another material that is more suited to the functionality of the device as a whole (e.g. a more resilient or less brittle material, nickel cobalt, nickel phosphor, palladium).

In some embodiments, blades and/or blade stacks may rotate at different rates or blades within a single stack may rotate at different rates.

In some embodiments the working end of the tissue removal device is formed with a length of about 4 mm, a width of about 2.5 mm and a height of about 0.75 to 1.0 mm. In other embodiments the height may be increased to several millimeters or decreased further, while the length and width may be increased many times (3-5 to even 10 times) or even decreased. Stacks of shredders of different sizes (e.g. number of shredding or intake rollers, or having diameters of such shredding or intake rollers) may be formed to provide a desired material interface configuration (e.g. cylindrical). Such configurations may have effective central heights that approximate their widths. Such configurations may have, for example, rectangular configurations, stepped diamond configurations, stepped configurations approximate ellipses or circles (e.g. approximate the diameter of a delivery cannula.

In some embodiments portions of the working end are formed separately and then assembled. In some embodiment the working end is formed in a final assembled state. In some embodiments the working end is coupled to other components of the delivery system (e.g., an introducer) after assembly. In some embodiments components that move relative to one another are formed with fully or partially overlapping etching holes so that improved flow paths are created for removing sacrificial material.

Figure 44:
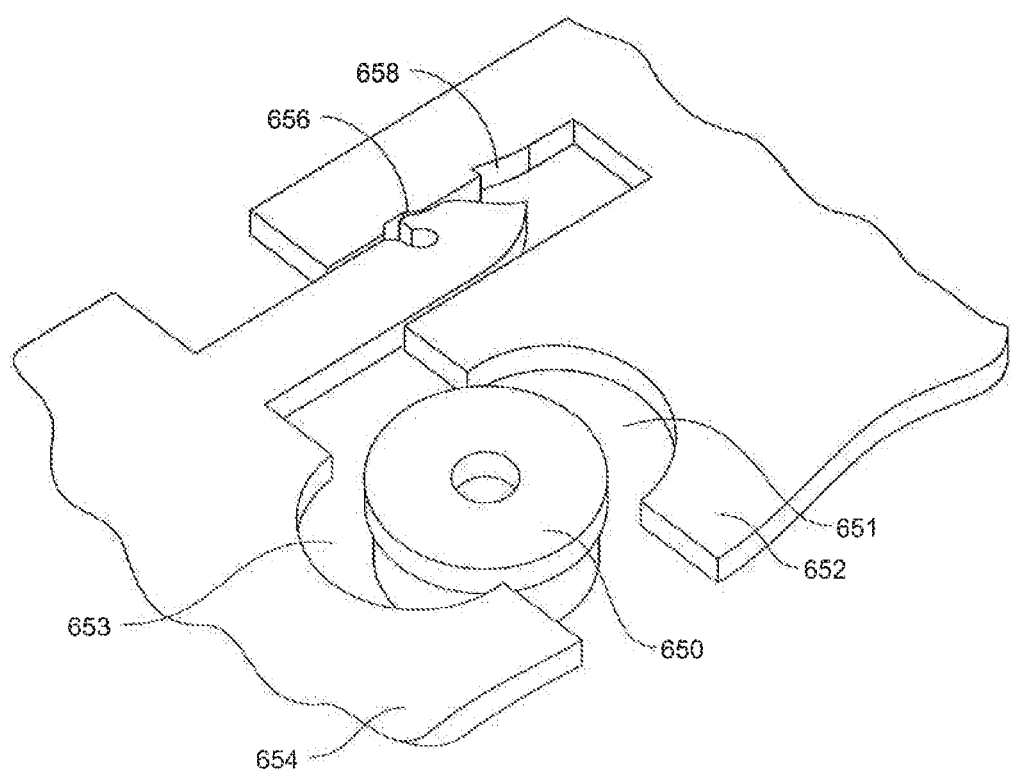
FIG. 44 illustrates an exemplary embodiment of components of a device that are formed in one configuration but separated from a final configuration and are moved relatively toward one another after release from sacrificial material.

FIG. 44 illustrates an exemplary embodiment of components of a device that are formed in one configuration but separated from a final configuration and are moved relatively toward one another after release from sacrificial material. It may be desirable to form very small gaps between a rotating gear axial, shaft or boss relative to a surrounding hole, bushing or bearing. Due to minimum feature size limitation, direct formation of moving components in desired configurations may be challenging or not cost effective. FIG. 44 shows gear boss 650 and adjacent surfaces 652 and 654 in an "as-formed" spaced-apart configuration. Additionally, although not shown, the internal gears could also be formed in a spaced-apart configuration from their adjacent material. After fabrication, surfaces of material 652 and 654 are moved closer to one another and locked in place by locking first lock element 656 and second lock element 658. Gear boss 650 can then be disposed in a final configuration closer to surfaces 652 and 654 than it would have been able exist in an "as-formed" configuration which was also the final configuration.

Figure 45:
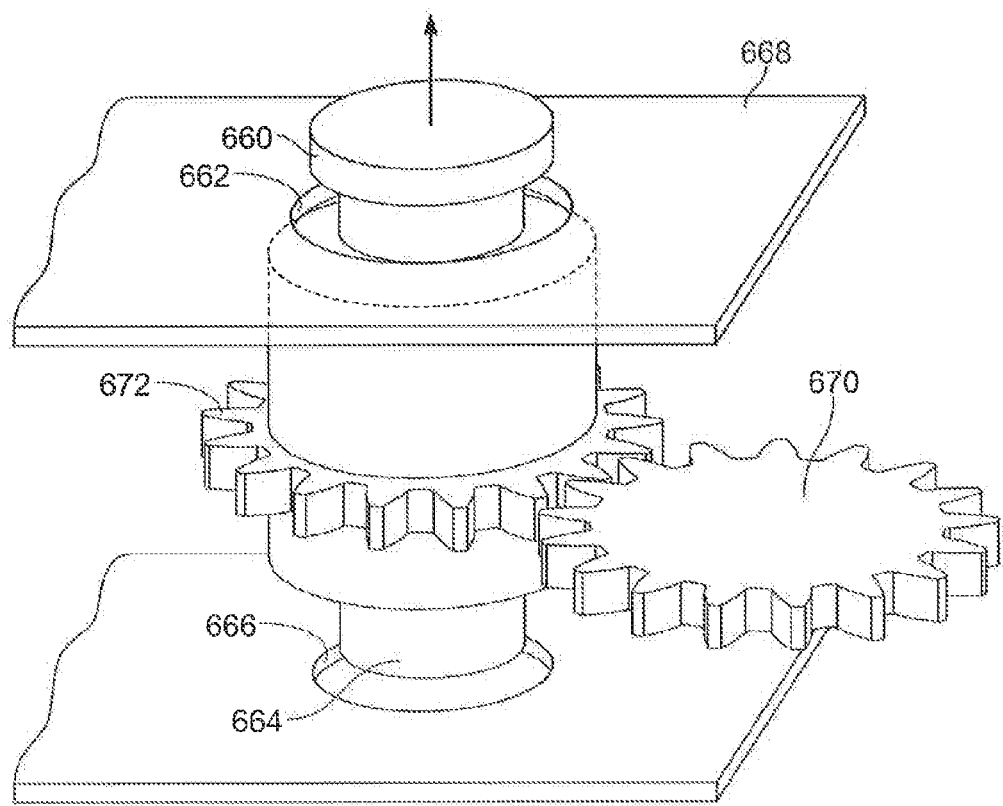
FIG. 45 shows an exemplary embodiment in which a gear or boss is fabricated in an "as-formed" configuration in which it is out of plane with material which the gear or boss will ultimately be in-plane with in a final configuration after formation.

FIG. 45 shows an exemplary embodiment in which a gear or boss is fabricated in an "as-formed" configuration in which it is out of plane with material which the gear or boss will ultimately be in-plane with in a final configuration after formation. Boss 660 is fabricated up and out of plane with 668, while gear 672 is fabricated out of plane with mating gear 670. Once fabricated, boss 660 is moved down into bore 662 so that it is in-plane with surface 668, while gear 672 is moved down and in-plane with its mating gear 670. Appropriate clip or other retention elements may exist to hold the components in their working positions after being moved there.

Figure 46:
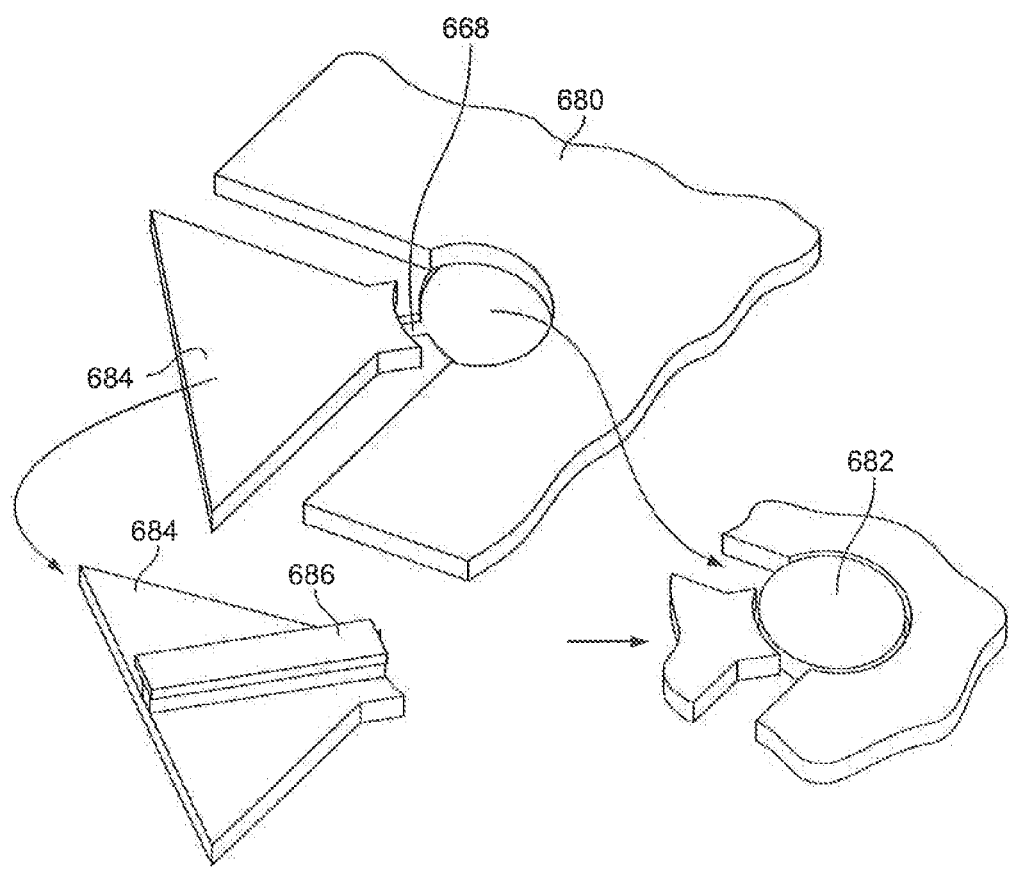
FIG. 46 illustrates an alternative embodiment similar to FIG. 44, wherein a slide plate includes a protrusion on one side adapted to fit within a channel

FIG. 46 illustrates an alternative embodiment similar to FIG. 44, wherein slide plate 684 includes protrusion 686 on one side adapted to fit within channel 668. Slide plate 684 is formed spaced apart from boss 682, but after formation slide plate is slid into position, and the boss clearance is properly set. The slide plate can then be locked in place, such as by snap- locking or laser welding in place.

Figure 47A:
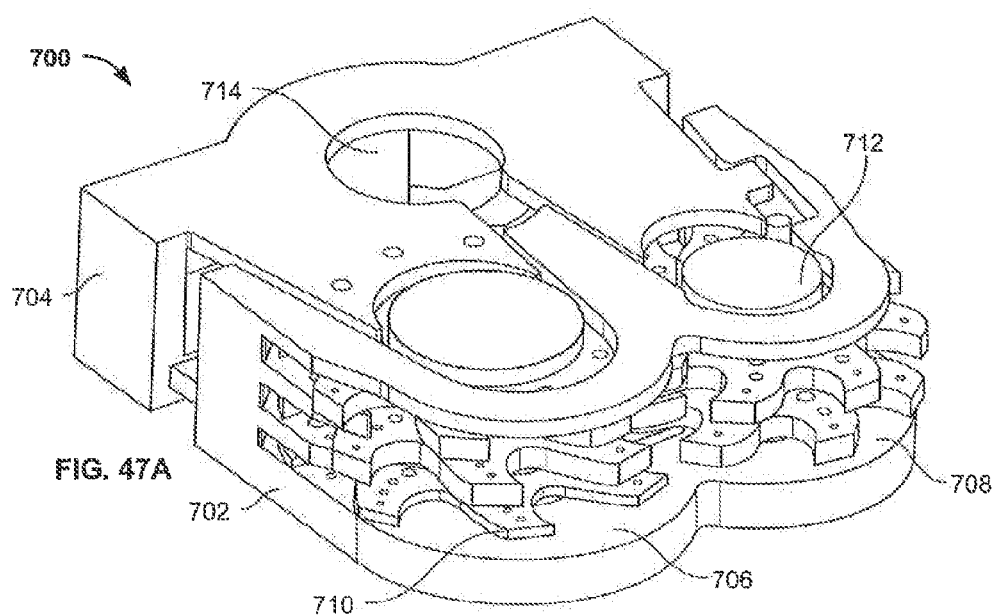
Figure 47B:
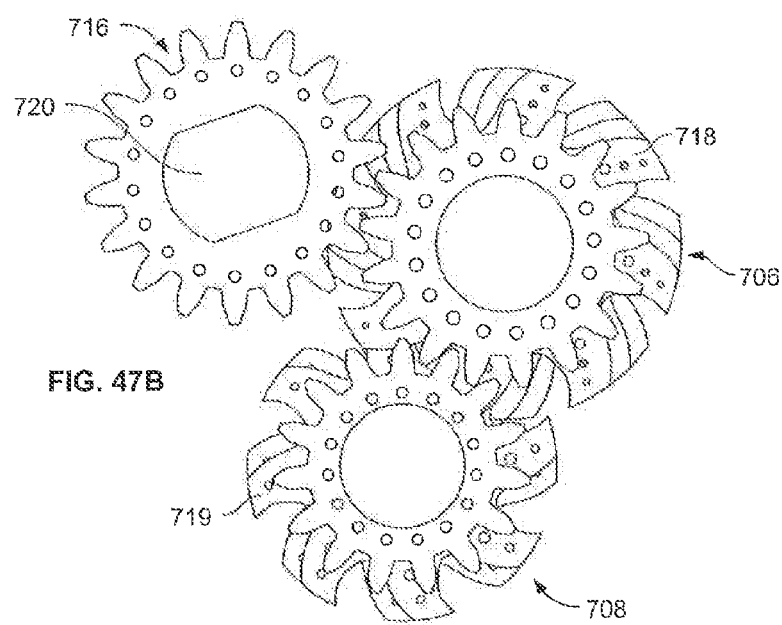

FIGS. 47A-47C illustrate an exemplary embodiment of a working end, including a gear train and two shredder rotors. FIG. 47A shows working end 700 in an "as fowled" configuration with elements spaced apart to fit minimum feature size limitation. Working end includes first section 704 and second section 702 spaced apart from one another, first boss 710, first blade stack 706, second blade stack 708, second boss 712, and pin bore 714 in first section 704. FIG. 47B shows driving gear 716, gear 718, and gear 719 in their as-formed configuration. The gears are formed spaced apart in order to create the proper gap dimensions between the teeth. FIG. 47C shows the design in a closed, final configuration in which section 704 and 702 are moved closer which reduces the gaps between surfaces of sections 704 and 702 and bosses 710 and 712. The gear teeth are also moved closer to one another (not shown).

In some embodiments gap layers (i.e. intermediate tiers) may, for example, be as little as about 2 microns or as much as about 10 microns, and more preferably be in the range of about 4 microns to about 6 microns. Non-gap layers may, for example, be as large as about 20 microns to about 50 microns or more, while in some embodiments the non-gap layers may preferably in the range of about 20 microns to about 30 microns.

Figure 48A:
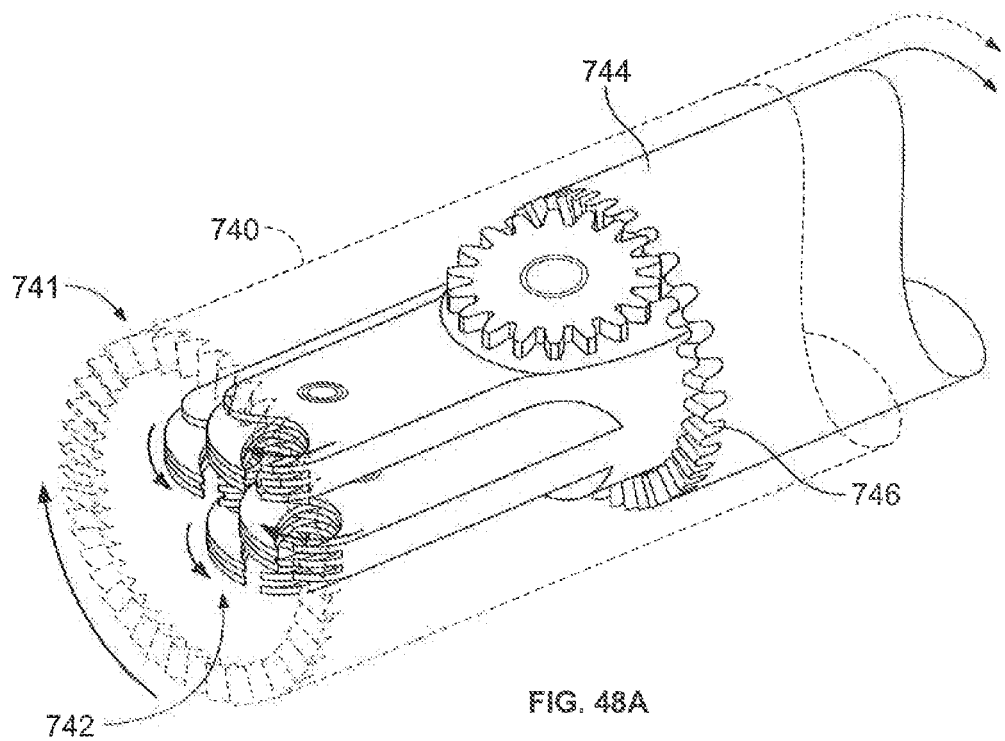
FIGS. 48A-48C illustrate an embodiment of a tissue removal device including a core cutting saw 740 with a plurality of tissue removal devices 742 therein.
Figure 48B:
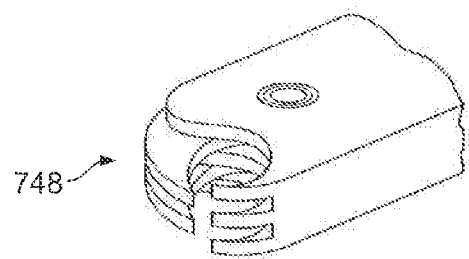
Figure 48C:
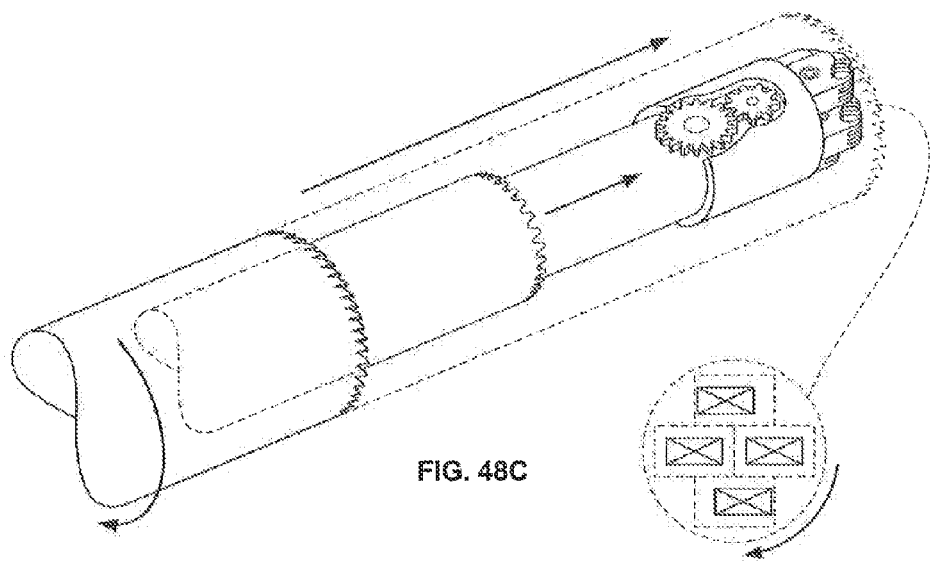

FIGS. 48A-48C illustrate an embodiment of a tissue removal device including a core cutting saw 740 with a plurality of tissue removal devices 742 therein. The device includes core cutting saw 740 with teeth 741 formed in its distal end, wherein the saw 740 is adapted to rotate in the direction of the arrow shown. The core saw is cutting to the outer diameter of the device, where the tissue removal devices are not adapted to cut to that diameter. The tissue removal devices are directing material inside their housings and processing it for transport to the proximal end of the device. FIG. 48B depicts one of the removal devices of FIG. 48A wherein element 748 rotates with it blade interdigitated with the blades on the stator as it forces material into the remover. FIG. 48C shows the assembly of a rotating saw, a joined rotating gear that engages drive gears on the removing devices which are fixed, or at least move at different rotational rates relative to the saw and cylindrical gear FIGS. 48A and 48B. The working end (i.e. the removing elements) may be fixed or non-rotating, rotating opposite to the saw or simply rotating at a different speed relative to the saw.

In some embodiments the etching holes in the working end may be sealed after release of sacrificial material.

In some embodiments of the working ends of the tissue removal devices set forth herein, may include holes, textures, grooves, or other features which provide rotating elements, the shafts on which they rotate, and/or to the surfaces surrounding the rotating elements with configurations that allow for aerodynamic or hydrodynamic bearing surfaces that reduce friction during rotation of the elements.

In some embodiments, the tissue removal devices may be configured to remove soft tissue without damaging hard tissue, either by use of selective blade configurations, operational speeds, and/or via clutch element that halt rotation of removal elements if encountered tissue does not have the anticipated properties. Such clutch mechanism may be mechanical in nature or implemented via sensor input and associated motor control.

Some embodiments of the disclosure relate to devices and methods for removing tissue from the human spine (e.g., the lumbar or cervical spine). Such methods may be minimally invasive while others may not. Tissue removal devices such as the various shredder devices discussed above may be used to remove tissue such as ligament, bone, cartilage, tendon, and disc (both nucleus and annulus), as well as fat, fascia, and muscle in the area of the spine. Removal of such tissue may be a part of medical procedures for repairing a bulging or herniated discs, for repairing spinal stenosis, or for other indications.

In some embodiments, a tissue removal device may be delivered to a desired surgical site via a rigid, flexible, steerable, or articulated structure, while optically visualizing the procedure using a rigid, flexible, steerable, or articulated endoscope that is separate from the removal device. In some embodiments, a tissue removal device may be delivered to a desired surgical site through a working channel, or alongside, a rigid, flexible, steerable, or articulated endoscope used to visualize the procedure. In some embodiments, the tissue removal device may be introduced under fluoro guidance or guidance fee another imaging method.

In some embodiments, a tissue removal device may be delivered to a desired surgical site through a rigid, flexible, steerable, or articulated structure and also incorporate one or more (e.g., two for stereoscopic visualization) imaging means such as a CCD or CMOS imaging chip, a fiber optic bundle, or single fiber endoscope (e.g., using the spectrally encoded endoscope technology developed by the Wellman Center for Photomedicine of Mass General Hospital), along with suitable optics such as lenses. The imaging devices may be located so that the optical axis substantially coincides with the centerline of the tissue removal device, or be offset from the centerline of the device. In some embodiments, the procedure may be visualized by the use of X-rays (e.g., fluoroscopy or CT scanning), ultrasound, MRI, or other imaging modalities, in addition to, or in lieu of, optical visualization via endoscopes or other imaging means as described above.

In some embodiments, to enhance visualization, a transparent dome that is hemispherical, wedge-shaped, or is otherwise appropriately shaped may be provided to protect the optics and to provide a means for displacing/retracting/dissecting tissue as the device is pushed forward. Irrigation and/or mechanical action may be used in some embodiments to keep the dome clean.

In some embodiments, the tissue removal device is activated (e.g., shredder cutters rotated) only once it has been delivered to the surgical site; prior to activation, it may be allowed to contact tissue (e.g., en route to the site). In some embodiments, the device may be protected from tissue contact by retracting it inside a sheath, tube, catheter, or similar structure. In some embodiments, the tissue removal device may include fixed or moveable shields or shutters which move out of the way to allow device use, prevent damage to surrounding structures, in some eases exposing only the tissue to be processed by the device.

In some embodiments, it is desirable to simultaneously remove tissue from a wider area than is possible with the previously-disclosed Shredder. In such embodiments, a shredder that is larger in width and/or height may be used, and may involve more than two groups of rotating cutters. In some embodiments, if the desired height exceeds that which is practical to achieve using multi-layer multi-material electrochemical fabrication methods as a single structure, two or more shredders may be stacked and operated as one.

Figure 49:
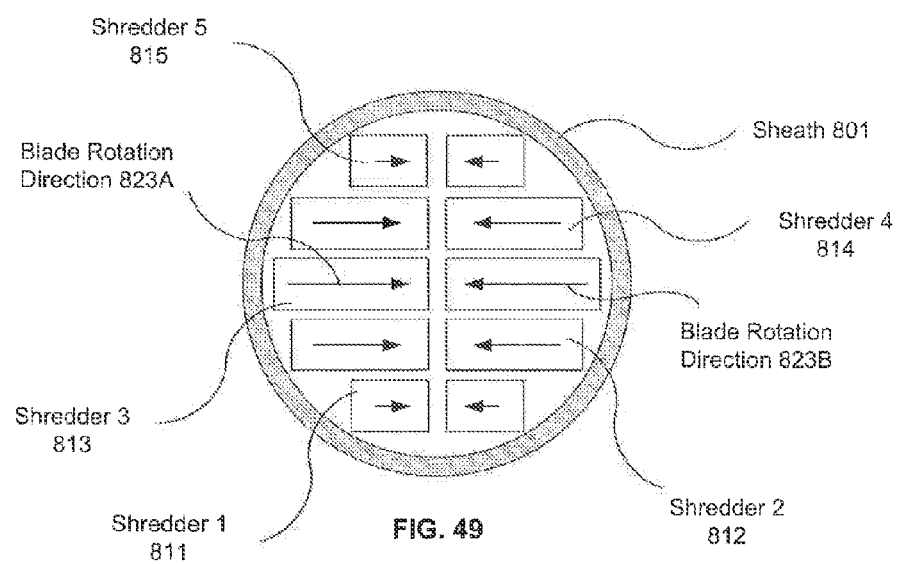
FIG. 49 provides a schematic illustration of a plurality (i.e. 5 as shown) stacked tissue shredding devices having individual and stacked configurations providing a large area tissue removal surface having a desired configuration (e.g. circular configuration).

Stacked shredders may be aligned, and joined by methods such as laser welding, fasteners such as screws and rivets, swaging of features designed for joining, soldering, brazing, and adhesives. Such stacked devices may be joined by connectors (e.g. male and female engagement elements formed with the devices themselves and engaged by stack mere act of aligned stacking. In other embodiments, engagement may occur after stacking by deploying components formed with the devices on a selective basis. In some embodiments, disengagement of stacked devices may also be possible. In such stacked device embodiments, gear trains may be driven independently (e.g., at different speeds or the same speeds, with correlated phase or un correlated phase) or jointly. In embodiments in which the gear trains of joined shredders are driven jointly, this may be accomplished when joining the shredders by aligning the holes in the driven gears (which receive a drive shaft) and driving all driven gears with an elongated shaft. Alternatively, the driven gears may be designed to be attached or keyed to one another so that when one or more is driven by a drive shaft, all spin together. Shredders designed to be stacked may incorporate upper and/or lower plates which are thinner (e.g., half the thickness or less) than if the shredder were designed for independent use, so that the combined thickness of the upper plate of one shredder and the lower plate of the shredder above it is not excessive. If the stacked shredders are intended to form a cylindrical device (e.g., to remove tissue in a cylindrical volume when plunged) or to occupy as much as possible of a cylindrical lumen (e.g., sheath or working channel), then the shredders may be designed as shown in the example of FIG. 49 which provides a schematic view of the distal or working end of a plurality of stacked shredders where each shredder is sized to conform roughly to a cylindrical overall shape. The working end is located within a sheath 801 (e.g. a catheter or other lumen and may be extended from the sheath as appropriate. The working end, in this example, include double shredders 811-815 wherein a portion of the shredders may have different configurations to provide an overall device or working end configuration of desired shape.

In some embodiments, in order to increase the hardness of the device where in contact with tissue (especially for hard tissue such as bone), the contacting surfaces may be made from harder material, or have a coating of harder material. Such materials include electroplated rhodium; vacuum-deposited nitrides, carbides, and oxides; and diamond, boron nitride, or other hard ceramic particles in a matrix of metal (e.g., co-deposited with electroless nickel) or resin.

In some implementations, jamming of the tissue removal device with tissue may be an issue. In some embodiments, reversing (e.g., periodically or as-needed) the direction of the motion (e.g., the shredder cutters) may help to dislodge tissue causing jamming. In some embodiments, tissue caught within the shredder cutters or similar structures, that might lead to jamming, could be dislodged/stripped from the cutters by suction, directed irrigation, or mechanical structures such as wiping or reciprocating elements.

While some tissue removal devices may not just cut tissue, but also capture and transport it away from the surgical site, in some embodiments suction capability (e.g., vacuum holes and manifold interfaced to a vacuum pump, peristaltic pump, etc.) may be incorporated into the device to facilitate removal of processed material. In some embodiments the tissue removal device may be interfaced to a device having the ability to mechanically transport tissue (e.g., an Archimedes-type screw rotating within a sheath) larger distances (e.g., to outside the body) than the device itself.

In some embodiments, the surgical approach to the tissue to be removed may be substantially anterior or anterior oblique, while in some embodiments, it may be substantially posterior or posterior oblique.

In embodiments relating to spinal disc problems, closure of the annulus of the disc after removal of disk material (e.g., disc nucleus) may be performed, for example, using suture material, or a tissue approximation device such as a clip, staple, or ratcheting fastener.

In variations of some of the above noted embodiments the effective cutting, shredding or removal area of a device may be adjustable, for example, by inclusion of an adjustable window on the removal device itself or on the catheter. Adjustability of a device may also allow different teeth configurations (shape and or size) to take more prominent positions depending on the type of tissue to be processed. In some embodiments the same catheters that provide the tissue removal devices may also provide suction or irrigation to be incorporated into the same catheter).

In some embodiments, material extraction from a working site may occur by back and forth motion at different angles which are varied by varying the entry angle of a relative rigid insertion element. In other embodiments, the tissue removal device may be located on flexible or guidable element that may be made to change shape by control wires or the like which can cause the device to bend to the left of the right while other movement may be obtained by rotating the device about its axis or by moving it back and forth. In some embodiments, the guidable element may be moveable up, down, and left and right directions by appropriate manipulation. In still other embodiments, for example, a single drive shaft operating all removal elements may be engaged by a rotating element and the device may be pivotable to the left or right by nearly 180 degrees by the extension or retraction of control wires engaged with the side of the device. Such devices would preferably include flexible or pivotal lumen elements that would allow appropriate extraction of material (e.g. via vacuum) along with possible application of irrigation for blade cleaning or material extraction regardless of the pointing direction of the distal end of the shredder. Such a pivotable device would allow access to forward, side facing, and back facing regions for tissue removal.

The operation of removal devices in removal procedures as set forth herein may be done under the manual control of a physician or operator wherein movement and extraction occur via a series of movements selected by the operator. Alternatively, the extraction may occur via a computer defined and controlled algorithm that directs the shredder through a series of predefined motions and operations or via a series of motions and operations that are dictated at least in part by sensor retrieved input (e.g. visually, optically, conductively, capacitively, magnetically, or the like).

Figure 50B:
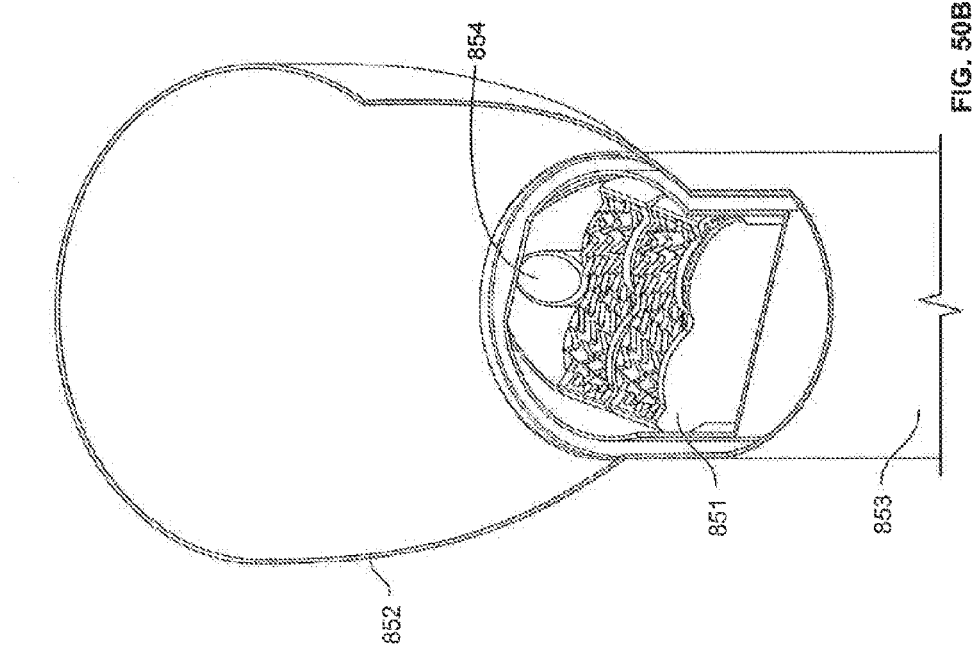
FIGS. 50A and 50B provide a schematic illustration of a shredding or tissue removal device, i.e. working end, located within a lumen having an expanded distal end and a smaller lumen which may be used to feed additional tools or elements into or beyond the expanded distal end of the lumen.
Figure 50A:
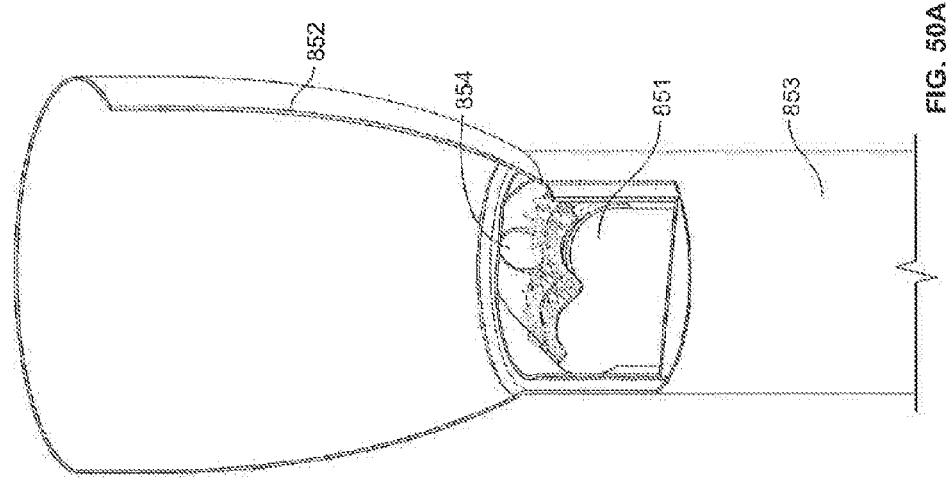

FIGS. 50A and 50B provide a schematic illustration of a shredding or tissue removal device, i.e. working end, 854 located within a lumen 853 having an expanded distal end 852 and a smaller lumen 851 which may be used to feed additional tools or elements into or beyond the expanded distal end of the lumen. The expanded distal end may be of fixed size or may be controllable.

FIGS. 51A and 51B provide close (compacted) and open (expanded) views of a sample device according to a procedural embodiment of the disclosure. The device includes an elongate delivery rod, tube or wire that may also provide control functionality along with an expandable mesh or net like elements that can be move from a contracted state 862C to an expanded state 862E.

Figure 52A:
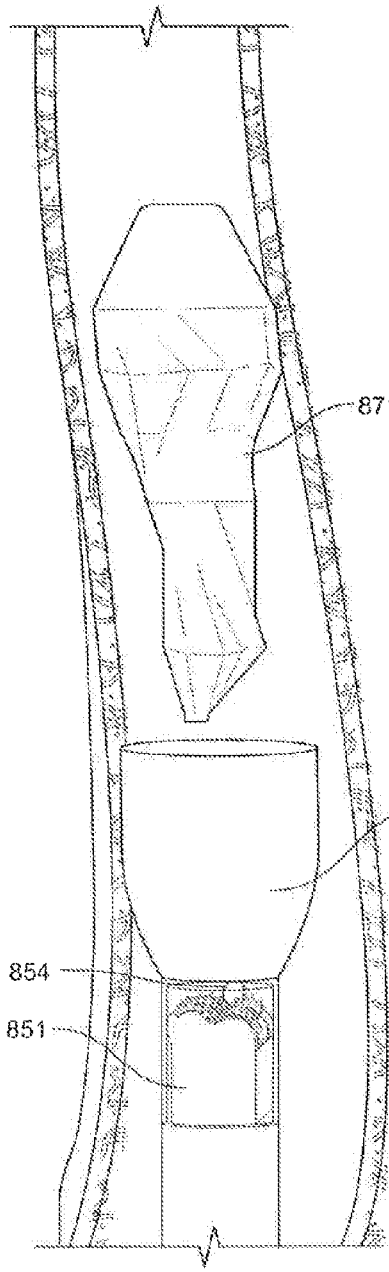
Figure 52B:
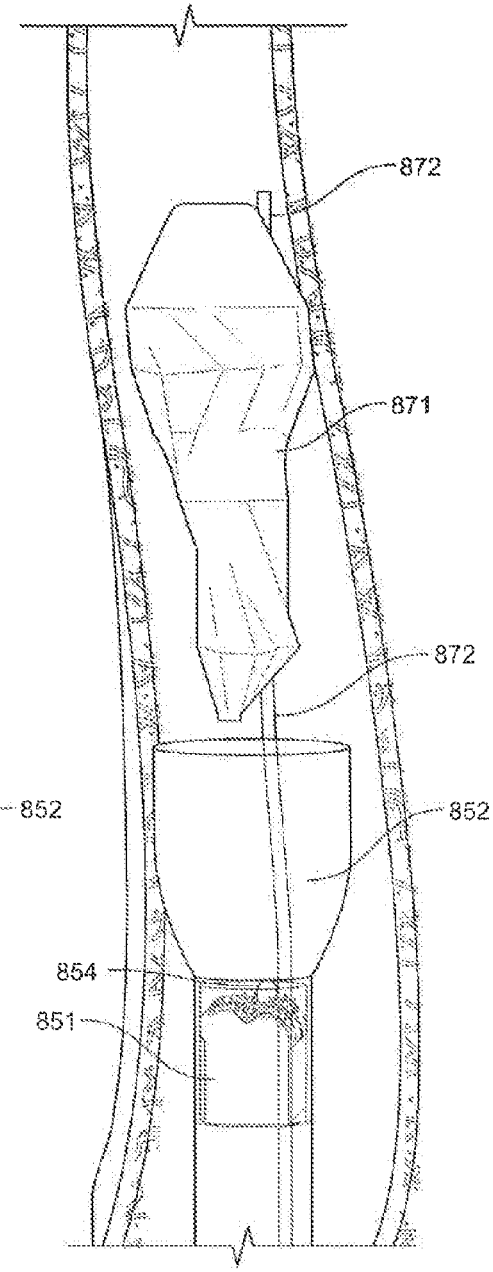

FIGS. 52A-52F illustrate the use of the devices of FIGS. 50A-50B and 51A-51B in a thrombectomy application. FIG. 52A depicts the device of FIGS. 50A and 50B inserted into a vessel containing a thrombus 871 wherein the distal end 852 of the device is located in proximity to the thrombus. Next, in FIG. 52B, a guidewire or lumen 872 is extended through and from lumen 254 though and beyond the distal end of the thrombus. In FIG. 52C the closed expander 862C is shown extending beyond the distal end of the thrombus after which it is manipulated to attain open state 862E. In FIG. 52E, the thrombus is shown being drawn in to the catheter so that it may be macerated by the shredder 854. FIG. 52F shows the state of the process after partial destruction and removal of the thrombus has occurred with a portion of it 871S being drawn down the lumen 851. Continued process will result in complete maceration of the thrombus or at least sufficient maceration to allow extraction of the remaining portion to safely occur (e.g. via entrapment in the distal end 852 of lumen 851.

FIGS. 53A-53D show another exemplary embodiment of a tissue removal device. Device 5310 may employ any of the cutting heads described herein, or other suitable cutting heads. In some embodiments, a double rotor shredding head is employed at the distal end of device 5310 to selectively debride tissue down to the cellular level.

In this exemplary embodiment, handheld device 5310 includes a stepper motor 5312 at its proximal end. In other embodiments, other types of electric, pneumatic or hydraulic motors, servos, or other prime movers may be used. The proximal end of motor 5312 may be provided with a manually turnable thumbwheel 5314, as shown. In this embodiment, the distal output end of motor 5312 is provided with a housing 5316, which is made up of a front cover 5318 and a rear cover 5320. Located distally from housing 5316 are an outer shaft housing 5322, an outer shaft lock seal 5324, and a support clamp 5326. A non-rotating, outer support tube 5328 extends from within the proximal end of device 5310 towards the distal end of the device. Within support tube 5328, a rotating drive tube 5330 (best seen in FIGS. 53B and 53C) also extends from within the proximal end of device 5310 towards the distal end of the device. The support tube 5328 and inner drive tube 5330 may collectively be referred to as an introducer. A cutter head assembly 5332, subsequently described in detail, is attached to the distal end of support tube 5328.

Figure 53A:
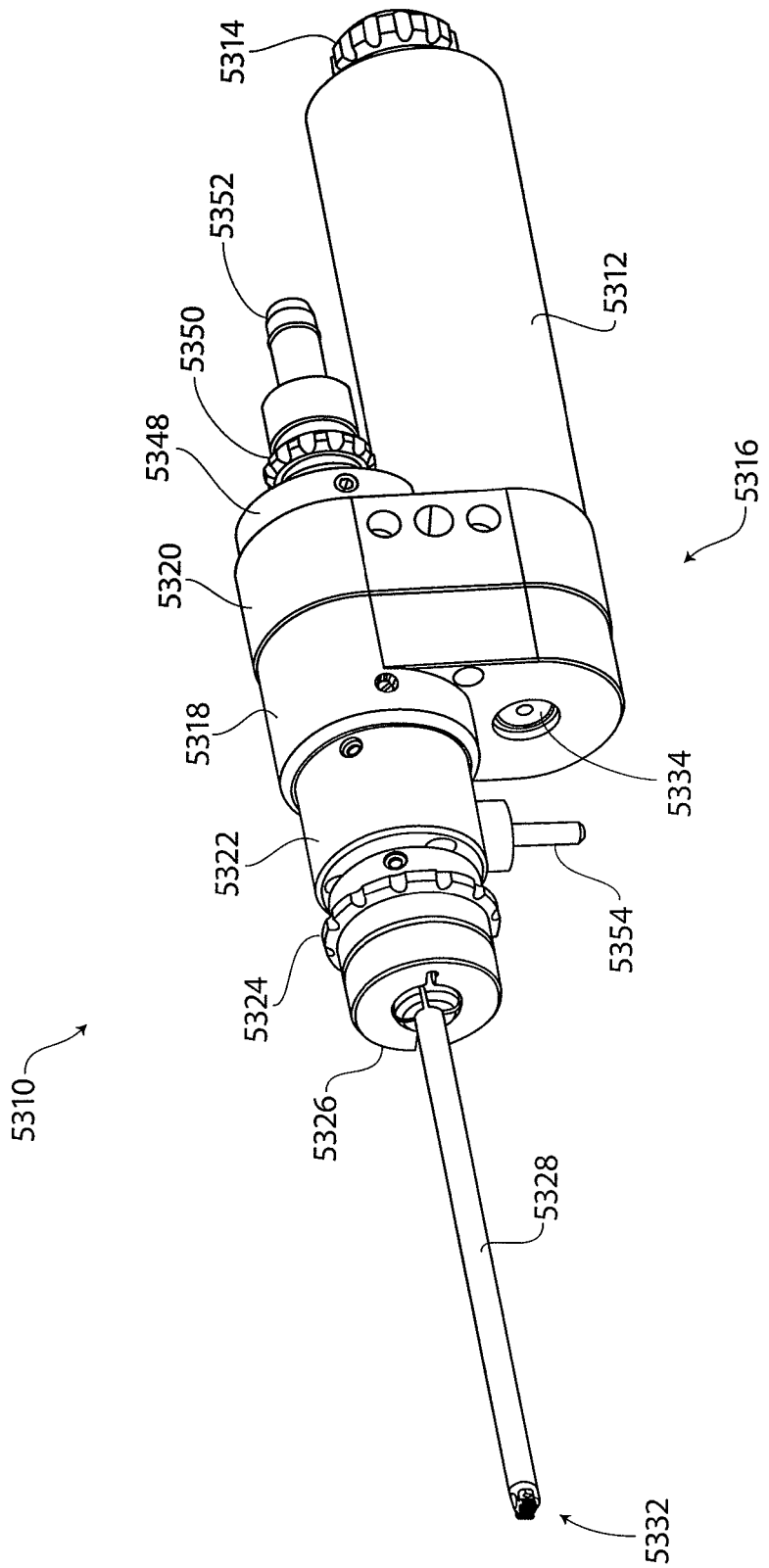
FIGS. 53A-53D show another exemplary embodiment of a tissue removal device.
Figure 53B:
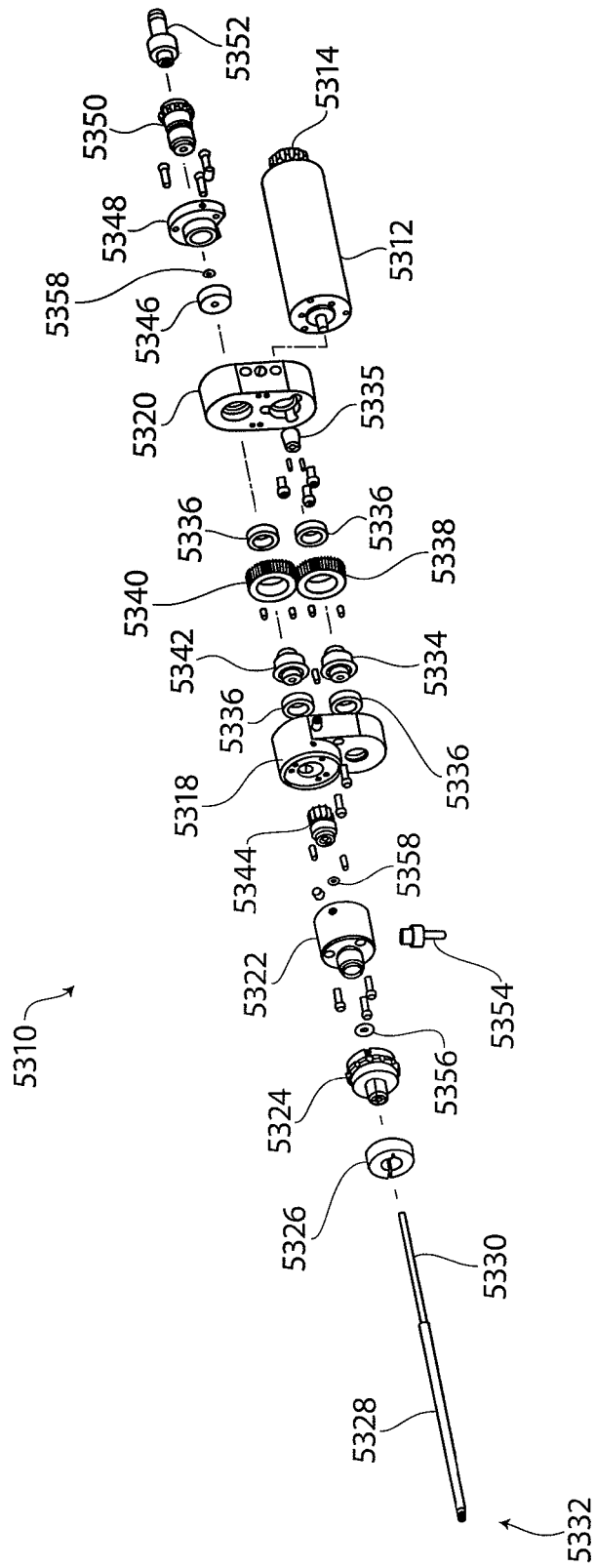

As best seen in FIG. 53B, other components of device 5310 include motor shaft drive axle 5334, motor dog 5335, four bearings 5336, drive gear 5338, driven gear 5340, inner drive shaft axel 5342, inner shaft lock seal 5344, vacuum gland disk 5346, vacuum seal lock housing 5348, vacuum seal lock 5350, vacuum hose barb 5352, irrigation fluid hose barb 5354, outer tube o-ring 5356, and two vacuum gland o-rings 5358. Various other pins, dowels, fasteners, set screws, ball detents, shims and wave disc springs are shown in the figures without reference numerals. As will be appreciated by those skilled in this art, these non-referenced components serve to align, retain and ensure the proper functioning of the other components of exemplary device 5310.

Figure 53C:
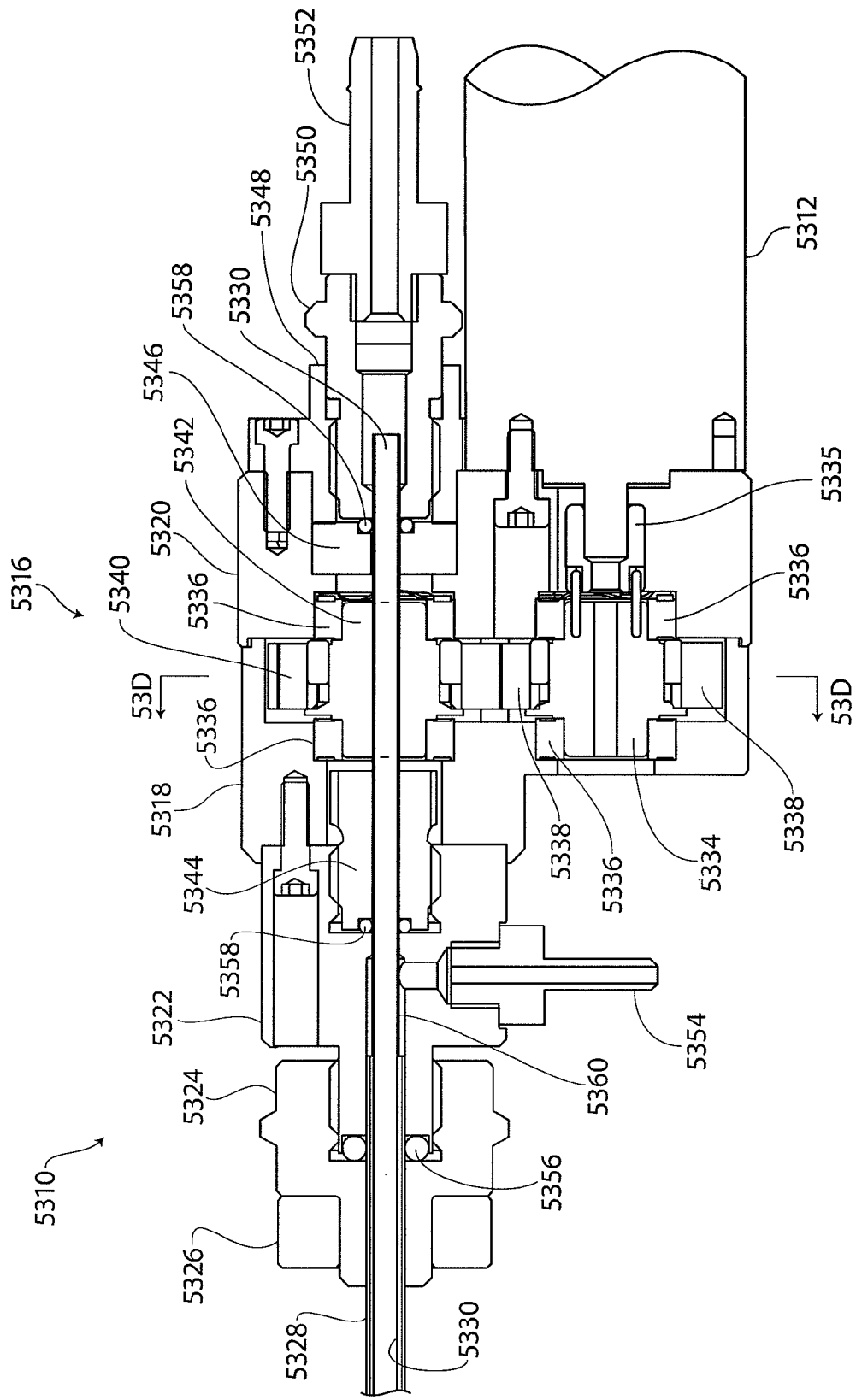
Figure 53D:
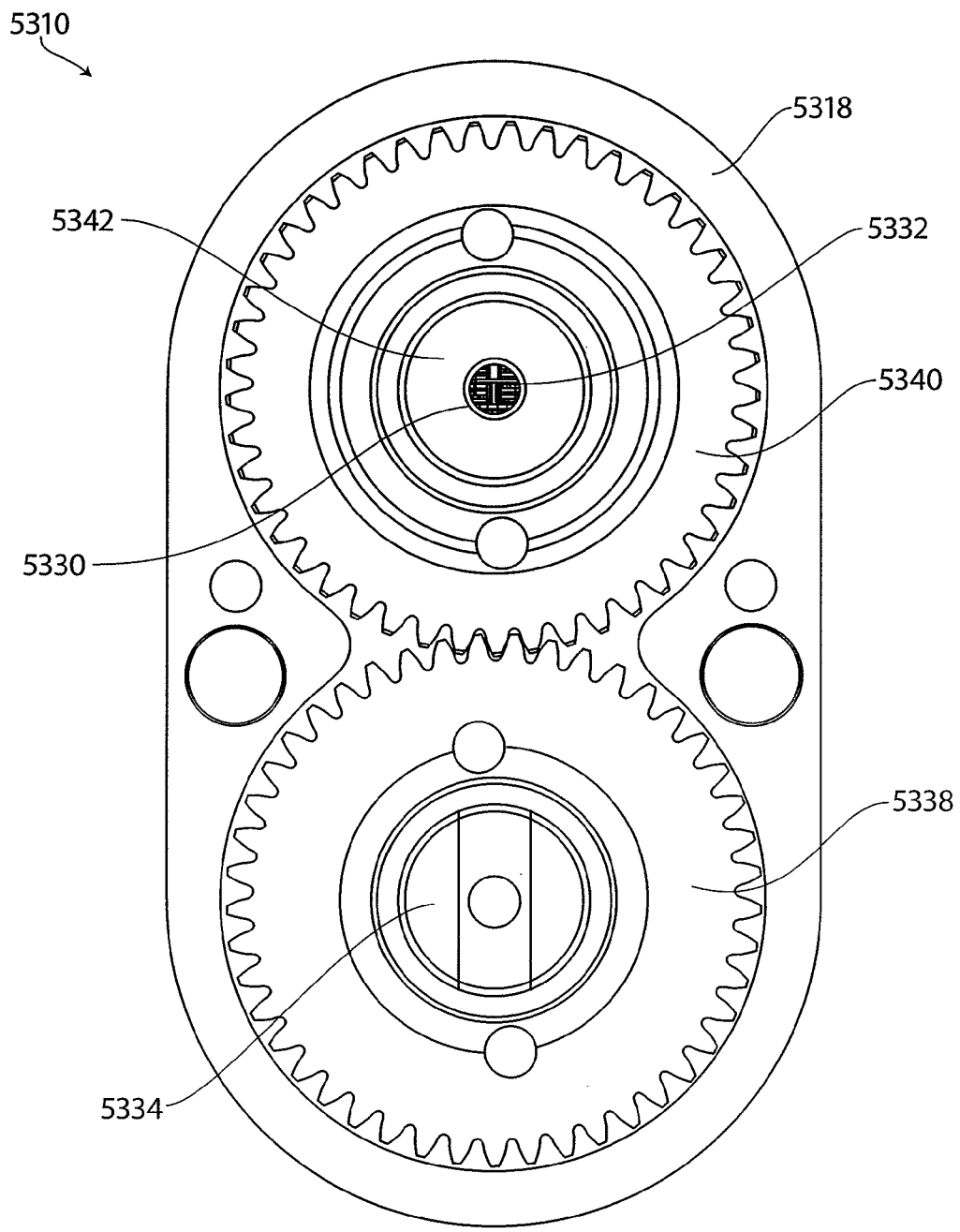

The two rotors of cutter head assembly 5332 located at the distal end of device 5310 are driven by motor 5312 through drive tube 5330 and other drive components of device 5310, as will now be described in more detail. As best seen in FIGS. 53B and 53C, a motor dog 5335 is attached to the output shaft of motor 5312. Motor dog 5335 is coupled to motor shaft drive axle 5334, which is rotatably mounted in housing 5316 with two bearings 5336. Drive gear 5338 is rigidly fixed to motor shaft drive axle 5334, and drives driven gear 5340 (as best seen in FIG. 53D.) Driven gear 5340 is rigidly fixed to inner drive shaft axel 5342, which is rotably mounted in housing 5316 with two bearings 5336. Inner rotating drive tube 5330 passes through the center of inner drive shaft axel 5342 and is rotatably fixed thereto. Drive tube 5330 extends from the proximal end of device 5310 to the distal end of the device through the non-rotating outer support tube 5328. The distal end of drive tube 5330 (or a separate tube 5330'attached thereto) is provided with crown teeth around its periphery, as shown in FIGS. 54B and 56C, for meshing with drive gear 5410. As drive tube 5330 is rotated about a longitudinal axis of device 5310 by motor 5312 through the above-described drive train components, it drives drive gear 5410 about an axis that is perpendicular to the longitudinal axis, as can be appreciated by viewing FIG. 56C. Drive gear 5410 in turn drives other components of the cutter head assembly, as can he appreciated by viewing FIG. 56E, and as is subsequently described in more detail.

In some embodiments motor 5312 is provided with feedback control for rotational velocity and torque. These two parameters can be used for controlling and monitoring changes in rotational velocity and the torque load. For measuring rotational velocity, an encoder may be located at one or more of the cutter rotors, at the drive motor, or at another location along the drive train between the drive motor and cutter rotors. In some embodiments, the encoder is located at or close to the rotors to avoid backlash associated with the drive train, thereby making the velocity monitoring more responsive and accurate. Encoder technologies that may be used include optical, resistive, capacitive and/or inductive measurement. To sense torque load, one or more strain gages may be located at the cutter rotors, at the drive motor, or at another location along the drive train between the drive motor and cutter rotors. Torque load may also be sensed by monitoring the current being drawn by the motor. By sensing changes in velocity and/or torque, a controller associated with device 5310 can determine that the cutter rotors are passing from one tissue type to another and take appropriate action. For example, the controller can sense when the cutter elements are passing from soft to hard tissue, from hard to medium density tissue, or from a cutting state to non-cutting state. In response to these changes, the controller and/or device 5310 can provide audio, visual and/or tactile feedback to the surgeon. In some embodiments, the controller can change the velocity, direction or stop cutter rotors from rotating in response to velocity and/or torque feedback. In one embodiment of the invention, a typical cutting rotor speed is on the order of 100 to 20,000 rotations per minute, and a typical torque load is on the order of 0.25 to 150 mN-meter. Other sensors, such as a pressure sensor or strain sensor located at the distal tip of device 5310, may also be utilized to provide feedback that tissue cutting elements are moving from one tissue type to another. In some embodiments, an impendence sensor may be located at the distal tip of the device, to sense different tissue types or conditions, and provide corresponding feedback for tissue cutting control when the tissue being cut by the cutter head changes. Such a pressure sensor feedback control arrangement can be used with types of cutting devices other than those disclosed herein.

Referring now to FIG. 53C, irrigation fluid hose barb 5354 is provided on the lower side of outer shall housing 5322 of exemplary device 5310. Hose barb 5354, or a similar fluid line coupling, may be connected to a supply of irrigation fluid. The lumen of hose barb 5354 is in fluid communication with an internal irrigation fluid cavity 5360. Fluid cavity 5360 surrounds internal drive tube 5330, and is bounded on its proximal end by o-ring seal 5358 around drive tube 5330. Fluid cavity 5360 is hounded on its distal end by o-ring seal 5356 around outer support tube 5328. This arrangement allows drive tube 5330 to rotate, but constrains irrigation fluid delivered from hose barb 5354 to travel only through the annular space defined by the outer surface of drive tube 5330 and the inner surface of support tube 5328. Irrigation fluid may thus flow distally through the annular space to the distal end of device 5310.

Figure 55A:
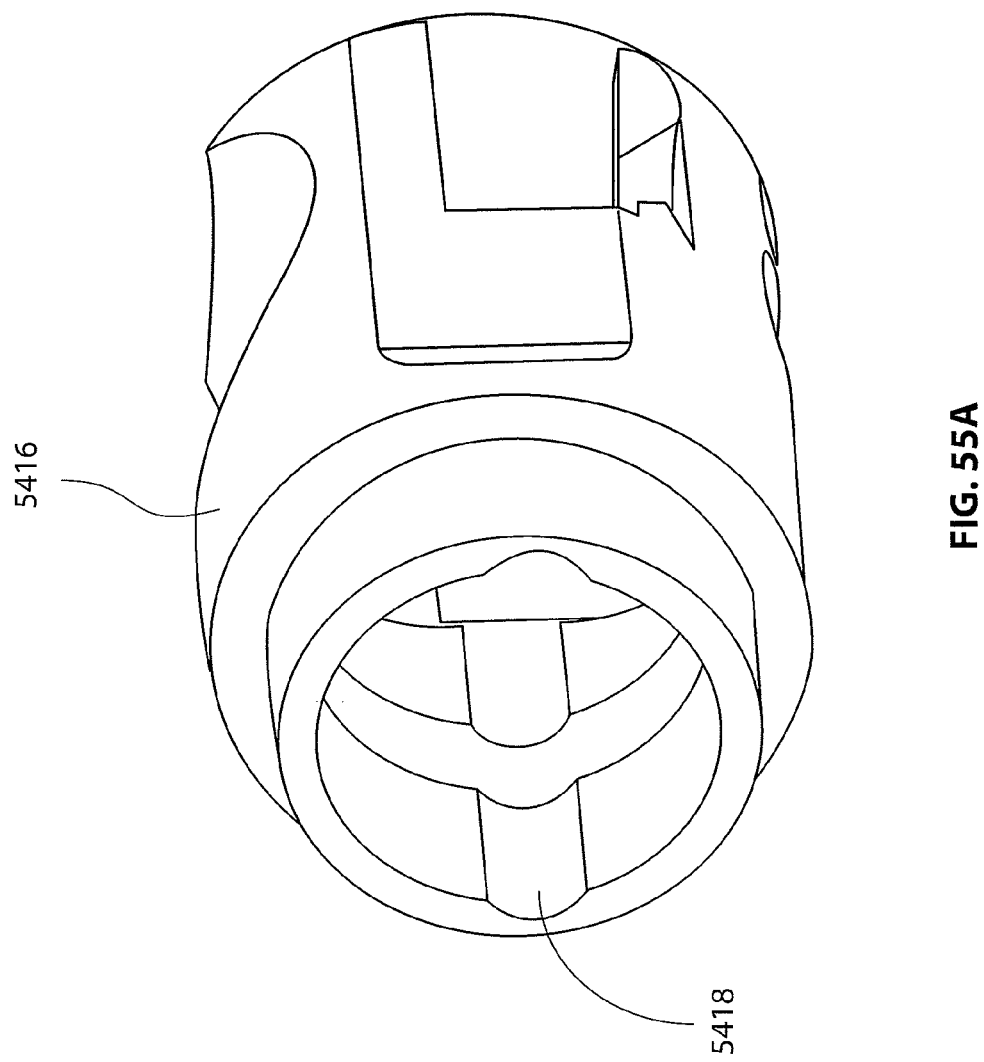
FIGS. 55A-55D show further details of the lug bearing of cutter head assembly 5332, shown in FIGS. 54A-54C.
Figure 55B:
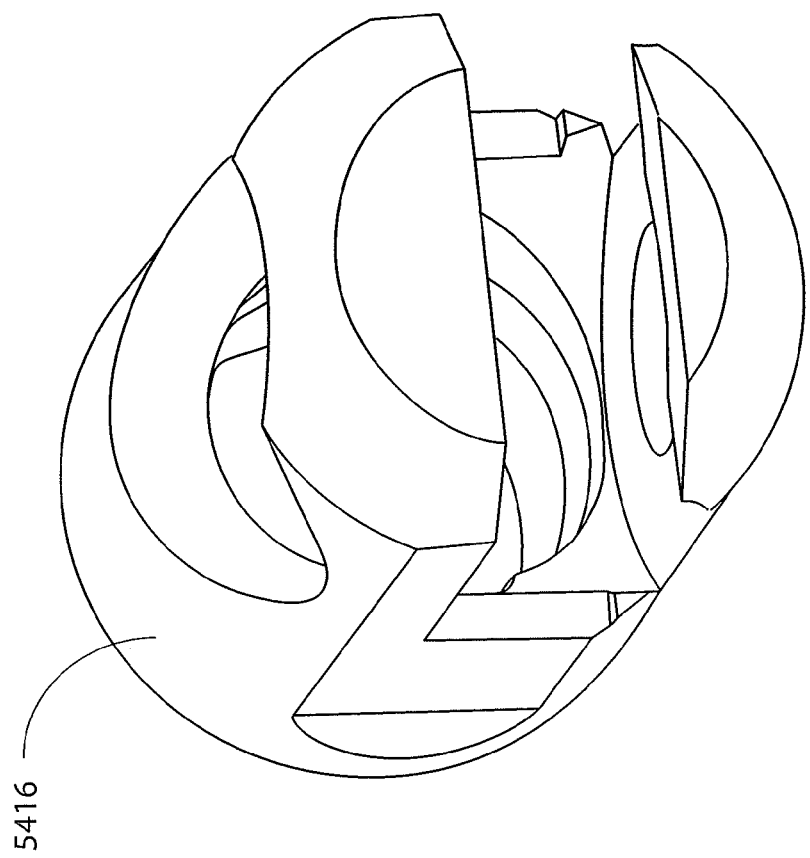
Figure 55C:
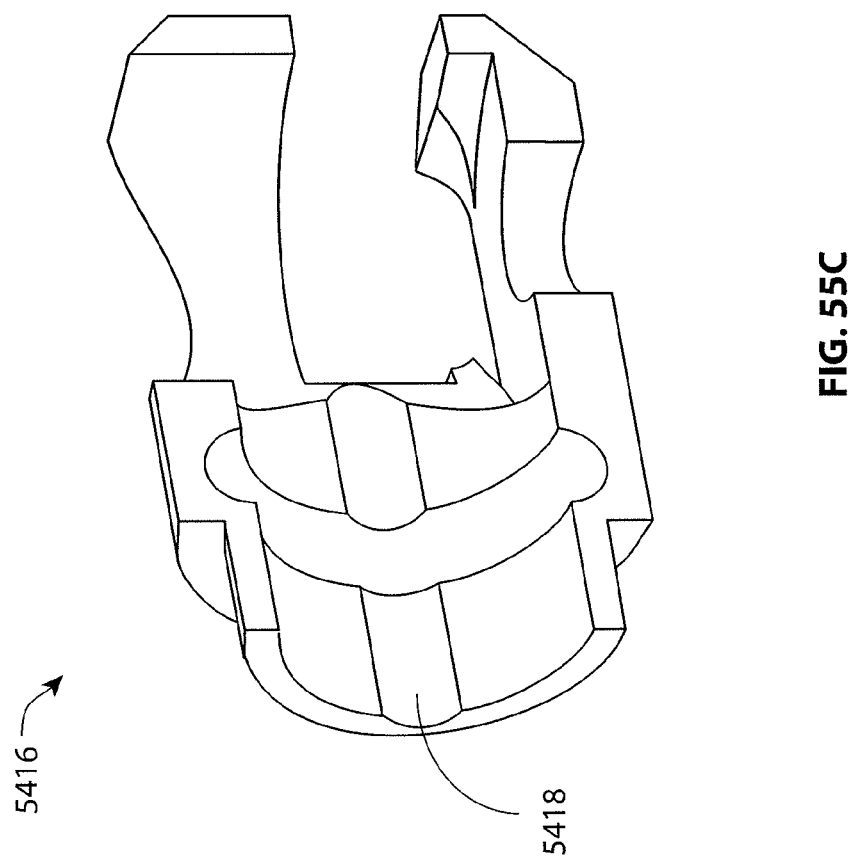
Figure 55D:
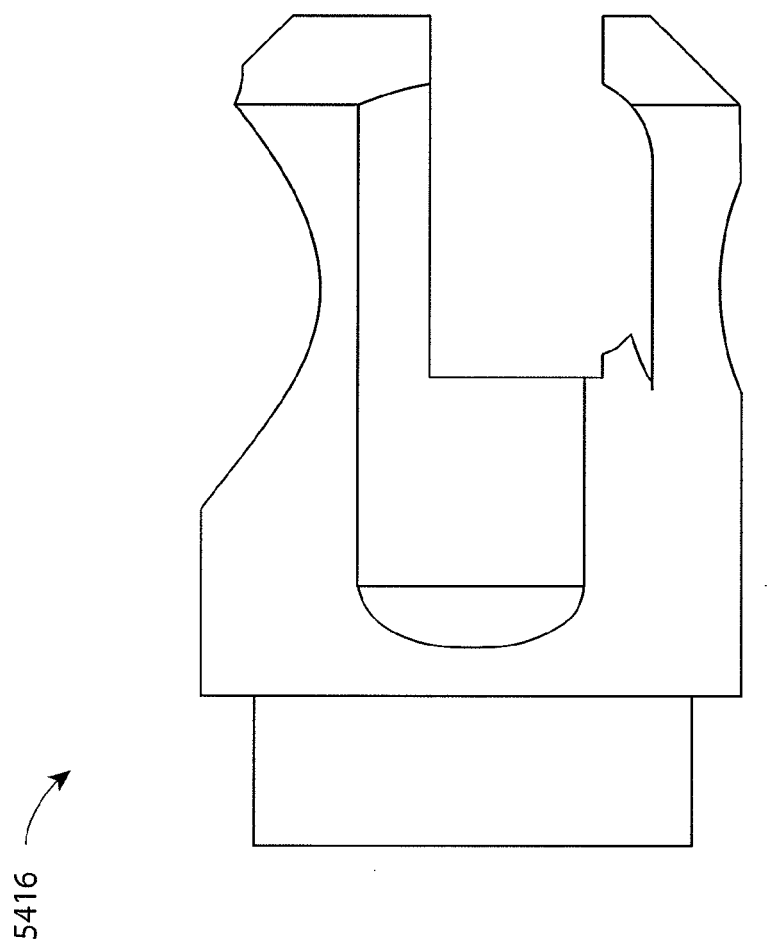
Figure 56A:
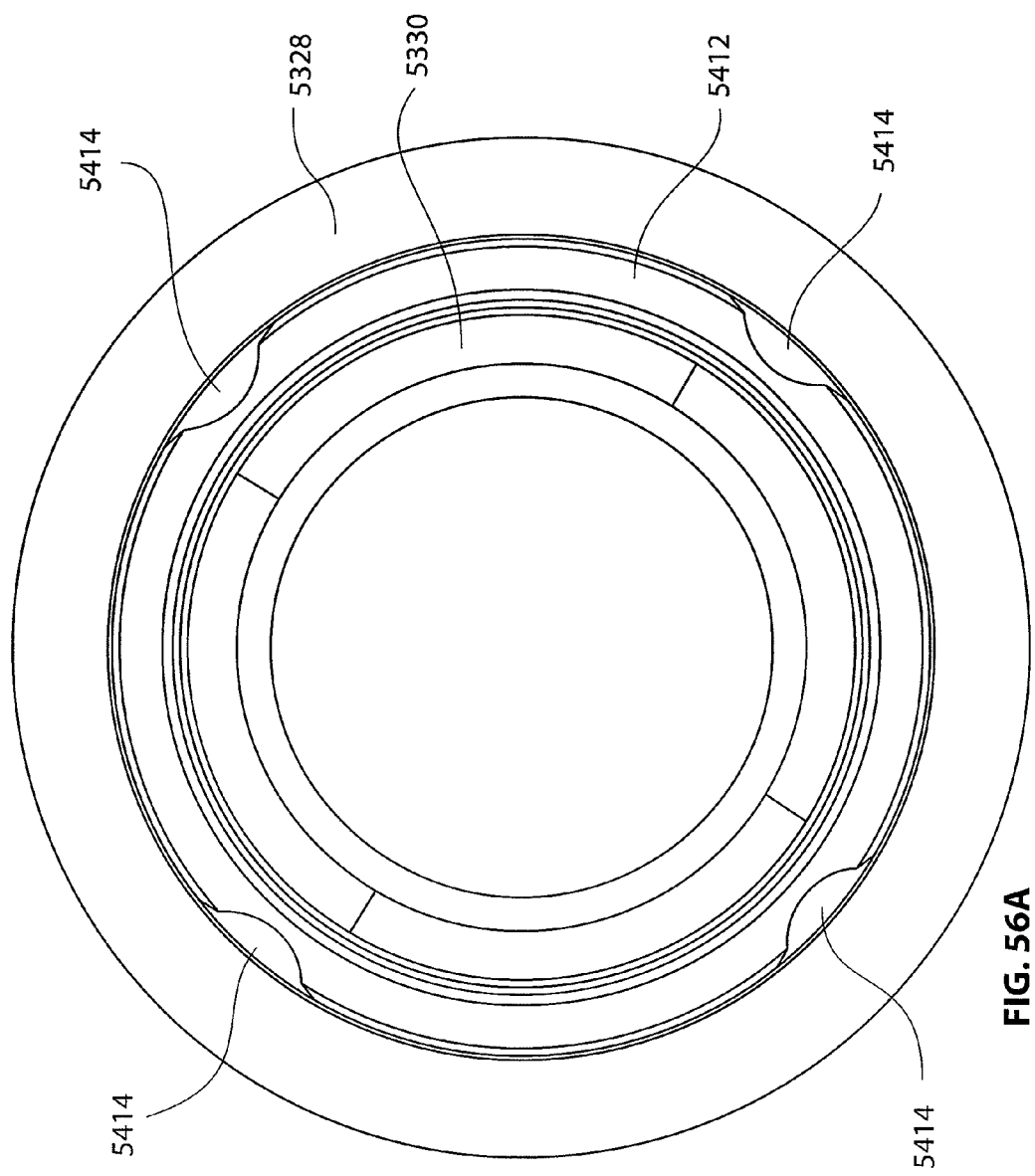
FIGS. 56A-56H show further details of cutter head assembly 5332, shown in FIGS. 54A-54C.
Figure 56B:
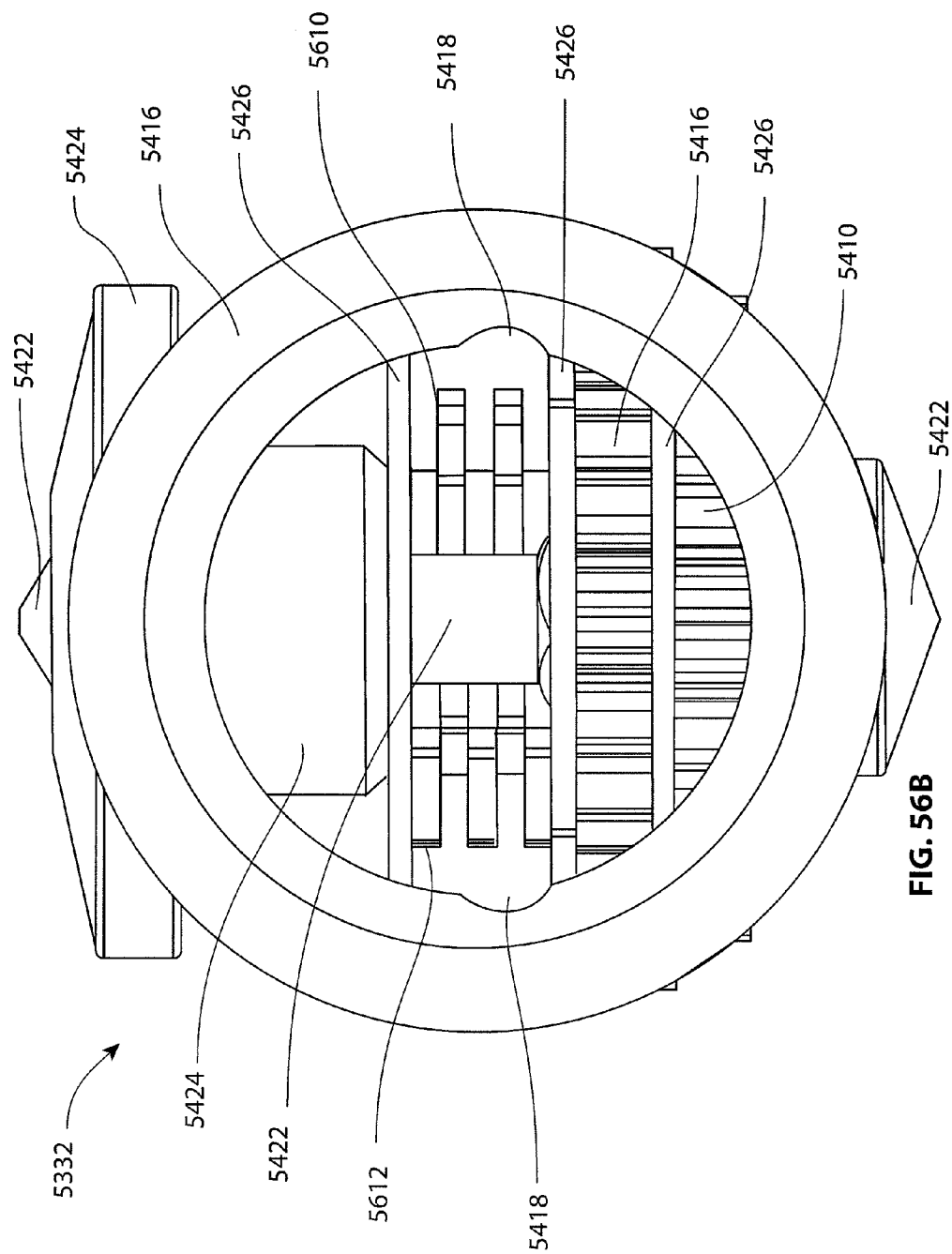
Figure 56C:
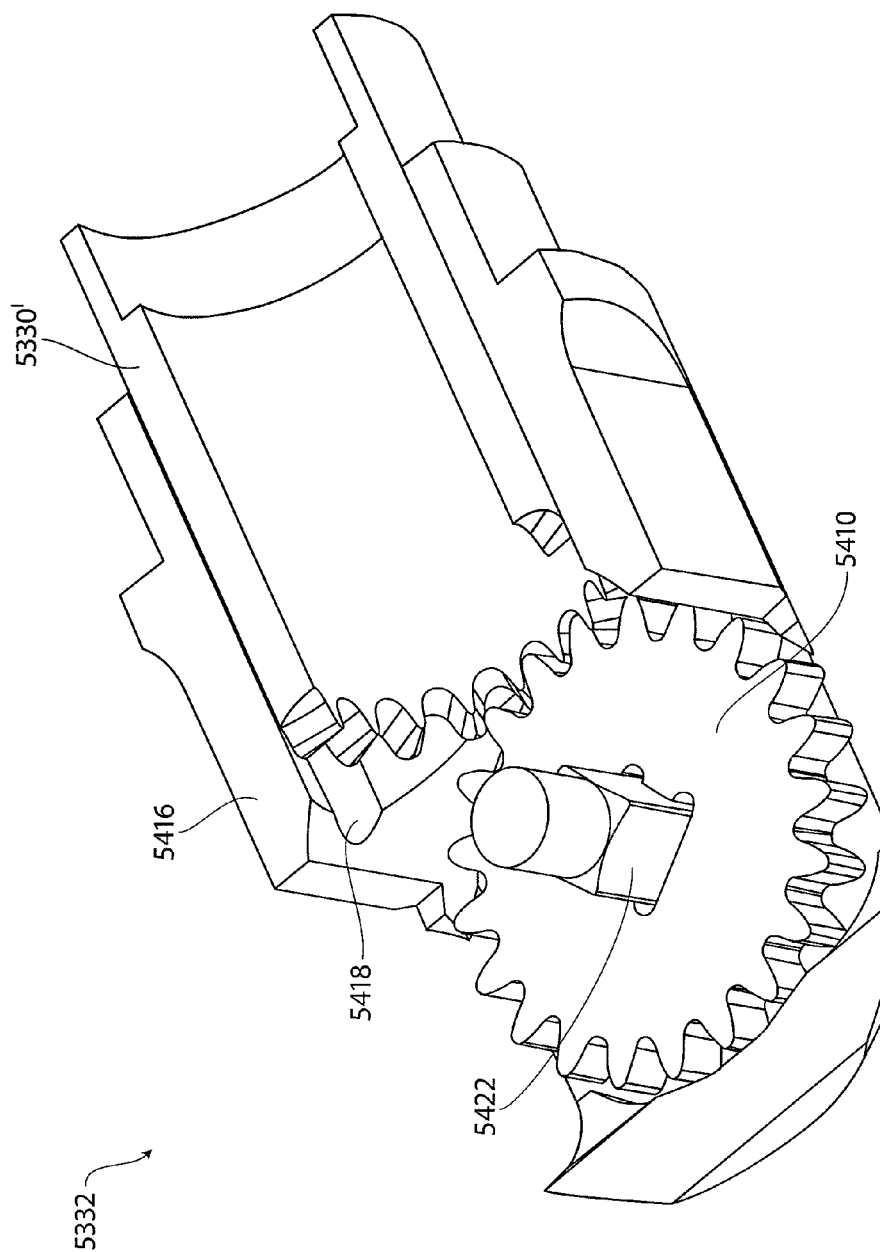

As shown in FIGS. 54B and 56A, one or more drive aligner rings 5412 may be provided between outer support tube 5328 and inner drive tube 5330 along their lengths to support drive tube 5330 as it rotates. In order to allow the flow of irrigation fluid between the tubes 5328 and 5330, rings 5412 may be provided with one or more channels 5414 as shown. When the distal flow of irrigation fluid reaches the cutter head assembly 5332, it continues to flow distally into lug 5416. To enable the fluid flow, lug 5416 is provided with fluid channels 5418 located along the outer walls of its central bore, as best seen in FIGS. 54C, 55C. As can be appreciated by viewing FIG. 56C, irrigation fluid passes distally between inner drive tube 5330 and lug 5416 through channels 5418 (only one channel shown in FIG. 56C). As shown in FIG. 56B, irrigation fluid flowing distally through channels 5418 is directed toward the outside portions of cutting elements. In this embodiment, the outside portions of cutting elements are rotating distally, away from the fluid flow, while the inside portions of cutting elements are rotating proximally, toward the center of lug 5416 and drive tube 5330.

In some embodiments, the irrigation fluid serves multiple functions. The irrigation fluid can serve to lubricate the cutting elements, drive gears, journal bearings and other components as the parts rotate. The irrigation fluid can also serve to cool the cutting elements and/or the tissue being cut, absorbing heat and carrying it away as the irrigation fluid is removed from the patient. The fluid can serve to flush tissue particles from the moving parts to prevent them from becoming clogged. The fluid can also serve to carry away the tissue portions being cut and remove them from the target tissue site. In some embodiments, the irrigation fluid is discharged from the cutting device and may be removed from the target tissue site with other, traditional aspiration means. With the current exemplary cutting device 5310, however, the irrigation fluid and/or other bodily fluids may be removed from the target tissue site by the cutting device 5310, as will now be described in detail.

As previously described, irrigation fluid may be delivered to cutting elements and/or a target tissue site through device 5310. Exemplary device 5310 is also constructed to remove the irrigation fluid and tissue portions cut from the target tissue site through the shaft of device 5310. As can be appreciated by viewing FIGS. 56B and 56F, the two interleaving stacks of cutting elements, also referred to as rotors 5610 and 5612, have an overlapping section 5614 in the center of cutter head assembly 5332. The two rotors 5610 and 5612 may be rotated in opposite directions (as depicted by arrows A and B in FIG. 56F) such that each rotor engages target tissue and pulls it towards the central overlapping section 5614. In overlapping section 5614, the tissue is shredded into small pieces by the interdigitated cutting elements, as is subsequently described in more detail. The small tissue portions are generally propelled in a proximal direction by rotors 5610 and 5612, away from the target tissue site and into the cutter head assembly 5332. As can be appreciated by viewing FIG. 56B, the shredded tissue portions emerge from rotors 5610 and 5612 substantially along the central axis of lug 5416 (and therefore also the central axis of drive tube 5330. With sufficient irrigation fluid being supplied to the tissue cutting area, and sufficient aspiration being provided from the proximal end of the device, irrigation fluid around rotors 5610 and 5612 carries the cut tissue particles proximally down the center of drive tube 5330. As shown in FIG. 53C, the proximal end of drive tube 5330 is in fluid communication with hose barb 5352 located at the proximal end of device 5310. A traditional aspiration device or other suction source may be attached to device 5310 through hose barb 5352 or other suitable fluid coupling to collect the spent irrigation fluid and cut tissue portions.

In some embodiments, the cut tissues portions emerging from hose barb 5352 may be collected for testing. The tissue portions may be separated from the irrigation fluid, such as by centrifugal force, settling and/or filtering. The tissue portions may be measured to precisely determine the mass and/or volume of tissue removed. The pathology of some or all of the tissue portions may also be determined. In some embodiments, the above testing may be performed during a surgical procedure so that results of the testing may be used to affect additional stages of the procedure.

According to aspects of the invention, the inside diameter of drive tube 5330 may be much larger than the maximum dimension of the tissue portions traveling through it. In some embodiments, the maximum tissue dimension is less than about 2 mm across. In one exemplary embodiment, the inside diameter of drive tube 5330 is about 3 mm, the outside diameter of the support tube 5328 is about 5.6 mm, and the maximum dimension of the tissue portions is about 150 microns. In another exemplary embodiment, the inside diameter of drive tube 5330 is about 1.5 mm, the outside diameter of the support tube 5328 is about 2.8 mm, and the maximum dimension of the tissue portions is about 75 microns. In other embodiments, the inside diameter of drive tube 5330 is between about atm and about 6 mm. In some embodiments, the maximum dimension of the tissue portions is at least one order of magnitude less than a diameter of the tissue removal lumen. In other embodiments, the maximum dimension of the tissue portions is at least twenty times less than a diameter of the tissue removal lumen. In some embodiments, the maximum dimension of the tissue portions is less than about 100 microns. In other embodiments, the maximum dimension of the tissue portions is about 2 microns.

Figure 54A:
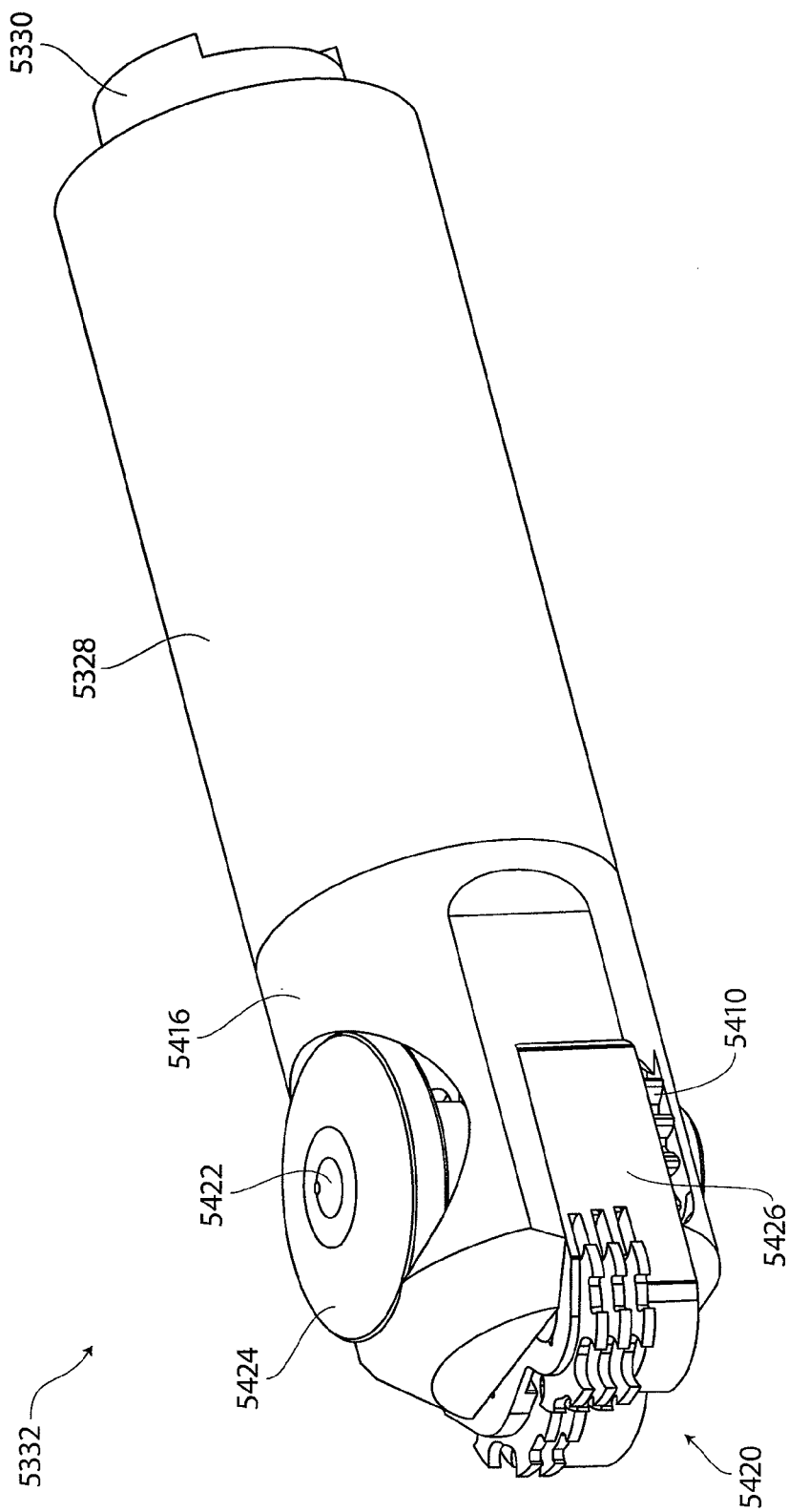
FIGS. 54A-54C show an exemplary cutter head assembly 5332 that may be used with debriding device 5310, shown in FIGS. 53A-53D.
Figure 54B:
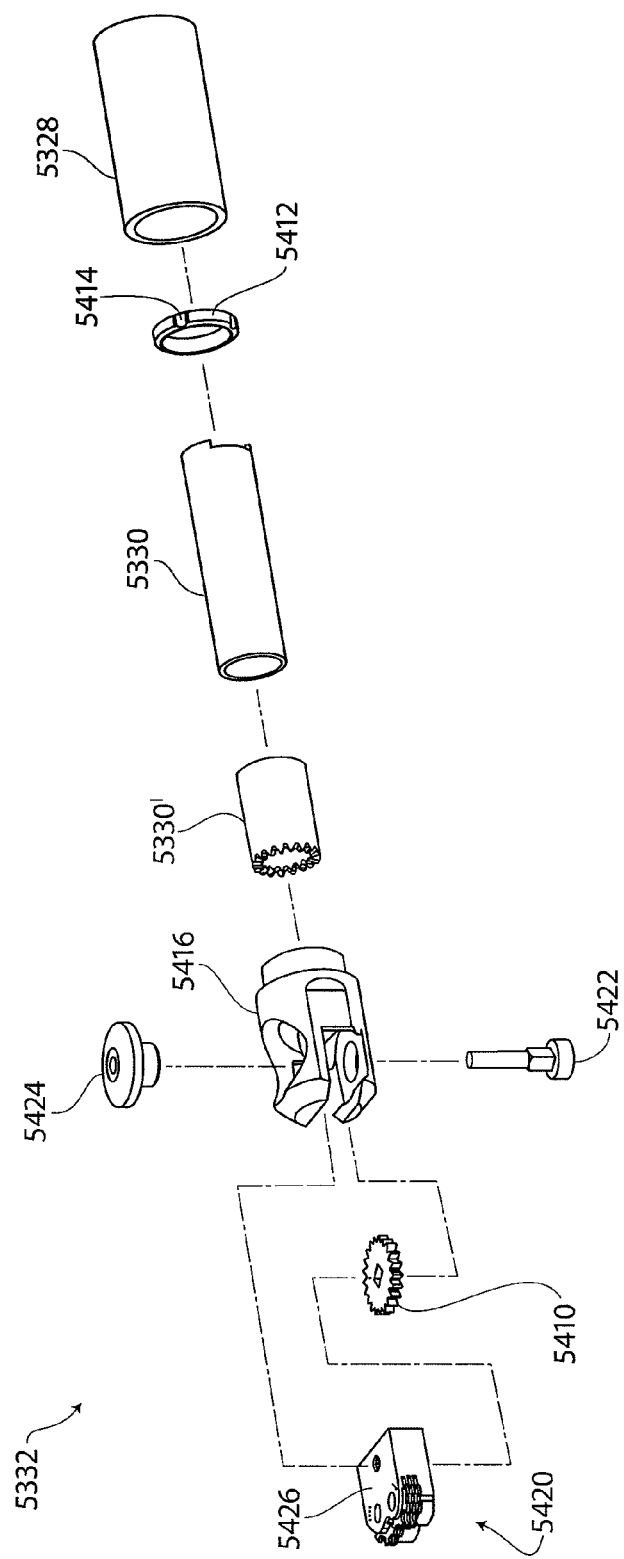
Figure 54C:
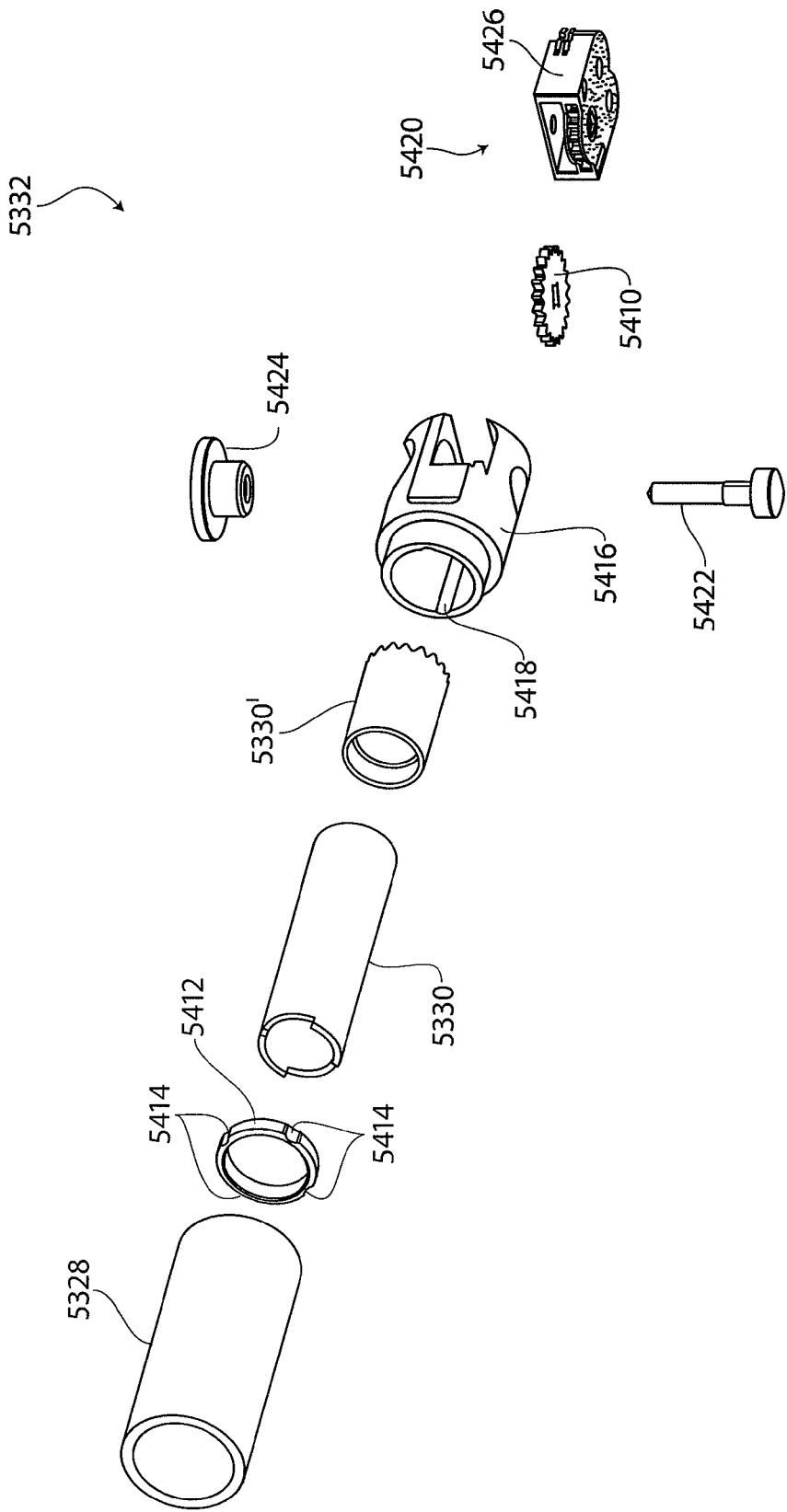
Figure 56D:
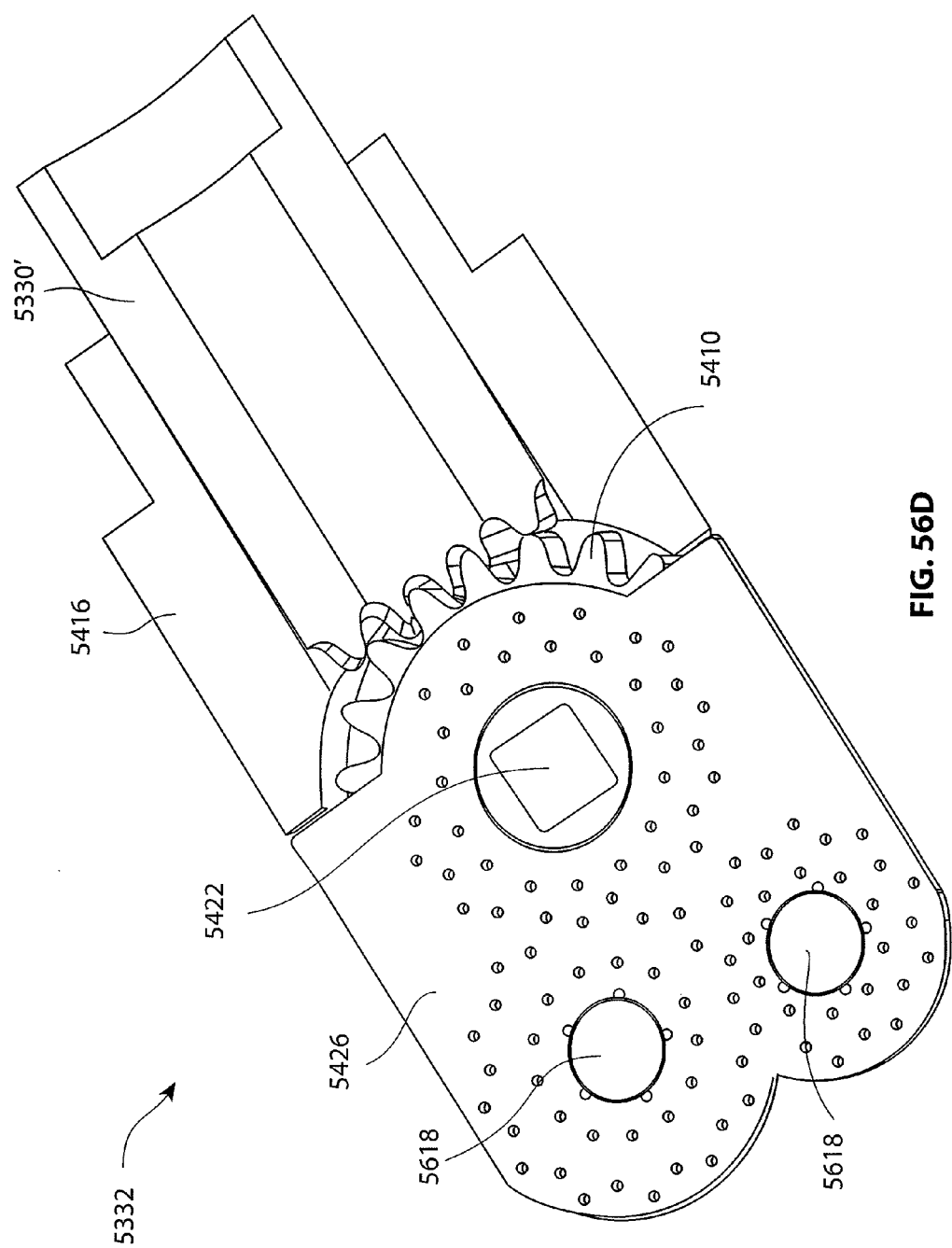
Figure 56E:
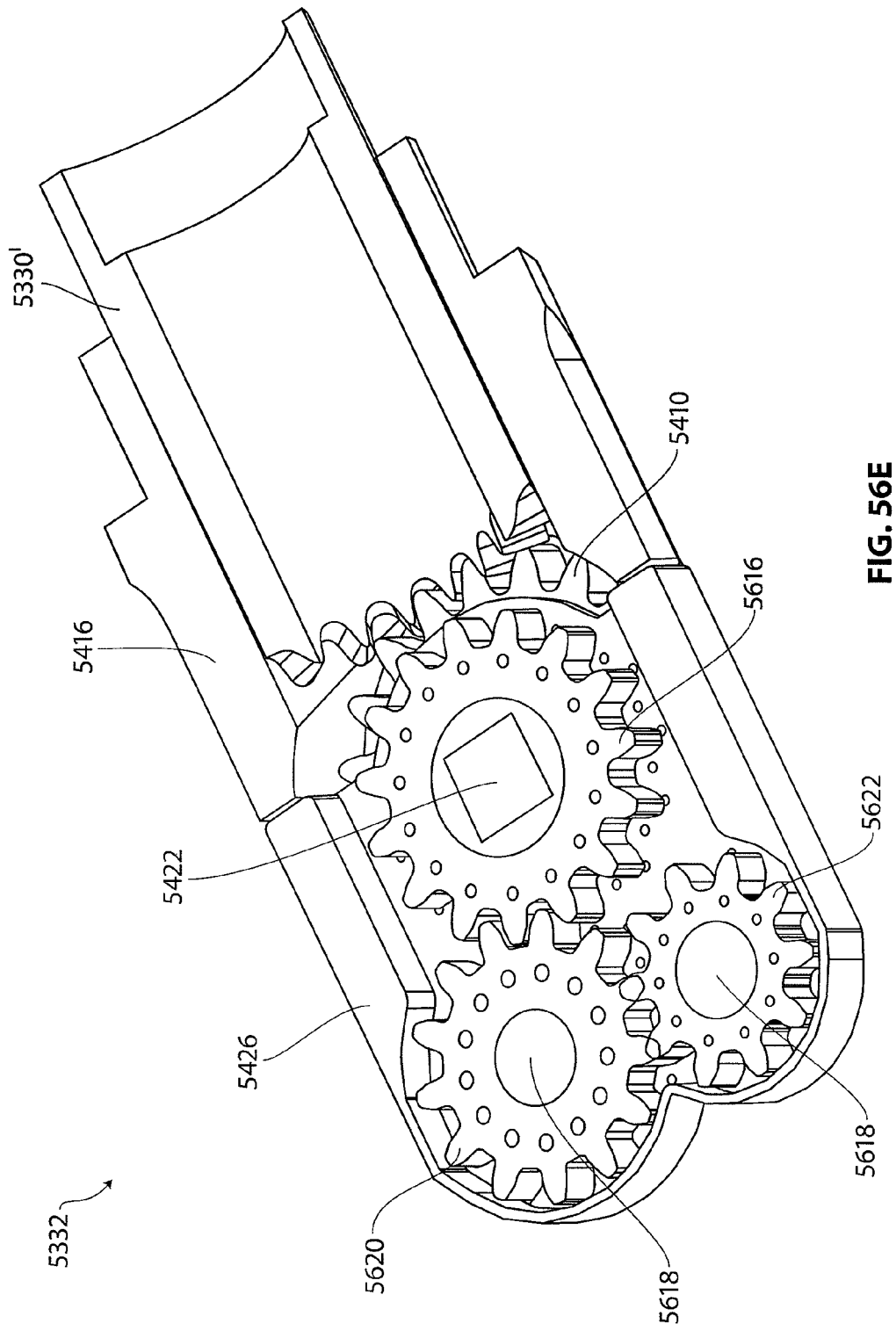
Figure 56F:
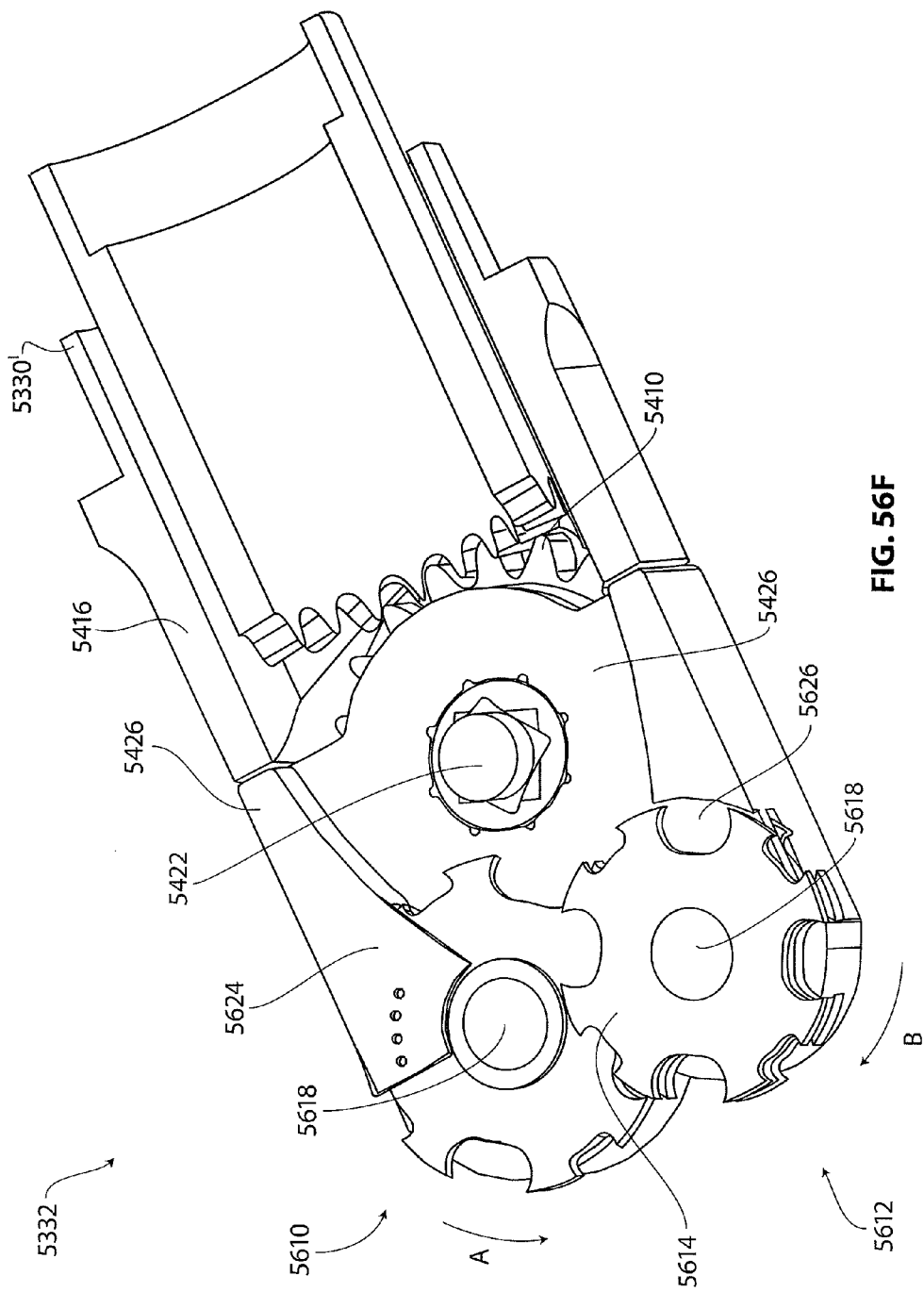
Figure 56G:
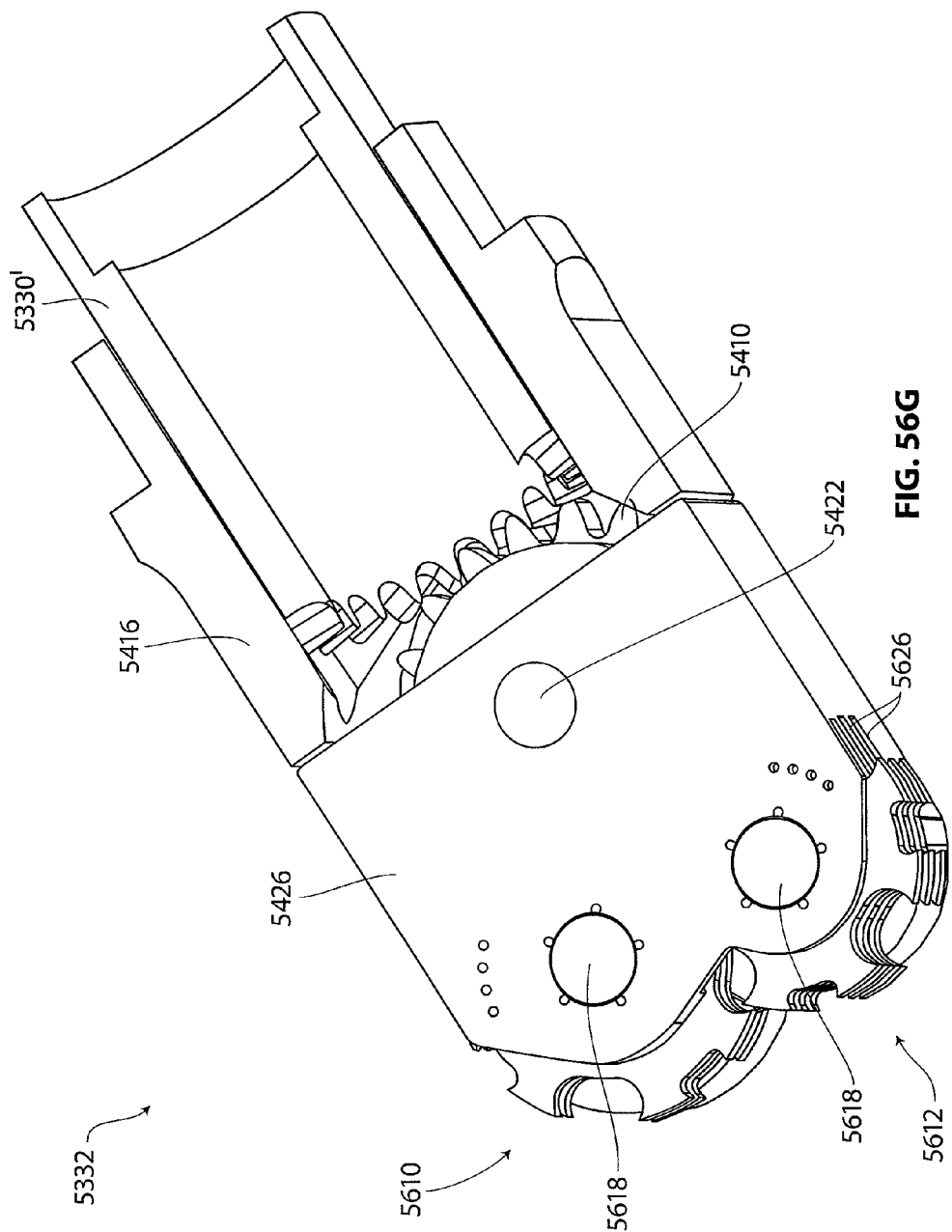
Figure 56H:
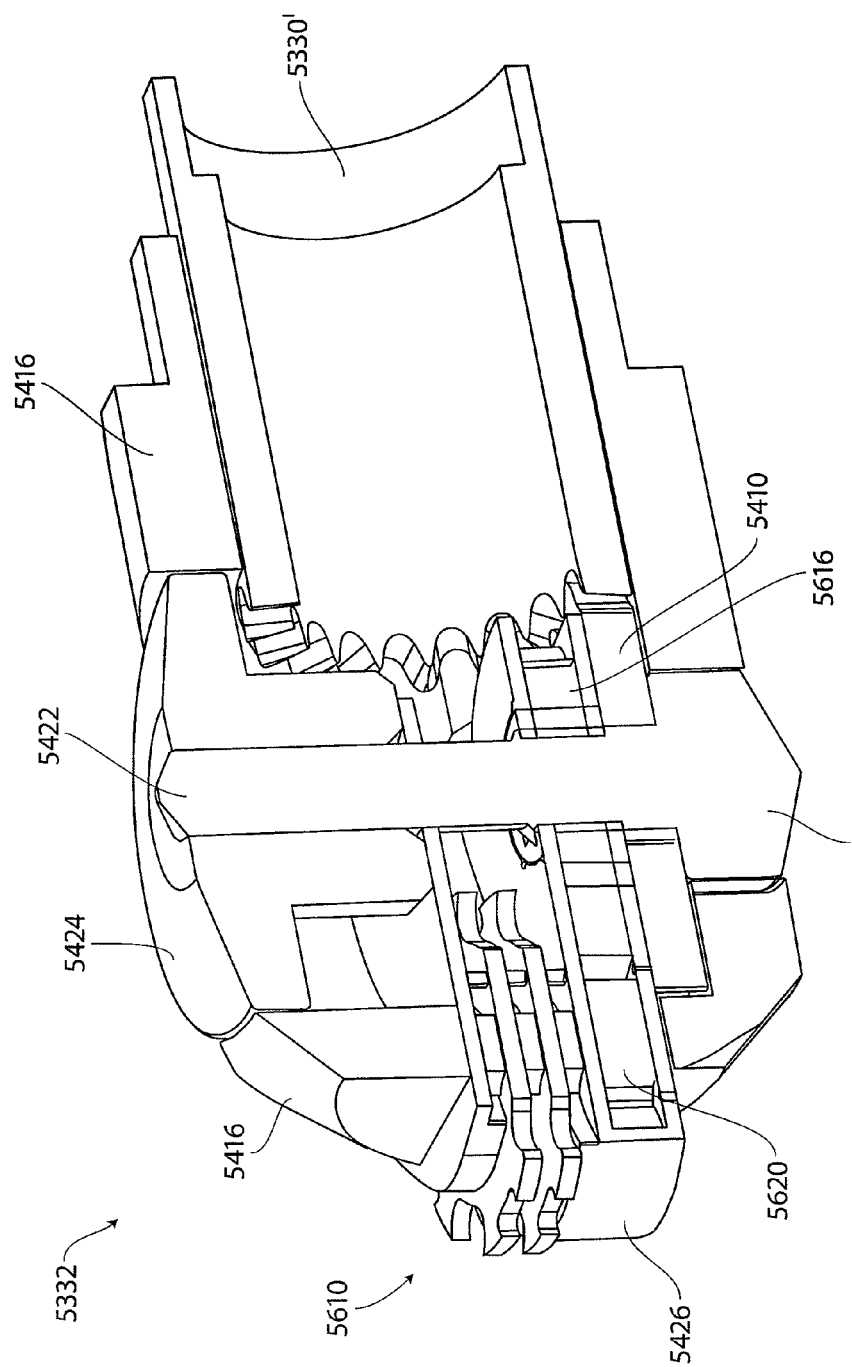

Referring now to FIGS. 54A-54C, an exemplary cutter head assembly 5332 is described in more detail. Cutter head assembly 5332 may be used with debriding device 5310, shown in FIGS. 53A-53D. As best seen in FIG. 54B, cutter head assembly 5332 includes lug 5416, drive gear 5410, rotor housing assembly 5420, aligner pin 5422, and aligner cap 5424. Lug 5416 is provided with a cutout on its distal end for receiving rotor housing assembly 5420. Beneath the rotor housing cutout, lug 5416 has a circular recess for receiving drive gear 5410. A bore is provided in the bottom of lug 5416 for receiving the head of aligner pin 5422. When cutter head 5332 is assembled, the shank of aligner pin 5422 passes through the bore of lug 5416, through a square aperture in the center of drive gear 5410, through a bore in the proximal end of rotor housing assembly 5420, and into a large diameter bore through the top of lug 5416. Aligner cap 5424 is received with the large diameter bore in the top of lug 5416, and is fastened to aligner pin 5422 by a press fit, weld, threads, a separate fastener, or other suitable means. In this assembled arrangement, best seen in. FIG. 56H, pin 5422 and cap 5424 retain rotor housing 5426 from moving longitudinally relative to the central axis of the instrument, and rotor housing 5426 and drive gear 5410 retain pin 5422 and cap 5424 from moving radially relative to the central axis of the instrument. Pin 5422 and cap 5424 spin together as a unit relative to lug 5416, and serve to align drive gear with the distal end of drive tube 5330', as previously described. Pin 5422 also serves to transmit torque from drive gear 5410 to gear 5616, which resides inside the rotor housing directly above drive gear 5410, as shown in FIG. 56H.

FIGS. 55A-55D show further details of lug bearing 5416, which forms the base of cutter head assembly 5332, shown in FIGS. 54A-54C. As subsequently described in further detail, various different cutter heads may alternately be inserted into and securing within the slot shaped opening in the distal end of the lug bearing.

FIGS. 56A-56H show the overall construction and operation of the various components of the rotor housing assembly 5420, and their interaction with the other components of the cutter head assembly 5332, shown in FIGS. 54A-54C. The device of this embodiment utilizes two front cutting rotors. The two rotors are driven inward toward one another at similar speeds. The rotors are situated approximately perpendicular to the inline axis. This device may be referred to as a shredder.

FIG. 56A is a distally looking axial view showing the relationship of outer support tube 5328, drive aligner ring 5412 and inner drive tube 5330. FIG. 56B is a distally looking axial view showing the relationship between rotor housing

5426, lug 5416, and other components of the cutter head assembly 5420. FIGS. 56C-56G are a series of oblique, cross-sectional views taken at various elevations through the cutter head assembly 5332, showing the various layers of components progressing from the bottom to the top of the assembly. Starting with FIG. 56C, lug 5416 and drive tube 5330' are shown in cross section with the rotor housing assembly 5420 removed to expose drive gear 5410. As previously described, drive gear 5410 resides in a circular cutout within lug 5416 and is driven by crown teeth located on the distal end of drive tube 5330, or a component 5330' connected to the distal end of drive tube 5330. Drive gear 5410 mates with a square shank portion of aligner pin 5422, which passes through a square aperture in the center of drive gear 5410, thereby rotatably driving pin 5422. FIG. 56D shows a bottom plate portion of rotor housing 5426 residing in its cutout within lug 5416 and covering most of drive gear 5410. A pair of apertures is provided through the bottom plate portion of rotor housing 5426 to rotatably receive axels 5618, 5618 from rotor assemblies 5610 and 5612. FIG. 56E shows gears 5616, 5620 and 5622 rotatably mounted on the bottom plate portion of rotor housing 5426. Gear 5616 has a square, central aperture for receiving the square shank portion of aligner pin 5422. As can be seen, gear 5622 meshes with gear 5620, which, in turn meshes with gear 5422. With this arrangement, drive tube 5330 or end component 5330' drives drive gear 5410, which drives aligner pin 5422, which drives gear 5616, which drives gear 5620, which drives gear 5622. Gears 5620 and 5622 each drive an axel 5618, which in turn drive rotors 5610 and 5612, respectively, in opposite directions as shown in FIG. 56F by arrows A and B. As can be seen in FIG. 56E, gear 5622 has a smaller pitch diameter than that of gear 5620 in this embodiment, which causes rotor 5612 to spin at a faster rotational velocity than that of rotor 5610. In other embodiments, the rotors may be driven at the same rotational velocity. As can be appreciated by viewing FIGS. 56E and 56F, a middle plate portion of rotor housing 5426 separates gears 5616, 5620 and 5622 (below the plate) from rotors 5610 and 5612 (above the plate). FIG. 56F shows rotor housing fins 5624 and 5626 interleaved between each of the blades of rotors 5610 and 5612, respectively. Fins 5624 and 5626 serve to guide cut tissue portions toward the center of drive tube 5330, rather than allow them to exit through the sides of the rotor housing and back into the patient. FIG. 56G shows the top plate portion of rotor housing 5426 covering most of rotors 5610 and 5612, with rotor axels 5618, 5618 and aligner pin 5422 protruding through. It can be seen by comparing FIGS. 56F and 56G that the blades of rotors 5610 and 5612 protrude further in the distal direction from the top plate portion of rotor housing 5426 than they do from the middle plate portion. In other embodiments, the protrusion distances can be equal, or reversed from those shown in FIG. 56G. In some embodiments, the blades may protrude from the housing by up to 500 microns. In other embodiments, the blades can be recessed from one or both portions of the rotor housing, as subsequently discussed in more detail.

FIG. 56H shows a cross-sectional view taken along a vertical centerline of the cutter head assembly 5332.

Figure 57A:
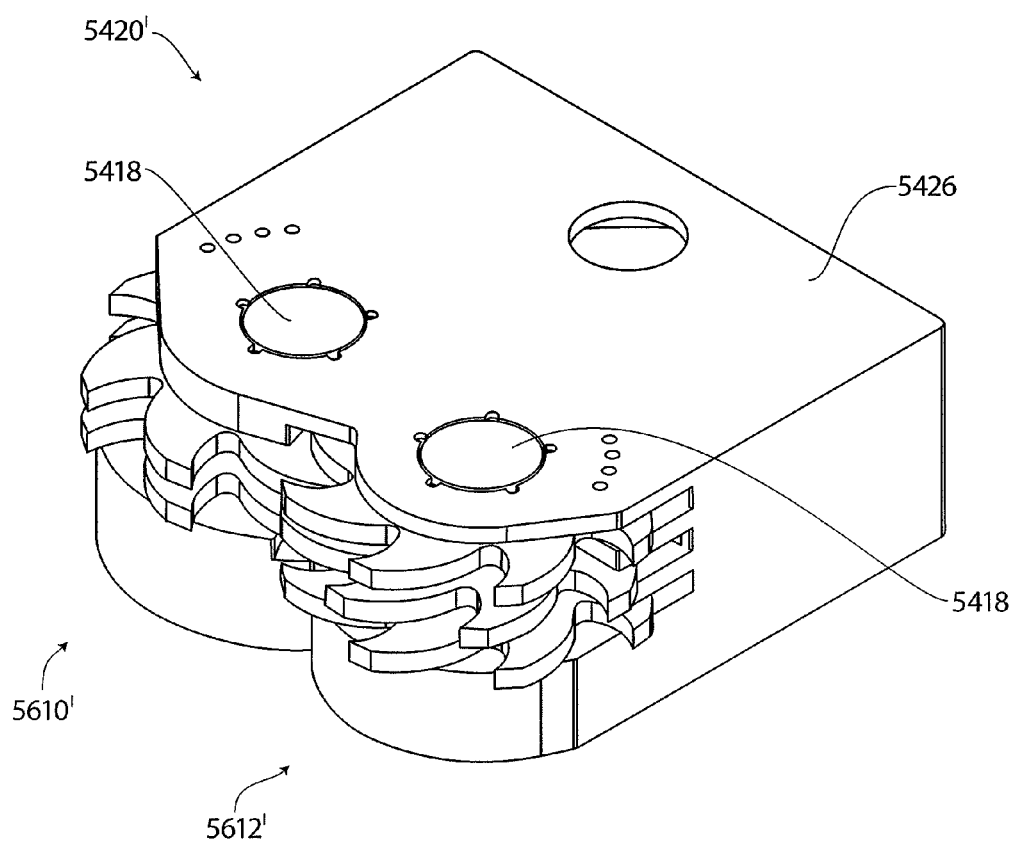
FIGS. 57A-57J show details of an exemplary rotor housing assembly 5420'.

FIGS. 57A-57J show further details of an exemplary rotor housing assembly 5420'. Assembly 5420' is constructed and operates in a manner similar to assembly 5420 as previously described in reference to FIGS. 54A-54C and 56A-56H, but has a different blade configuration. As shown in FIG. 57A, rotor housing assembly 5420' includes a pair of rotors 5610' and 5612', each rotatably mounted in rotor housing 5426 by an axel 5618. In this embodiment, rotors 5610' and 5612' are configured to rotate in opposite directions to draw tissue into a center, overlapping region where the tissue is shredded.

Figure 57B:
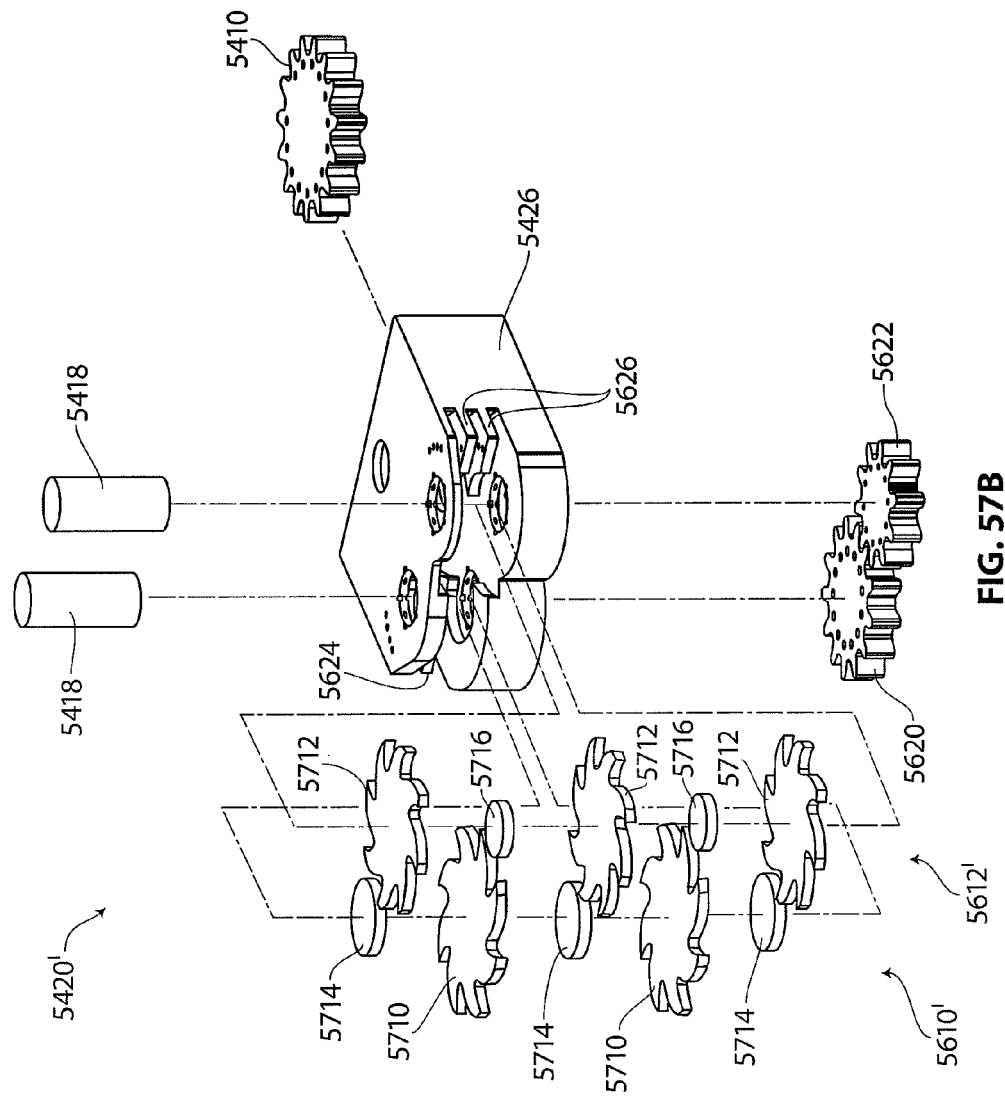
Figure 57C:
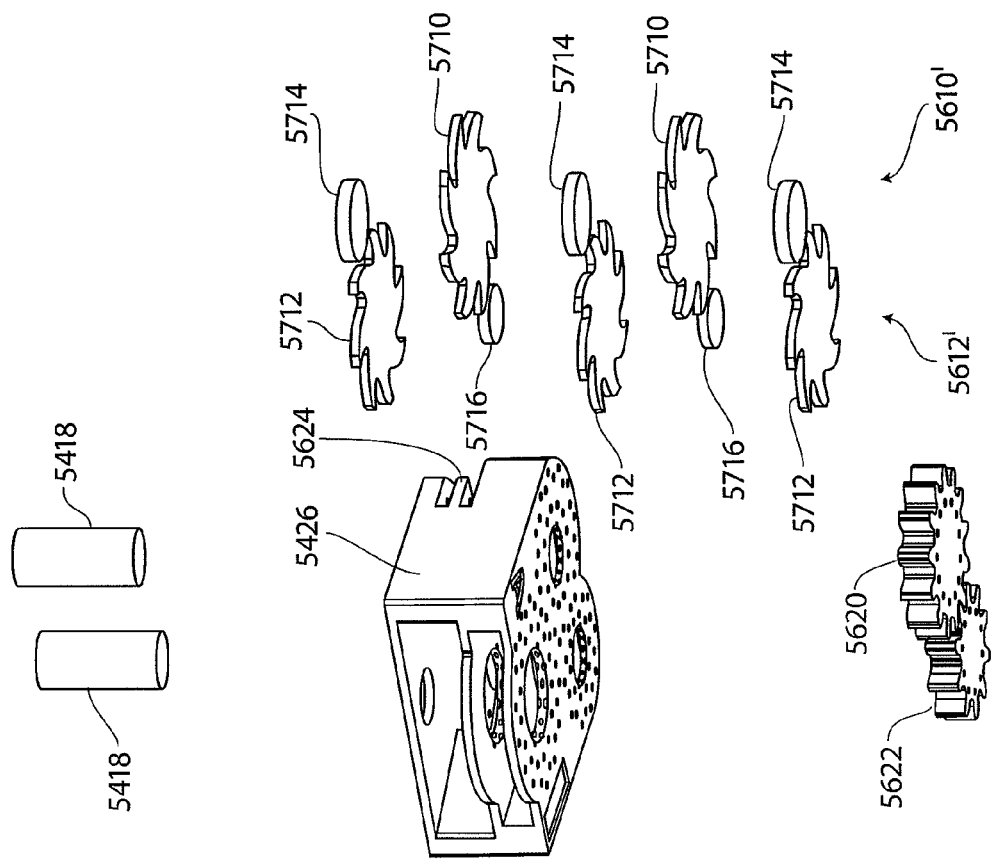

Referring to FIGS. 57B and 57C, the components of rotor housing assembly 5420' are shown. Assembly 5420' includes housing 5426, a pair of axels 5418, and gears 5410, 5620 and 5622, as previously described. Rotor 5610' includes two blades 5710 interspersed with three spacer rings 5714 on first axel 5418. Rotor 5612' includes three blades 5712 interspersed with two spacer rings 5716 on second axel 5418.

It should be noted that while rotor housing assembly 5420' is shown in an exploded format for clarity in FIGS. 57B and 57C, suggesting that the components are fabricated separately and then assembled using traditional assembly processes, this may or may not be the case, depending on the embodiment. In some embodiments, rotor assembly 5420' is assembled this way. In other embodiments, assembly 5420' may be built in layers, such as by using the MEMS fabrication processes described earlier in this disclosure. For example, after portions of housing 5426 and gears 5410, 5620 and 5622 are built up in layers, bottom blade 5712, bottom spacer 5714, and housing fin 5624 are formed together in one or more layers. Following this layer, bottom blade 5710, bottom spacer 5716, and bottom housing fin 5626 may be formed together in one or more layers. The process may be repeated until the entire rotors 5610' and 5612' and surrounding components are formed. A thin sacrificial layer may be formed between adjacent layers of components to separate the components from one layer from components of adjacent layers. Sacrificial material may also be formed in portions of each non-sacrificial layer to separate components on that layer, create desired voids in the finished assembly, and to provide a substrate for forming components in subsequent layers above. With such a fabrication technique, rotor 5610' may be formed as a single unitary structure interleaved with portions of rotor housing 5426, rather than separate components (i.e. axel 5418, spacers 5714, blades 5710, and gear 5620.) Similarly, rotor 5612' may be formed as a single unitary structure interleaved with portions of rotor housing 5426, rather than separate components (i.e. axel 5418, blades 5712, spacers 5716, and gear 5622.) In some embodiments, combinations of fabrication and assembly techniques may be used to create the rotor housing and/or cutter head assemblies.

Figure 57D:
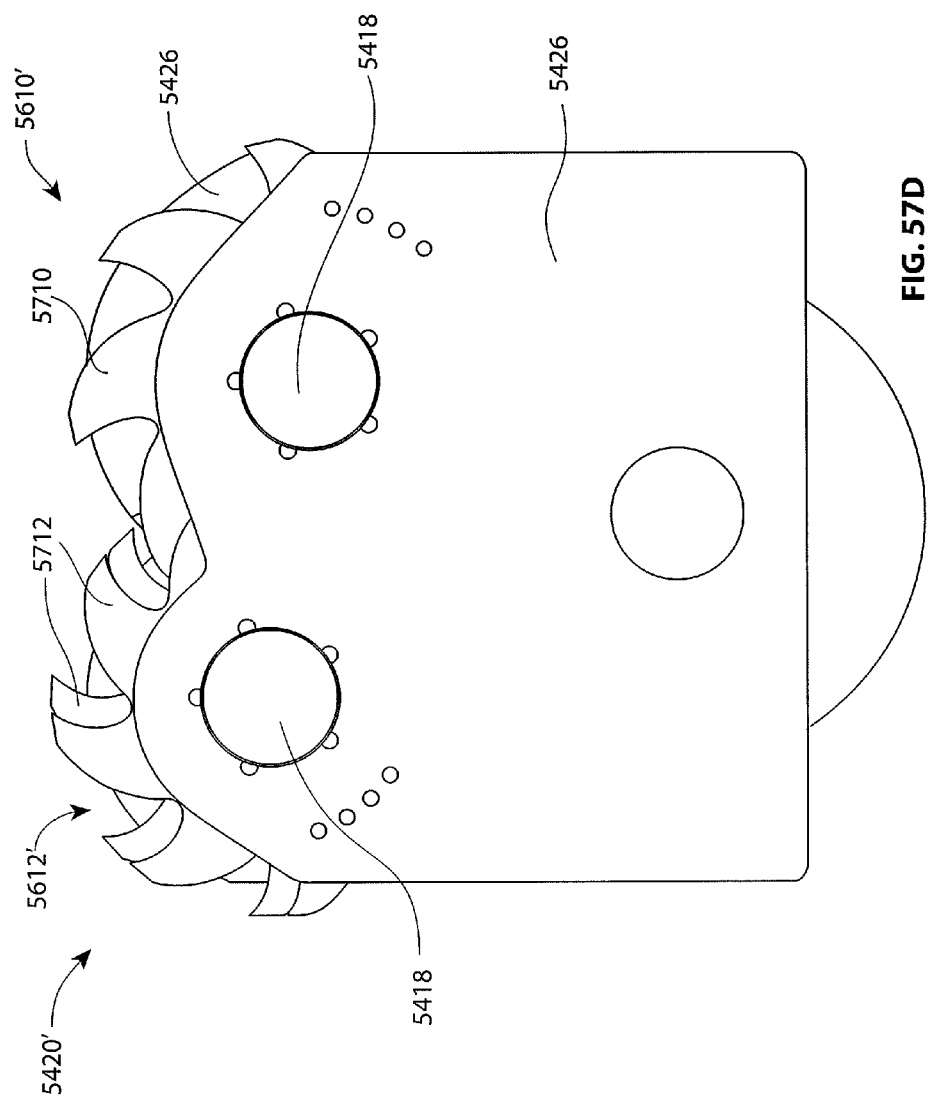
Figure 57E:
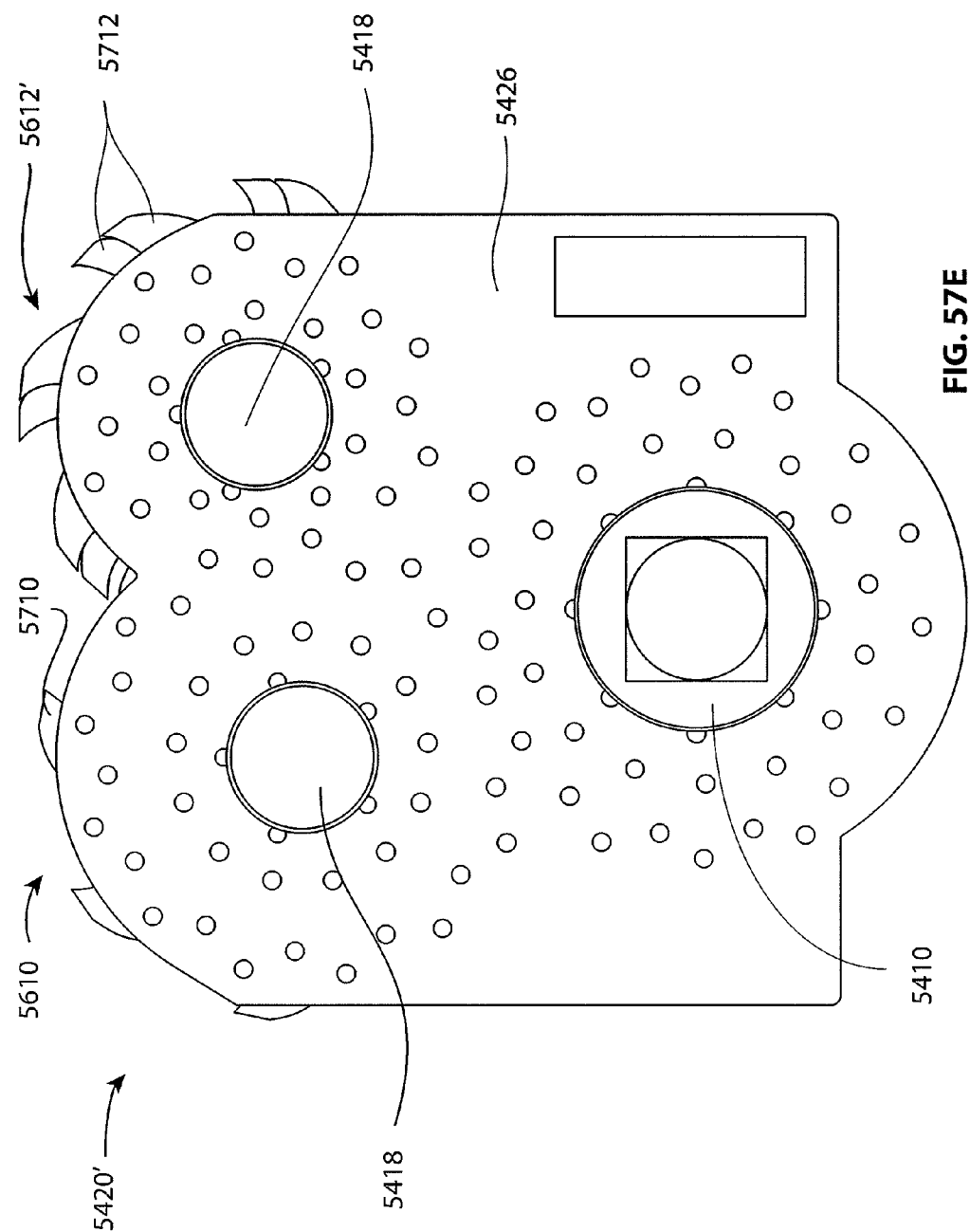

Referring to the top view shown in FIG. 57D and the bottom view shown in FIG. 57E, it can be seen that in this embodiment the axel 5418 of rotor 5612' is more distally located than axel 5418 of rotor 5610'. It can also be seen that while a top plate portion of rotor housing 5426 covers most of rotor blades 5710 and 5712, the blades protrude less from a middle and bottom plate portion of housing 5426. Further details of protruding blades and rotor characteristics are subsequently discussed in reference to FIG. 57J.

Figure 57F:
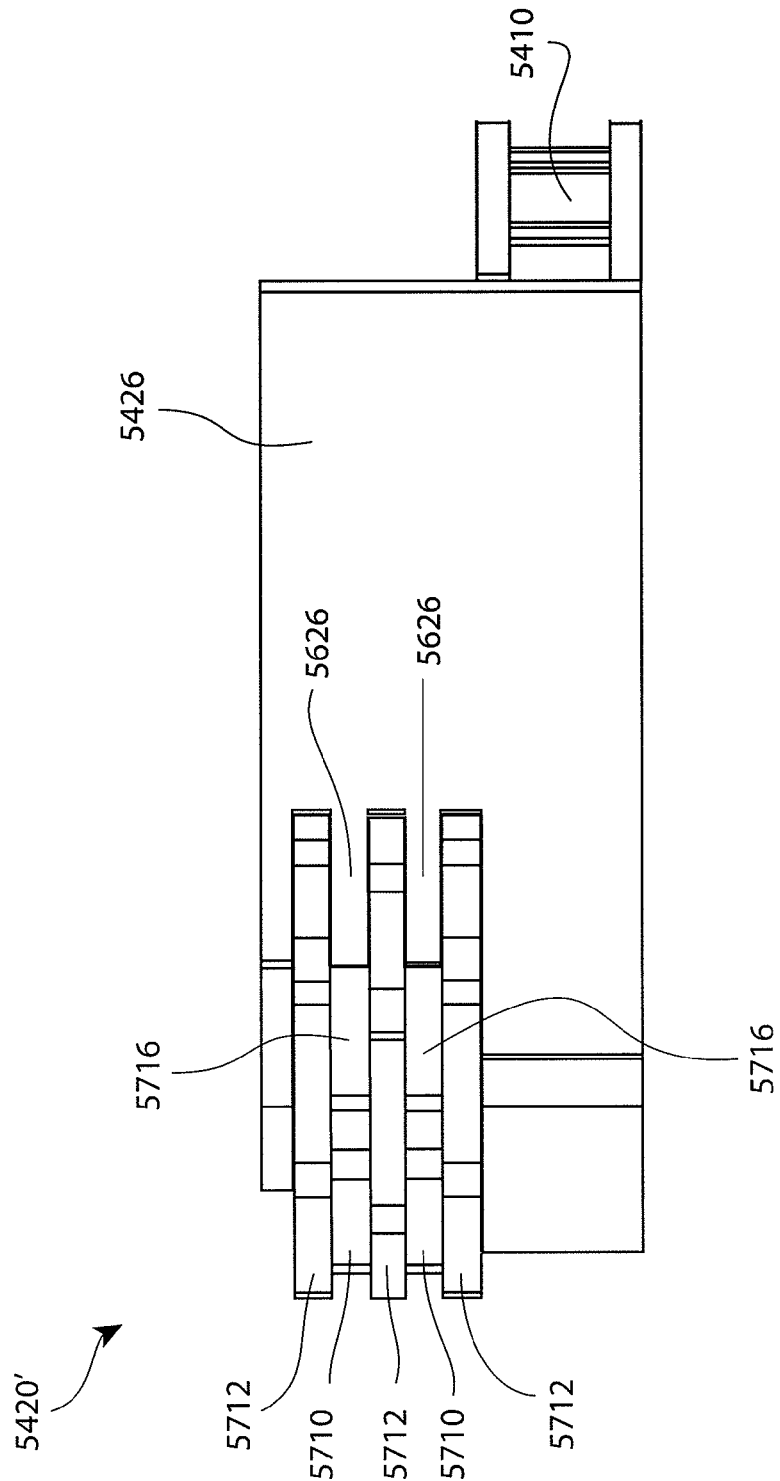

Referring to the side view shown in FIG. 57F, it can be seen that the three blades 5712 of rotor 5612' are interleaved in a proximal region by rotor housing fins 5626, in a central region by spacers 5716, and in an opposite side region (seen only in a distal region of the blades in FIG. 57F) by blades 5710 of opposing rotor 5610'.

Figure 57G:
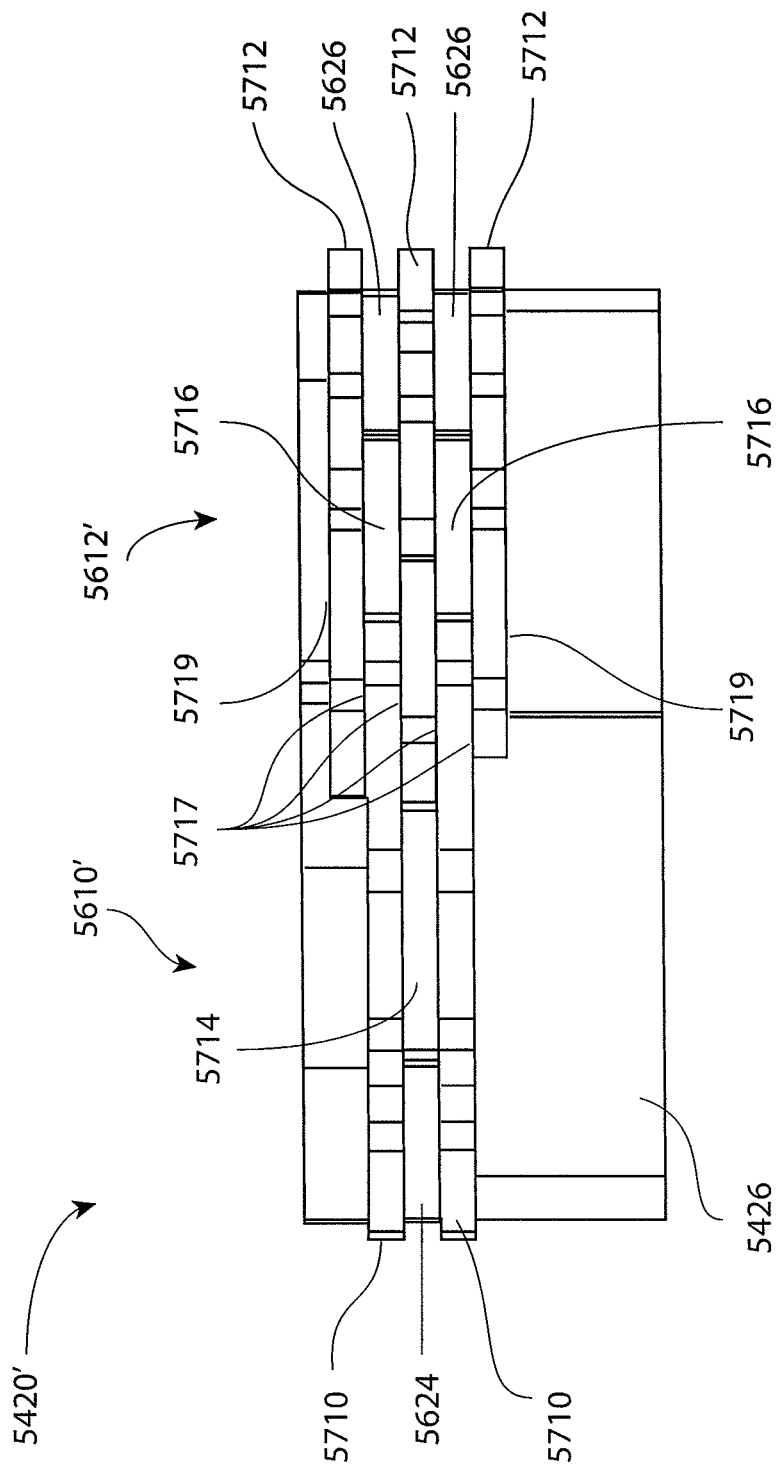
Figure 57H:
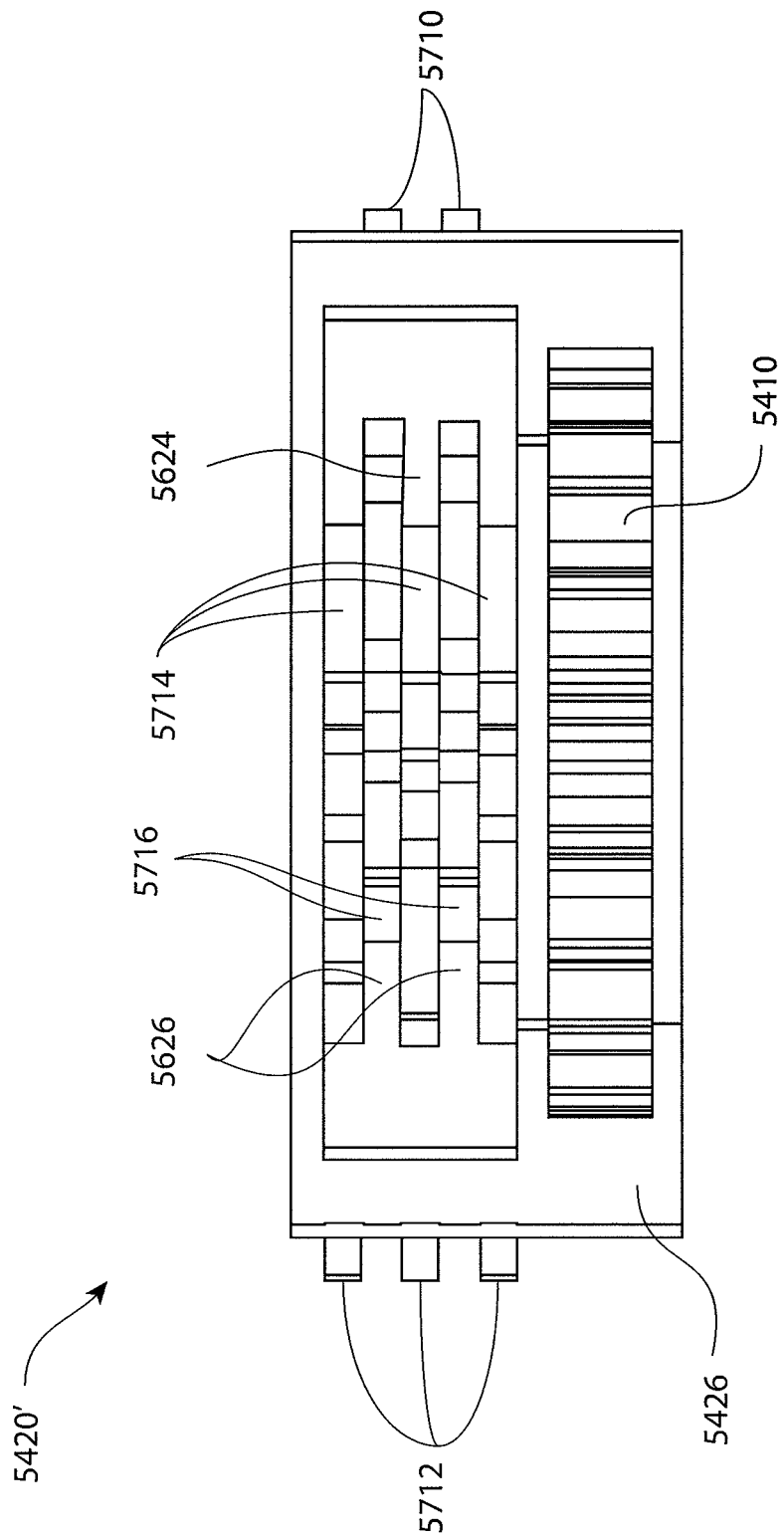

A front or distal end view is shown in FIG. 57G and a rear or proximal end view is shown in FIG. 57H. As depicted in FIG. 57G, very small gaps or interference fits 5717 between overlapping blades 5710 and 5712 are desirable in some embodiments. Similarly, very small gaps or interference fits 5719 between blades 5712 and adjacent portions of rotor housing 5426 are desirable in some embodiments, as will be subsequently described in more detail.

Figure 57I:
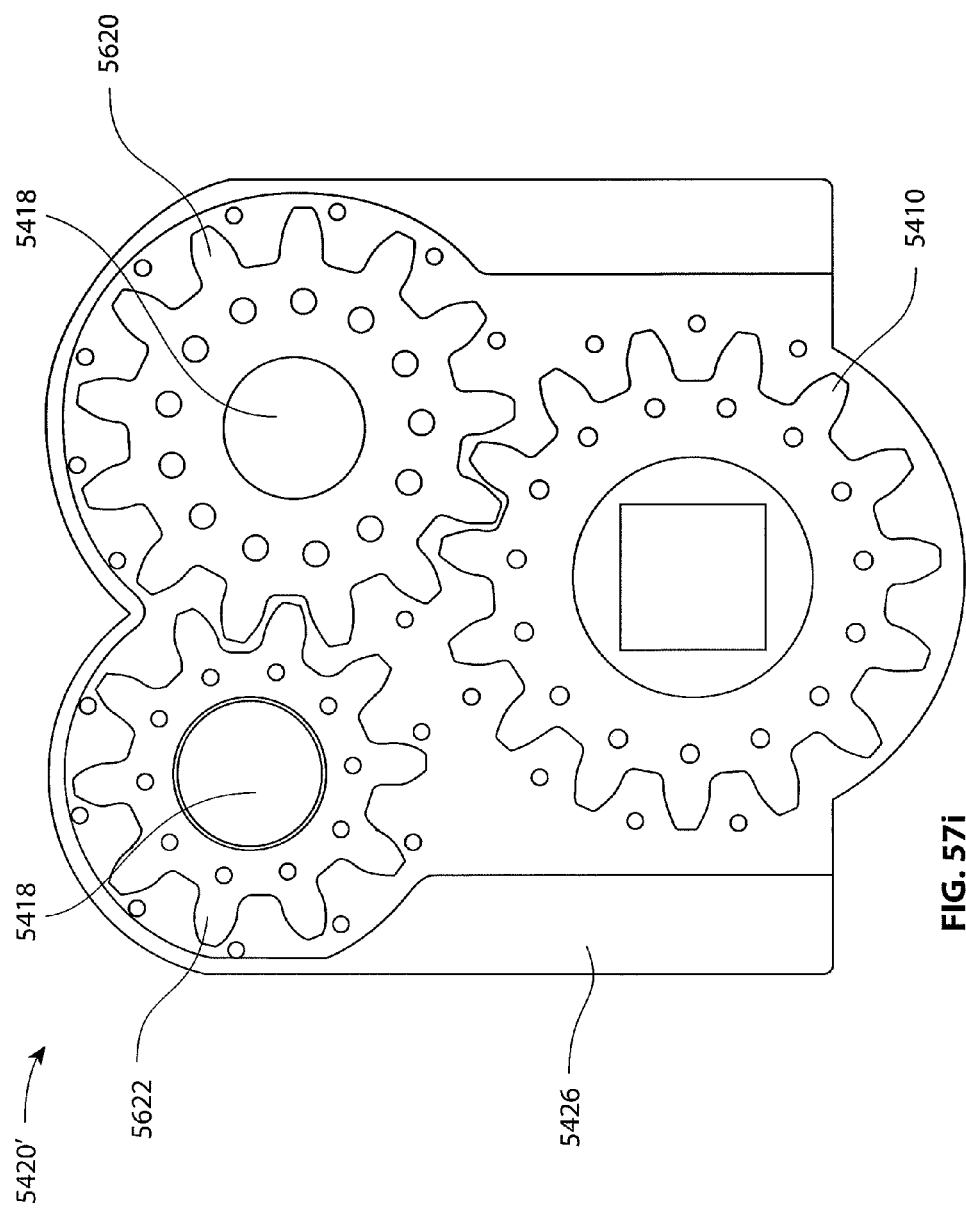

FIG. 57I shows a cross-sectional plan view of the gear train located in the lower portion of rotor housing 5426 of assembly 5420'.

Figure 57J:
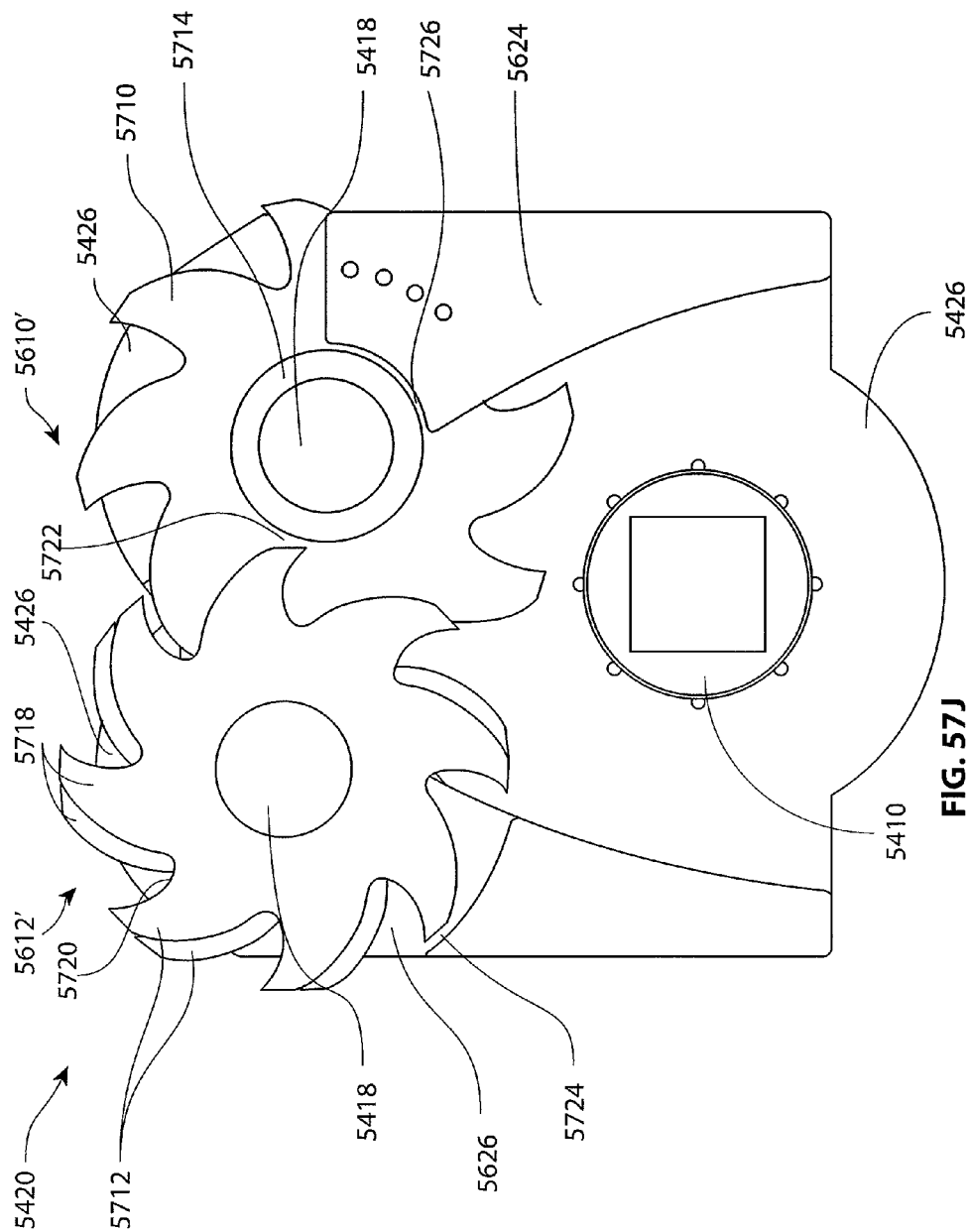

Referring to the cross-sectional plan view of FIG. 57J, the bottom two blades 5712, of rotor 5612' and the bottom blade 5710 of rotor 5610' are shown. As shown, blades 5710 have a larger outer diameter than that of blades 5712. But because axel 5418 of rotor 5612' is located more distally than axel 5418 of rotor 5610', blades 5712 protrude more distally from the bottom of rotor housing 5426 than do blades 5710 of rotor 5610'. It can also be seen that teeth 5718 and associated troughs 5720 of blades 5712 are configured to be rotationally out of phase with those of other blades 5712 of rotor 5612'. As will subsequently be discussed in more detail, this arrangement can tune rotors 5612 to selective cut certain types of tissue and avoid cutting other types of tissue.

Various rotor gaps can be seen in FIG. 57J. For example, gap 5722 is shown between the tips of blade teeth 5718 of rotor 5612' and spacer ring 5714/axel 5418 of opposing rotor 5610'. Gap 5724 is also shown, between the tips of blade teeth 5718 of rotor 5612' and the adjacent portion of housing 5426. Gap 5726 is also shown, between spacer ring 5714/axel 5418 of rotor 5610' and the adjacent portion of housing 5426. In some embodiments, it is desirable to keep gaps 5722, 5724 and 5726 very small, to ensure that tissue portions/particles that pass through rotors 5610' and 5612' are first cut to a very small size, and to avoid jamming or clogging rotors 5610' and 5612'. In some embodiments, these gaps are fabricated as small interferences between the adjacent parts so that when the rotors are first rotated, the adjacent parts hit each other and wear down or burnish each other. In this manner, after a break in period, smaller interference or zero clearance fits are created between the adjacent moving parts. Gap distances that applicants believe are advantageous include less than about 20 microns, less than about 10 microns, less than about 5 microns, less than about 1 micron, substantially zero, an initial interference fit of at least 2 microns, and an initial interference fit of about 5 microns.

In operation, the clatter elements of rotor housing assembly shown in FIGS. 57A-57J serve to grab tissue from a target source, draw the tissue towards a central region between the blades, cut the tissue from the source, and morcellate the tissue in small pieces for transport away from the body. In other embodiments, separate cutter elements may be used for these various functions. For example, one blade or blades may be used to cut tissue from the source, while another blade or set of blades may be used to morcellate the cut tissue.

Components of cutter head assembly 5332, including rotor housing assemblies 5420 and 5420', may be fabricated using processes such as laser cutting/machining, photo chemical machining (PCM), Swiss screw, electro-discharge machining (EDM), electroforming and/or other processes for fabricating small parts. Wafer manufacturing processes may be used to produce high precision micro parts, such as EFAB, X-ray LICA (Lithography, Electroplating, and Molding), and/or UV LIGA.

FIGS. 58-65 depict various other aspects of cutting blades useful for selective tissue removal, according to aspects of the invention.

In some embodiments, the key to the shredder's ability to selectively remove tissue is attributed to the protrusion of the rotating cutters from the housing and the design of a tooth pitch (space between the tips of adjacent teeth) of each rotor. In some embodiments, the protrusion sets the depth of the inward cut for the tips of the rotor. This inward depth controls the thickness of tissue being removed. The tooth pitch or number of teeth circumferentially about the rotor diameter provides an opening for individual tissue fibers and/or fiber bundles to be hooked, tensioned and drawn between the cutters.

From the point of view of the selected tissue, the tooth pitch and protrusion may be designed to grasp the smallest fibers or fiber bundles that are to be removed. From the point of view of the non-selected tissue, the tooth pitch may be many times smaller than the fiber or fiber bundle, and the protrusion may also be equally smaller than the fiber/bundle diameter.

As previously described, FIGS. 57D and 57E show the exemplary protrusion of blades 5710 and 5712 as viewed from the top and bottom of a rotor housing assembly 5420', respectively. As shown in FIG. 57D versus 57E, the protrusion is more exposed on the top side than the bottom in this embodiment. In other embodiments, the cutter device has the same protrusion for both sides. Biasing the protrusion more on one side than the other can provide advantages such as cutting/shredding directionality and/or additional safety. Blade protrusion distances that applicants believe are advantageous include less than about 100 microns, less than about 10 microns, substantially flush with the housing, recessed a minimum of about 5 microns, and recessed a minimum of about 10 microns.

Figure 58:
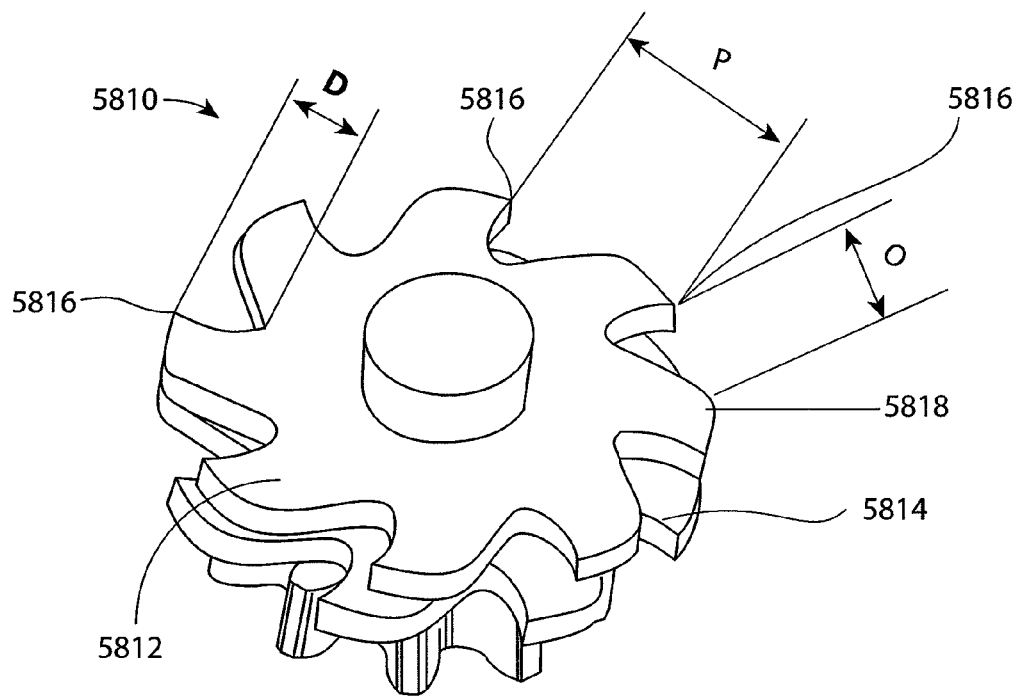
FIGS. 58-65 depict various other aspects of cutting blades useful for selective tissue removal, according to aspects of the present invention.

For tooth pitch, FIG. 58 shows a rotor 5810 with two blade disks 5812 and 5814. The pitch P is the distance from one tooth tip 5816 to the next tooth tip 5816 along an imaginary circle circumscribing the outer circumference of the blade. The trough diameter or depth D generally is the distance between the tooth tip 5816 and the low point between the tooth tips. In many embodiments, the trough is a critical geometry component that enables tissue selectivity. Additionally, the trough opening O (i.e. the distance from tooth tip 5816 to the tooth back 5818 of an adjoining tooth) can determine the size of the "window" for capturing a fiber or fiber bundle diameter.

As shown in FIG. 58, teeth from one blade 5812 can be designed to be out of phase with teeth from another blade 5814. Designing the blades to be out of phase from one another can be used to reduce the effective trough diameter by having the teeth of one disk overlap the troughs of another disk. This makes the device more suitable for removing tissue in thin planes (shaver). A device designed to use this planing mode may rely on a depth stop from the rotor housing to control the thickness of tissue removed.

Although the mechanical aspects are important attributes of tissue selectivity at this scale, there is another important feature that enables or further enables selectivity in some embodiments. As previously described, the electronic control system for a closed loop motor drive can be designed and programmed to enable the sensing of the torque load (changes in electrical current) and/or changes in velocity at the blade rotors as they are being loaded by the tissue. In some embodiments, this is very important when going from one tissue plane into another, i.e. muscle to cartilage, cartilage to bone, fiavum to dura, tumor to nerve, etc. For the cutting of each tissue plane there can be a known mechanical load that is imparted to the cutter head and sensed by the motor drive electronics and/or microprocessor. When a known load signature changes (with the exception of a no load condition), the system can recognize this change. The surgeon can be alerted to this change, the motor can be stopped under control or the motor speed can be changed to an optimal level for the next tissue type to be cut.

For a closed loop motor controller, the output current can be limited and monitored continuously with a high speed microprocessor (torque sensing). Likewise, for velocity monitoring, the servo gains can be set so the motor is underdamped. The change in velocity may be indicated by a tachometer and can be used to indicate a change in load at the cutter head. Either of these methods of monitoring a change in load (torque sensing, such as by monitoring current) or a change in velocity (velocity sensing, such as with a tachometer) alone or in combination enable a highly sensitive method of measuring tissue load and detecting transitions in tissue structures.

In some embodiments, tooth protrusion, tooth pitch, trough diameter/depth, and trough opening are key geometric blade features that enable selective tissue removal. The descriptions below that accompany FIGS. 59-65 illustrate these concepts.

Figure 59:
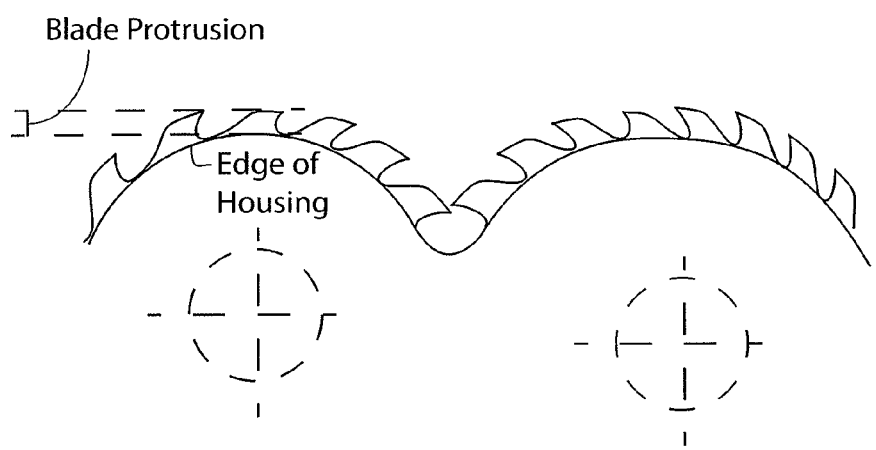

FIG. 59 shows the details of blade protrusion from the edge of a housing.

Figure 60:
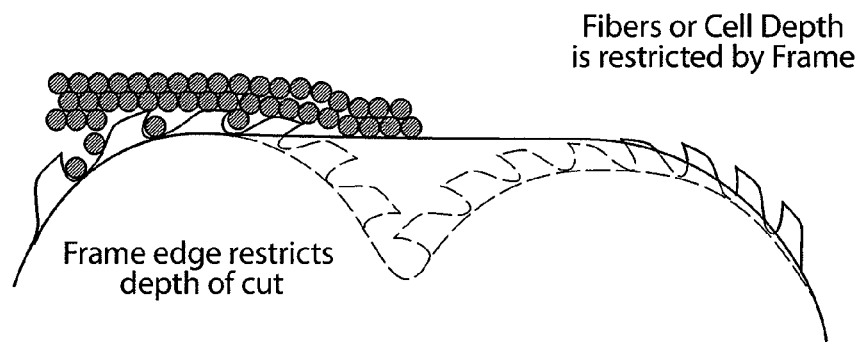

FIG. 60 shows how a housing is being used as a depth stop for controlling the thickness of tissue being removed from the source. In some embodiments, the protrusion depth is as small as an individual cell or fiber diameter of 2 microns.

Figure 61:
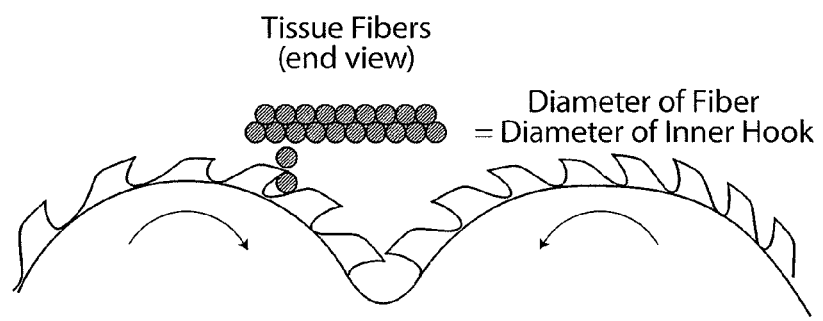

FIG. 61 shows the diameter of the tooth trough matching the diameter of the fiber or cell. In some embodiments, the tooth trough diameter is as small as an individual cell or fiber diameter of 2 microns.

Figure 62:
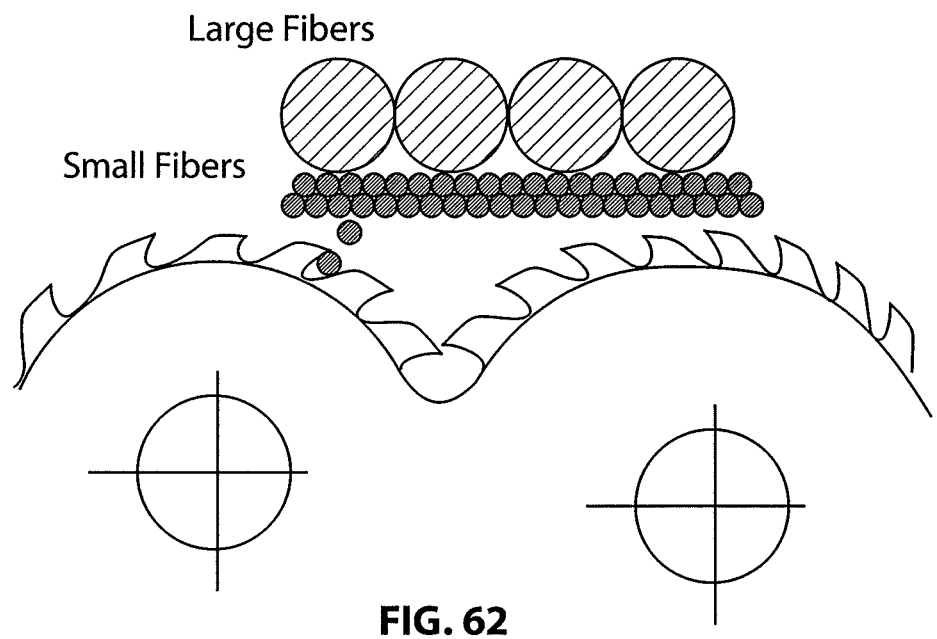
Figure 63:
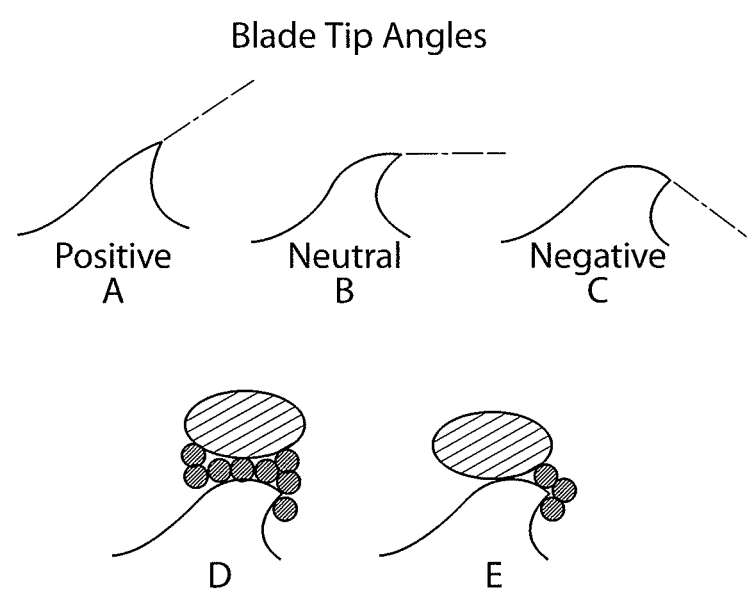

FIG. 62 shows the details of selectivity from small fibers (selected) to large fibers (non-selected).

FIGS. 63A-63E show the details of how a tooth tip's angle of attack can be adjusted to further enhance the selective cutting attributes. By creating a negative angle of attack as shown in FIGS. 63C-63E, the tooth tip is generally only effective when the fiber diameter is less than or equal to the trough diameter. When the fiber diameter is greater than the trough diameter, the fiber is pushed away from the tooth, as depicted in FIG. 63E. The negative angle of attack can ensure the repulsion of the larger fiber from the tooth's grasp. A positive angle of attack (FIG. 63A) or a neutral angle of attack (FIG. 63B), on the other hand, is less selective than the negative angle of attack (FIG. 63C). Adjusting the tip pitch, trough depth, trough opening, protrusion distance, tooth speed, etc., of tooth tips having positive or neutral angles of attack can enable these tips to also be selective of the type of tissue they will and will not cut.

Figure 64:
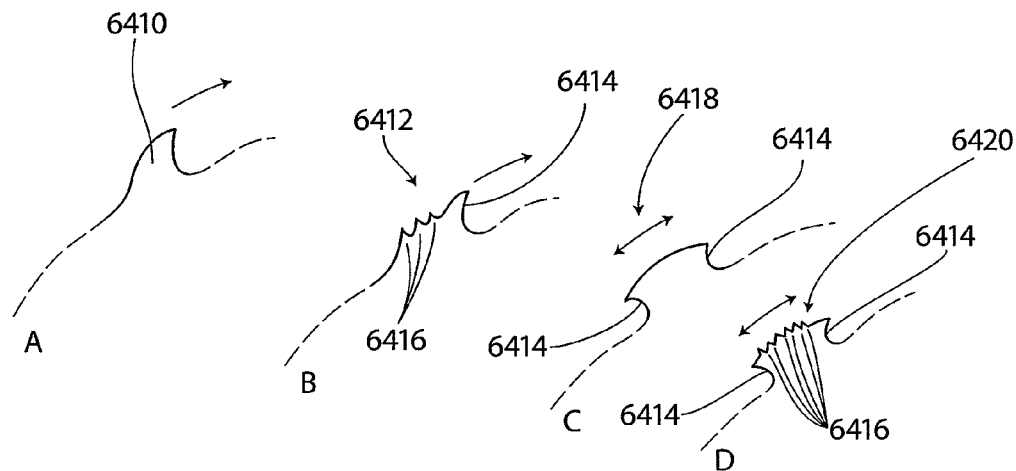

FIG. 64 shows different tooth geometries that can be designed into each rotor. In FIG. 64A, a basic unidirectional grasping tooth is shown. In FIG. 64B, a dual purpose unidirectional tooth 6412 is shown. This design has a leading grasper type tooth 6414 followed by teeth 6413 that can be used for removing harder materials such as ligament and bone. FIG. 64C shows a bidirectional tooth 6418 with a grasping cutter 6414 at each end of the tooth. This dual direction cutter can cut in clockwise and counter-clockwise directions by grasping, pulling and cutting tissue from the source, working in the same manner as tooth 6410 depicted in FIG. 64A. FIG. 64D shows a bidirectional cutter 6420 with the same bidirectional cutting attributes as tooth 6418 in FIG. 64C, but with smaller tooth features 6416 between the two large leading edges, for use in removing harder materials such as ligament and bone.

Figure 65:
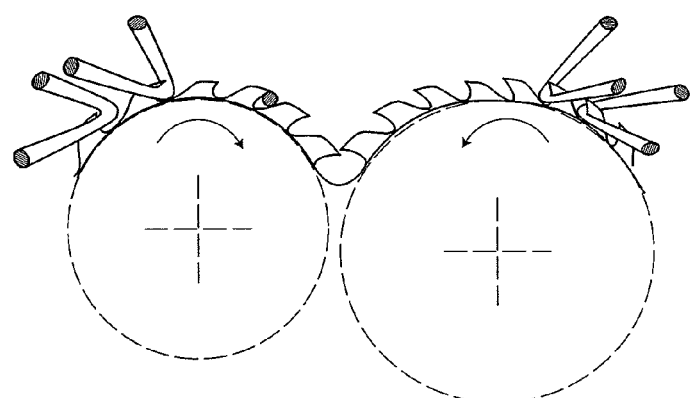
Figure 66D:
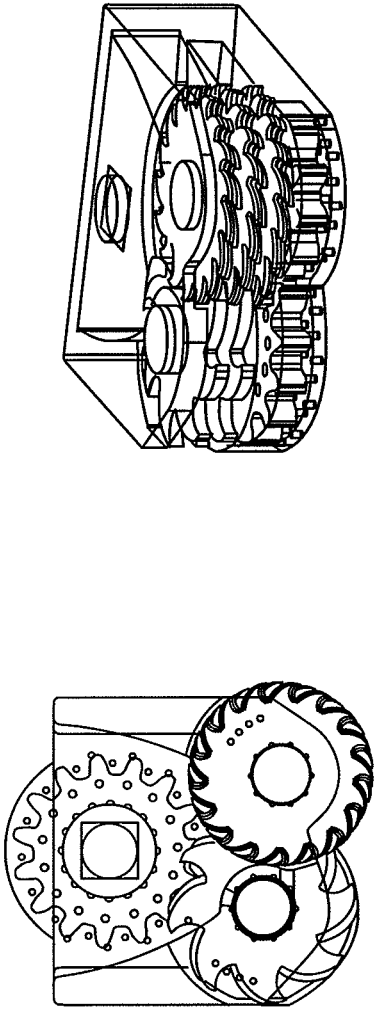

In FIG. 65, two rotary blades are shown with fibers in tension. In some double blade cutter embodiments, the ability to pretension the fibers tightly before cutting is a key attribute. Tensioning fibers before pulling them between the rotors and shearing them from the source enables the device to remove soft tissue in a swath that is as wide as or wider than the width or diameter of the cutter head. This process of pre-tensioning the tissue fibers before cutting enables soft tissue to be cut and/or removed in a manner similar to how rigid materials are precisely cut and shaped using controlled industrial machining processes.

Tooth tip velocity along with tooth geometry is another means of controlling selective tissue removal, according to aspects of the present invention. A cutting device can be made non-selective for a particular tissue by adding a negative angle of attack to the teeth and driving the rotors at a fast speed, such that the tissue fibers are bumped or pushed away from the tooth troughs. By decreasing the speed along with the use of suction and/or pressure against the target tissue, the selected fibers matching the trough diameter are pulled inward between the blade rotors. At this point, the device works at an optimal speed for selective tissue removal without abrasion or tearing to the larger non-selected tissue fibers.

In some embodiments, the target tissue being cut is hydrated and generally has a nominal fiber diameter of about 6 to about 9 microns. In some embodiments, the target tissue being cut is dry and generally has a nominal fiber diameter of about 5 to about 6 microns. In some embodiments, the tissue fibers are connected together in bundles having a nominal diameter of about 250 microns.

Typical dimensions in some embodiments include:
Housing diameter: 6 mm or less
Blade diameter range: 0.75 mm to 4 mm
Tip to Tip range: 0.2 mm to 1 mm
Trough diameter range: 2 microns to 0.5 mm
Blade protrusion range: 2 microns to 2 mm
The tip to tip distance is typically at least two times the trough diameter for hook type teeth.

FIGS. 66A-66M show 13 further examples of cutter heads constructed according to aspects of the present invention.

The tissue cutting devices disclosed herein may be configured for use in a variety of procedures. An example of a cardiac application is using the inventive devices to selectively remove endocardium, with the cutting device configured to leave the underlying myocardium uncut. An example of a tissue removing application involving the esophagus includes selectively removing mucosa, leaving the submucosa. Such a therapy would be useful for treating Barrett's disease. Examples in the spinal area include selectively removing flavum, with the cutting device configured to stop removing tissue when dura is reached, leaving the dura intact. Selective removal of flavum but not nerve root is another embodiment. A cutting device constructed according to aspects of the invention can also be configured to remove flavum without cutting bone. In this embodiment, the rotor velocity could be changed and/or the cutting elements could be changed after the flavum is removed such that some bone tissue could then be removed. Examples in the neurovascular area include selectively removing cancerous tissue while not cutting adjacent blood vessel tissue or nerve tissue. In the rheumatology field, tears in labral target tissue may be selectively removed while preserving adjacent non-target tissue, such as in the hips, shoulders, knees, ankles, and small joints. In some embodiments, small teeth on the rotors can interact with micron scale fibers of cartilage, removing tissue in a precise way, much like precision machining of materials that are harder than tissue. Other target tissues that may be selectively removed by the inventive devices and methods described herein include cartilage, which tends to be of a medium density, periosteum, stones, calcium deposits, calcified tissue, cancellous bone, cortical bone, plaque, thrombi, blood clots, and emboli.

It can be appreciated by those skilled in the art of tissue removal that soft tissue is much more difficult to remove in a small quantities and/or in a precise way than harder tissue such as bone that may be grinded or sculpted, since soft tissue tends to move or compress when being cut, rather than cut cleanly. Cutting tissue rather than removing it with a laser or other high energy device has the advantage of not overheating the tissue. This allows the tissue to be collected and its pathology tested, as previously described.

In some embodiments of the invention, the selective tissue cutting tool may be moved laterally along a tissue plane, removing thin swaths of tissue with each pass until the desired amount or type of tissue is removed. In some embodiments, the tool may be plunged into the target tissue in a distal direction, until a desired depth or type of tissue is reached. In any of these embodiments, the tool may cut a swath or bore that is as large as or larger than the width of the tool head. In some embodiments, the cutting elements are distally facing, laterally facing, or both.

Further Comments and Conclusions

Structural or sacrificial dielectric materials may be incorporated into embodiments of the present disclosure in a variety of different ways. Such materials may form a third material or higher deposited on selected layers or may form one of the first two materials deposited on some layers. Additional teachings concerning the formation of structures on dielectric substrates and/or the formation of structures that incorporate dielectric materials into the formation process and possibility into the final structures as formed are set forth in a number of patent applications filed Dec. 31, 2003. The first of these filings is U.S. Patent Application No. 60/534,184 which is entitled "Electrochemical Fabrication Methods Incorporating Dielectric Materials and/or Using Dielectric Substrates". The second of these filings is U.S. Patent Application No. 60/533,932, which is entitled "Electrochemical Fabrication Methods Using Dielectric Substrates". The third of these filings is U.S. Patent Application No. 60/534,157, which is entitled "Electrochemical Fabrication Methods Incorporating Dielectric Materials". The fourth of these filings is U.S. Patent Application No. 60/533,891, which is entitled "Methods for Electrochemically Fabricating Structures Incorporating Dielectric Sheets and/or Seed Layers That Are Partially Removed Via Planarization". A fifth such filing is U.S. Patent Application No. 60/533,895, which is entitled "Electrochemical Fabrication Method for Producing Multi-layer Three-Dimensional Structures on a Porous Dielectric". Additional patent filings that provide teachings concerning incorporation of dielectrics into the EFAB process include U.S. patent application Ser. No. 11/139,262, filed May 26, 2005 by Lockard, et al., and which is entitled "Methods for Electrochemically Fabricating Structures Using Adhered Masks, Incorporating Dielectric Sheets, and/or Seed Layers that are Partially Removed Via Planarization"; and U.S. patent application Ser. No. 11/029,216, now abandoned, filed Jan. 3, 2005 by Cohen, et al., and which is entitled "Electrochemical Fabrication Methods Incorporating Dielectric Materials and/or Using Dielectric Substrates". These patent filings are each hereby incorporated herein by reference as if set forth in full herein.

Some embodiments may employ diffusion bonding or the like to enhance adhesion between successive layers of material. Various teachings concerning the use of diffusion bonding in electrochemical fabrication processes are set forth in U.S. patent application Ser. No. 10/841,384, now abandoned, which was filed May 7, 2004 by Cohen et al. which is entitled "Method of Electrochemically Fabricating Multilayer Structures Having Improved Interlayer Adhesion" and which is hereby incorporated herein by reference as if set forth in full. This application is hereby incorporated herein by reference as if set forth in full.

Some embodiments may incorporate elements taught in conjunction with other medical devices as set forth in various U.S. patent applications filed by the owner of the present application and/or may benefit from combined use with these other medical devices: Some of these alternative devices have been described in the following previously filed patent applications: (1) U.S. patent application Ser. No. 11/478,934, by Cohen et al., and entitled "Electrochemical Fabrication Processes Incorporating Non-Platable Materials and/or Metals that are Difficult to Plate On"; (2) U.S. patent application Ser. No. 11/582,049, by Cohen, and entitled "Discrete or Continuous Tissue Capture Device and Method for Making"; (3) U.S. patent application Ser. No. 11/625,807, by Cohen, and entitled "Microdevices for Tissue Approximation and Retention, Methods for Using, and Methods for Making"; (4) U.S. patent application Ser. No. 11/696,722, by Cohen, and entitled "Biopsy Devices, Methods for Using, and Methods for Making"; (5) U.S. patent application Ser. No. 11/734,273, by Cohen, and entitled "Thrombectomy Devices and Methods for Making"; (6) U.S. Patent Application No. 60/942,200, by Cohen, and entitled "Micro-Umbrella Devices for Use in Medical Applications and Methods for Making Such Devices"; and (7) U.S. patent application Ser. No. 11/444,999, by Cohen, and entitled "Microtools and Methods for Fabricating Such Tools". Each of these applications is incorporated herein by reference as if set forth in full herein.

Though the embodiments explicitly set forth herein have considered multi-material layers to be formed one after another. In some embodiments, it is possible to form structures on a layer-by-layer basis but to deviate from a strict planar layer on planar layer build up process in favor of a process that interlaces material between the layers. Such alternative build processes are disclosed in U.S. application Ser. No. 10/434,519, filed on May 7, 2003, now U.S. Pat. No. 7,252,861, entitled Methods of and Apparatus for Electrochemically Fabricating Structures Via Interlaced Layers or Via Selective Etching and Filling of Voids. The techniques disclosed in this referenced application may be combined with the techniques and alternatives set forth explicitly herein to derive additional alternative embodiments. In particular, the structural features are still defined on a planar-layer-by-planar-layer basis but material associated with some layers are formed along with material for other layers such that interlacing of deposited material occurs. Such interlacing may lead to reduced structural distortion during formation or improved interlayer adhesion. This patent application is herein incorporated by reference as if set forth in full.

The patent applications and patents set forth below are hereby incorporated by reference herein as if set forth in full. The teachings in these incorporated applications can be combined with the teachings of the instant application in many ways: For example, enhanced methods of producing structures may be derived from some combinations of teachings, enhanced structures may be obtainable, enhanced apparatus may be derived, and the like.

| U.S. Pat. App. Ser. No., Filing Date U.S. App. Pub. No., Pub. Date U.S. Pat. No., Issue Date | Inventor, Title |
|---|---|
| 09/493,496 - Jan. 28, 2000 U.S. Pat. No. 6,790,377 - Sep. 14, 2004 | Cohen, "Method For Electrochemical Fabrication" |
| 10/677,556 - Oct. 1, 2003 2004-0134772 - Jul. 15, 2004 | Cohen, "Monolithic Structures Including Alignment and/or Retention Fixtures for Accepting Components" |
| 10/830,262 - Apr. 21, 2004 2004-0251142A - Dec. 16, 2004 U.S. Pat. No. 7,198,704 - Apr. 3, 2007 | Cohen, "Methods of Reducing Interlayer Discontinuities in Electrochemically Fabricated Three-Dimensional Structures" |
| 10/271,574 - Oct. 15, 2002 2003-0127336A - Jul. 10, 2003 U.S. Pat. No. 7,288,178 - Oct. 30, 2007 | Cohen, "Methods of and Apparatus for Making High Aspect Ratio Microelectromechanical Structures" |
| 10/697,597 - Dec. 20, 2002 2004-0146650A - Jul. 29, 2004 | Lockard, "EFAB Methods and Apparatus Including Spray Metal or Powder Coating Processes" |
| 10/677,498 - Oct. 1, 2003 2004-0134788 - Jul. 15, 2004 U.S. Pat. No. 7,235,166 - Jun. 26, 2007 | Cohen, "Multi-cell Masks and Methods and Apparatus for Using Such Masks To Form Three-Dimensional Structures" |
| 10/724,513 - Nov. 26, 2003 2004-0147124 - Jul. 29, 2004 U.S. Pat. No. 7,368,044 - May 6, 2008 | Cohen, "Non-Conformable Masks and Methods and Apparatus for Forming Three-Dimensional Structures" |
| 10/607,931 - Jun. 27, 2003 2004-0140862 - Jul. 22, 2004 U.S. Pat. No. 7,239,219 - Jul. 3, 2007 | Brown, "Miniature RF and Microwave Components and Methods for Fabricating Such Components" |
| 10/841,100 - May 7, 2004 2005-0032362 - Feb. 10, 2005 U.S. Pat. No. 7,109,118 - Sep. 19, 2006 | Cohen, "Electrochemical Fabrication Methods Including Use of Surface Treatments to Reduce Overplating and/or Planarization During Formation of Multi-layer Three-Dimensional Structures" |
| 10/387,958 - Mar. 13, 2003 2003-022168A - Dec. 4, 2003 | Cohen, "Electrochemical Fabrication Method and Application for Producing Three-Dimensional Structures Having Improved Surface Finish" |
| 10/434,494 - May 7, 2003 2004-0000489A - Jan. 1, 2004 | Zhang, "Methods and Apparatus for Monitoring Deposition Quality During Conformable Contact Mask Plating Operations" |
| 10/434,289 - May 7, 2003 2004-0065555A - Apr. 8, 2004 | Zhang, "Conformable Contact Masking Methods and Apparatus Utilizing In Situ Cathodic Activation of a Substrate" |
| 10/434,294 - May 7, 2003 2004-0065550A - Apr. 8, 2004 | Zhang, "Electrochemical Fabrication Methods With Enhanced Post Deposition Processing" |
| 10/434,295 - May 7, 2003 2004-0004001A - Jan. 8, 2004 | Cohen, "Method of and Apparatus for Forming Three-Dimensional Structures Integral With Semiconductor Based Circuitry" |
| 10/434,315 - May 7, 2003 2003-0234179 A - Dec. 25, 2003 U.S. Pat. No. 7,229,542 - Jun. 12, 2007 | Bang, "Methods of and Apparatus for Molding Structures Using Sacrificial Metal Patterns" |
| 10/434,103 - May 7, 2004 2004-0020782A - Feb. 5, 2004 U.S. Pat. No. 7,160,429 - Jan. 9, 2007 | Cohen, "Electrochemically Fabricated Hermetically Sealed Microstructures and Methods of and Apparatus for Producing Such Structures" |
| 10/841,006 - May 7, 2004 2005-0067292 - May 31, 2005 | Thompson, "Electrochemically Fabricated Structures Having Dielectric or Active Bases and Methods of and Apparatus for Producing Such Structures" |
| 10/434,519 - May 7, 2003 2004-0007470A - Jan. 15, 2004 U.S. Pat. No. 7,252,861 - Aug. 7, 2007 | Smalley, "Methods of and Apparatus for Electrochemically Fabricating Structures Via Interlaced Layers or Via Selective Etching and Filling of Voids" |
| 10/724,515 - Nov. 26, 2003 2004-0182716 - Sep. 23, 2004 U.S. Pat. No. 7,291,254 - Nov. 6, 2007 | Cohen, "Method for Electrochemically Forming Structures Including Non-Parallel Mating of Contact Masks and Substrates" |
| 10/841,347 - May 7, 2004 2005-0072681 - Apr. 7, 2005 | Cohen, "Multi-step Release Method for Electrochemically Fabricated Structures" |
| 60/533,947 - Dec. 31, 2003 | Kumar, "Probe Arrays and Method for Making" |
| 60/534,183 - Dec. 31, 2003 | Cohen, "Method and Apparatus for Maintaining Parallelism of Layers and/or Achieving Desired Thicknesses of Layers During the Electrochemical Fabrication of Structures" |
| 11/733,195 - Apr. 9, 2007 2008-0050524 - Feb. 28, 2008 | Kumar, "Methods of Forming Three-Dimensional Structures Having Reduced Stress and/or Curvature" |
| 11/506,586 - Aug. 8, 2006 2007-0039828 - Feb. 22, 2007 | Cohen, "Mesoscale and Microscale Device Fabrication Methods Using Split Structures and Alignment Elements" |
| 10/949,744 - Sep. 24, 2004 2005-0126916 - Jun. 16, 2005 U.S. Pat. No. 7,498,714 - Mar. 3, 2009 | Lockard, "Three-Dimensional Structures Having Feature Sizes Smaller Than a Minimum Feature Size and Methods for Fabricating" |

Though various portions of this specification have been provided with headers, it is not intended that the headers be used to limit the application of teachings found in one portion of the specification from applying to other portions of the specification. For example, it should be understood that alternatives acknowledged in association with one embodiment, are intended to apply to all embodiments to the extent that the features of the different embodiments make such application functional and do not otherwise contradict or remove all benefits of the adopted embodiment. Various other embodiments of the present invention exist. Some of these embodiments may be based on a combination of the teachings herein with various teachings incorporated herein by reference.

In view of the teachings herein, many further embodiments, alternatives in design and uses of the embodiments of the instant invention will be apparent to those of skill in the art. As such, it is not intended that the invention be limited to the particular illustrative embodiments, alternatives, and uses described above but instead that it be solely limited by the claims presented hereafter.

What is claimed is:

1. A method of selectively removing target tissue from a body, the method comprising:
    providing a tissue cutting instrument capable of automatically distinguishing between target tissue to be removed and non-target tissue, the tissue cutting instrument comprising:
        at least two oppositely rotating cutting elements covered by a cutter housing, the at least two cutting elements each having at least one cutting surface configured to shear tissue against a cutting surface of an opposing cutting element, wherein the at least two oppositely rotating cutting elements have two separate, parallel and laterally offset axes of rotation, wherein each of the at least two oppositely rotating cutting elements is configured to rotate at least one full turn about one of the axes of rotation, wherein the cutting surfaces each comprise at least two cutting teeth and at least one trough between the teeth, the at least one trough having a nominal diameter of about 2 to about 100 microns, wherein a tip to tip distance between the teeth is at least two times the trough diameter, the cutter housing having a tissue access opening adjacent to a portion of the cutting elements through which tissue must extend to contact the cutting elements, wherein a maximum outside diameter of each of the at least two cutting elements is recessed from the tissue access opening in the cutter housing by a fixed, predetermined distance, wherein the instrument is configured to remove a maximum of about 2 to about 100 microns of target tissue at a time;
    urging the instrument against the target tissue and the non-target tissue; and
    allowing the instrument to cut the target tissue while automatically avoiding cutting of the non-target tissue.

2. The method of claim 1, further comprising automatically discontinuing tissue cutting once the instrument is contacting only the non-target tissue.

3. The method of claim 1, further comprising allowing the instrument to remove the target tissue from the body as it is being cut.

4. The method of claim 1, wherein the tissue cutting instrument is configured to distinguish between the target tissue and the non-target tissue by sensing an electrical current level being delivered to a cutter motor.

5. The method of claim 1, wherein the tissue cutting instrument is configured to distinguish between the target tissue and the non-target tissue by electronically sensing a cutter drive velocity.

6. The method of claim 1, wherein the tissue cutting instrument is configured to sense at least one parameter selected from the group consisting of: capacitance, inductance, optical changes, pressure, proximity and position.

7. The method of claim 1, wherein the tissue cutting instrument is configured to allow cutting of the target tissue while automatically avoiding cutting of non-target tissue by permitting modulation of a cutter speed.

8. The method of claim 1, wherein the tissue cutting instrument is configured to allow cutting of the target tissue while automatically avoiding cutting of non-target tissue by permitting modulation of suction in a port adjacent to a cutter head of the instrument.

9. The method of claim 1, wherein the at least two cutting elements are tuned to capture elements of the target tissue and reject elements of the non-target tissue.

10. The method of claim 9, wherein the nominal diameter of the at least one through of each of the cutting surfaces is matched to a diameter of a fiber or fiber bundle of the target tissue.

11. The method of claim 9, wherein the tip to tip distance between the cutting teeth is matched to a diameter of a fiber bundle of the target tissue.

12. The method of claim 1, wherein the maximum outside diameter is recessed by an amount that is at least about 5 microns and less than about 100 microns.

13. The method of claim 1, wherein the target tissue comprises endocardium and the non-target tissue comprises myocardium.

14. The method of claim 1, wherein the target tissue comprises mucosa and the non-target tissue comprises submucosa.

15. The method of claim 1, wherein the target tissue comprises flavum and the non-target tissue comprises dura mater.

16. The method of claim 1, wherein the target tissue comprises flavum and the non-target tissue comprises nerve roots.

17. The method of claim 1, wherein the target tissue comprises flavum and the non-target tissue comprises bone.

18. The method of claim 1, wherein the target tissue comprises prostate tissue and the non-target tissue comprises nerve tissue.

19. The method of claim 1, wherein the target tissue comprises soft tissue and the non-target tissue comprises tendon.

20. The method of claim 1, wherein the target tissue comprises soft tissue and the non-target tissue comprises cartilage.

21. The method of claim 1, wherein the target tissue comprises cartilage and the non-target tissue comprises bone.

22. The method of claim 1, wherein the target tissue comprises cancerous cells.

23. The method of claim 1, wherein the target tissue comprises labrum.

24. The method of claim 1, wherein the target tissue comprises plaque and the non-target tissue comprises a vascular wall.

25. The method of claim 1, wherein the target tissue comprises calcified tissue and the non-target tissue comprises a vascular wall.

26. The method of claim 1, wherein the target tissue comprises a thrombus and the non-target tissue comprises a vascular wall.

27. The method of claim 1, wherein the target tissue comprises an embolus and the non-target tissue comprises a vascular wall.

* * * * *